United States Patent
Bollu et al.

(10) Patent No.: US 8,846,739 B2
(45) Date of Patent: Sep. 30, 2014

(54) TGR5 AGONISTS

(75) Inventors: Venkataiah Bollu, San Diego, CA (US); Brant Clayton Boren, San Diego, CA (US); Jackaline Dalgard Julien, Del Mar, CA (US); Brenton T. Flatt, Poway, CA (US); Nadia Haq, Waltham, MA (US); Sarah Hudson, San Diego, CA (US); Raju Mohan, Encinitas, CA (US); Michael Morrissey, Danville, CA (US); Benjamin Pratt, Encinitas, CA (US)

(73) Assignee: Exelixis Patent Company LLC, South San Francisco, CA (US)

( * ) Notice: Subject to any disclaimer, the term of this patent is extended or adjusted under 35 U.S.C. 154(b) by 92 days.

(21) Appl. No.: 13/515,132

(22) PCT Filed: Aug. 11, 2010

(86) PCT No.: PCT/US2010/045195
§ 371 (c)(1),
(2), (4) Date: Jul. 23, 2012

(87) PCT Pub. No.: WO2011/071565
PCT Pub. Date: Jun. 16, 2011

(65) Prior Publication Data
US 2013/0303505 A1      Nov. 14, 2013

Related U.S. Application Data

(60) Provisional application No. 61/303,514, filed on Feb. 11, 2010, provisional application No. 61/284,140, filed on Dec. 11, 2009.

(51) Int. Cl.
| | | |
|---|---|---|
| C07D 249/10 | (2006.01) | |
| C07D 249/08 | (2006.01) | |
| C07D 233/54 | (2006.01) | |
| C07D 401/12 | (2006.01) | |
| A61K 31/454 | (2006.01) | |
| A61K 31/496 | (2006.01) | |
| A61K 31/4995 | (2006.01) | |
| C07D 295/15 | (2006.01) | |
| C07D 249/12 | (2006.01) | |
| A61K 31/4164 | (2006.01) | |
| A61K 31/4178 | (2006.01) | |
| A61K 31/5377 | (2006.01) | |
| A61K 31/4196 | (2006.01) | |
| C07D 403/12 | (2006.01) | |
| C07D 233/64 | (2006.01) | |
| C07D 233/84 | (2006.01) | |
| A61K 31/4439 | (2006.01) | |
| C07D 487/08 | (2006.01) | |

(52) U.S. Cl.
CPC .......... C07D 487/08 (2013.01); C07D 401/12 (2013.01); A61K 31/454 (2013.01); A61K 31/496 (2013.01); A61K 31/4995 (2013.01); C07D 295/15 (2013.01); C07D 249/12 (2013.01); A61K 31/4164 (2013.01); A61K 31/4178 (2013.01); A61K 31/5377 (2013.01); A61K 31/4196 (2013.01); C07D 403/12 (2013.01); C07D 233/64 (2013.01); C07D 233/84 (2013.01); A61K 31/4439 (2013.01)
USPC ........................... 514/385; 514/383; 514/392

(58) Field of Classification Search
None
See application file for complete search history.

(56) References Cited

FOREIGN PATENT DOCUMENTS

| WO | 03104207 A2 | 12/2003 |
|---|---|---|
| WO | WO 03/104207 | * 12/2003 |
| WO | 2004089367 | 10/2004 |
| WO | 2005044192 A2 | 5/2005 |
| WO | 2005087750 | 9/2005 |
| WO | 2010/062861 A2 | 6/2010 |
| WO | 2010093845 A1 | 8/2010 |

* cited by examiner

*Primary Examiner* — Jeffrey S. Lundgren
*Assistant Examiner* — Meghan Finn
(74) *Attorney, Agent, or Firm* — Honigman Miller Schwartz and Cohn LLP; Heidi Berven; Jonathan P. O'Brien

(57) ABSTRACT

TGR5 agonists of structural formula VIII(Q), wherein X, $R^1$, $R^2$, and $R^5$ are defined in the specification, pharmaceutically acceptable salts thereof, compositions thereof, and use of the compounds and compositions for treating diseases. The invention also comprises use of the compounds in and for the manufacture of medicaments, particularly for treating diseases.

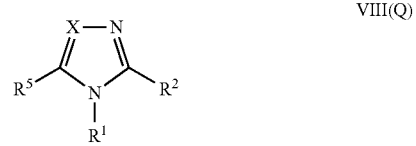

VIII(Q)

23 Claims, No Drawings

TGR5 AGONISTS

This application is a U.S. national stage application of International Application No. PCT/US2010/045195, filed on Aug. 11, 2010, which claims the benefit under 35 U.S.C. §119(e) of U.S. Provisional Application No. 61/284,140, filed on Dec. 11, 2009, and No. 61/303,514, filed on Feb. 11, 2010, all of which are incorporated herein by reference.

BACKGROUND OF THE INVENTION

1. Field of the Invention

The invention relates to agonists of the G protein-coupled receptor TGR5, compositions comprising them, methods of making the compounds and compositions and using them for the treatment of diseases TGR5 mediates or is implicated in.

2. Summary of the Related Art

Bile acids play essential roles in the absorption of dietary lipids and in the regulation of bile acid biosynthesis. While bile acids have long been known to be essential in dietary lipid absorption and cholesterol catabolism, in recent years an important role for bile acids as signaling molecules has emerged. Bile acids activate mitogen-activated protein kinase pathways, are ligands for the G-protein-coupled receptor (GPCR) TGR5, and activate nuclear hormone receptors such as farnesoid X receptor a (FXR-α). Through activation of these diverse signaling pathways, bile acids can regulate their own enterohepatic circulation, but also triglyceride, cholesterol, energy, and glucose homeostasis. Thus, bile acid (BA) controlled signaling pathways are promising novel drug targets to treat common metabolic diseases, such as obesity, type II diabetes, hyperlipidemia, and atherosclerosis. Houten et al., *The EMBO Journal* (2006) 25, 1419-1425).

Watanabe et al., *Nature* 2006, 439(7075) 484-489 showed that the administration of bile acids to mice increases energy expenditure in brown adipose tissue, preventing obesity and resistance to insulin. This novel metabolic effect of bile acids is critically dependent on induction of the cyclic-AMP-dependent thyroid hormone activating enzyme type 2 iodothyronine deiodinase (D2) because it is lost in D2–/– mice. Treatment of brown adipocytes and human skeletal myocytes with bile acids increases D2 activity and oxygen consumption. These effects are independent of FXR-α, and instead are mediated by increased cAMP production that stems from the binding of bile acids with TGR5. In both rodents and humans, the most thermogenically important tissues are specifically targeted by this mechanism because they coexpress D2 and TGR5. The BA-TGR5-cAMP-D2 signaling pathway is therefore a crucial mechanism for fine-tuning energy homeostasis that can be targeted to improve metabolic control.

Glucagon-like peptide-1 (GLP-1) is produced by L-cells in the distal digestive tract and affects multiple metabolic parameters, including enhanced insulin secretion, glucagon suppression, and lowering of blood glucose. TGR5 expression in L-cells is linked to increased GLP-1 secretion. Katsuma, et al., *Biochem. Biophys. Res. Commun.* 2005, 329(1), 386-390) showed that bile acids promote glucagon-like peptide-1 (GLP-1) secretion through TGR5 in a murine enteroendocrine cell line STC-1. RNA interference experiments showed that reduced expression of TGR5 resulted in reduced secretion of GLP-1. Furthermore, transient transfection of STC-1 cells with an expression plasmid containing TGR5 significantly enhanced GLP-1 secretion.

SUMMARY OF THE INVENTION

The present invention comprises TGR5 agonists of structural formula VIII(Q),

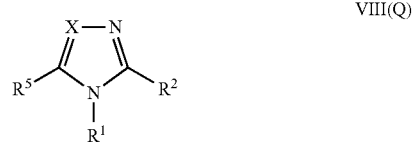

VIII(Q)

wherein X, $R^1$, $R^2$, and $R^5$ are defined hereinbelow, and pharmaceutically acceptable salts thereof. The invention further comprises compositions comprising the compounds and/or pharmaceutically acceptable salts thereof. The invention also comprises use of the compounds and compositions for treating diseases. The invention also comprises use of the compounds in and for the manufacture of medicaments, particularly for treating diseases.

The invention also comprises use of the compounds and compositions for treating diseases in which TGR5 is a mediator or is implicated. The invention also comprises use of the compounds in and for the manufacture of medicaments, particularly for treating diseases in which TGR5 is a mediator or is implicated.

DETAILED DESCRIPTION OF THE INVENTION

All of the compounds of Formulae VI(Q), VII(Q), VIII(Q), VIII(Q2), IX, X, XI, XII, XIII, XIV and XV disclosed herein have quaternary ammonium ion moieties, and it is understood to one skilled in the art that these compounds are all in the presence of a pharmaceutically acceptable counter ion. The pharmaceutically acceptable counter ion for each of the quaternary ammonium ion moieties present in the compounds of the invention can be any pharmaceutically acceptable counter ion known to one skilled in the art. Non-limiting examples of the pharmaceutically acceptable counter ions that can be used include chloride, bromide, sulfate, tosylate, phosphate, tartrate, maleate, acetate, 2,2,2-trifluoroacetate, methanesulfonate, formate, fumarate, mesylate, nitrate, oxalate, ascorbate, citrate, ammonium, arginine, diethylamine, ethylenediamine, magnesium, sodium, calcium, and potassium. It is also understood that the source of the counter ions can be from either intermolecular sources, or, when possible, intramolecular sources.

One aspect of the invention relates to a compound of Formula VIII(Q):

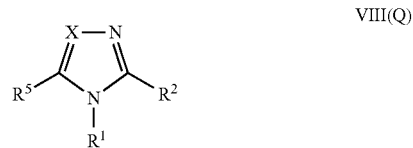

VIII(Q)

or pharmaceutically acceptable salt thereof, wherein:
X is =N— or =C($R^4$)—;
$R^1$ is $R^C$;
or X can be =C($R^C$)— only when $R^1$ is phenyl optionally substituted with one, two, or three $R^{C10}$ groups;
$R^C$ is selected from phenyl, —($C_1$-$C_6$)-cycloalkyl, —$CH_2$-phenyl, heteroaryl, and —($C_1$-$C_4$)alkyl optionally substituted with —$OR^{C13}$, —N($R^{C13}$)$_2$ or —S($R^{C13}$), wherein the cyclic group of $R^C$ can be optionally substituted with 1, 2, 3, 4 or 5

$R^{C10}$ groups, wherein the 1, 2, 3, 4, or 5 $R^{C10}$ groups are independently selected from $R^{C10A}$ and $R^{C10B}$ provided that $R^C$ cannot be substituted with more than 2 $R^{C10B}$ groups, wherein each $R^{C10A}$ is independently selected from halo, cyano and —(C$_1$-C$_4$)alkyl optionally substituted with 1-3 groups selected from —OH and halo;

each $R^{C10B}$ is independently selected from —C(O)NH$_2$, (5-6 membered)heterocycloalkyl, —O—(C$_1$-C$_4$)alkyl-R$^{C11}$, —C(O)OR$^{C12}$, —OC(O)OR$^{C12}$ and —O—(C$_1$-C$_4$)alkyl optionally substituted with —OH or —C(O)OH;

$R^{C11}$ is cyano, nitro, —N(R$^{C12}$)$_2$, —OR$^{C12}$, —SR$^{C12}$, —C(O)R$^{C12}$, —C(O)OR$^{C12}$, —C(O)N(R$^{C12}$)$_2$, —S(O)N (R$^{C12}$)$_2$, —S(O)$_2$N(R$^{C12}$)$_2$, —S(O)$_2$R$^{C12}$, —OC(O)R$^{C12}$, —OC(O)OR$^{C12}$, —OC(O)N(R$^{C12}$)$_2$, —N(R$^{C12}$)C(O)R$^{C12}$, —N(R$^{C12}$)C(O)OR$^{C12}$, —N(R$^{C12}$)C(O)N(R$^{C12}$, or —N(R$^{C12}$)C(=NR$^{C12}$)N(R$^{C12}$)$_2$;

each $R^{C12}$ is independently selected from hydrogen, —(C$_1$-C$_4$)alkyl, and —(C$_1$-C$_4$)haloalkyl;

each $R^{C13}$ is independently selected from hydrogen, —(C$_1$-C$_4$)alkyl, and —(C$_1$-C$_4$)halo alkyl;

$R^2$ is $L^D$-$R^{D1}$;

$L^D$ is —[C(R)$_2$]$_p$—Y—[C(R)$_2$]$_q$—;

p is 0 or 1:

q is 0 or 1;

each R is independently selected from H, —(C$_1$-C$_3$)alkyl, halo, —OH, and —CH$_2$OH;

Y is a bond, —S—, —S(O)$_2$—, —CH(OH)—, —O—, —C(H)=C(H)—, —C(O)—(C$_1$-C$_4$)alkyl-, —(C$_1$-C$_4$)alkyl-S—(C$_1$-C$_4$)alkyl-, —(C$_1$-C$_4$)alkyl-N(R$^Y$)—(C$_1$-C$_4$)alkyl-, —C(H)(halo)-, —(C$_1$-C$_4$)alkyl-S(O)$_2$—, —S(O)$_2$—N (R$^Y$)—, —(C$_1$-C$_4$)alkyl-O—, or —C(O)—N(R$^Y$)—, wherein R$^Y$ is H, —(C$_1$-C$_4$)alkyl, hydroxyl(C$_1$-C$_4$)alkyl or —C≡C—(C$_1$-C$_3$)alkyl-;

$R^{D1}$ is selected from —(C$_6$-C$_{10}$)aryl, —N(H)-phenyl, cycloalkyl, heterocycloalkyl, and heteroaryl, wherein $R^{D1}$ is substituted with 1-5 $R^{D10}$ groups, wherein the 1-5 $R^{D10}$ groups are independently selected from A groups and B groups, provided that $R^{D1}$ is substituted with 1-2 B groups;

each A group, when they occur, is independently selected from halo, —CF$_3$, —CN, —NO$_2$, —OH, —O—(C$_1$-C$_4$)alkyl optionally substituted at the alkyl group with 1-3 substituents independently selected from —OH and halo, and —(C$_1$-C$_4$) alkyl optionally substituted with 1-3 substituents independently selected from —OH and halo;

each B group is selected from —(C$_1$-C$_4$)alkyl-N(R$^{D11}$) R$^{D11B}$, —C(O)—N(R$^{D11D}$)R$^{D11}$—C(O)—(C$_1$-C$_4$)alkyl-Q$^A$, —C(O)O—(C$_1$-C$_4$)alkyl-Q$^A$, —C(O)-heterocycloalkyl-R$^{D11}$, —S(O)$_2$—(C$_1$-C$_4$)alkyl-N(R$^{D11B}$)R$^{D11}$, —S(O)$_2$—R$^{D11}$, —S(O)$_2$—N(R$^{D11D}$)Q$^R$, —S(O)$_2$—N(H)C(O)—(C$_1$-C$_4$)alkyl-Q$^A$, —S(O)$_2$—N(R$^{D11D}$)C(O)O—(C$_1$-C$_4$)alkyl-Q$^A$, —S(O)$_2$—N(H)C(O)—N(H)R$^{D11}$, —S(O)$_2$-(4-6 membered)heterocycloalkyl-(C$_0$-C$_4$)alkyl-Q$^A$, wherein a carbon of the heterocycloalkyl group of —S(O)$_2$-(4-6 membered)heterocycloalkyl-(C$_0$-C$_4$)alkyl-Q$^A$ can be substituted with R$^{D11D}$, —S(O)$_2$—(C$_1$-C$_4$)alkyl-Q$^A$, —O—(C$_1$-C$_4$) alkyl-Q$^A$ optionally substituted at the alkyl group with 1 or 2 R$^{D11B}$, —C(O)—N(R$^{D11D}$)—(C$_1$-C$_6$)alkyl substituted at the alkyl group with 1 or 2 R$^{D11}$, heterocycloalkyl-Q$^A$ optionally substituted with oxo or R$^{D11D}$, —S(O)$_2$—N(R$^{D11D}$)R$^{D11}$, —N(R$^{D11D}$)—C(O)—(C$_1$-C$_4$)alkyl substituted at the alkyl group with 1 or 2 R$^{D11}$, —N(H)—C(O)—N(R$^{D11D}$)—(C$_1$-C$_3$)alkyl substituted at the —(C$_1$-C$_3$)alkyl group with R$^{D11}$, —(C$_1$-C$_6$)alkyl substituted with 1 or 2 R$^{D11}$, and —C≡C—(C$_0$-C$_3$)alkyl substituted with R$^{D11}$;

each $R^{D11}$ is independently selected from —(C$_3$-C$_6$)cycloalkyl-Q$^A$, —(C$_0$-C$_6$)alkyl-Q$^A$ optionally substituted with halo or —COOH, —(C$_0$-C$_6$)alkyl-(5-6 membered) heterocycloalkyl-Q$^A$, and a PEG polymer substituted with Q$^A$;

$R^{D11B}$ is selected from Q$^A$, H, —OH, —CF$_3$, —N(R$^{D11E}$)$_2$, —C(O)OH, —O—(C$_1$-C$_4$)alkyl, —S(O)$_2$OH, —C(=NH)—NH$_2$, —N(H)C(=NH)NH$_2$, —C(H)=NC (=NH)NH$_2$, —C(H)=NN(H)C(=NH)NH$_2$, 1,4-diazabicyclo[2.2.2]octanyl, —N(H)C(=NH)—N(H)C(=NH)NH$_2$, —C(O)—(C$_1$-C$_3$)alkyl, —O—(C$_1$-C$_4$)alkyl-C(O)OH, (5-6 membered)heteroaryl, —(C$_1$-C$_4$)alkyl optionally substituted with 1-3 groups independently selected from halo, —OH, —S(O)$_2$OH, C(O)OH, —NH$_2$, —N[(C$_1$-C$_3$)alkyl]$_3^+$, 1,4-diazabicyclo[2.2.2]octanyl, and —N(H)C(=NH)NH$_2$, —(C$_0$-C$_3$)alkyl-(5-8 membered)heterocycloalkyl optionally substituted at the heterocycloalkyl group with 1-3 R$^{D11}$, —(C$_0$-C$_3$)alkyl-(C$_3$-C$_6$)cycloalkyl optionally substituted with R$^{D11}$, and aryl optionally substituted with 1-5 halo;

$R^{D11D}$ is selected from H, —(C$_3$-C$_6$)cycloalkyl, —(C$_1$-C$_6$) alkyl optionally substituted with 1 or 2 substituents selected from —N[(C$_1$-C$_3$)alkyl]$_3^+$, gem-cyclopropyl, —OH, —C(O) OH, —C(O)O—(C$_1$-C$_3$)alkyl, and —C(O)NH$_2$, and —(C$_1$-C$_6$)alkyl-phenyl optionally substituted at the phenyl group with —(C$_1$-C$_3$)alkoxy, —C(O)OH, or —C(O)O—(C$_1$-C$_3$) alkyl;

each $R^{D11E}$ is independently selected from H, —(C$_1$-C$_3$) alkyl, and —(C$_1$-C$_3$)haloalkyl;

$R^4$ is H, —(C$_1$-C$_3$)alkyl or halo;

$R^5$ is —[C(R$^8$)$_2$]-phenyl, —[C(R$^8$)$_2$]-naphthalenyl, or —[C(R$^8$)$_2$]-(5-10 membered) heteroaryl, wherein the heteroaryl is selected from (benzo[d][1,3]dioxolyl, benzo[d] isoxazole, quinoxalinyl, quinolinyl and 2,3,4a,8a-tetrahydrobenzo[b][1,4]dioxinyl, wherein the cyclic group of $R^5$ is optionally substituted with 1-5 R$^{410}$ groups, wherein the 1-5 R$^{A10}$ groups are independently selected from R$^{A10A}$ groups and R$^{A10B}$ groups, provided that R$^5$ cannot be substituted with more than 2 R$^{A10B}$ groups;

each R$^{A10a}$, when they occur, is independently selected from halo, alkoxyl, hydroxyl, —CN, —OCF$_3$, —(C$_1$-C$_4$) alkyl and —NH$_2$, each R$^{A10B}$, when they occur, is selected from –O—(C$_1$-C$_4$)alkyl-R$^{A11}$, —S(O)$_2$—NH$_2$, —S(O)$_2$CH$_3$, —N(H)—S (O)$_2$CH$_3$, —S(O)$_2$N(H)—CH$_3$, —C(O)OH, —(C$_1$-C$_4$)alkyl-OH, —C(O)NH$_2$, and —(C$_1$-C$_4$)alkyl substituted with 1-3 groups selected from —OH and halo;

$R^{A11}$ is selected —C(O)OH, (5-6 membered)heterocycloalkyl, halogen, cyano, nitro, —(C$_1$-C$_4$)alkyl, —N(R$^{A12}$)$_2$, —OR$^{A12}$, —SR$^{A12}$, —N(OR$^{A12}$)R$^{A12}$, —C(O)R$^{A12}$, —C(O) OR$^{A12}$, —C(O)N(R$^{A12}$)$_2$, —N(R$^{A12}$)S(O)R$^{A12}$, —N(R$^{A12}$)S (O)$_2$R$^{A12}$, —S(O)N(R$^{A12}$)$_2$, —S(O)$_2$N(R$^{A12}$)$_2$, —S(O)$_2$R$^{A12}$, —OC(O)R$^{A12}$, —OC(O)OR$^{A12}$, —OC(O)N(R$^{A12}$)$_2$, —N(R$^{A12}$)C(O)R$^{A12}$, —N(R$^{A12}$)S(O)$_2$R$^{A12}$, —N(R$^{A12}$)C (O)OR$^{A12}$, —N(R$^{A12}$)C(O)N(R$^{A12}$)$_2$, —N(R$^{A12}$)C (=NR$^{A12}$)N(R$^{A12}$)$_2$, and heteroaryl, wherein each R$^{A12}$ is independently hydrogen, —(C$_1$-C$_4$)alkyl, or —(C$_1$-C$_4$)halo alkyl; and each $R^8$ is independently hydrogen, halogen, or methyl, or both $R^8$ taken together with the carbon to which they are both attached form either a (C$_3$-C$_6$)cycloalkyl or a (3-6 membered) heterocycloalkyl;

$R^9$ is —(C$_1$-C$_3$)alkyl;

Q$^A$ is Q$^L$ or Q$^R$;

Q$^L$ is —N[(C$_1$-C$_3$)alkyl]$_3^+$ wherein an alkyl group of —N[(C$_1$-C$_3$)alkyl]$_3^+$ is optionally substituted with —(C$_0$-C$_6$) alkyl-S(O)$_2$OH;

$Q^R$ is selected from

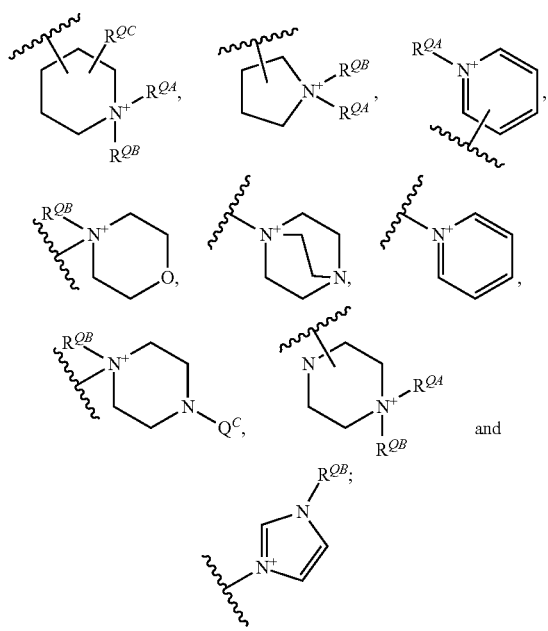

$R^{QA}$ is —(C$_1$-C$_6$)alkyl;

$R^{QB}$ is —(C$_1$-C$_6$)alkyl optionally substituted with C(O)OH; and $R^{QC}$ is H, —OH, —(C$_0$-C$_4$)alkyl-C(O)OH or —(C$_1$-C$_6$)alkyl.

In embodiment (2) of the compound of formula VIII(Q), embodiment (A), wherein $R^C$ is aryl, heteroaryl, or aryl(C$_1$-C$_2$)alkyl, each optionally substituted with one, two, or three $R^{C10}$ groups.

In embodiment (3) of the compound of formula VIII(Q), $R^C$ is phenyl substituted with one, two, or three $R^{C10}$ groups.

Embodiment (4) of the compound of formula VIII(Q) is embodiment (3), wherein $R^C$ is phenyl substituted with one or two halogen groups.

In embodiment (5) of the compound of formula VIII(Q), $R^C$ is heteroaryl optionally substituted with one, two, or three $R^{C10}$ groups.

In embodiment (6) of the compound of formula VIII(Q), $R^C$ is

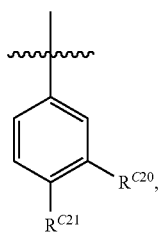

wherein $R^{C21}$ is halogen, and $R^{C20}$ is —OR$^{C12}$ or —OC$_1$-C$_4$alkyl-R$^{C11}$.

In embodiment (7) of the compound of formula VIII(Q), $R^C$ is C$_1$-C$_4$alkyl, C$_3$-C$_8$cycloalkyl, —C$_1$-C$_4$alkyl-N(R$^{C13}$)$_2$, —C$_1$-C$_4$alkyl-OR$^{C13}$, or —C$_1$-C$_4$alkyl-SR$^{C13}$, wherein each $R^{C13}$ is independently hydrogen, C$_1$-C$_4$alkyl, or C$_1$-C$_4$haloalkyl.

Embodiment (9) of the compound of formula VIII(Q) is embodiment (8), wherein $L^D$ is —[CH$_2$]$_p$—Y—[CH$_2$]$_q$—.

Embodiment (10) of the compound of formula VIII(Q) is embodiment (9), wherein Y is —N(R$^Y$)—, —O—, or S—.

Embodiment (11) of the compound of formula VIII(Q) is embodiment (10), wherein $L^D$ is —S—(CH$_2$)$_q$— or (CH$_2$)$_p$—S—.

Embodiment (12) of the compound of formula VIII(Q) is embodiment (9), wherein Y is —S(O)$_2$— or —C(O)—.

Embodiment (13) of the compound of formula VIII(Q) is embodiment (9), wherein Y is —C(O)N(R$^Y$)—, —N(R$^Y$)C(O)—, —S(O)$_2$N(R$^Y$)—, or —N(R$^Y$)S(O)$_2$—.

Embodiment (14) of the compound of formula VIII(Q) is embodiment (8), wherein $L^D$ is —S(O)$_2$N(H)—[C(R)$_2$]$_q$, wherein q is 1 or 2.

In embodiment (15) of the compound of formula VIII(Q), $R^C$ is aryl, heteroaryl, or aryl(C$_1$-C$_2$)alkyl, each optionally substituted with one, two, or three $R^{C10}$ groups.

In embodiment (16) of the compound of formula VIII(Q), $R^C$ is aryl, heteroaryl, or aryl(C$_1$-C$_2$)alkyl, each optionally substituted with one, two, or three $R^{C10}$ groups.

In embodiment (17) of the compound of formula VIII(Q), $R^C$ is aryl, heteroaryl, or aryl(C$_1$-C$_2$)alkyl, each optionally substituted with one, two, or three $R^{C10}$ groups.

Embodiment (18) of the compound of formula VIII(Q) is embodiment (15), wherein $R^C$ is phenyl substituted with one, two, or three $R^{C10}$ groups.

Embodiment (19) of the compound of formula VIII(Q) is embodiment (18), wherein $R^C$ is phenyl substituted with one or two halogen groups.

Embodiment (20) of the compound of formula VIII(Q) is embodiment (17), wherein $R^C$ is heteroaryl optionally substituted with one, two, or three $R^{C10}$ groups.

Embodiment (21) of the compound of formula VIII(Q) is embodiment (15) wherein $R^C$ is

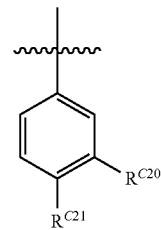

wherein $R^{C21}$ is halogen and $R^{C20}$ is —OR$^{C12}$ or —OC$_1$-C$_4$alkyl-R$^{C11}$.

Embodiment (22) of the compound of formula VIII(Q) is any of embodiments (1)-(21), wherein $R^A$ is [C(R$^8$)$_2$]-phenyl, wherein the phenyl is substituted with two $R^{410}$ groups.

Embodiment (23) of the compound of formula VIII(Q) is embodiment (22), wherein $R^A$ is

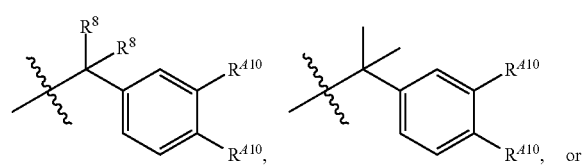

-continued

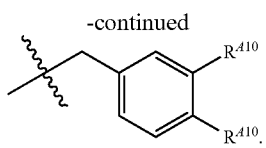

Embodiment (24) of the compound of formula VIII(Q) is embodiment (23), wherein each $R^{A10}$ is independently halogen, —$OR^{A12}$, —$C(O)OR^{A12}$, —$C(O)N(R^{A12})_2$, —$S(O)_2N(R^{A12})_2$, —$S(O)_2R^{A12}$, cyano, nitro, pyrrolyl, tetrazolyl, —$C_1$-$C_4$alkyl-$R^{A11}$, or —$OC_1$-$C_4$alkyl-$R^{A11}$.

Embodiment (25) of the compound of formula VIII(Q) is embodiment (23), wherein one $R^{A10}$ is halogen and one $R^{A10}$ is —$OR^{A12}$, —$C(O)OR^{A12}$, —$C(O)N(R^{A12})_2$, —$S(O)_2N(R^{A12})_2$, —$S(O)_2R^{A12}$, cyano, nitro, pyrrolyl, tetrazolyl, —$C_1$-$C_4$alkyl-$R^{A11}$, or —$OC_1$-$C_4$alkyl-$R^{A11}$.

Embodiment (26) of the compound of formula VIII(Q) is any one of embodiments 1-25 wherein both $R^8$ groups are methyl.

Embodiment (27) of the compound of formula VIII(Q) is any one of embodiments 1-26 wherein $R^A$ is

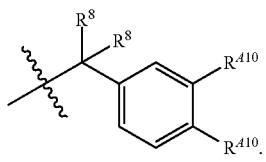

Embodiment (28) of the compound of formula VIII(Q) is any one of embodiments (1)-(26), wherein $R^A$ is

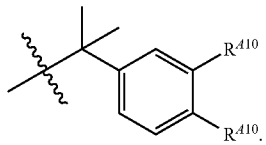

Embodiment (29) of the compound of formula VIII(Q) is embodiment (27) or (28), wherein at least one $R^{A10}$ is halogen.

Embodiment (30) of the compound of formula VIII(Q) is embodiment (27) or (28), wherein one $R^{A10}$ is —$OR^{A12}$, —$C(O)OR^{A12}$, —$C(O)N(R^{A12})_2$, —$S(O)_2N(R^{A12})_2$, —$S(O)_2 R^{A12}$, cyano, nitro, pyrrolyl, tetrazolyl, —$C_1$-$C_4$alkyl-$R^{A11}$ (e.g., —$C_1$-$C_4$ alkyl-OH), or —$OC_1$-$C_4$alkyl-$R^{A11}$ (e.g., —$OC_1$-$C_4$alkyl-OH, —$OC_1$-$C_4$alkyl-COOH, —$OC_1$-$C_4$alkyl-morpholinyl, or —$OC_1$-$C_4$alkyl-imidazolyl).

Embodiment (31) of the compound of formula VIII(Q) is embodiment (27) or (28), wherein one $R^{A10}$ is halogen and one $R^{A10}$ is —$OR^{A12}$, $C(O)OR^{A12}$, —$C(O)N(R^{A12})_2$, —$S(O)_2 N(R^{A12})_2$, —$S(O)_2R^{A12}$, cyano, nitro, pyrrolyl, tetrazolyl, —$C_1$-$C_4$alkyl-$R^{A11}$ (e.g., —$C_1$-$C_4$ alkyl-OH), or —$OC_1$-$C_4$alkyl-$R^{A11}$ (e.g., —$OC_1$-$C_4$alkyl-OH, —$OC_1$-$C_4$alkyl-COOH, —$OC_1$-$C_4$ alkyl-morpholinyl, or —$OC_1$-$C_4$ alkyl-imidazolyl).

In another embodiment of the compound of Formula VIII (Q), $R^C$ is substituted with 1, 2, 3, 4 or 5 $R^{C10A}$ groups.

In another embodiment of the compound of Formula VIII (Q), $R^C$ is substituted with 0, 1, 2, 3 or 4 $R^{C10A}$ groups and 1 $R^{C10B}$ group.

In another embodiment of the compound of Formula VIII (Q), $R^C$ is substituted with 0, 1, 2 or 3 $R^{C10A}$ groups and 1 or 2 $R^{C10B}$ groups.

In another embodiment of the compound of Formula VIII (Q), $R^{D1}$ is substituted with 0-4 A groups and 1 B group.

In another embodiment of the compound of Formula VIII (Q), $R^{D1}$ is substituted with 0-3 A groups and 1-2 B groups.

In another embodiment of the compound of Formula VIII (Q), $R^5$ is optionally substituted with 1-5 $R^{A10A}$ groups.

In another embodiment of the compound of Formula VIII (Q), $R^5$ is optionally substituted with 0-4 $R^{A10A}$ groups and 1 $R^{A10B}$ group.

In another embodiment of the compound of Formula VIII (Q), $R^5$ is optionally substituted with 0-3 $R^{A10A}$ groups and 1-2 $R^{A10B}$ groups.

Another aspect of the invention relates to a compound of Formula VIII(Q2):

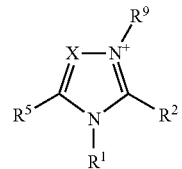

VIII(Q2)

or pharmaceutically acceptable salt thereof, wherein:
X is =N— or =$C(R^4)$—;
$R^1$ is $R^C$;
or X can be =$C(R^C)$— only when $R^1$ is phenyl optionally substituted with one, two, or three $R^{C10}$ groups;
$R^C$ is selected from phenyl, —$(C_1$-$C_6)$-cycloalkyl, —$CH_2$-phenyl, heteroaryl, and —$(C_1$-$C_4)$alkyl optionally substituted with —$OR^{C13}$, —$N(R^{C13})_2$ or —$S(R^{C13})$, wherein the cyclic group of $R^C$ can be optionally substituted with 1, 2, 3, 4 or 5 $R^{C10}$ groups, wherein the 1, 2, 3, 4, or 5 $R^{C10}$ groups are independently selected from $R^{C10A}$ and $R^{C10B}$, provided that $R^C$ cannot be substituted with more than 2 $R^{C10B}$ groups, wherein
each $R^{C10A}$ is independently selected from halo, cyano and —$(C_1$-$C_4)$alkyl optionally substituted with 1-3 groups selected from —OH and halo;
each $R^{C10B}$ is independently selected from —$C(O)NH_2$, (5-6 membered)heterocycloalkyl, —O—$(C_1$-$C_4)$alkyl-$R^{C11}$, —$C(O)OR^{C12}$, —$OC(O)OR^{C12}$ and —O—$(C_1$-$C_4)$alkyl optionally substituted with —OH or —$C(O)OH$;
$R^{C11}$ is cyano, nitro, —$N(R^{C12})_2$, —$OR^{C12}$, —$SR^{C12}$, —$C(O)R^{C12}$, —$C(O)OR^{C12}$, —$C(O)N(R^{C12})_2$, —$S(O)N(R^{C12})_2$, —$S(O)_2N(R^{C12})_2$, —$S(O)_2R^{C12}$, —$OC(O)R^{C12}$, —$OC(O)OR^{C12}$, —$OC(O)N(R^{C12})_2$, —$N(R^{C12})C(O)R^{C12}$, —$N(R^{C12})C(O)OR^{C12}$, —$N(R^{C12})C(O)N(R^{C12})_2$, or —$N(R^{C12})C(=NR^{C12})N(R^{C12})_2$;
each $R^{C12}$ is independently selected from hydrogen, —$(C_1$-$C_4)$alkyl, and —$(C_1$-$C_4)$halo alkyl;
each $R^{C13}$ is independently selected from hydrogen, —$(C_1$-$C_4)$alkyl, and —$(C_1$-$C_4)$halo alkyl;
$R^2$ is $L^D$-$R^{D1}$;
$L^D$ is —$[C(R)_2]_p$—Y—$[C(R)_2]_q$—;
p is 0 or 1;
q is 0 or 1;
each R is independently selected from H, —$(C_1$-$C_3)$alkyl, halo, —OH, and —$CH_2OH$;
Y is a bond, —S—, —$S(O)_2$—, —CH(OH)—, —O—, —$C(H)$=$C(H)$—, —$C(O)$—$(C_1$-$C_4)$alkyl-, —$(C_1$-$C_4)$alkyl-S—$(C_1$-$C_4)$alkyl-, —$(C_1$-$C_4)$alkyl-N$(R^Y)$—$(C_1$-$C_4)$alkyl-, —C(H)(halo)-, —(C$_1$-C$_4$)alkyl-S(O)$_2$—, —S(O)$_2$—N(R$^Y$)—, —(C$_1$-C$_4$)alkyl-O—, or —C(O)—N(R$^Y$)—, wherein R$^Y$ is H, —(C$_1$-C$_4$)alkyl, hydroxyl(C$_1$-C$_4$)alkyl or ≡C≡(C$_1$-C$_3$)alkyl-;

R$^{D1}$ is selected from —(C$_6$-C$_{10}$)aryl, —N(H)-phenyl, cycloalkyl, heterocycloalkyl, and heteroaryl, wherein R$^{D1}$ is substituted with 1-5 R$^{C10}$ groups, wherein the 1-5 R$^{D10}$ groups are independently selected from A groups and B groups, provided that R$^{D1}$ is substituted with 1-2 B groups;

each A group, when they occur, is independently selected from halo, —CF$_3$, —CN, —NO$_2$, —OH, —O—(C$_1$-C$_4$)alkyl optionally substituted at the alkyl group with 1-3 substituents independently selected from —OH and halo, and —(C$_1$-C$_4$)alkyl optionally substituted with 1-3 substituents independently selected from —OH and halo;

each B group is selected from —(C$_1$-C$_4$)alkyl-N(R$^{D11}$)R$^{D11B}$, —C(O)—N(R$^{D11D}$)R$^{D11}$, —C(O)—(C$_1$-C$_4$)alkyl-Q$^A$, —C(O)O—(C$_1$-C$_4$)alkyl-Q$^A$, —C(O)-heterocycloalkyl-R$^{D11}$, —S(O)$_2$—(C$_1$-C$_4$)alkyl-N(R$^{D11B}$)R$^{D11}$, —S(O)$_2$—R$^{D11}$, —S(O)$_2$—N(R$^{D11D}$)Q$^R$, —S(O)$_2$—N(H)C(O)—(C$_1$-C$_4$)alkyl-Q$^A$, —S(O)$_2$—N(R$^{D11D}$)C(O)O—(C$_1$-C$_4$)alkyl-Q$^A$, —S(O)$_2$—N(H)C(O)—N(H)R$^{D11}$, —S(O)$_2$-(4-6 membered)heterocycloalkyl-(C$_0$-C$_4$)alkyl-Q$^A$, wherein a carbon of the heterocycloalkyl group of —S(O)$_2$-(4-6 membered)heterocycloalkyl-(C$_0$-C$_4$)alkyl-Q$^A$ can be substituted with R$^{D11D}$, —S(O)$_2$—(C$_1$-C$_4$)alkyl-Q$^A$, —O—(C$_1$-C$_4$)alkyl-Q$^A$ optionally substituted at the alkyl group with 1 or 2 R$^{D11B}$, —C(O)—N(R$^{D11D}$)—(C$_1$-C$_6$)alkyl substituted at the alkyl group with 1 or 2 R$^{D11}$, heterocycloalkyl-Q$^A$ optionally substituted with oxo or R$^{D11D}$, —S(O)$_2$—N(R$^{D11D}$)R$^{D11}$, —N(R$^{D11D}$)—C(O)—(C$_1$-C$_4$)alkyl substituted at the alkyl group with 1 or 2 R$^{D11}$, —N(H)—C(O)—N(R$^{D11D}$)—(C$_1$-C$_3$)alkyl substituted at the —(C$_1$-C$_3$)alkyl group with ell, —(C$_1$-C$_6$)alkyl substituted with 1 or 2 R$^{D11}$, and —C≡C—(C$_0$-C$_3$)alkyl substituted with R$^{D11}$;

each R$^{D11}$ is independently selected from —(C$_3$-C$_6$)cycloalkyl-Q$^A$, —(C$_0$-C$_6$)alkyl-Q$^A$ optionally substituted with halo or —COOH, —(C$_0$-C$_6$)alkyl-(5-6 membered) heterocycloalkyl-Q$^A$, and a PEG polymer substituted with Q$^A$;

R$^{D11B}$ is selected from Q$^A$, H, —OH, —CF$_3$, —N(R$^{D11E}$)$_2$, —C(O)OH, —O—(C$_1$-C$_4$)alkyl, —S(O)$_2$OH, —C(=NH)—NH$_2$, —N(H)C(=NH)NH$_2$, —C(H)=NC(=NH)NH$_2$, —C(H)=NN(H)C(=NH)NH$_2$, 1,4-diazabicyclo[2.2.2]octanyl, —N(H)C(=NH)—N(H)C(=NH)NH$_2$, —C(O)—(C$_1$-C$_3$)alkyl, —O—(C$_1$-C$_4$)alkyl-C(O)OH, (5-6 membered)heteroaryl, —(C$_1$-C$_4$)alkyl optionally substituted with 1-3 groups independently selected from halo, —OH, —S(O)$_2$OH, C(O)OH, —NH$_2$, —N[(C$_1$-C$_3$)alkyl]$_3$$^+$, 1,4-diazabicyclo[2.2.2]octanyl, and —N(H)C(=NH)NH$_2$, —(C$_0$-C$_3$)alkyl-(5-8 membered)heterocycloalkyl optionally substituted at the heterocycloalkyl group with 1-3 R$^{D11}$, —(C$_0$-C$_3$)alkyl-(C$_3$-C$_6$)cycloalkyl optionally substituted with R$^{D11}$, and aryl optionally substituted with 1-5 halo;

R$^{D11D}$ is selected from H, —(C$_3$-C$_6$)cycloalkyl, —(C$_1$-C$_6$)alkyl optionally substituted with 1 or 2 substituents selected from —N[(C$_1$-C$_3$)alkyl]$_3$$^+$, gem-cyclopropyl, —OH, —C(O)OH, —C(O)O—(C$_1$-C$_3$)alkyl, and —C(O)NH$_2$, and —(C$_1$-C$_6$)alkyl-phenyl optionally substituted at the phenyl group with —(C$_1$-C$_3$)alkoxy, —C(O)OH, or —C(O)O—(C$_1$-C$_3$)alkyl;

each R$^{D11E}$ is independently selected from H, —(C$_1$-C$_3$)alkyl, and —(C$_1$-C$_3$)haloalkyl;

R$^4$ is H, —(C$_1$-C$_3$)alkyl or halo;

R$^5$ is —[C(R$^8$)$_2$]-phenyl, —[C(R$^8$)$_2$]-naphthalenyl, or —[C(R$^8$)$_2$]-(5-10 membered) heteroaryl, wherein the heteroaryl is selected from (benzo[d][1,3]dioxolyl, benzo[d]isoxazole, quinoxalinyl, quinolinyl and 2,3,4a,8a-tetrahydrobenzo[b][1,4]dioxinyl, wherein the cyclic group of R$^5$ is optionally substituted with 1-5 R$^{410}$ groups, wherein the 1-5 R$^{410}$ groups are independently selected from R$^{410A}$ groups and R$^{410B}$ groups, provided that R$^5$ cannot be substituted with more than 2 R$^{410B}$ groups;

each R$^{410A}$, when they occur, is independently selected from halo, alkoxyl, hydroxyl, —CN, —OCF$_3$, —(C$_1$-C$_4$)alkyl and —NH$_2$, each R$^{410B}$, when they occur, is selected from –O—(C$_1$-C$_4$)alkyl-R$^{411}$, —S(O)$_2$—NH$_2$, —S(O)$_2$CH$_3$, —N(H)—S(O)$_2$CH$_3$, —S(O)$_2$N(H)—CH$_3$, —C(O)OH, —(C$_1$-C$_4$)alkyl-OH, —C(O)NH$_2$, and —(C$_1$-C$_4$)alkyl substituted with 1-3 groups selected from —OH and halo;

R$^{411}$ is selected —C(O)OH, (5-6 membered)heterocloalkyl, halogen, cyano, nitro, —(C$_1$-C$_4$)alkyl, —N(R$^{412}$)$_2$, —OR$^{412}$, —SR$^{412}$, —N(OR$^{412}$)R$^{412}$, —C(O)R$^{412}$, —C(O)OR$^{412}$, —C(O)N(R$^{412}$)$_2$, —N(R$^{412}$)S(O)R$^{412}$, —N(R$^{412}$)S(O)$_2$R$^{412}$, —S(O)N(R$^{412}$)$_2$, —S(O)$_2$N(R$^{412}$)$_2$, —S(O)$_2$R$^{412}$, —OC(O)R$^{412}$, —OC(O)OR$^{412}$, —OC(O)N(R$^{412}$)$_2$, —NR(R$^{412}$)C(O)R$^{412}$, —N(R$^{412}$)S(O)$_2$R$^{412}$, —N(R$^{412}$)C(O)OR$^{412}$, —N(R$^{412}$)C(O)N(R$^{412}$)$_2$, —N(R$^{412}$)C(=NR$^{412}$)N(R$^{412}$)$_2$, and heteroaryl, wherein each R$^{412}$ is independently hydrogen, —(C$_1$-C$_4$)alkyl, or —(C$_1$-C$_4$)halo alkyl; and each R$^8$ is independently hydrogen, halogen, or methyl, or both R$^8$ taken together with the carbon to which they are both attached form either a (C$_3$-C$_6$)cycloalkyl or a (3-6 membered) heterocycloalkyl;

Q$^A$ is Q$^L$ or Q$^R$;

Q$^L$ is —N[(C$_1$-C$_3$)alkyl]$_3$$^+$ wherein an alkyl group of —N[(C$_1$-C$_3$)alkyl]$_3$$^+$ is optionally substituted with —(C$_0$-C$_6$)alkyl-S(O)$_2$OH;

Q$^R$ is selected from

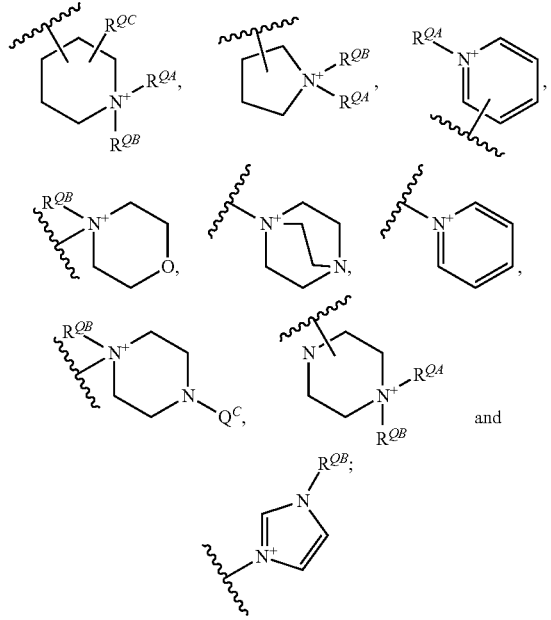

R$^{QA}$ is —(C$_1$-C$_6$)alkyl;
R$^{QB}$ is —(C$_1$-C$_6$)alkyl optionally substituted with C(O)OH; and
R$^{QC}$ is H, —OH, —(C$_0$-C$_4$)alkylC(O)OH or —(C$_1$-C$_6$)alkyl.

Other embodiments of the Formula VIII(Q2) are embodiments 2-31 of formula VIII(Q) above, wherein the compound of Formula VIII(Q) is the compound of Formula VIII(Q2).

Another embodiment of the compound VIII relates to structural formulae (VIQ) or (VIIQ):

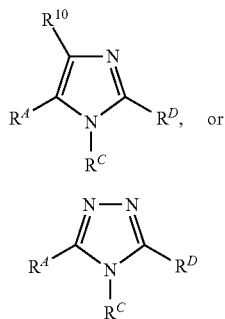

(VIQ)

(VIIQ)

or pharmaceutically acceptable salt thereof, wherein:

$R^A$ is —[C(CH$_3$)$_2$]-phenyl, —[C(CH$_3$)$_2$]-naphthalenyl, or [C(CH$_3$)$_2$]-(5-10 membered)heteroaryl, wherein the heteroaryl is selected from (benzo[d][1,3]dioxolyl, benzo[d]isoxazole, quinoxalinyl, quinolinyl and 2,3,4a,8a-tetrahydrob enzo[b][1,4]dioxinyl, wherein the cyclic group of $R^A$ is optionally substituted with 1, 2 or 3 $R^{A10}$;

each $R^{A10}$ is independently selected from halo, alkoxyl, hydroxyl, —NH$_2$, —S(O)$_2$—NH$_2$, —S(O)$_2$CH$_3$, —N(H)—S(O)$_2$CH$_3$, —SO$_2$N(H)—CH$_3$, —CN, —C(O)OH, —(C$_1$-C$_4$)alkyl-OH, —OCF$_3$, —C(O)NH$_2$, and —(C$_1$-C$_4$)alkyl optionally substituted with 1-3 groups independently selected from —OH and halo;

$R^C$ is phenyl, —CH$_2$-phenyl, —(C$_1$-C$_6$)-cycloalkyl, —CH$_2$-phenyl, or pyridinyl, wherein the cyclic group of $R^C$ can be optionally substituted with 1, 2 or 3 $R^{C10}$, wherein the 1, 2, or 3 $R^{C10}$ groups are independently selected from $R^{C10A}$ and $R^{C10B}$, provided that $R^C$ cannot be substituted with more than 1 $R^{C10B}$ group;

each $R^{C10A}$ is independently selected from halo, and —(C$_1$-C$_3$)alkyl optionally substituted with 1-3 groups selected from —OH, methoxy, —CF$_3$ and halo;

$R^{C10B}$ is selected from —C(O)NH$_2$, (5-6 membered)heterocycloalkyl, —C(O)OH, or —N[—(C$_1$-C$_4$)alkyl]$_2$, —O—(C$_1$-C$_4$)alkyl optionally substituted with —OH, and —(C$_1$-C$_4$)alkyl substituted with —N[—(C$_1$-C$_4$)alkyl]$_2$;

$R^D$ is $L^D$-$R^{D1}$;

$L^D$ is —Y—[C(R)$_2$]$_q$—;

q is 0 or 1;

each R is independently selected from H, —(C$_1$-C$_3$)alkyl (—CH$_3$), halo, —OH, and —CH$_2$OH;

Y is a bond, —S—, —S(O)$_2$—, —CH(OH)—, —O—, —C(H)=C(H)—, —C(O)—(C$_1$-C$_4$)alkyl-, —(C$_1$-C$_4$)alkyl-S—(C$_1$-C$_4$)alkyl-, —(C$_1$-C$_4$)alkyl-N(R$^Y$)—(C$_1$-C$_4$)alkyl-, —C(H)(halo)-, —(C$_1$-C$_4$)alkyl-S(O)$_2$—, —S(O)$_2$—N(R$^Y$)—, —(C$_1$-C$_4$)alkyl-O—, or —C(O)—N(R$^Y$)—, wherein R$^Y$ is H, —(C$_1$-C$_4$)alkyl, hydroxyl(C$_1$-C$_4$)alkyl or —C≡C—(C$_1$-C$_3$)alkyl-;

$R^{D1}$ is selected from —(C$_6$-C$_{10}$)aryl, —N(H)-phenyl, cycloalkyl, heterocycloalkyl, and heteroaryl, wherein $R^{D1}$ is substituted with 1-5 $R^{D10}$ groups, wherein the 1-4 $R^{D10}$ groups are independently selected from A groups and B groups, provided that $R^{D1}$ is substituted with 1-2 B groups;

each A group, when they occur, is independently selected from halo, —CF$_3$, —CN, —NO$_2$, —OH, —O—(C$_1$-C$_4$)alkyl optionally substituted at the alkyl group with 1-3 substituents independently selected from —OH and halo, and —(C$_1$-C$_4$)alkyl optionally substituted with 1-3 substituents independently selected from —OH and halo;

each B group is independently selected from —(C$_1$-C$_4$)alkylN(R$^{D11}$)R$^{D11B}$, —C(O)—N(R$^{D11D}$)R$^{D11}$, —C(O)—(C$_1$-C$_4$)alkyl-Q$^A$, —C(O)O—(C$_1$-C$_4$)alkyl-Q$^A$, —C(O)-heterocycloalkyl-R$^{D11}$, —S(O)$_2$—(C$_1$-C$_4$)alkyl-N(R$^{D11B}$)R$^{D11}$, —S(O)$_2$—R$^{D11}$, —S(O)$_2$—N(R$^{D11D}$)Q$^R$, —S(O)$_2$—N(H)C(O)—(C$_1$-C$_4$)alkyl-Q$^A$, —S(O)$_2$—N((R$^{D11D}$)C(O)O—(C$_1$-C$_4$)alkyl-Q$^A$, —S(O)$_2$—N(H)C(O)—N(H)R$^{D11}$, —S(O)$_2$—(C$_1$-C$_4$)alkyl-Q$^A$, —O—(C$_1$-C$_4$)alkyl-Q$^A$ optionally substituted at the alkyl group with 1 or 2 R$^{D11B}$, —C(O)—N(R$^{D11D}$)—(C$_1$-C$_6$)alkyl substituted at the alkyl group with 1 or 2 R$^{D11}$, heterocycloalkyl-Q$^A$ optionally substituted with oxo or R$^{D11D}$, —S(O)$_2$—N(R$^{D11D}$)R$^{D11}$, —S(O)$_2$-(4-6 membered)heterocycloalkyl-(C$_0$-C$_4$)alkyl-Q$^A$, wherein a carbon of the heterocycloalkyl group of —S(O)$_2$-(4-6 membered)heterocycloalkyl-(C$_0$-C$_4$)alkyl-Q$^A$ can be substituted with R$^{D11D}$, —N(R$^{D11D}$)—C(O)—(C$_1$-C$_4$)alkyl substituted at the alkyl group with 1 or 2 R$^{D11}$, —N(H)—C(O)—N(R$^{D11D}$)—(C$_1$-C$_3$)alkyl substituted at the —(C$_1$-C$_3$) alkyl group with R$^{D11}$, —(C$_1$-C$_6$)alkyl substituted with 1 or 2 R$^{D11}$, and —C≡C—(C$_0$-C$_3$)alkyl substituted with R$^{D11}$;

each $R^{D11}$ is independently selected from —(C$_3$-C$_6$)cycloalkyl-Q$^A$, —(C$_0$-C$_6$)alkyl-(5-6 membered) heterocycloalkyl-Q$^A$, —(C$_0$-C$_6$)alkyl-Q$^A$ optionally substituted with halo or —COOH, and a PEG polymer substituted with Q$^A$;

$R^{D11B}$ is selected from Q$^A$, H, —OH, —CF$_3$, —N(R$^{D11E}$)$_2$, —C(O)OH, —O—(C$_1$-C$_4$)alkyl, —S(O)$_2$OH, —C(=NH)—NH$_2$, —N(H)C(=NH)NH$_2$, —C(H)=NC(=NH)NH$_2$, —C(H)=NN(H)C(=NH)NH$_2$, 1,4-diazabicyclo[2.2.2]octanyl, —O—(C$_1$-C$_4$)alkyl-C(O)OH, —N(H)C(=NH)—N(H)C(=NH)NH$_2$, (5-6 membered)heteroaryl, —C(O)—(C$_1$-C$_3$)alkyl, —(C$_1$-C$_4$)alkyl optionally substituted with 1-3 groups independently selected from halo, —OH, —S(O)$_2$OH, C(O)OH, —NH$_2$, —N[(C$_1$-C$_3$)alkyl]$_3^+$, 1,4-diazabicyclo[2.2.2]octanyl, and —N(H)C(=NH)NH$_2$, —(C$_0$-C$_3$)alkyl-(5-8 membered)heterocycloalkyl optionally substituted at the heterocycloalkyl group with 1-3 R$^{D11}$, —(C$_0$-C$_3$)alkyl-(C$_3$-C$_6$)cycloalkyl optionally substituted with R$^{D11}$, and aryl optionally substituted with 1-3 halo;

$R^{D11D}$ is selected from H, —(C$_3$-C$_6$)cycloalkyl, —(C$_1$-C$_6$) alkyl optionally substituted with 1 or 2 substituents independently selected from —N[(C$_1$-C$_3$)alkyl]$_3^+$, —OH, gem-cyclopropyl, —C(O)OH, —C(O)O—(C$_1$-C$_3$)alkyl, and —C(O)NH$_2$, and —(C$_1$-C$_6$)alkyl-phenyl optionally substituted at the phenyl group with —(C$_1$-C$_3$)alkoxy, —C(O)OH, or —C(O)O—(C$_1$-C$_3$)alkyl;

$Q^A$ is $Q^L$ or $Q^R$;

$Q^L$ is —N[(C$_1$-C$_3$)alkyl]$_3^+$ wherein an alkyl group of —N[(C$_1$-C$_3$)alkyl]$_3^+$ is optionally substituted with —(C$_0$-C$_6$)alkyl-S(O)$_2$OH;

$Q^R$ is selected from

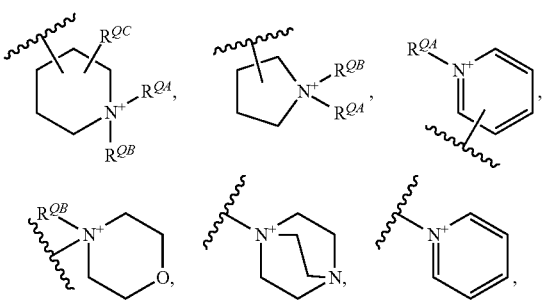

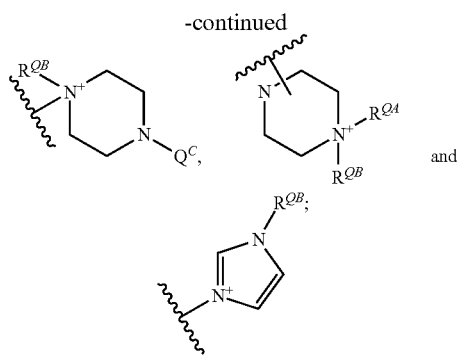

$R^{QA}$ is —(C$_1$-C$_6$)alkyl;

$R^{QB}$ is —(C$_1$-C$_6$)alkyl optionally substituted with C(O)OH; and $R^{QC}$ is H, —OH, —(C$_0$-C$_4$)alkyl-C(O)OH or —(C$_1$-C$_6$)alkyl.

In another embodiment of the compound of Formula VIII (Q), $R^C$ is substituted with 1, 2, 3, 4 or 5 $R^{C10A}$ groups.

In another embodiment of the compound of Formula VI(Q), $R^C$ is substituted with 0, 1, 2, 3 or 4 $R^{C10A}$ groups and 1 $R^{C10B}$ group.

In another embodiment of the compound of Formula VI(Q), $R^C$ is substituted with 0, 1, 2 or 3 $R^{C10A}$ groups and 1 or 2 $R^{C10B}$ groups.

In another embodiment of the compound of Formula VI(Q), $R^{D1}$ is substituted with 0-4 A groups and 1 B group.

In another embodiment of the compound of Formula VI(Q), $R^{D1}$ is substituted with 0-3 A groups and 1-2 B groups.

In another embodiment of the compound of Formula VI(Q), $R^5$ is optionally substituted with 1-5 $R^{410A}$ groups.

In another embodiment of the compound of Formula VI(Q), $R^5$ is optionally substituted with 0-4 $R^{410A}$ groups and 1 $R^{410B}$ group.

In another embodiment of the compound of Formula VI(Q), $R^5$ is optionally substituted with 0-3 $R^{410A}$ groups and 1-2 $R^{410B}$ groups.

In another embodiment of the compound of Formula VII (Q), $R^C$ is substituted with 1, 2, 3, 4 or 5 $R^{C10A}$ groups.

In another embodiment of the compound of Formula VII (Q), $R^C$ is substituted with 0, 1, 2, 3 or 4 R groups and 1 $R^{C10B}$ group.

In another embodiment of the compound of Formula VII (Q), $R^C$ is substituted with 0, 1, 2 or 3 $R^{C10A}$ groups and 1 or 2 $R^{C10B}$ groups.

In another embodiment of the compound of Formula VII (Q), $R^{D1}$ is substituted with 0-4 A groups and 1 B group.

In another embodiment of the compound of Formula VII (Q), $R^{D1}$ is substituted with 0-3 A groups and 1-2 B groups.

In another embodiment of the compound of Formula VII (Q), $R^5$ is optionally substituted with 1-5 $R^{410A}$ groups.

In another embodiment of the compound of Formula VII (Q), $R^5$ is optionally substituted with 0-4 $R^{410A}$ groups and 1 $R^{410B}$ group.

In another embodiment of the compound of Formula VII (Q), $R^5$ is optionally substituted with 0-3 $R^{410A}$ groups and 1-2 $R^{410B}$ groups.

In another embodiment of the compound of formula VIII (Q),

X is =C($R^4$)—;

each R is independently selected from H, —(C$_1$-C$_3$)alkyl, —OH, and —CH$_2$OH;

Y is —S—, —S(O)$_2$—, —C(H)=C(H)—, —C(O)—, —(C$_1$-C$_4$)alkyl-S—, —(C$_1$-C$_4$)alkyl-N($R^Y$)—, —C(H) (halo)-, —(C$_1$-C$_4$)alkyl-S(O)$_2$—, —S(O)$_2$—N(H)—, —S(O)$_2$—N($R^Y$)—, —(C$_1$-C$_4$)alkyl-O—, —CH(OH)—, or —C(O)—N($R^Y$)—, wherein $R^Y$ is H, —(C$_1$-C$_4$)alkyl or hydroxyl(C$_1$-C$_4$)alkyl;

$R^{D1}$ is selected from phenyl —(C$_6$-C$_{10}$)aryl, —N(H)-phenyl, —(C$_1$-C$_6$)cycloalkyl, heterocycloalkyl, or heteroaryl, wherein $R^{D1}$ is substituted with 1, 2, 3 or 4 $R^{D10}$, wherein the 1-4 $R^{D10}$ groups are 0-3 A groups and 1 B group;

each A group, when they occur, is independently selected from halo, —CF$_3$, —CN, —NO$_2$, —OH, —O—(C$_1$-C$_4$)alkyl optionally substituted at the alkyl group with 1-3 substituents independently selected from —OH and halo, and —(C$_1$-C$_4$) alkyl optionally substituted with 1-3 substituents independently selected from —OH and halo;

each B group is selected from —(C$_1$-C$_4$)alkylN($R^{D11}$)$R^{D11B}$, —C(O)—N($R^{D11D}$)$R^{D11}$, —C(O)—(C$_1$-C$_4$)alkyl-$Q^A$, —C(O)O—(C$_1$-C$_4$)alkyl-$Q^A$, —S(O)$_2$—(C$_1$-C$_4$)alkyl-N($R^{D11B}$)$R^{D11}$, —S(O)$_2$—$R^{D11}$, —S(O)$_2$—N($R^{D11D}$)$Q^R$, —C(O)-heterocycloalkyl-$R^{D11}$, —S(O)$_2$—N(H)C(O)—(C$_1$-C$_4$)alkyl-$Q^A$, —S(O)$_2$—N(($R^{D11D}$)C(O)O—(C$_1$-C$_4$)alkyl-$Q^A$, —S(O)$_2$—N(H)C(O)—N(H)$R^{D11}$, —S(O)$_2$—(C$_1$-C$_4$)alkyl-$Q^A$, —O—(C$_1$-C$_4$)alkyl-$Q^A$ optionally substituted at the alkyl group with 1 or 2 $R^{D11B}$, —C(O)—N($R^{D11D}$)—(C$_1$-C$_6$)alkyl substituted at the alkyl group with 1 or 2 $R^{D11}$, heterocyloalkyl-$Q^A$ optionally substituted with oxo or $R^{D11D}$, —S(O)$_2$—N($R^{D11D}$)$R^{D11}$, —S(O)$_2$-(4-6 membered)heterocycloalkyl-(C$_0$-C$_4$)alkyl-$Q^A$, wherein a carbon of the heterocycloalkyl group of —S(O)$_2$-(4-6 membered)heterocycloalkyl-(C$_0$-C$_4$)alkyl-$Q^A$ can be substituted with $R^{D11F}$, —N($R^{D11D}$)—C(O)—(C$_1$-C$_4$)alkyl substituted at the alkyl group with 1 or 2 $R^{D11}$, —N(H)—C(O)—N($R^{D11D}$)—(C$_1$-C$_3$)alkyl substituted at the —(C$_1$-C$_3$)alkyl group with $R^{D11}$, —(C$_1$-C$_6$)alkyl substituted with 1 or 2 $R^{D11}$, and —C≡C—(C$_0$-C$_3$)alkyl substituted with $R^{D11}$;

each $R^{D11}$ is independently selected from —(C$_3$-C$_6$)cycloalkyl-$Q^A$, —(C$_0$-C$_6$)alkyl-(5-6 membered) heterocycloalkyl-$Q^A$, —(C$_0$-C$_6$)alkyl-$Q^A$ optionally substituted with halo or —COOH, and a PEG polymer substituted with $Q^A$;

$R^{D11B}$ is selected from $Q^A$, H, —OH, —CF$_3$, —N($R^{D11E}$)$_2$, —C(O)OH, —O—(C$_1$-C$_4$)alkyl, —S(O)$_2$OH, —C(=NH)—NH$_2$, —N(H)C(=NH)NH$_2$, —C(H)=NC(=NH)NH$_2$, —C(H)=NN(H)C(=NH)NH$_2$, 1,4-diazabicyclo[2.2.2]octanyl, —O—(C$_1$-C$_4$)alkyl-C(O)OH, —N(H)C(=NH)—N(H)C(=NH)NH$_2$, —C(O)—(C$_1$-C$_3$)alkyl, (5-6 membered)heteroaryl, —(C$_1$-C$_4$)alkyl optionally substituted with 1-3 groups independently selected from halo, —OH, —S(O)$_2$OH, C(O)OH, —NH$_2$, —N[(C$_1$-C$_3$)alkyl]$_3$$^+$, 1,4-diazabicyclo[2.2.2]octanyl, and —N(H)C(=NH)NH$_2$, —(C$_0$-C$_3$)alkyl-(5-8 membered)heterocycloalkyl optionally substituted at the heterocycloalkyl group with 1 to 3 $R^{D11}$, —(C$_0$-C$_3$)alkyl-(C$_3$-C$_6$)cycloalkyl optionally substituted with $R^{D11}$, and aryl optionally substituted with 1-5 halo;

$R^{D11D}$ is selected from H, —(C$_3$-C$_6$)cycloalkyl, —(C$_1$-C$_6$)alkyl optionally substituted with 1 or 2 substituents selected from —OH, gem-cyclopropyl, —C(O)OH, —C(O)O—(C$_1$-C$_3$)alkyl, and —C(O)NH$_2$, and —(C$_1$-C$_6$)alkyl-phenyl optionally substituted at the phenyl group with —(C$_1$-C$_3$) alkoxy, —C(O)OH, or —C(O)O—(C$_1$-C$_3$)alkyl;

$R^{D11E}$ is H or —(C$_1$-C$_3$)alkyl; and $R^{D11F}$ is H or —C(O)OH.

In other embodiments of the compounds of formulae VI(Q), VII(Q) and VII(Q), or a pharmaceutically acceptable salt thereof, X is =C($R^4$)—;

Y is a bond, —S—, —S(O)$_2$—, —CH(CH$_3$)—S(O)$_2$—, —CH(CH$_3$)—S—, —CH(OH)—, —CH(CH$_3$)—O—, —C(O)—, —(CH$_2$)—S—, —CH$_2$—N($R^Y$)—, —CH(halo)-, —CH$_2$—S(O)$_2$—, —S(O)$_2$—N(R$^Y$)—, —(CH$_2$)—O—, or —C(O)—N(R)—, wherein R$^Y$ is H, —(C$_1$-C$_3$)alkyl or hydroxyl(C$_1$-C$_3$)alkyl, each R is independently selected from H, —CH$_3$, —OH, F and —CH$_2$OH;

R$^{D1}$ is selected from phenyl, —N(H)-phenyl, —(C$_3$-C$_6$) cycloalkyl, -(5-6 membered)heterocycloalkyl, and -(5-6 membered)heteroaryl-(5-6 membered)heterocycloalkyl, -(5-6 membered)heteroaryl, wherein R$^{D1}$ is substituted with 1, 2, or 3 R$^{D10}$, wherein the 1-3 R$^{D10}$ groups are 0-2 A groups and 1 B group;

each A group, when they occur, is independently selected from halo, —CF$_3$, —CN, —NO$_2$, —OH, —O—(C$_1$-C$_4$)alkyl optionally substituted with 1-3 substituents independently selected from —OH and halo, and —(C$_1$-C$_4$)alkyl optionally substituted with 1-3 substituents independently selected from —OH and halo;

each B group is selected from —(C$_1$-C$_4$)alkylN(R$^{D11}$) R$^{D11B}$, —C(O)—N(R$^{D11D}$)R$^{D11}$, —C(O)—(C$_1$-C$_4$)alkyl-Q$^A$, —C(O)O—(C$_1$-C$_4$)alkyl-Q$^A$, —C(O)-heterocycloalkyl-R$^{D11}$, —S(O)$_2$—(C$_1$-C$_4$)alkyl-N(R$^{D11B}$)R$^{D11}$, —S(O)$_2$—R$^{D11}$, —S(O)$_2$—N(R$^{D11D}$)Q$^R$, —S(O)$_2$—N(H)C(O)—(C$_1$-C$_4$)alkyl-Q$^A$, —S(O)$_2$—N((R$^{D11D}$)C(O)O—(C$_1$-C$_4$)alkyl-Q$^A$, —S(O)$_2$—N(H)C(O)—N(H)R$^{D11}$, —S(O)$_2$—(C$_1$-C$_4$)alkyl-Q$^A$, —C(O)—N(R$^{D11D}$)—(C$_1$-C$_6$)alkyl substituted at the alkyl group with 1 or 2 R$^{D11}$, heterocyloalkyl-Q$^A$ optionally substituted with oxo or R$^{D11D}$, —O—(C$_1$-C$_4$)alkyl-Q$^A$ optionally substituted at the alkyl group with 1 or 2 R$^{D11B}$, —S(O)$_2$—N(R$^{D11D}$)R$^{D11}$, —S(O)$_2$-(4-6 membered)heterocycloalkyl-(C$_0$-C$_4$)alkyl-Q$^A$, wherein a carbon of the heterocycloalkyl group of —S(O)$_2$-(4-6 membered)heterocycloalkyl-(C$_0$-C$_4$)alkyl-Q$^A$ can be substituted with R$^{D11F}$, —N(R$^{D11D}$)—C(O)—(C$_1$-C$_4$)alkyl substituted at the alkyl group with 1 or 2 R$^{D11}$, —N(H)—C(O)—N(R$^{D11D}$)—(C$_1$-C$_3$)alkyl substituted at the —(C$_1$-C$_3$)alkyl group with R$^{D11}$, —(C$_1$-C$_6$)alkyl substituted with 1 or 2 R$^{D11}$, and —C≡C—(C$_0$-C$_3$)alkyl substituted with R$^{D11}$1;

each R$^{D11}$ is independently —(C$_3$-C$_6$)cycloalkyl-Q$^A$, —(C$_0$-C$_6$)alkyl-(5-6 membered) heterocycloalkyl-Q$^A$, —(C$_0$-C$_6$)alkyl-Q$^A$ optionally substituted with halo or —COOH, and a PEG polymer substituted with Q$^A$;

R$^{D11B}$ is selected from H, —OH, —CF$_3$, —N(R$^{D11E}$)$_2$, —C(O)OH, —O—(C$_1$-C$_4$)alkyl, —S(O)$_2$OH, —C(O)—(C$_1$-C$_3$)alkyl, —O—(C$_1$-C$_4$)alkyl-C(O)OH, (5-6 membered) heteroaryl, —(C$_1$-C$_4$)alkyl optionally substituted with 1-3 groups independently selected from halo, —OH, —S(O)$_2$OH, C(O)OH, —NH$_2$, —N[(C$_1$-C$_3$)alkyl]$_3$$^+$, 1,4-diazabicyclo[2.2.2]octanyl, and —N(H)C(═NH)NH$_2$, —(C$_0$-C$_3$) alkyl-(5-8 membered)heterocycloalkyl optionally substituted at the heterocycloalkyl group with 1 to 3 R$^{D11}$, —(C$_0$-C$_3$)alkyl-(C$_3$-C$_6$)cycloalkyl optionally substituted with R$^{D11}$, and aryl optionally substituted with 1-3 halo;

R$^{D11D}$ is selected from H, —(C$_3$-C$_6$)cycloalkyl, —(C$_1$-C$_6$) alkyl optionally substituted with 1 or 2 substituents selected from —OH, gem-cylcopropyl, —C(O)OH, —C(O)O—(C$_1$-C$_3$)alkyl, and —C(O)NH$_2$, and —(C$_1$-C$_6$)alkyl-phenyl optionally substituted at the phenyl group with —(C$_1$-C$_3$) alkoxy, —C(O)OH, or —C(O)O—(C$_1$-C$_3$)alkyl;

R$^{D11E}$ is H or —(C$_1$-C$_3$)alkyl; and

R$^{D11F}$ is H or —C(O)OH.

In other embodiments of the compounds of formulae VI(Q), VII(Q) and VII(Q), or any embodiments of the compounds of formulae VI(Q), VII(Q) and VII(Q) described herein as it may apply, or a pharmaceutically acceptable salt of any of these compounds, p is 0;

Y is a bond, —S—, —S(O)$_2$—, —CH(CH$_3$)—S(O)$_2$—, —CH(CH$_3$)—S—, —CH(OH)—, —CH(CH$_3$)—O—, —C(H)═C(H)—, —C(O)—, —(CH$_2$)—S—, —CH$_2$—N(R$^Y$)—, —CH(halo)-, —CH$_2$—S(O)$_2$, —S(O)$_2$—N(R$^Y$)—, —(CH$_2$)—O—, or —C(O)—N(R$^Y$)—, wherein R$^Y$ is H, —(C$_1$-C$_4$)alkyl or hydroxyl(C$_1$-C$_4$)alkyl;

each R is independently selected from H, —(C$_1$-C$_2$)alkyl, fluoro, —OH and —CH$_2$OH;

R$^{D1}$ is selected from phenyl, —N(H)-phenyl, cyclohexyl, cyclopentyl, piperidinyl, piperazinyl, pyrrolidinyl, morpholinyl, 1,2,3,6-tetrahydropyridine, heteroarylheterocycloalkyl, pyridinyl, oxazolyl, pyrazinyl, quinolinyl, 1,2,4-oxadiazolyl, 1,2,3,4-tetrahydroquinolinyl, and pyrazolyl, wherein R$^D$1 is substituted with 1, 2 or 3 R$^{D10}$, wherein the 1-3 R$^D$10 groups are independently selected from A groups and B groups, provided that R$^{D1}$is substituted with 1 B group;

each A group, when they occur, is independently selected from halo, —CF$_3$, —CN, —NO$_2$, —OH, —O—(C$_1$-C$_4$)alkyl optionally substituted with 1-3 substituents independently selected from —OH and halo, and —(C$_1$-C$_4$)alkyl optionally substituted with 1-3 substituents independently selected from —OH and halo;

each B group is selected from —O—(C$_1$-C$_4$)alkyl-Q$^L$, —S(O)$_2$—N(R$^{D11D}$)Q$^R$, —C(O)—N(R$^{D11D}$)Q$^R$, —C(O)—(C$_1$-C$_4$)alkyl-Q$^A$, —C(O)-heterocycloalkyl-Q$^L$, —S(O)$_2$—R$^{D11}$, —S(O)$_2$—N(R$^{D11D}$)—C(R$^{D11F}$)—(C$_1$-C$_5$)alkyl-Q$^A$, —C(O)—N(R$^{D11E}$)—(C$_1$-C$_6$)alkyl substituted at the alkyl group with Q$^A$, —S(O)$_2$—N(R$^{D11D}$)R$^{D11}$, —S(O)$_2$-(4-6 membered)heterocycloalkyl-(C$_0$-C$_4$)alkyl-Q$^L$, wherein a carbon of the heterocycloalkyl group of —S(O)$_2$-(4-6 membered)heterocycloalkyl-(C$_0$-C$_4$)alkyl-Q$^L$ can be substituted with R$^{D11F}$, —N(H)—C(O)—N(R$^{D11D}$)—(C$_1$-C$_3$)alkyl substituted at the —(C$_1$-C$_3$)alkyl group with Q$^L$, —(C$_1$-C$_6$)alkyl substituted with Q$^A$, and —C≡C—(C$_0$-C$_3$)alkyl substituted with Q$^A$;

R$^{D11D}$ is selected from H, —(C$_3$-C$_6$)cycloalkyl, —(C$_1$-C$_6$) alkyl optionally substituted with 1 or 2 substituents selected from —OH, gem-cyclopropyl, —C(O)OH, —C(O)O—(C$_1$-C$_3$)alkyl, and —C(O)NH$_2$, and —(C$_1$-C$_6$)alkyl-phenyl optionally substituted at the phenyl group with —(C$_1$-C$_3$) alkoxy, —C(O)OH, or —C(O)O—(C$_1$-C$_3$)alkyl;

R$^{D11E}$ is H or —(C$_1$-C$_3$)alkyl; and

R$^{D11F}$ is H or —C(O)OH.

In other embodiments of the compounds of formulae VI(Q), VII(Q) and VIII(Q), or any embodiments of the compounds of formulae VI(Q), VII(Q) and VIII(Q) described herein as it may apply, or a pharmaceutically acceptable salt of any of these compounds, X is ═C(H)—;

p is 0;

Y is a bond, —S—, —S(O)$_2$—, —CH(CH$_3$)—S(O)$_2$—, —CH(CH$_3$)—S—, —CH(OH)—, —CH(CH$_3$)—O—, —C(H)═C(H)—, —C(O)—, —(CH$_2$)—S—, —CH$_2$—N(R$^Y$)—, —CH(halo)-, —CH$_2$—S(O)$_2$, —S(O)$_2$—N(R$^Y$)—, —(CH$_2$)—O—, or —C(O)—N(R$^Y$)—, wherein R$^Y$ is H, —(C$_1$-C$_4$)alkyl or hydroxyl(C$_1$-C$_4$)alkyl;

each R is independently selected from H, —(C$_1$-C$_2$)alkyl, fluoro, —OH and —CH$_2$OH;

R$^{D1}$ is selected from phenyl, —N(H)-phenyl, cyclohexyl, cyclopentyl, piperidinyl, piperazinyl, pyrrolidinyl, morpholinyl, 1,2,3,6-tetrahydropyridine, heteroarylheterocycloalkyl, pyridinyl, oxazolyl, pyrazinyl, quinolinyl, 1,2,4-oxadiazolyl, 1,2,3,4-tetrahydroquinolinyl, and pyrazolyl, wherein R$^D$1 is substituted with 1, 2 or 3 $R^{D10}$, wherein the 1-3 $R^{D10}$ groups are 0-2 A groups and 1 B group;

each A group, when they occur, is independently selected from halo, —$CF_3$, —CN, —$NO_2$, —OH, —O—($C_1$-$C_4$)alkyl optionally substituted with 1-3 substituents independently selected from —OH and halo, and —($C_1$-$C_4$)alkyl optionally substituted with 1-3 substituents independently selected from —OH and halo;

the B group is selected from —O—($C_1$-$C_4$)alkyl-$Q^L$, —C(O)—N($R^{D11D}$)$Q^R$, —C(O)—($C_1$-$C_4$)alkyl-$Q^A$, —C(O)-heterocycloalkyl-$Q^L$, —S(O)$_2$—N($R^{D11D}$)$Q^R$, —S(O)$_2$—$R^{D11}$, —S(O)$_2$—N($R^{D11D}$)—($C_1$-$C_6$)alkyl-$Q^A$, —S(O)$_2$—N($R^{D11D}$)—C($R^{D11F}$)—($C_1$-$C_5$)alkyl-$Q^A$, —C(O)—N($R^{D11E}$)—($C_1$-$C_6$)alkyl substituted at the alkyl group with $Q^A$, —S(O)$_2$-(4-6 membered)heterocycloalkyl-($C_0$-$C_4$)alkyl-$Q^L$, wherein a carbon of the heterocycloalkyl group of —S(O)$_2$-(4-6 membered)heterocycloalkyl-($C_0$-$C_4$)alkyl-$Q^L$ can be substituted with $R^{D11F}$—N(H)—C(O)—N($R^{D11D}$)—($C_1$-$C_3$)alkyl substituted at the —($C_1$-$C_3$)alkyl group with $Q^L$, —($C_1$-$C_6$)alkyl substituted with $Q^A$, and —C≡C—($C_0$-$C_3$)alkyl substituted with $Q^A$;

$R^{D11D}$ is selected from H, —($C_1$-$C_6$)alkyl optionally substituted with 1 or 2 substituents selected from —OH, gem-cyclopropyl, —C(O)OH, —C(O)O—($C_1$-$C_3$)alkyl, and —C(O)NH$_2$, and —($C_1$-$C_6$)alkyl-phenyl optionally substituted at the phenyl group with —($C_1$-$C_3$)alkoxy or —C(O)OH;

$R^{D11E}$ is H or —($C_1$-$C_3$)alkyl; and
$R^{D11F}$ is H or —C(O)OH.

In other embodiments of the compounds of formulae VI(Q), VII(Q) and VIII(Q), or any embodiments of the compounds of formulae VI(Q), VII(Q) and VIII(Q) described herein as it may apply, or a pharmaceutically acceptable salt of any of these compounds, X is =C($R^4$)—;
p is 0;
Y is a bond, —S—, —S(O)$_2$—, —CH(CH$_3$)—S(O)$_2$—, —CH(CH$_3$)—S—, —CH(OH)—, —CH(CH$_3$)—O—, —C(H)=C(H)—, —C(O)—, —(CH$_2$)—S—, —CH$_2$—N($R^Y$)—, —CH(halo)-, —CH$_2$—S(O)$_2$—, —S(O)$_2$—N($R^Y$)—, —(CH$_2$)—O—, or —C(O)—N($R^Y$)—, wherein $R^Y$ is H, —($C_1$-$C_4$)alkyl or hydroxyl($C_1$-$C_4$)alkyl;

each R is independently selected from H, —($C_1$-$C_2$)alkyl, fluoro, —OH and —CH$_2$OH;

$R^{D1}$ is selected from phenyl, —N(H)-phenyl, cyclohexyl, cyclopentyl, piperidinyl, piperazinyl, pyrrolidinyl, morpholinyl, 1,2,3,6-tetrahydropyridine, heteroarylheterocycloalkyl, pyridinyl, oxazolyl, pyrazinyl, quinolinyl, 1,2,4-oxadiazolyl, 1,2,3,4-tetrahydroquinolinyl, and pyrazolyl, wherein $R^{D1}$ is substituted with 1, 2 or 3 $R^{D10}$, wherein the 1-3 $R^{D10}$ groups are 0-2 A groups and 1 B group;

each A group, when they occur, is independently selected from halo, —$CF_3$, —CN, —$NO_2$, —OH, —O—($C_1$-$C_4$)alkyl optionally substituted with 1-3 substituents independently selected from —OH and halo, and —($C_1$-$C_4$)alkyl optionally substituted with 1-3 substituents independently selected from —OH and halo;

the B group is selected from —O—($C_1$-$C_4$)alkyl-$Q^L$, —C(O)—N($R^{D11D}$)$Q^R$, —C(O)—($C_1$-$C_4$)alkyl-$Q^A$, —C(O)-heterocycloalkyl-$Q^L$, —C(O)—N($R^{D11E}$)($C_1$-$C_6$)alkyl substituted at the alkyl group with $Q^A$, —S(O)$_2$—N($R^{D11D}$)$Q^R$, —S(O)$_2$—$R^{D11}$, —S(O)$_2$—N($R^{D11D}$)—($C_1$-$C_6$)alkyl-$Q^A$, —S(O)$_2$—N($R^{D11E}$)—C($R^{D11F}$)alkyl-$Q^A$, —S(O)$_2$-(4-6 membered)heterocycloalkyl-($C_0$-$C_4$)alkyl-$Q^L$, wherein a carbon of the heterocycloalkyl group of —S(O)$_2$-(4-6 membered)heterocycloalkyl-($C_0$-$C_4$)alkyl-$Q^L$ can be substituted with $R^{D11F}$, —N(H)—C(O)—N($R^{D11D}$)—($C_1$-$C_3$)alkyl substituted at the —($C_1$-$C_3$)alkyl group with $Q^L$, —($C_1$-$C_6$)alkyl substituted with $Q^A$, and —C≡C—($C_0$-$C_3$)alkyl substituted with $Q^A$;

$R^{D11D}$ is selected from H, —($C_1$-$C_6$)alkyl optionally substituted with 1 or 2 substituents selected from —OH, gem-cyclopropyl, —C(O)OH, —C(O)O—($C_1$-$C_3$)alkyl, and —C(O)NH$_2$, and —($C_1$-$C_6$)alkyl-phenyl optionally substituted at the phenyl group with —($C_1$-$C_3$)alkoxy or —C(O)OH;

$R^{D11E}$ is H or —($C_1$-$C_2$)alkyl; and
$R^{D11F}$ is —C(O)OH.

In other embodiments of the compounds of formulae VI(Q), VII(Q) and VIII(Q), or any embodiments of the compounds of formulae VI(Q), VII(Q) and VIII(Q) described herein as it may apply, or a pharmaceutically acceptable salt of any of these compounds, $L^D$ is selected from —($C_1$-$C_3$)alkyl-O—, —($C_0$-$C_3$)alkyl-NR$^Y$—($C_0$-$C_3$)alkyl-, —($C_0$-$C_3$)alkyl-S—($C_0$-$C_3$)alkyl-, —($C_0$-$C_3$)alkyl-S(O)$_2$—($C_0$-$C_3$)alkyl-; —C(O)N(R$^Y$)—($C_0$-$C_3$)alkyl-, —S(O)$_2$—N(R$^Y$)—($C_0$-$C_3$)alkyl-, —C(O)—($C_0$-$C_3$)alkyl-, —($C_1$-$C_4$)alkyl-optionally substituted with halo or —OH, —C≡C—($C_0$-$C_3$)alkyl- and —($C_0$-$C_3$)alkyl-.

In other embodiments of the compounds of formulae VI(Q), VII(Q) and VIII(Q), or any embodiments of the compounds of formulae VI(Q), VII(Q) and VIII(Q) described herein as it may apply, or a pharmaceutically acceptable salt of any of these compounds, $L^D$ is selected from —(CH$_2$)$_{1-3}$—O—, —(CH$_2$)$_{1-3}$—NR$^Y$—, —(C$_0$-C$_3$)alkyl-S—(C$_0$-C$_3$)alkyl-; —(CH$_2$)$_{1-3}$—S—, —S—(CH$_2$)$_{1-3}$—, —S(O)$_2$—(CH$_2$)$_{1-3}$—, —S(O)$_2$—, —C(O)N(H)—(CH$_2$)$_{1-3}$—, —S(O)$_2$—N(H)—(CH$_2$)$_{1-3}$—, —C(O)—(CH$_2$)$_{1-2}$—, —C≡C—(C$_0$-C$_3$)alkyl-, a bond, and —(C$_1$-C$_4$)alkyl-optionally substituted with halo or —OH.

In other embodiments of the compounds of formulae VI(Q), VII(Q) and VIII(Q), or any embodiments of the compounds of formulae VI(Q), VII(Q) and VIII(Q) described herein as it may apply, or a pharmaceutically acceptable salt of any of these compounds, $L^D$ is selected from —(CH$_2$)—O—, —(CH$_2$)—NR$^Y$—, —(CH$_2$)—S—, —S—(CH$_2$)—, —S(O)$_2$—, —S(O)$_2$—(CH$_2$)—, —C(O)N(R$^Y$)—(C$_0$-C$_3$)alkyl-; —S(O)$_2$—N(H)—(CH$_2$)$_{1-3}$—, —C(O)—(CH$_2$)$_{1-2}$—, —C≡C—(C$_2$-C$_3$)alkyl-, and —(C$_1$-C$_4$)alkyl-optionally substituted with halo or —OH.

In other embodiments of the compounds of formulae VI(Q), VII(Q) and VIII(Q), or any embodiments of the compounds of formulae VI(Q), VII(Q) and VIII(Q) described herein as it may apply, or a pharmaceutically acceptable salt of any of these compounds, $L^D$ is selected from —(CH$_2$)—O—, —(CH$_2$)—NR$^Y$—, —(CH$_2$)—S—, —S—(CH$_2$)—, —S(O)$_2$—, —S(O)$_2$—(CH$_2$)—, —C(O)N(R$^Y$)—(C$_0$-C$_3$)alkyl-, —S(O)$_2$—N(H)—(CH$_2$)$_{1-3}$—, —C(O)—(CH$_2$)$_{1-2}$—, —C≡C—(C$_2$-C$_3$)alkyl-, and —(C$_1$-C$_4$)alkyl-optionally substituted with halo or —OH.

In other embodiments of the compounds of formulae VI(Q), VII(Q) and VIII(Q), or any embodiments of the compounds of formulae VI(Q), VII(Q) and VIII(Q) described herein as it may apply, or a pharmaceutically acceptable salt of any of these compounds, $L^D$ is selected from —(CH$_2$)—O—, —(CH$_2$)—NH—, —(CH$_2$)—S—, —S—(CH$_2$)—, —S(O)$_2$—, —S(O)$_2$—(CH$_2$)—, —C(O)N(H)—(CH$_2$)$_{1-3}$—, —S(O)$_2$—N(H)—(CH$_2$)$_{1-3}$—, —C(O)—(CH$_2$)$_{1-2}$—, —C≡C—(C$_2$-C$_3$)alkyl- and —(C$_1$-C$_4$)alkyl-optionally substituted with halo or —OH.

In other embodiments of the compounds of formulae VI(Q), VII(Q) and VII(Q), or any embodiments of the compounds of formulae VI(Q), VII(Q) and VII(Q) described herein as it may apply, or a pharmaceutically acceptable salt of any of these compounds, the B group of $R^{D1}$ is selected from:

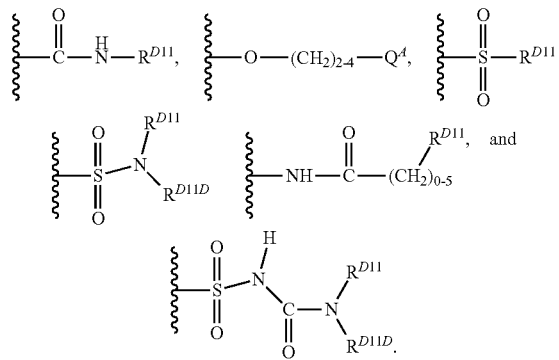

In other embodiments of the compounds of formulae VI(Q), VII(Q) and VIII(Q), or any embodiments of the compounds of formulae VI(Q), VII(Q) and VIII(Q) described herein as it may apply, or a pharmaceutically acceptable salt of any of these compounds, $R^C$ is phenyl, —$CH_2$-phenyl, —$(C_5$-$C_6)$-cycloalkyl, or pyridinyl, wherein $R^C$ can be optionally substituted with 1, 2 or 3 $R^{C10}$, wherein the 1, 2 or 3 $R^{C10}$ groups are independently selected from $R^{C10}$ and $R^{C10B}$, provided that $R^C$ cannot be substituted with more than 1 $R^{C10B}$ group;

each $R^{C10A}$, when they occur, is independently selected from halo, —$(C_1$-$C_3)$alkyl optionally substituted with 1-3 groups selected from halo and —OH, methoxy, —$CF_3$ and halo; and $R^{C10B}$ is selected from —$C(O)NH_2$, (5-6 membered)heterocycloalkyl, —O—$(C_1$-$C_4)$alkyl optionally substituted with —OH, —C(O)OH, or —N[—$(C_1$-$C_4)$alkyl]$_2$, and —$(C_1$-$C_4)$alkyl substituted with —N[—$(C_1$-$C_4)$alkyl]$_2$.

In other embodiments of the compounds of formulae VI(Q), VII(Q) and VIII(Q), or any embodiments of the compounds of formulae VI(Q), VII(Q) and VIII(Q) described herein as it may apply, or a pharmaceutically acceptable salt of any of these compounds, $R^C$ is phenyl, —$CH_2$-phenyl, —$(C_5$-$C_6)$-cycloalkyl, or pyridinyl, wherein the cyclic group of $R^C$ can be optionally substituted with one, two, or three $R^{C10}$ groups and, wherein the one, two, or three $R^{C10}$ groups are independently selected from $R^{C10A}$ and $R^{C10B}$, provided that $R^C$ cannot be substituted with more than 1 $R^{C10B}$ group;

each $R^{C10A}$, when they occur, is independently selected from methoxy, —$CF_3$, halo, and —$(C_1$-$C_3)$alkyl optionally substituted with 1-3 groups selected from halo and —OH; and $R^{C10B}$ is selected from (5-6 membered)heterocycloalkyl, —$(C_1$-$C_4)$alkyl substituted with —N[—$(C_1$-$C_4)$alkyl]$_2$, —$C(O)NH_2$, and —O—$(C_1$-$C_4)$alkyl optionally substituted with —OH, —C(O)OH, or —N[—$(C_1$-$C_4)$alkyl]$_2$.

In other embodiments of the compounds of formulae VI(Q), VII(Q) and VIII(Q), or any embodiments of the compounds of formulae VI(Q), VII(Q) and VIII(Q) described herein as it may apply, or a pharmaceutically acceptable salt of any of these compounds, $R^C$ is phenyl, —$CH_2$-phenyl or pyridinyl, wherein the cyclic group of $R^C$ can be optionally substituted with 1, 2 or 3 $R^{C10}$, wherein the 1, 2 or 3 $R^{C10}$ groups are independently selected from $R^{C10A}$ and $R^{C10B}$, provided that $R^C$ cannot be substituted with more than 1 $R^{10B}$ group;

each $R^{C10A}$, when they occur, is independently selected from —$(C_1$-$C_3)$alkyl optionally substituted with 1-3 groups selected from —OH, methoxy, —$CF_3$ and halo;

$R^{C10B}$ is selected from —$C(O)NH_2$, (5-6 membered)heterocycloalkyl, —$(C_1$-$C_4)$alkyl substituted with —N[—$(C_1$-$C_4)$alkyl]$_2$, and —O—$(C_1$-$C_4)$alkyl optionally substituted with —OH, —C(O)OH, or —N[—$(C_1$-$C_4)$alkyl]$_2$.

In other embodiments of the compounds of formulae VI(Q), VII(Q) and VIII(Q), or any embodiments of the compounds of formulae VI(Q), VII(Q) and VIII(Q) described herein as it may apply, or a pharmaceutically acceptable salt of any of these compounds, $R^C$ is phenyl or pyridinyl, wherein the cyclic group of $R^C$ can be optionally substituted with 1, 2 or 3 $R^{C10}$, wherein the 1, 2 or 3 $R^{C10}$ groups are independently selected from $R^{C10A}$ and $R^{C10B}$, provided that $R^C$ cannot be substituted with more than 1 $R^{C10B}$ group;

each $R^{C10A}$, when they occur, is independently selected from methoxy and halo; and $R^{C10B}$ is selected from —$C(O)NH_2$, (5-6 membered)heterocycloalkyl, —$(C_1$-$C_4)$alkyl substituted with —N[—$(C_1$-$C_4)$alkyl]$_2$, and —O—$(C_1$-$C_4)$alkyl optionally substituted with —OH, —C(O)OH, or —N[—$(C_1$-$C_4)$alkyl]$_2$.

In other embodiments of the compounds of formulae VI(Q), VII(Q) and VIII(Q), or any embodiments of the compounds of formulae VI(Q), VII(Q) and VIII(Q) described herein as it may apply, or a pharmaceutically acceptable salt of any of these compounds, Rc is phenyl or pyridinyl, wherein the cyclic group of $R^C$ can be optionally substituted with 1 or 2 groups selected from methoxy, methyl and halo.

In other embodiments of the compounds of formulae VI(Q), VII(Q) and VIII(Q), or any embodiments of the compounds of formulae VI(Q), VII(Q) and VIII(Q) described herein as it may apply, or a pharmaceutically acceptable salt of any of these compounds, Rc is phenyl or pyridinyl, wherein the cyclic group of $R^C$ can be optionally substituted 1 or 2 groups selected from methoxy, methyl, fluoro and chloro.

In other embodiments of the compounds of formulae VI(Q), VII(Q) and VIII(Q), or any embodiments of the compounds of formulae VI(Q), VII(Q) and VIII(Q) described herein as it may apply, or a pharmaceutically acceptable salt of any of these compounds, $R^C$ is phenyl substituted with one or two groups selected from methoxy, fluoro or chloro.

In other embodiments of the compounds of formulae VI(Q), VII(Q) and VIII(Q), or any embodiments of the compounds of formulae VI(Q), VII(Q) and VIII(Q) described herein as it may apply, or a pharmaceutically acceptable salt of any of these compounds, the compound is one of formula IX, X, XI, XII, XIII, XIV or XV:

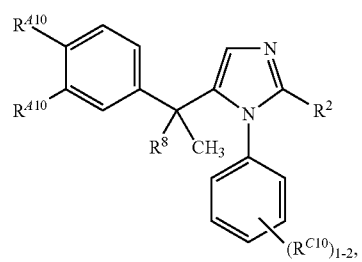

IX

X

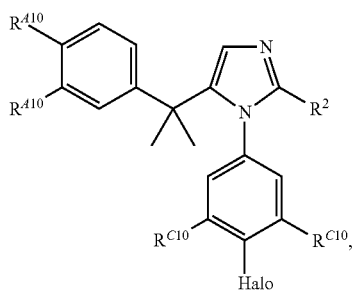

XI

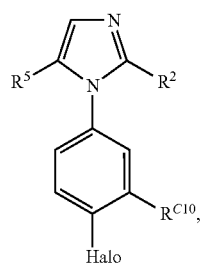

XII

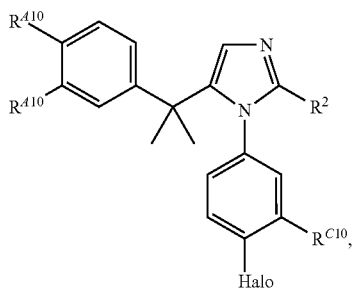

XIII

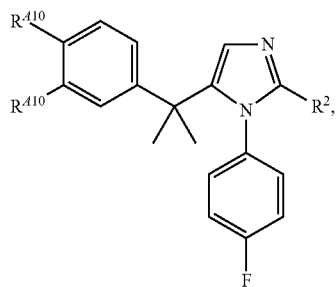

XIV

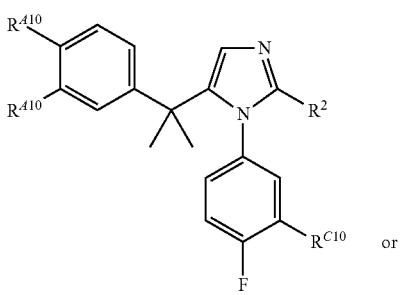

XV

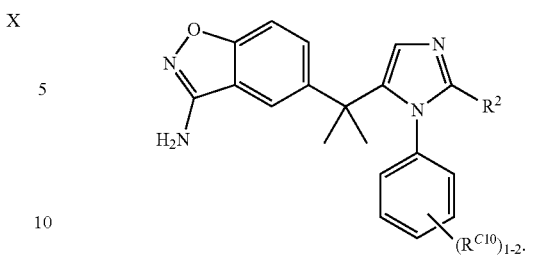

It is to be understood throughout this specification that any embodiment of this specification which includes a variable that is not defined, that the definition of that variable can be as defined in any of the embodiments disclosed herein wherein this variable in question is defined. For instance, each of $R^{A10}$, $R^2$, $R^{C10}$ and $R^8$ in formula IX, X, XI, XII, XIII, XIV or XV above can be as defined in any other embodiment disclosed herein wherein these variables are defined.

In other embodiments of the compounds of formulae VI(Q), VII(Q), VIII(Q), IX, X, XI, XII, XIII, XIV and XV, or in any of the above embodiments of the compounds of formulae VI(Q), VII(Q), VIII(Q) described herein as it may apply, or a pharmaceutically acceptable salt of any of these compounds, each $R^{A10}$ is selected from fluoro, chloro and methoxy;
each $R^{C10}$ is selected from fluoro, chloro and methoxy;
$R^2$ is -$L^D$-$R^{D1}$, wherein:
$L^D$ is selected from —(CH$_2$)—O—, —(CH$_2$)—NH—, —(CH$_2$)—S—, —S—(CH$_2$)—, —S(O)$_2$—, —S(O)$_2$—(CH$_2$)—, —C(O)N(H)—(CH$_2$)$_{1-3}$—, —S(O)$_2$—N(H)—(CH$_2$)$_{1-3}$—, —C(O)—(CH$_2$)$_{1-2}$—, —(C$_1$-C$_3$)alkyl-optionally substituted with halo or —OH, and —C≡C—(C$_2$-C$_3$) alkyl; and
$R^{D1}$ is one of:

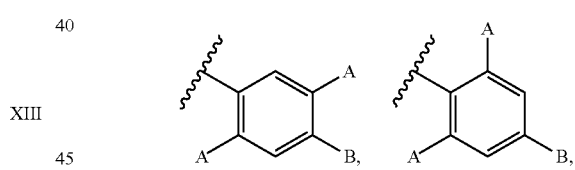

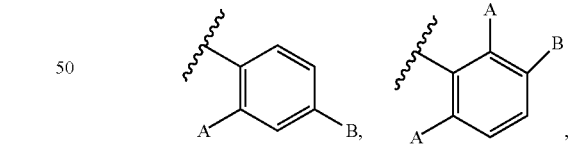

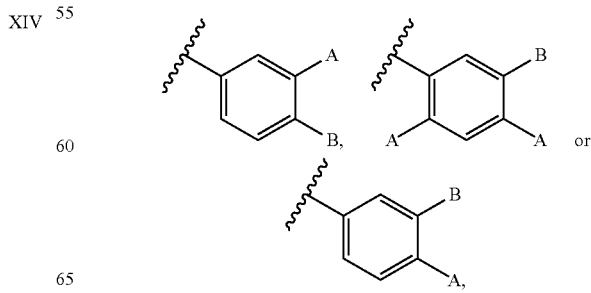

wherein each A is chloro or fluoro, and B is selected from:

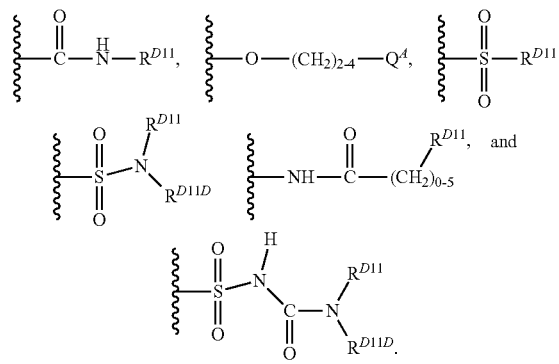

In other embodiments of the compounds of formulae VI(Q), VII(Q), VIII(Q), IX, X, XI, XII, XIII, XIV and XV, or in any of the above embodiments of the compounds of formulae VI(Q), VII(Q), VIII(Q) described herein as it may apply, or a pharmaceutically acceptable salt of any of these compounds, $L^D$ is selected from —(CH$_2$)—O—, —(CH$_2$)—NH—, —(CH$_2$)—S—, —S—(CH$_2$)—, —S(O)$_2$—, —S(O)$_2$—(CH$_2$)—, —C(O)N(H)—(CH$_2$)$_{1-3}$—, —S(O)$_2$—N(H)—(CH$_2$)$_{1-3}$—, —C(O)—(CH$_2$)$_{1-2}$—, —(C$_1$-C$_4$)alkyl-optionally substituted with halo or —OH, and —C≡C—(C$_2$-C$_3$) alkyl-.

In other embodiments of the compounds of formulae VI(Q), VII(Q), VIII(Q), IX, X, XI, XII, XIII, XIV and XV, or in any of the above embodiments of the compounds of formulae VI(Q), VII(Q), VIII(Q) described herein as it may apply, or a pharmaceutically acceptable salt of any of these compounds, $L^D$ is selected from —S—(C$_1$-C$_3$)alkyl-, —(CH$_2$)$_2$— and —(C$_1$-C$_3$)alkyl-O—.

In other embodiments of the compounds of formulae VI(Q), VII(Q), VIII(Q), IX, X, XI, XII, XIII, XIV and XV, or in any of the above embodiments of the compounds of formulae VI(Q), VII(Q), VIII(Q) described herein as it may apply, or a pharmaceutically acceptable salt of any of these compounds, $R^5$ is —[C(CH$_3$)$_2$]-phenyl, —[C(CH$_3$)$_2$]-naphthalenyl, or -[C(CH$_3$)$_2$]-(5-10 membered) heteroaryl, wherein the heteroaryl is selected from (benzo[d][1,3]dioxolyl, benzo[d]isoxazole, quinoxalinyl, quinolinyl and 2,3,4a,8a-tetrahydrobenzo[b][1,4]dioxinyl, wherein the cyclic group of $R^5$ is optionally substituted with one, two, or three $R^{410}$ groups, wherein the one, two, or three $R^{410}$ groups are independently selected from $R^{410A}$ and $R^{410B}$, provided that $R^5$ cannot be substituted with more than 1 $R^{410B}$ group;

each $R^{410A}$, when they occur, is independently selected from halo, —(C$_1$-C$_3$)alkoxyl and hydroxyl; and $R^{410B}$ is —(C$_1$-C$_4$)alkyl optionally substituted with 1-3 groups selected from —OH and halo, —O—(C$_1$-C$_4$)alkyl-C(O)OH, O—(C$_1$-C$_4$)alkyl-N[(C$_1$-C$_3$)alkyl]$_2$, —NH$_2$, —S(O)$_2$ —NH$_2$, —SO$_2$CH$_3$, —N(H)—SO$_2$CH$_3$, —SO$_2$N(H)—CH$_3$, —CN, —C(O)OH, —(C$_1$-C$_4$)alkyl-OH, —OCF$_3$, or —C(O)NH$_2$.

In other embodiments of the compounds of formulae VI(Q), VII(Q), VIII(Q), IX, X, XI, XII, XIII, XIV and XV, or in any of the above embodiments of the compounds of formulae VI(Q), VII(Q), VIII(Q) described herein as it may apply, or a pharmaceutically acceptable salt of any of these compounds, $R^5$ is —[C(CH$_3$)$_2$]-phenyl, and the phenyl group of $R^5$ is optionally substituted with one, two, or three $R^{410}$ groups, wherein the one, two, or three $R^{410}$ groups are independently selected from $R^{410A}$ and $R^{410B}$, provided that $R^5$ cannot be substituted with more than 1 $R^{410B}$ group;

each $R^{410A}$, when they occur, is independently selected from halo, methoxy and hydroxyl; and $R^{410B}$ is —O—(C$_1$-C$_4$)alkyl-C(O)OH, O—(C$_1$-C$_4$)alkyl-N[(C$_1$-C$_3$)alkyl]$_2$, —NH$_2$, —S(O)$_2$—NH$_2$, —SO$_2$CH$_3$, —N(H)—SO$_2$CH$_3$, —SO$_2$N(H)—CH$_3$, —CN, —C(O)OH, —(C$_1$-C$_4$)alkyl-OH, —OCF$_3$, —C(O)NH$_2$ or —(C$_1$-C$_4$) alkyl optionally substituted with 1-3 groups selected from —OH and halo.

In other embodiments of the compounds of formulae VI(Q), VII(Q), VIII(Q), IX, X, XI, XII, XIII, XIV and XV, or in any of the above embodiments of the compounds of formulae VI(Q), VII(Q), VIII(Q) described herein as it may apply, or a pharmaceutically acceptable salt of any of these compounds, $R^5$ is —[C(CH$_3$)$_2$]-phenyl, wherein the phenyl group is optionally substituted with one or two groups selected from halo, methoxy and hydroxyl.

In other embodiments of the compounds of formulae VI(Q), VII(Q), VIII(Q), IX, X, XI, XII, XIII, XIV and XV, or in any of the above embodiments of the compounds of formulae VI(Q), VII(Q), VIII(Q) described herein as it may apply, or a pharmaceutically acceptable salt of any of these compounds, $R^5$ is —[C(CH$_3$)$_2$]-phenyl, wherein the phenyl group is optionally substituted with one or two groups selected from halo and methoxy.

In other embodiments of the compounds of formulae VI(Q), VII(Q), VIII(Q), IX, X, XI, XII, XIII, XIV and XV, or in any of the above embodiments of the compounds of formulae VI(Q), VII(Q), VIII(Q) described herein as it may apply, or a pharmaceutically acceptable salt of any of these compounds, $R^5$ is:

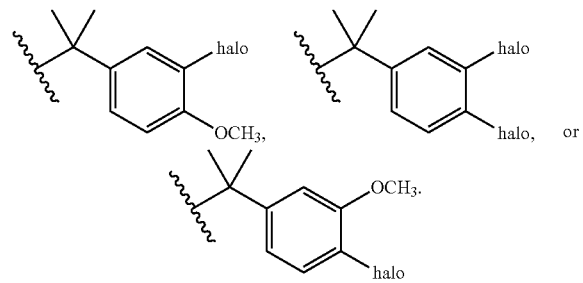

In other embodiments of the compounds of formulae VI(Q), VII(Q), VIII(Q), IX, X, XI, XII, XIII, XIV and XV, or in any of the above embodiments of the compounds of formulae VI(Q), VII(Q), VIII(Q), IX, X, XI, XII, XIII, XIV and XV described herein as it may apply, or a pharmaceutically acceptable salt of any of these compounds, the B group is —O—(C$_1$-C$_4$)alkyl-Q$^L$.

In other embodiments of the compounds of formulae VI(Q), VII(Q), VIII(Q), IX, X, XI, XII, XIII, XIV and XV, or in any of the above embodiments of the compounds of formulae VI(Q), VII(Q), VIII(Q), IX, X, XI, XII, XIII, XIV and XV described herein as it may apply, or a pharmaceutically acceptable salt of any of these compounds, the B group is —C(O)—N(R$^{D11D}$)Q$^R$.

In other embodiments of the compounds of formulae VI(Q), VII(Q), VIII(Q), IX, X, XI, XII, XIII, XIV and XV, or in any of the above embodiments of the compounds of formulae VI(Q), VII(Q), VIII(Q), IX, X, XI, XII, XIII, XIV and XV described herein as it may apply, or a pharmaceutically acceptable salt of any of these compounds, the B group is —C(O)—(C$_1$-C$_4$)alkyl-QA.

In other embodiments of the compounds of formulae VI(Q), VII(Q), VIII(Q), IX, X, XI, XII, XIII, XIV and XV, or in any of the above embodiments of the compounds of formulae VI(Q), VII(Q), VIII(Q), IX, X, XI, XII, XIII, XIV and XV described herein as it may apply, or a pharmaceutically acceptable salt of any of these compounds, the B group is —C(O)-heterocycloalkyl-Q$^L$.

In other embodiments of the compounds of formulae VI(Q), VII(Q), VIII(Q), IX, X, XI, XII, XIII, XIV and XV, or in any of the above embodiments of the compounds of formulae VI(Q), VII(Q), VIII(Q), IX, X, XI, XII, XIII, XIV and XV described herein as it may apply, or a pharmaceutically acceptable salt of any of these compounds, the B group is —C(O)—N(R$^{D11E}$)—(C$_1$-C$_6$)alkyl substituted at the alkyl group with Q$^R$.

In other embodiments of the compounds of formulae VI(Q), VII(Q), VIII(Q), IX, X, XI, XII, XIII, XIV and XV, or in any of the above embodiments of the compounds of formulae VI(Q), VII(Q), VIII(Q), IX, X, XI, XII, XIII, XIV and XV described herein as it may apply, or a pharmaceutically acceptable salt of any of these compounds, the B group is —C(O)—N(R$^{D11E}$)—(C$_1$-C$_6$)alkyl substituted at the alkyl group with Q$^L$.

In other embodiments of the compounds of formulae VI(Q), VII(Q), VIII(Q), IX, X, XI, XII, XIII, XIV and XV, or in any of the above embodiments of the compounds of formulae VI(Q), VII(Q), VIII(Q), IX, X, XI, XII, XIII, XIV and XV described herein as it may apply, or a pharmaceutically acceptable salt of any of these compounds, the B group is —S(O)$_2$—N(R$^{D11D}$)Q$^R$ In other embodiments of the compounds of formulae VI(Q), VII(Q), VIII(Q), IX, X, XI, XII, XIII, XIV and XV, or in any of the above embodiments of the compounds of formulae VI(Q), VII(Q), VIII(Q), IX, X, XI, XII, XIII, XIV and XV described herein as it may apply, or a pharmaceutically acceptable salt of any of these compounds, the B group is —S(O)$_2$—N(R$^{D11D}$)—(C$_1$-C$_6$)alkyl-QR In other embodiments of the compounds of formulae VI(Q), VII(Q), VIII(Q), IX, X, XI, XII, XIII, XIV and XV, or in any of the above embodiments of the compounds of formulae VI(Q), VII(Q), VIII(Q), IX, X, XI, XII, XIII, XIV and XV described herein as it may apply, or a pharmaceutically acceptable salt of any of these compounds, the B group is —S(O)$_2$—N(R$^{D11D}$)—(C$_1$-C$_6$)alkyl-Q$^L$.

In other embodiments of the compounds of formulae VI(Q), VII(Q), VIII(Q), IX, X, XI, XII, XIII, XIV and XV, or in any of the above embodiments of the compounds of formulae VI(Q), VII(Q), VIII(Q), IX, X, XI, XII, XIII, XIV and XV described herein as it may apply, or a pharmaceutically acceptable salt of any of these compounds, the B group is —S(O)$_2$—N(R$^{D11E}$)—C(R$^{D11F}$)—(C$_1$-C$_5$)alkyl-Q$^R$.

In other embodiments of the compounds of formulae VI(Q), VII(Q), VIII(Q), IX, X, XI, XII, XIII, XIV and XV, or in any of the above embodiments of the compounds of formulae VI(Q), VII(Q), VIII(Q), IX, X, XI, XII, XIII, XIV and XV described herein as it may apply, or a pharmaceutically acceptable salt of any of these compounds, the B group is —S(O)$_2$—N(R$^{D11E}$)—C(R$^{D11F}$)—(C$_1$-C$_4$)alkyl-Q$^L$.

In other embodiments of the compounds of formulae VI(Q), VII(Q), VIII(Q), IX, X, XI, XII, XIII, XIV and XV, or in any of the above embodiments of the compounds of formulae VI(Q), VII(Q), VIII(Q), IX, X, XI, XII, XIII, XIV and XV described herein as it may apply, or a pharmaceutically acceptable salt of any of these compounds, the B group is —S(O)$_2$-(4-6 membered)heterocycloalkyl-(C$_0$-C$_4$)alkyl-Q$^L$.

In other embodiments of the compounds of formulae VI(Q), VII(Q), VIII(Q), IX, X, XI, XII, XIII, XIV and XV, or in any of the above embodiments of the compounds of formulae VI(Q), VII(Q), VIII(Q), IX, X, XI, XII, XIII, XIV and XV described herein as it may apply, or a pharmaceutically acceptable salt of any of these compounds, the B group is —S(O)$_2$-(4-6 membered)heterocycloalkyl-(C$_0$-C$_4$)alkyl-Q$^L$ wherein a carbon of the heterocycloalkyl group of —S(O)$_2$-(4-6 membered)heterocycloalkyl-(C$_0$-C$_4$)alkyl-Q$^L$ is substituted with COOH.

In other embodiments of the compounds of formulae VI(Q), VII(Q), VIII(Q), IX, X, XI, XII, XIII, XIV and XV, or in any of the above embodiments of the compounds of formulae VI(Q), VII(Q), VIII(Q), IX, X, XI, XII, XIII, XIV and XV described herein as it may apply, or a pharmaceutically acceptable salt of any of these compounds, the B group is —N(H)—C(O)—N(R$^{D11D}$)—(C$_1$-C$_3$)alkyl substituted at the —(C$_1$-C$_3$)alkyl group with Q$^L$.

In other embodiments of the compounds of formulae VI(Q), VII(Q), VIII(Q), IX, X, XI, XII, XIII, XIV and XV, or in any of the above embodiments of the compounds of formulae VI(Q), VII(Q), VIII(Q), IX, X, XI, XII, XIII, XIV and XV described herein as it may apply, or a pharmaceutically acceptable salt of any of these compounds, the B group is —(C$_1$-C$_6$)alkyl substituted with Q$^A$.

In other embodiments of the compounds of formulae VI(Q), VII(Q), VIII(Q), IX, X, XI, XII, XIII, XIV and XV, or in any of the above embodiments of the compounds of formulae VI(Q), VII(Q), VIII(Q), IX, X, XI, XII, XIII, XIV and XV described herein as it may apply, or a pharmaceutically acceptable salt of any of these compounds, the B group is —C≡C—(C$_0$-C$_3$)alkyl substituted with Q$^A$.

In other embodiments of the compounds of formulae VI(Q), VII(Q), VIII(Q), IX, X, XI, XII, XIII, XIV and XV, or in any of the above embodiments of the compounds of formulae VI(Q), VII(Q), VIII(Q), IX, X, XI, XII, XIII, XIV and XV described herein as it may apply, or a pharmaceutically acceptable salt of any of these compounds, R$^{D11}$ is —(C$_3$-C$_6$)cycloalkyl-Q$^R$.

In other embodiments of the compounds of formulae VI(Q), VII(Q), VIII(Q), IX, X, XI, XII, XIII, XIV and XV, or in any of the above embodiments of the compounds of formulae VI(Q), VII(Q), VIII(Q), IX, X, XI, XII, XIII, XIV and XV described herein as it may apply, or a pharmaceutically acceptable salt of any of these compounds, R$^{D11}$ is —(C$_3$-C$_6$)cycloalkyl-Q$^L$.

In other embodiments of the compounds of formulae VI(Q), VII(Q), VIII(Q), IX, X, XI, XII, XIII, XIV and XV, or in any of the above embodiments of the compounds of formulae VI(Q), VII(Q), VIII(Q), IX, X, XI, XII, XIII, XIV and XV described herein as it may apply, or a pharmaceutically acceptable salt of any of these compounds, R$^{D11}$ is —(C$_0$-C$_6$)alkyl-Q$^A$ optionally substituted with halo or COOH.

In other embodiments of the compounds of formulae VI(Q), VII(Q), VIII(Q), IX, X, XI, XII, XIII, XIV and XV, or in any of the above embodiments of the compounds of formulae VI(Q), VII(Q), VIII(Q), IX, X, XI, XII, XIII, XIV and XV described herein as it may apply, or a pharmaceutically acceptable salt of any of these compounds, R$^{D11}$ is —(C$_0$-C$_6$)alkyl-(5-6 membered) heterocycloalkyl-Q$^A$.

In other embodiments of the compounds of formulae VI(Q), VII(Q), VIII(Q), IX, X, XI, XII, XIII, XIV and XV, or in any of the above embodiments of the compounds of formulae VI(Q), VII(Q), VIII(Q), IX, X, XI, XII, XIII, XIV and XV described herein as it may apply, or a pharmaceutically acceptable salt of any of these compounds, $R^{D11}$ is a PEG polymer substituted with $Q^A$.

In other embodiments of the compounds of formulae VI(Q), VII(Q) and VIII(Q), or in any of the above embodiments of the compounds of formulae VI(Q), VII(Q), and VIII(Q), described herein as it may apply, or a pharmaceutically acceptable salt of any of these compounds, $R^{D11B}$ is H.

In other embodiments of the compounds of formulae VI(Q), VII(Q) and VIII(Q), or in any of the above embodiments of the compounds of formulae VI(Q), VII(Q), and VIII(Q) described herein as it may apply, or a pharmaceutically acceptable salt of any of these compounds, $R^{D11B}$ is —OH.

In other embodiments of the compounds of formulae VI(Q), VII(Q) and VIII(Q), or in any of the above embodiments of the compounds of formulae VI(Q), VII(Q), and VIII(Q) described herein as it may apply, or a pharmaceutically acceptable salt of any of these compounds, $R^{D11B}$ is —CF$_3$.

In other embodiments of the compounds of formulae VI(Q), VII(Q) and VIII(Q), or in any of the above embodiments of the compounds of formulae VI(Q), VII(Q), and VIII(Q) described herein as it may apply, or a pharmaceutically acceptable salt of any of these compounds, $R^{D11B}$ is —N(R$^{D11E}$).

In other embodiments of the compounds of formulae VI(Q), VII(Q) and VIII(Q), or in any of the above embodiments of the compounds of formulae VI(Q), VII(Q), and VIII(Q) described herein as it may apply, or a pharmaceutically acceptable salt of any of these compounds, $R^{D11B}$ is —C(O)OH.

In other embodiments of the compounds of formulae VI(Q), VII(Q) and VIII(Q), or in any of the above embodiments of the compounds of formulae VI(Q), VII(Q), and VIII(Q) described herein as it may apply, or a pharmaceutically acceptable salt of any of these compounds, $R^{D11B}$ is —O—(C$_1$-C$_4$)alkyl.

In other embodiments of the compounds of formulae VI(Q), VII(Q) and VIII(Q), or in any of the above embodiments of the compounds of formulae VI(Q), VII(Q), and VIII(Q) described herein as it may apply, or a pharmaceutically acceptable salt of any of these compounds, $R^{D11B}$ is —S(O)$_2$OH.

In other embodiments of the compounds of formulae VI(Q), VII(Q) and VIII(Q), or in any of the above embodiments of the compounds of formulae VI(Q), VII(Q), and VIII(Q) described herein as it may apply, or a pharmaceutically acceptable salt of any of these compounds, $R^{D11B}$ is —C(O)—(C$_1$-C$_3$)alkyl.

In other embodiments of the compounds of formulae VI(Q), VII(Q) and VIII(Q), or in any of the above embodiments of the compounds of formulae VI(Q), VII(Q), and VIII(Q) described herein as it may apply, or a pharmaceutically acceptable salt of any of these compounds, $R^{D11B}$ is —O—(C$_1$-C$_4$)alkyl-C(O)OH.

In other embodiments of the compounds of formulae VI(Q), VII(Q) and VIII(Q), or in any of the above embodiments of the compounds of formulae VI(Q), VII(Q), and VIII(Q) described herein as it may apply, or a pharmaceutically acceptable salt of any of these compounds, $R^{D11B}$ is (5-6 membered)heteroaryl.

In other embodiments of the compounds of formulae VI(Q), VII(Q) and VIII(Q), or in any of the above embodiments of the compounds of formulae VI(Q), VII(Q), and VIII(Q) described herein as it may apply, or a pharmaceutically acceptable salt of any of these compounds, $R^{D11B}$ is —(C$_1$-C$_4$)alkyl optionally substituted with 1-3 groups independently selected from halo and —OH.

In other embodiments of the compounds of formulae VI(Q), VII(Q) and VIII(Q), or in any of the above embodiments of the compounds of formulae VI(Q), VII(Q), and VIII(Q) described herein as it may apply, or a pharmaceutically acceptable salt of any of these compounds, $R^{D11B}$ is —(C$_1$-C$_4$)alkyl optionally substituted with 1-3 groups independently selected from halo, —OH, —S(O)$_2$OH, C(O)OH, —NH$_2$, —N[(C$_1$-C$_3$)alkyl]$_3$, 1,4-diazabicyclo[2.2.2]octanyl, and —N(H)C(=NH)NH$_2$.

In other embodiments of the compounds of formulae VI(Q), VII(Q) and VIII(Q), or in any of the above embodiments of the compounds of formulae VI(Q), VII(Q), and VIII(Q) described herein as it may apply, or a pharmaceutically acceptable salt of any of these compounds, $R^{D11B}$ is —(C$_0$-C$_3$)alkyl-(5-8 membered)heterocycloalkyl optionally substituted at the heterocycloalkyl group with 1 to 3 $R^{D11}$ In other embodiments of the compounds of formulae VI(Q), VII(Q) and VIII(Q), or in any of the above embodiments of the compounds of formulae VI(Q), VII(Q), and VIII(Q) described herein as it may apply, or a pharmaceutically acceptable salt of any of these compounds, $R^{D11B}$ is —(C$_0$-C$_3$)alkyl-(C$_3$-C$_6$)cycloalkyl optionally substituted with $R^{D11}$.

In other embodiments of the compounds of formulae VI(Q), VII(Q) and VIII(Q), or in any of the above embodiments of the compounds of formulae VI(Q), VII(Q), and VIII(Q) described herein as it may apply, or a pharmaceutically acceptable salt of any of these compounds, $R^{D11B}$ is aryl optionally substituted with 1-3 halo.

In other embodiments of the compounds of formulae VI(Q), VII(Q), VIII(Q), IX, X, XI, XII, XIII, XIV and XV, or in any of the above embodiments of the compounds of formulae VI(Q), VII(Q), VIII(Q), IX, X, XI, XII, XIII, XIV and XV described herein as it may apply, or a pharmaceutically acceptable salt of any of these compounds, $R^{D11D}$ is H.

In other embodiments of the compounds of formulae VI(Q), VII(Q), VIII(Q), IX, X, XI, XII, XIII, XIV and XV, or in any of the above embodiments of the compounds of formulae VI(Q), VII(Q), VIII(Q), IX, X, XI, XII, XIII, XIV and XV described herein as it may apply, or a pharmaceutically acceptable salt of any of these compounds, $R^{D11D}$ is —(C$_3$-C$_6$)cycloalkyl.

In other embodiments of the compounds of formulae VI(Q), VII(Q), VIII(Q), IX, X, XI, XII, XIII, XIV and XV, or in any of the above embodiments of the compounds of formulae VI(Q), VII(Q), VIII(Q), IX, X, XI, XII, XIII, XIV and XV described herein as it may apply, or a pharmaceutically acceptable salt of any of these compounds, $R^{D11D}$ is —(C$_1$-C$_6$)alkyl optionally substituted with 1 or 2 substituents selected from —OH, gem-cylcopropyl.

In other embodiments of the compounds of formulae VI(Q), VII(Q), VIII(Q), IX, X, XI, XII, XIII, XIV and XV, or in any of the above embodiments of the compounds of formulae VI(Q), VII(Q), VIII(Q), IX, X, XI, XII, XIII, XIV and XV described herein as it may apply, or a pharmaceutically acceptable salt of any of these compounds, $R^{D11D}$ is —C(O)OH.

In other embodiments of the compounds of formulae VI(Q), VII(Q), VIII(Q), IX, X, XI, XII, XIII, XIV and XV, or in any of the above embodiments of the compounds of formulae VI(Q), VII(Q), VIII(Q), IX, X, XI, XII, XIII, XIV and XV described herein as it may apply, or a pharmaceutically acceptable salt of any of these compounds, $R^{D11D}$ is —C(O)O—(C$_1$-C$_3$)alkyl.

In other embodiments of the compounds of formulae VI(Q), VII(Q), VIII(Q), IX, X, XI, XII, XIII, XIV and XV, or in any of the above embodiments of the compounds of formulae VI(Q), VII(Q), VIII(Q), IX, X, XI, XII, XIII, XIV and XV described herein as it may apply, or a pharmaceutically acceptable salt of any of these compounds, $R^{D11D}$ is —C(O)NH$_2$.

In other embodiments of the compounds of formulae VI(Q), VII(Q), VIII(Q), IX, X, XI, XII, XIII, XIV and XV, or in any of the above embodiments of the compounds of formulae VI(Q), VII(Q), VIII(Q), IX, X, XI, XII, XIII, XIV and XV described herein as it may apply, or a pharmaceutically acceptable salt of any of these compounds, $R^{D11D}$ is —(C$_1$-C$_6$)alkyl-phenyl optionally substituted at the phenyl group with —(C$_1$-C$_3$)alkoxy, —C(O)OH, or —C(O)O—(C$_1$-C$_3$) alkyl.

In other embodiments of the compounds of formulae VI(Q), VII(Q) and VIII(Q), or in any of the above embodiments of the compounds of formulae VI(Q), VII(Q), and VIII(Q) described herein as it may apply, or a pharmaceutically acceptable salt of any of these compounds, $R^{D11E}$ is H.

In other embodiments of the compounds of formulae VI(Q), VII(Q) and VIII(Q), or in any of the above embodiments of the compounds of formulae VI(Q), VII(Q), and VIII(Q) described herein as it may apply, or a pharmaceutically acceptable salt of any of these compounds, $R^{D11E}$ is —CH$_3$.

In other embodiments of the compounds of formulae VI(Q), VII(Q) and VIII(Q), or in any of the above embodiments of the compounds of formulae VI(Q), VII(Q), and VIII(Q) described herein as it may apply, or a pharmaceutically acceptable salt of any of these compounds, $R^{D11E}$ is —(C$_1$-C$_3$)haloalkyl.

In other embodiments of the compounds of formulae VI(Q), VII(Q) and VIII(Q), or in any of the above embodiments of the compounds of formulae VI(Q), VII(Q), and VIII(Q) described herein as it may apply, or a pharmaceutically acceptable salt of any of these compounds, $R^{D11F}$ is H.

In other embodiments of the compounds of formulae VI(Q), VII(Q) and VIII(Q), or in any of the above embodiments of the compounds of formulae VI(Q), VII(Q), and VIII(Q) described herein as it may apply, or a pharmaceutically acceptable salt of any of these compounds $R^{D11F}$ is —C(O)OH.

In other embodiments of the compounds of formulae VI(Q), VII(Q), VIII(Q), IX, X, XI, XII, XIII, XIV and XV, or in any of the above embodiments of the compounds of formulae VI(Q), VII(Q), VIII(Q), IX, X, XI, XII, XIII, XIV and XV described herein as it may apply, or a pharmaceutically acceptable salt of any of these compounds, $Q^L$ is —N[(C$_1$-C$_3$)alkyl]$_3^+$.

In other embodiments of the compounds of formulae VI(Q), VII(Q), VIII(Q), IX, X, XI, XII, XIII, XIV and XV, or in any of the above embodiments of the compounds of formulae VI(Q), VII(Q), VIII(Q), IX, X, XI, XII, XIII, XIV and XV described herein as it may apply, or a pharmaceutically acceptable salt of any of these compounds, $Q^R$ is Sac

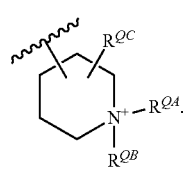

In other embodiments of the compounds of formulae VI(Q), VII(Q), VIII(Q), IX, X, XI, XII, XIII, XIV and XV, or in any of the above embodiments of the compounds of formulae VI(Q), VII(Q), VIII(Q), IX, X, XI, XII, XIII, XIV and XV described herein as it may apply, or a pharmaceutically acceptable salt of any of these compounds, $Q^R$ is

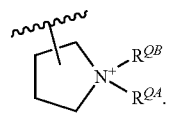

In other embodiments of the compounds of formulae VI(Q), VII(Q), VIII(Q), IX, X, XI, XII, XIII, XIV and XV, or in any of the above embodiments of the compounds of formulae VI(Q), VII(Q), VIII(Q), IX, X, XI, XII, XIII, XIV and XV described herein as it may apply, or a pharmaceutically acceptable salt of any of these compounds, $Q^R$ is

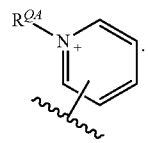

In other embodiments of the compounds of formulae VI(Q), VII(Q), VIII(Q), IX, X, XI, XII, XIII, XIV and XV, or in any of the above embodiments of the compounds of formulae VI(Q), VII(Q), VIII(Q), IX, X, XI, XII, XIII, XIV and XV described herein as it may apply, or a pharmaceutically acceptable salt of any of these compounds, $Q^R$ is

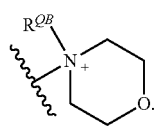

In other embodiments of the compounds of formulae VI(Q), VII(Q), VIII(Q), IX, X, XI, XII, XIII, XIV and XV, or in any of the above embodiments of the compounds of formulae VI(Q), VII(Q), VIII(Q), IX, X, XI, XII, XIII, XIV and XV described herein as it may apply, or a pharmaceutically acceptable salt of any of these compounds, $Q^R$ is

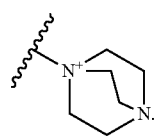 [SMILES: *[N+]12CCN(CC1)CC2]

In other embodiments of the compounds of formulae VI(Q), VII(Q), VIII(Q), IX, X, XI, XII, XIII, XIV and XV, or in any of the above embodiments of the compounds of formulae VI(Q), VII(Q), VIII(Q), IX, X, XI, XII, XIII, XIV and XV described herein as it may apply, or a pharmaceutically acceptable salt of any of these compounds, $Q^R$ is

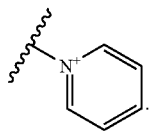 [SMILES: *[n+]1ccccc1]

In other embodiments of the compounds of formulae VI(Q), VII(Q), VIII(Q), IX, X, XI, XII, XIII, XIV and XV, or in any of the above embodiments of the compounds of formulae VI(Q), VII(Q), VIII(Q), IX, X, XI, XII, XIII, XIV and XV described herein as it may apply, or a pharmaceutically acceptable salt of any of these compounds, $Q^R$ is

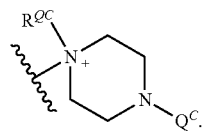

In other embodiments of the compounds of formulae VI(Q), VII(Q), VIII(Q), IX, X, XI, XII, XIII, XIV and XV, or in any of the above embodiments of the compounds of formulae VI(Q), VII(Q), VIII(Q), IX, X, XI, XII, XIII, XIV and XV described herein as it may apply, or a pharmaceutically acceptable salt of any of these compounds, $Q^R$ is

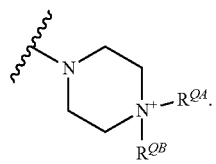

In other embodiments of the compounds of formulae VI(Q), VII(Q), VIII(Q), IX, X, XI, XII, XIII, XIV and XV, or in any of the above embodiments of the compounds of formulae VI(Q), VII(Q), VIII(Q), IX, X, XI, XII, XIII, XIV and XV described herein as it may apply, or a pharmaceutically acceptable salt of any of these compounds, $Q^R$ is

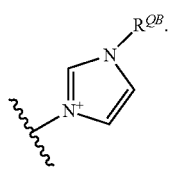

The invention also comprises as another embodiment, a composition comprising a TGR agonist compound according to any one of the preceding embodiments together with a pharmaceutically acceptable diluent, excipient, and/or carrier. Such compositions are substantially free of non-pharmaceutically acceptable components, i.e., contain amounts of non-pharmaceutically acceptable components lower than permitted by US regulatory requirements at the time of filing this application. In some embodiments of this aspect, if the compound is dissolved or suspended in water, the composition further optionally comprises an additional pharmaceutically acceptable carrier, diluent, or excipient.

The invention also comprises as another embodiment a method for treating or preventing a metabolic disease in a subject in need of such treatment comprising administering to the subject an effective amount of a TGR agonist compound according to any one of the preceding embodiments. Metabolic diseases that may be treated or prevented include, without limitation, metabolic syndrome, insulin resistance, and Type 1 and Type 2 diabetes.

The invention also comprises as another embodiment a method for treating obesity or type II diabetes in a subject in need of such treatment comprising administering to the subject an effective amount of a TGR agonist compound or pharmaceutical composition according to any one of the preceding embodiments.

The invention also comprises as another embodiment a method for treating hyperlipidemia in a subject in need of such treatment comprising administering to the subject an effective amount of a TGR agonist compound or pharmaceutical composition according to any one of the preceding embodiments.

The invention also comprises as another embodiment a method for treating athersclerosis in a subject in need of such treatment comprising administering to the subject an effective amount of a TGR agonist compound or pharmaceutical composition according to any one of the preceding embodiments.

The invention also comprises as another embodiment a method for lowering blood glucose in a subject in need of such treatment comprising administering to the subject an effective amount of a TGR agonist compound or pharmaceutical composition according to any one of the preceding embodiments.

The invention also comprises as another embodiment a method for enhancing insulin secretion in a subject in need of such treatment comprising administering to the subject an effective amount of a TGR agonist compound or pharmaceutical composition according to any one of the preceding embodiments.

The invention also comprises as another embodiment a method for treating a disease associated with perturbed bile acid metabolism in a subject in need of such treatment comprising administering to the subject an effective amount of a TGR agonist compound or pharmaceutical composition according to any one of the preceding embodiments. Such diseases include, but are not limited to, gall bladder stones, cholecystitis, cholangitis, choledocholithiasis, jaundice, and obstetric cholestosis and the itch associated with it.

The invention also comprises as another embodiment a method for treating obesity or type II diabetes in a subject in need of such treatment comprising co-administering to the subject, simultaneously or sequentially, an effective amount of a TGR agonist compound according to any one of the preceding embodiments and a second anti-diabetic drug or pharmaceutical composition comprising an effective amount of a TGR agonist compound according to any one of the preceding embodiments and a second anti-diabetic drug. Non-limiting examples of anti-diabetic drugs include:

Sulfonylureas (e.g., tolbutamide (3-butyl-1-(4-methylphenyl)sulfonylurea), acetohexamide (4-acetyl-N-(cyclohexylcarbamoyl)benzenesulfonamide), tolazamide (3-azepan-1-yl-1-(4-methylphenyl)sulfonyl-urea), chlorpropamide (N-(4-chlorophenyl)sulfonylmethanamide), glipizide (N-[2-[4-(cyclohexylcarbamoylsulfamoyl)phenyl]ethyl]-5-methyl-pyrazine-2-carboxamide), glyburide (5-chloro-N-[2-[4-(cyclohexylcarbamoylsulfamoyl)phenyl]ethyl]-2-methoxy-benzamide), glimepiride (3-ethyl-N,N-bis(3- ethyl-4-methyl-2-oxo-5H-pyrrol-2-yl)-4-methyl-2-oxo-5H-pyrrole-1-carboxamide), gliclazide (3-(7-azabicyclo[3.3.0]oct-7-yl)-1-(4-methylphenyl) sulfonyl-urea), and gliquidone (3-cyclohexyl-1-[4-[2-(7-methoxy-4,4-dimethyl-1,3-dioxo-isoquinolin-2-yl) ethyl]phenyl]sulfonyl-urea))

Meglitinides (e.g., repaglinide (S(+)-2-ethoxy-4(2((3-methyl-1-(2-(1-piperidinyl)phenyl)-butyl)amino)-2-oxo-ethyl)benzoic acid), nateglinide (3-phenyl-2-(4-propan-2-ylcyclohexyl)carbonylamino-propanoic acid), and mitiglinide ((2S)-2-benzyl-4-[(3aR,7aS)-octahydro-2H-isoindol-2-yl]-4-oxobutanoic acid))

Biguanides (e.g., metformin (N,N-dimethylimidodicarbonimidic diamide), phenformin (2-(N-phenethylcarbamimidoyl)guanidine), and buformin (2-butyl-1-(diaminomethylidene)guanidine))

Alpha-glucosidase inhibitors (e.g., miglitol ((2R,3R,4R,5S)-1-(2-hydroxyethyl)-2-(hydroxymethyl)piperidine-3,4,5-triol), acarbose ((2R,3R,4R,5S,6R)-5-{[(2R,3R,4R,5S,6R)-5-{[(2R,3R,4S,5S,6R)-3,4-dihydroxy-6-methyl-5-{[(1S,4R,5S,6S)-4,5,6-trihydroxy-3-(hydroxymethyl)cyclohex-2-en-1-yl]amino}tetrahydro-2H-pyran-2-yl]oxy}-3,4-dihydroxy-6-(hydroxymethyl)tetrahydro-2H-pyran-2-yl]oxy}-6-(hydroxymethyl)tetrahydro-2H-pyran-2,3,4-triol), and voglibose ((1S,2S,3R,4S,5S)-5-(1,3-dihydroxypropan-2-ylamino)-1-(hydroxymethyl)cyclohexane-1,2,3,4-tetrol))

Glucagon-like peptide (GLP) analogs and agonists (e.g., exenatide and liraglutide)

Amylin analogues (e.g., pramlintide acetate (Symlin))

Dipeptidyl peptidase-4 (DPP-4) inhibitors (e.g., vildagliptin, (2S)-1-{2-[(3-hydroxy-1-adamantyl)amino]acetyl}pyrrolidine-2-carbonitrile and sitagliptin ((3R)-3-amino-1-[9-(trifluoromethyl)-1,4,7,8-tetrazabicyclo[4.3.0]nona-6,8-dien-4-yl]-4-(2,4,5-trifluorophenyl)butan-1-one)), and Thiazolidinediones (e.g., rosiglitazone, 5-((4-(2-(methyl-2-pyridinylamino)ethoxy)phenyl)methyl)-2,4-thiazolidinedione, pioglitazone (5-((4-(2-(5-ethyl-2-pyridinyl)ethoxy)phenyl)methyl)-,(+−)-2,4-thiazolidinedione,) and troglitazone (5-(4-((6-hydroxy-2,5,7,8-tetramethylchroman-2-yl-methoxy)benzyl)-2,4-thiazolidinedione)).

The invention also comprises as another embodiment, a method for inducing increased GLP-1 secretion in cell, in vitro, comprising contacting the cell with an inducing effective amount of a TGR agonist compound according to any one of the preceding embodiments.

The invention also comprises as another embodiment the use of an effective amount of a TGR agonist compound according to any one of the preceding embodiments for the preparation of a medicament for treating a metabolic disease in a subject in need of such treatment.

The invention also comprises as another embodiment, the use of an effective amount of a TGR agonist compound according to any one of the preceding embodiments for the preparation of a medicament for treating obesity or type II diabetes in a subject in need of such treatment.

The invention also comprises as another embodiment, the use of an effective amount of a TGR agonist compound according to any one of the preceding embodiments for the preparation of a medicament for treating hyperlipidemia in a subject in need of such treatment.

The invention also comprises as another embodiment, the use of an effective amount of a TGR agonist compound according to any one of the preceding embodiments for the preparation of a medicament for treating athersclerosis in a subject in need of such treatment.

The invention also comprises as another embodiment, the use of an effective amount of a TGR agonist compound according to any one of the preceding embodiments for the preparation of a medicament for lowering blood glucose in a subject in need of such treatment.

The invention also comprises as another embodiment, the use of an effective amount of a TGR agonist compound according to any one of the preceding embodiments for the preparation of a medicament for enhancing insulin secretion in a subject in need of such treatment.

The invention also comprises as another embodiment, the use of an effective amount of a TGR agonist compound according to any one of the preceding embodiments for the preparation of a medicament for treating a disease associated with perturbed bile acid metabolism in a subject in need of such treatment.

The invention also comprises as another embodiment, the use of an effective amount of a TGR agonist compound according to any one of the preceding embodiments and a second anti-diabetic drug for the preparation of a medicament for treating obesity or type II diabetes in a subject in need of such treatment.

Pharmaceutical Formulations and Dosage Forms

Administration of the compounds of this disclosure, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracistemally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages.

The compositions will include a conventional pharmaceutical carrier, excipient, and/or diluent and a compound of this disclosure as the/an active agent, and, in addition, can include carriers and adjuvants, etc.

Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It can also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, a pharmaceutical composition of the compounds in this disclosure can also contain minor amounts of auxiliary substances such as wetting or emulsifying agents, pH buffering agents, antioxidants, and the like, such as, for example, citric acid, sorbitan monolaurate, triethanolamine oleate, butylalted hydroxytoluene, etc.

The choice of formulation depends on various factors such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

Compositions suitable for parenteral injection can comprise physiologically acceptable sterile aqueous or nonaqueous solutions, dispersions, suspensions or emulsions, and sterile powders for reconstitution into sterile injectable solutions or dispersions. Examples of suitable aqueous and non-aqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

One preferable route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms can also comprise buffering agents.

Solid dosage forms, as described above, can be prepared with coatings and shells, such as enteric coatings and others well known in the art. They can contain pacifying agents, and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., a compound(s) of this disclosure, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active compounds, can contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the compounds of this disclosure with, for example, suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Dosage forms for topical administration of a compound of this disclosure include ointments, powders, sprays, and inhalants. The active component is admixed under sterile conditions with a physiologically acceptable carrier and any preservatives, buffers, or propellants as can be required. Ophthalmic formulations, eye ointments, powders, and solutions are also contemplated for the compounds in this disclosure.

Compressed gases can be used to disperse a compound of this disclosure in aerosol form. Inert gases suitable for this purpose are nitrogen, carbon dioxide, etc.

Generally, depending on the intended mode of administration, the pharmaceutically acceptable compositions will contain about 1% to about 99% by weight of a compound(s) of this disclosure, or a pharmaceutically acceptable salt thereof, and 99% to 1% by weight of a suitable pharmaceutical excipient. In one example, the composition will be between about 5% and about 75% by weight of a compound(s) of this disclosure, or a pharmaceutically acceptable salt thereof, with the rest being suitable pharmaceutical excipients.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of this disclosure, or a pharmaceutically acceptable salt thereof, for treatment of a disease-state in accordance with the teachings of this disclosure.

The compounds of this disclosure, or their pharmaceutically acceptable salts, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. The compounds of this disclosure can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to one of ordinary skill in the art.

The compositions will include a conventional pharmaceutical carrier or excipient and a compound of this disclosure as the/an active agent, and, in addition, can include other medicinal agents and pharmaceutical agents. Compositions of the compounds in this disclosure can be used in combination with anticancer and/or other agents that are generally administered to a patient being treated for cancer, e.g. surgery, radiation and/or chemotherapeutic agent(s). Chemotherapeutic agents that can be useful for administration in combination with compounds of Formula I in treating cancer include alkylating agents, platinum containing agents.

If formulated as a fixed dose, such combination products employ the compounds of this disclosure within the dosage range described above and the other pharmaceutically active agent(s) within its approved dosage range. Compounds of this disclosure can alternatively be used sequentially with known pharmaceutically acceptable agent(s) when a combination formulation is inappropriate.

The compounds described herein, as well as their pharmaceutically acceptable salts or other derivatives thereof, can exist in isotopically-labeled form, in which one or more atoms of the compounds are replaced by an atom having the same atomic number but an atomic mass different from the atomic mass usually found in nature. Examples of isotopes that can be incorporated into compounds of the invention include isotopes of hydrogen, carbon, nitrogen, oxygen, phosphorous, sulfur, fluorine and chloride, such as $^2$H (deuterium), $^3$H (tritium), $^{13}$C, $^{14}$C, N, $^{18}$O, $^{17}$O, $^{31}$P, $^{32}$P, $^{35}$S, $^{18}$F and $^{36}$Cl, respectively. Isotopically labeled compounds of the present invention, as well as pharmaceutically acceptable salts, esters, prodrugs, solvates, hydrates or other derivatives thereof, generally can be prepared by carrying out the procedures disclosed in the Schemes and/or in the Examples and Preparations below, by substituting a readily available isotopically labeled reagent for a non-isotopically labeled reagent.

In the compounds of the invention, unless otherwise stated, any atom not specifically designated as a particular isotope is meant to represent any stable isotope of that atom at its natural abundance. When a position is designated as "H" or "hydrogen", the position is to be understood to have hydrogen at its natural abundance isotopic composition, with the understanding that some variation of natural isotopic abundance occurs in a synthesized compound depending upon the origin of chemical materials used in the synthesis. When a particular position is designated as "D" or "deuterium", it is to be understood that the abundance of deuterium at that position is substantially greater than the natural abundance of deuterium, which is 0.015%, and typically has at least 50% deuterium incorporation at that position.

The methods disclosed herein also include methods of treating diseases by administering deuterated compounds of the invention or other isotopically-labeled compounds of the invention alone or as pharmaceutical compositions. In some of these situations, substitution of hydrogen atoms with heavier isotopes such as deuterium can afford certain therapeutic advantages resulting from greater metabolic stability (for example, increased in vivo half-life or reduced dosage requirements).

Moreover, certain isotopically-labeled compounds, for example those into which radioactive isotopes such as $^3$H and $^{14}$C are incorporated, are useful in drug and/or substrate tissue distribution assays such as positron emission tomgraphy (PET). Tritiated, ($^3$H) and carbon-14 ($^{14}$C) isotopes are useful for these embodiments because of their detectability.

DEFINITIONS

Terms used herein may be preceded and/or followed by a single dash, "-", or a double dash, "=", to indicate the bond order of the bond between the named substituent and its parent moiety; a single dash indicates a single bond and a double dash indicates a double bond. In the absence of a single or double dash it is understood that a single bond is formed between the substituent and its parent moiety; further, substituents are intended to be read "left to right" unless a dash indicates otherwise. For example, $C_1$-$C_6$alkoxycarbonyloxy and —OC(O)OC$_1$-C$_6$alkyl indicate the same functionality. Also, for instance, when variable X of formula VIII(Q) is defined as =N— or =C(R$^4$)—, the bonds are only to indicate attachment points and the bonds are not meant to add additional bonds to the parent structure. So, for instance, when variable X of formula VIII(Q) is defined as =N—, this would mean the same thing as X being defined as N.

Certain variables used herein are indicated as divalent linking moieties, for example, $L^D$ is a divalent moiety linking $R^D1$ to the parent structure. For such divalent variables, particular members defining $L^D$ may be written, for example, in the form —X—Y— or —Y—X—. When certain groups, such as alkyl groups, are part of a linker, these groups are also divalent moieties.

"Administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., surgery, radiation, chemotherapy, and the like), "administration" and its variants are each understood to include concurrent and sequential introduction of the compound or prodrug thereof and other agents.

"Alkoxy" means the group —OR wherein R is alkyl, as defined herein. Representative examples include methoxy, ethoxy, propoxy, butoxy, pentyloxy, hexyloxy, 4-methylhexyloxy, 4-methylheptyloxy, 4,7-dimethyloctyloxy, and the like.

"Alkoxycarbonyl" means an alkoxy group, as defined herein, appended to a parent moiety via a carbonyl group (i.e., a group of the form, —C(O)OR$^0$, wherein R$^0$ is alkyl, as defined herein). Examples of alkoxycarbonyl groups include, but are not limited to, methoxycarbonyl, ethoxycarbonyl, isopropoxycarbonyl, t-butoxycarbonyl, and n-hexylcarbonyl.

"Alkyl" means a linear or branched hydrocarbon group having from 1 to 10 carbon atoms unless otherwise defined. Representative examples for alkyl groups include methyl, ethyl, propyl, butyl, pentyl, hexyl, 4-methylhexyl, 4-methylheptyl, 4,7-dimethyloctyl, and the like. —(C$_1$-C$_4$)alkyl, which means exactly the same as (C$_{1-4}$)alkyl, includes groups selected from methyl, ethyl, propyl, isopropyl, butyl, sec-butyl,

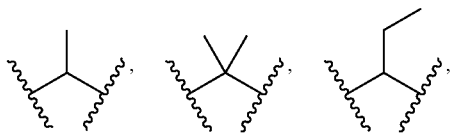
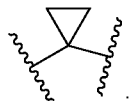

isobutyl, and tert-butyl.

"Alkylamino" means an alkyl group, as defined herein, appended to a parent moiety through an —NH— group (i.e., substituents of the form —N(H)R$^O$, where R$^O$ is an alkyl group). Examples of alkylamino groups include, but are not limited to, methylamino, ethylamino, isopropylamino, hexylamino, and the like.

"Alkylaminocarbonyl" means an alkylamino group, as defined herein, appended to a parent moiety via a carbonyl group (i.e., a group of the form, —C(O)N(H)R$^O$, wherein R$^O$ is alkyl, as defined herein). Examples of alkylaminocarbonyl groups include, but are not limited to, methylaminocarbonyl, ethylaminocarbonyl, isopropylaminocarbonyl, t-butylaminocarbonyl, and n-hexylaminocarbonyl.

"Amino" means a —NH$_2$ group.

"Aryl" means a monovalent, monocyclic, or polycyclic radical having 6 to 14 ring carbon atoms. The monocyclic aryl radical is aromatic and whereas the polycyclic aryl radical may be partially saturated, at least one of the rings comprising a polycyclic radical is aromatic. The polycyclic aryl radical includes fused, bridged, and spiro ring systems. Any 1 or 2 ring carbon atoms of any nonaromatic rings comprising a polycyclic aryl radical may be replaced by a —C(O)—, —C(S)—, or —C(=NH)— group. Unless stated otherwise, the valency may be located on any atom of any ring of the aryl group, valency rules permitting. Representative examples include phenyl, naphthyl, indanyl, and the like.

"Carbonyl" means a —C(O)— group.

"Cycloalkyl" means a monocyclic or polycyclic hydrocarbon radical having 3 to 13 carbon ring atoms. The cycloalkyl radical may be saturated or partially unsaturated, but cannot contain an aromatic ring. The cycloalkyl radical includes fused, bridged and spiro ring systems. Examples of such radicals include cyclopropyl, cyclobutyl, cyclopentyl and cyclohexyl.

"Dialkylamino" means two alkyl groups, each independently as defined herein, appended to a parent moiety through a nitrogen atom (i.e., substituents of the form —N(R$^O$)$_2$, where each R$^O$ is an alkyl group). Examples of dialkylamino groups include, but are not limited to N,N-dimethylamino, N,N-diethylamino, N-isopropyl-N-methylamino, N-ethyl-N-hexylamino, and the like.

"Di(C$_1$-C$_4$alkyl)aminocarbonyl" means a dialkylamino group, as defined herein, appended to a parent moiety via a carbonyl group (i.e., a group of the form, —C(O)N(R$^O$)$_2$, wherein each R$^O$ is alkyl, as defined herein). Examples of dialkylamino groups include, but are not limited to N,N-dimethylaminocarbonyl, N,N-diethylaminocarbonyl, N-isopropyl-N-methylaminocarbonyl, N-ethyl-N-hexylaminocarbonyl, and the like.

"gem-cyclopropyl" means any alkyl group that has a carbon substituted in such a way to form the following structure:

"Fused ring system" and "fused ring" refer to a polycyclic ring system that contains bridged or fused rings; that is, where two rings have more than one shared atom in their ring structures. In this application, fused-polycyclics and fused ring systems are not necessarily all aromatic ring systems. Typically, but not necessarily, fused-polycyclics share a vicinal set of atoms, for example naphthalene or 1,2,3,4-tetrahydronaphthalene. A spiro ring system is not a fused-polycyclic by this definition, but fused polycyclic ring systems of the invention may themselves have spiro rings attached thereto via a single ring atom of the fused-polycyclic. In some examples, as appreciated by one of ordinary skill in the art, two adjacent groups on an aromatic system may be fused together to form a ring structure. The fused ring structure may contain heteroatoms and may be optionally substituted with one or more groups. It should additionally be noted that saturated carbons of such fused groups (i.e., saturated ring structures) can contain two substitution groups.

"Halo" and "halogen" mean a fluoro, chloro, bromo or iodo group.

"Haloalkyl" means an alkyl radical, as defined herein, substituted with one or more halo atoms. For example, halo-substituted (C$_{1-4}$)alkyl includes trifluoromethyl, 2,2-dichloroethyl, 2,2,2-trifluoroethyl, perchloroethyl, 2-bromopropyl, and the like.

"Heteroaryl" means a monovalent monocyclic or polycyclic radical having 5 to 14 ring atoms of which one or more of the ring atoms, for example one, two, three, or four ring atoms, are heteroatoms independently selected from —O—, —S(O)$_n$— (n is 0, 1, or 2), —N—, —N(Rx)-, and the remaining ring atoms are carbon atoms, where Rx is hydrogen, alkyl, hydroxy, alkoxy, —C(O)R$^O$ or —S(O)$_2$R$^O$, where R$^O$ is alkyl. The monocyclic heteroaryl radical is aromatic and whereas the polycyclic heteroaryl radical may be partially saturated, at least one of the rings comprising a polycyclic radical is aromatic. The polycyclic heteroaryl radical includes fused, bridged and spiro ring systems. Any 1 or 2 ring carbon atoms of any nonaromatic rings comprising a polycyclic heteroaryl radical may be replaced by a —C(O)—, —C(S)—, or —C(=NH)— group. Unless stated otherwise, the valency may be located on any atom of any ring of the heteroaryl group, valency rules permitting. In particular, when the point of valency is located on the nitrogen, then Rx is absent. More specifically, the term heteroaryl includes, but is not limited to, 1,2,4-triazolyl, 1,3,5-triazolyl, phthalimidyl, pyridinyl, pyrrolyl, imidazolyl, thienyl, furanyl, indolyl, 2,3-dihydro-1H-indolyl (including, for example, 2,3-dihydro-1H-indol-2-yl, 2,3-dihydro-1H-indol-5-yl, and the like), isoindolyl, indolinyl, isoindolinyl, benzimidazolyl, benzodioxol-4-yl, benzofuranyl, cinnolinyl, indolizinyl, naphthyridin-3-yl, phthalazin-3-yl, phthalazin-4-yl, pteridinyl, purinyl, quinazolinyl, quinoxalinyl, tetrazoyl, pyrazolyl, pyrazinyl, pyrimidinyl, pyridazinyl, oxazolyl, isooxazolyl, oxadiazolyl, benzoxazolyl, quinolinyl, isoquinolinyl, tetrahydroisoquinolinyl (including, for example, tetrahydroisoquinolin-4-yl, tetrahydroisoquinolin-6-yl, and the like), 2,3,3a,7a-tetrahydro-1H-isoindolyl, pyrrolo[3,2-c]pyridinyl (including, for example, pyrrolo[3,2-c]pyridin-2-yl, pyrrolo[3,2-c]pyridin- 7-yl, and the like), benzopyranyl, thiazolyl, isothiazolyl, thiadiazolyl, benzothiazolyl, benzothienyl, and the N-oxide derivatives thereof.

"Heterocyclyl" means a monovalent, monocyclic or polycyclic hydrocarbon radical having 3 to 13 ring atoms of which one or more of the ring atoms, for example 1, 2, 3 or 4 ring atoms, are heteroatoms independently selected from —O—, —S(O)$_n$— (n is 0, 1, or 2), —N═ and —N(R$^y$)— (where R$^y$ is hydrogen, alkyl, hydroxy, alkoxy, —C(O)R$^0$ r —S(O)$_2$R$^0$, where R$^0$ is alkyl, as defined herein), and the remaining ring atoms are carbon. The heterocycloalkyl radical may be saturated or partially unsaturated, but cannot contain an aromatic ring. The heterocycloalkyl radical includes fused, bridged and spiro ring systems. Any 1 or 2 ring carbon atoms independently may be replaced by a —C(O)—, —C(S)—, or —C(═NH)— group. Unless otherwise stated, the valency of the group may be located on any atom of any ring within the radical, valency rules permitting. In particular, when the point of valency is located on a nitrogen atom, Ry is absent. More specifically the term heterocycloalkyl includes, but is not limited to, azetidinyl, pyrrolidinyl, 2-oxopyrrolidinyl, 2,5-dihydro-1H-pyrrolyl, piperidinyl, 4-piperidonyl, morpholinyl, piperazinyl, 2-oxopiperazinyl, tetrahydropyranyl, 2-oxopiperidinyl, thiomorpholinyl, thiamorpholinyl, perhydroazepinyl, pyrazolidinyl, imidazolinyl, imidazolidinyl, dihydropyridinyl, tetrahydropyridinyl, oxazolinyl, oxazolidinyl, isoxazolidinyl, thiazolinyl, thiazolidinyl, quinuclidinyl, isothiazolidinyl, octahydroindolyl, octahydroisoindolyl, decahydroisoquinolyl, tetrahydrofuryl, 1,4-dioxa-8-azaspiro[4.5]decan-8-yl and tetrahydropyranyl, and the N-oxide derivatives thereof.

"Heterocyclylalkyl" means a heterocyclyl group appended to a parent moiety via an alkyl group, as defined herein. Examples of heterocyclylalkyl groups include, but are not limited to, morpholin-4-ylmethyl, 2-(morpholin-4-yl)ethyl, morpholin-2-ylmethyl, 2-(morpholin-2-yl)ethyl, morpholin-3-ylmethyl, 2-(morpholin-3-yl)ethyl, piperazin-1-ylmethyl, 2-(piperazin-1-yl)ethyl, piperidin-1-ylmethyl, 2-(piperidin-1-yl)ethyl, piperidin-2-ylmethyl, 2-(piperidin-2-yl)ethyl, piperidin-4-ylmethyl, 2-(piperidin-4-yl)ethyl, pyrrolidin-1-ylmethyl, 2-(pyrrolidin-1-yl)ethyl, pyrrolidin-2-ylmethyl, 2-(pyrrolidin-2-yl)ethyl.

"Hydroxyalkyl" means an alkyl group, as defined herein, substituted with at least one, for example one, two, or three, hydroxy group(s), provided that if two hydroxy groups are present they are not both on the same carbon atom. Representative examples include, but are not limited to, hydroxymethyl, 2-hydroxyethyl, 2-hydroxypropyl, 3-hydroxypropyl, 1-(hydroxymethyl)-2-methylbutyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl, 2-(hydroxymethyl)-3-hydroxypropyl, 2-hydroxyethylene, 2,3-dihydroxypropyl, 1-(hydroxymethyl)-2-hydroxyethyl, and the like.

The term "optionally substituted" means the substitution may or may not occur and includes instances where said substitution occurs and instances in which it does not. One of ordinary skill in the art would understand that with respect to any molecule described as containing one or more substituents, only sterically practical and/or synthetically feasible compounds are meant to be included. Unless otherwise specified in this specification, when a variable is said to optionally substituted or substituted with a substituent(s), this is to be understood that this substitution occurs by replacing a hydrogen that is covalently bound to the variable with one these substituent(s). This meaning shall apply to all variables that are stated to be substituted or optionally substituted in the specification. For instance, when it is stated that variable R$^C$ can be optionally substituted with R$^{C10}$, this means that this substitution, when it occurs, takes place by replacing a hydrogen that is covalently bound to R$^C$ with R$^{C10}$. Other non-limiting examples of variables that are described in certain instances in the specification as being optionally substituted or substituted with various substituents include, but are not limited to, R$^{D1}$, A groups, B groups, and R$^5$.

Polyethylene glycol (PEG) are polymers of ethylene oxide. Polyethylene glycol refers to the polymer with molecular weight less than 50,000. A polymer is made by joining molecules of ethylene oxide and water together in a repeating pattern. Polyethylene glycol has the following structure: —(CH$_2$—CH$_2$—O)n-.

"Saturated bridged ring system" refers to a bicyclic or polycyclic ring system that is not aromatic. Such a system may contain isolated or conjugated unsaturation, but not aromatic or heteroaromatic rings in its core structure (but may have aromatic substitution thereon). For example, hexahydro-furo[3,2-b]furan, 2,3,3a,4,7,7a-hexahydro-1H-indene, 7-aza-bicyclo[2.2.1]heptane and 1,2,3,4,4a,5,8,8a-octahydro-naphthalene are all included in the class "saturated bridged ring system."

"Spiro ring" refers to a ring originating from a particular annular carbon of another ring. For example, as depicted below:

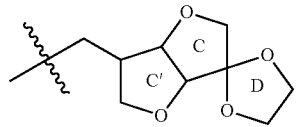

a ring atom of a saturated bridged ring system (rings C and C'), but not a bridgehead atom, can be a shared atom between the saturated bridged ring system and a spiro ring (ring D) attached thereto. A representative example of a spiro ring system is 2,3-dioxa-8-azaspiro[4.5]decan-8-yl.

"Isomers" means compounds having identical molecular formulae but differing in the nature or sequence of bonding of their atoms or in the arrangement of their atoms in space. Isomers that differ in the arrangement of their atoms in space are termed "stereoisomers." Stereoisomers that are not mirror images of one another are termed "diastereomers" and stereoisomers that are nonsuperimposable mirror images are termed "enantiomers" or sometimes "optical isomers." A carbon atom bonded to four nonidentical substituents is termed a "chiral center." A compound with one chiral center has two enantiomeric forms of opposite chirality is termed a "racemic mixture." A compound that has more than one chiral center has $2^{n-1}$ enantiomeric pairs, where n is the number of chiral centers. Compounds with more than one chiral center may exist as ether an individual diastereomer or as a mixture of diastereomers, termed a "diastereomeric mixture." When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry," 3rd edition, March, Jerry, John Wiley & Sons, New York, 1985). The names and illustration used in this application to describe compounds of the invention, unless indicated otherwise, are meant to be encompassed all possible stereoisomers and any mixture, racemic or otherwise, thereof.

The present invention also includes N-oxide derivatives of the compounds of the invention. N-oxide derivatives mean derivatives of compounds of the invention in which nitrogens are in an oxidized state (i.e., N→O), e.g., pyridine N-oxide, and which possess the desired pharmacological activity.

"Metabolite" refers to the break-down or end product of a compound or its salt produced by metabolism or biotransformation in the animal or human body; for example, biotransformation to a more polar molecule such as by oxidation, reduction, or hydrolysis, or to a conjugate (see Goodman and Gilman, "The Pharmacological Basis of Therapeutics" 8.sup.th Ed., Pergamon Press, gilman et al. (eds), 1990 for a discussion of biotransformation). As used herein, the metabolite of a compound of the invention or its salt may be the biologically active form of the compound in the body. In one example, a prodrug may be used such that the biologically active form, a metabolite, is released in vivo. In another example, a biologically active metabolite is discovered serendipitously, that is, no prodrug design per se was undertaken. An assay for activity of a metabolite of a compound of the present invention is known to one of skill in the art in light of the present disclosure.

"Patient" and "subject" for the purposes of the present invention includes humans and other animals, particularly mammals, and other organisms. Thus the methods are applicable to both human therapy and veterinary applications. In another embodiment the patient is a mammal, and in another embodiment the patient is human.

A "pharmaceutically acceptable salt" of a compound means a salt that is pharmaceutically acceptable and that possesses the desired pharmacological activity of the parent compound. It is understood that the pharmaceutically acceptable salts are non-toxic. Additional information on suitable pharmaceutically acceptable salts can be found in *Remington's Pharmaceutical Sciences*, 17$^{th}$ ed., Mack Publishing Company, Easton, Pa., 1985, or S. M. Berge, et al., "Pharmaceutical Salts," J. Pharm. Sci., 1977; 66:1-19. It is also understood that the compound can have one or more pharmaceutically acceptable salts associated with it.

Examples of pharmaceutically acceptable acid addition salts include those formed with inorganic acids such as hydrochloric acid, hydrobromic acid, sulfuric acid, nitric acid, phosphoric acid, and the like; as well as organic acids such as acetic acid, trifluoroacetic acid, propionic acid, hexanoic acid, cyclopentanepropionic acid, glycolic acid, pyruvic acid, lactic acid, oxalic acid, maleic acid, malonic acid, succinic acid, fumaric acid, tartaric acid, citric acid, benzoic acid, cinnamic acid, 3-(4-hydroxybenzoyl)benzoic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, p-toluenesulfonic acid, salicylic acid and the like.

Examples of a pharmaceutically acceptable base addition salts include those formed when an acidic proton present in the parent compound is replaced by a metal ion, such as sodium, potassium, lithium, ammonium, calcium, magnesium, iron, zinc, copper, manganese, aluminum salts and the like. Preferable salts are the ammonium, potassium, sodium, calcium and magnesium salts. Salts derived from pharmaceutically acceptable organic non-toxic bases include, but are not limited to, salts of primary, secondary and tertiary amines, substituted amines including naturally occurring substituted amines, cyclic amines and basic ion exchange resins. Examples of organic bases include isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, tromethamine, N-methylglucamine, polyamine resins, and the like. Exemplary organic bases are isopropylamine, diethylamine, ethanolamine, trimethylamine, dicyclohexylamine, choline, and caffeine.

"Prodrug" refers to compounds that are transformed (typically rapidly) in vivo to yield the parent compound of the above formulae, for example, by hydrolysis in blood. Aommon examples include, but are not limited to, ester and amide forms of a compound having an active form bearing a carboxylic acid moiety. Examples of pharmaceutically acceptable esters of the compounds of this invention include, but are not limited to, alkyl esters (for example with between about one and about six carbons) the alkyl group is a straight or branched chain. Acceptable esters also include cycloalkyl esters and arylalkyl esters such as, but not limited to benzyl. Examples of pharmaceutically acceptable amides of the compounds of this invention include, but are not limited to, primary amides and secondary and tertiary alkyl amides (for example with between about one and about six carbons). Amides and esters of the compounds of the present invention may be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

"Therapeutically effective amount" is an amount of a compound of the invention, that when administered to a patient, effectively treats the disease. The amount of a compound of the invention which constitutes a "therapeutically effective amount" will vary depending upon a sundry of factors including the activity, metabolic stability, rate of excretion and duration of action of the compound, the age, weight, general health, sex, diet and species of the patient, the mode and time of administration of the compound, the concurrent administration of adjuvants or additional therapies and the severity of the disease for which the therapeutic effect is sought. The therapeutically effective amount for a given circumstance can be determined without undue experimentation.

"Treating" or "treatment" of a disease, disorder, or syndrome, as used herein, includes (i) preventing the disease, disorder, or syndrome from occurring in a human, i.e., causing the clinical symptoms of the disease, disorder, or syndrome not to develop in an animal that may be exposed to or predisposed to the disease, disorder, or syndrome but does not yet experience or display symptoms of the disease, disorder, or syndrome; (ii) inhibiting the disease, disorder, or syndrome, i.e., arresting its development; and (iii) relieving the disease, disorder, or syndrome, i.e., causing regression of the disease, disorder, or syndrome. As is known in the art, adjustments for systemic versus localized delivery, the age, weight, general health, sex, diet and species of the patient, the mode and time of administration of the compound, the concurrent administration of adjuvants or additional therapeutically active ingredients and the severity of the disease for which the therapeutic effect is sought may be necessary, and will be ascertainable with routine experimentation.

The compounds disclosed herein and their pharmaceutically acceptable salts can exist as single stereoisomers, racemates, and as mixtures of enantiomers and diastereomers. The compounds disclosed herein can also exist as geometric isomers. All such single stereoisomers, racemates and mixtures thereof, and geometric isomers are intended to be within the scope of the compounds disclosed herein.

It is assumed that when considering generic descriptions of compounds of the 2 disclosed herein for the purpose of constructing a compound, such construction results in the creation of a stable structure. That is, one of ordinary skill in the art would recognize that theoretically some constructs which would not normally be considered as stable compounds (that is, sterically practical and/or synthetically feasible, supra).

Methods for the preparation and/or separation and isolation of single stereoisomers from racemic mixtures or non-racemic mixtures of stereoisomers are well known in the art. For example, optically active (R)- and (S)-isomers can be prepared using chiral synthons or chiral reagents, or resolved using conventional techniques. Enantiomers (R- and S-isomers) can be resolved by methods known to one of ordinary skill in the art, for example by: formation of diastereoisomeric salts or complexes which can be separated, for example, by crystallization; via formation of diastereoisomeric derivatives which can be separated, for example, by crystallization, selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step can be required to liberate the desired enantiomeric form. Alternatively, specific enantiomer can be synthesized by asymmetric synthesis using optically active reagents, substrates, catalysts or solvents or by converting on enantiomer to the other by asymmetric transformation. For a mixture of enantiomers, enriched in a particular enantiomer, the major component enantiomer can be further enriched (with concomitant loss in yield) by recrystallization.

In addition, the compounds of this disclosure can exist in unsolvated as well as solvated forms with pharmaceutically acceptable solvents such as water, ethanol, and the like. In general, the solvated forms are considered equivalent to the unsolvated forms for the purposes of the compounds of this disclosure.

In addition, it is intended that the present disclosure cover compounds made either using standard organic synthetic techniques, including combinatorial chemistry or by biological methods, such as bacterial digestion, metabolism, enzymatic conversion, and the like.

The examples and scheme below depict the general synthetic procedure for the compounds disclosed herein. Synthesis of the compounds of Formulae VIII(Q) disclosed herein, and embodiments thereof, are not limited by these examples and schemes. One skilled in the art will know that other procedures can be used to synthesize the compounds of Formulae VIII(Q) disclosed herein, and that the procedures described in the examples and schemes is only one such procedure. In the descriptions below, one of ordinary skill in the art would recognize that specific reaction conditions, added reagents, solvents, and reaction temperatures can be modified for the synthesis of specific compounds that fall within the scope of this disclosure. All intermediate compounds described below, for which there is no description of how to synthesize such intermediates within these examples below, are commercially available compounds unless otherwise specified.

Synthesis

In the following general methods, X, $L^D$, $Q^4$, $R^1$, $R^2$, $R^4$, $R^8$, $R^{410}$, $R^{D1}$, $R^{D10}$, $R^{D11}$, $R^{D11D}$, and $R^Y$ are as previously defined for a compound of formula VIII(Q), and embodiments thereof, unless otherwise stated. The following abbreviations and acronyms are used herein.

| | | | |
|---|---|---|---|
| AcOH or HOAc | acetic acid | Et₃N | triethylamine |
| AIBN | azobisisobutyronitrile | GLP-1 | glucagon-like peptide-1 |
| cAMP | cyclic adenosine monophosphate | Hex | hexane |
| CD-FBS | charcoal-dextran-treated fetal bovine serum | HATU | O-(7-Azabenzotriazol-1-yl)-N,N,N',N'-tetramethyluronium hexafluorophosphate |
| C2MC | carboxymethyl cellulose | HMTA | hexamethylenetetramine |
| conc. | concentrated | IBMX | isobutylmethylxanthine |
| DCM | dichloromethane | KOtBu | potassium tert-butoxide |
| DIBAH | diisobutylaluminum hydride | mCPBA | m-chloroperoxybenzoic acid |
| DIPEA | diisopropylethylamine | MeCN | acetonitrile |
| DMEM | Dulbecco's modified essential medium | MeMgBr | methylmagnesium bromide |
| DMF | N,N-dimethylformamide | MeOH | methanol |
| DMSO | dimethylsulfoxide | NBS | N-bromosuccinimide |
| DPBS | Dulbecco's Phosphate Buffered Saline | OAc | acetate |
| DPP-IV | dipeptidyl peptidase IV | PCC | pyridinium chlorochromate |
| EDTA | ethylenediaminetetraacetic acid | PEG | polyethylene glycol |
| Et₂O | diethyl ether | PG | protecting group |
| EtOAc | ethyl acetate | satd | saturated |
| EtOH | ethanol | STC-1 | stanniocalcin 1 |
| FAF-BSA | Fatty acid-free bovine serum albumin | TFA | trifluoroacetic acid |
| FBS | fetal bovine serum | THF | tetrahydrofuran |

When $L^D$ represents —SCH$_2$— and X represents =C(H)—, then compounds of formula (I$^4$) may be prepared as depicted in Scheme 1.

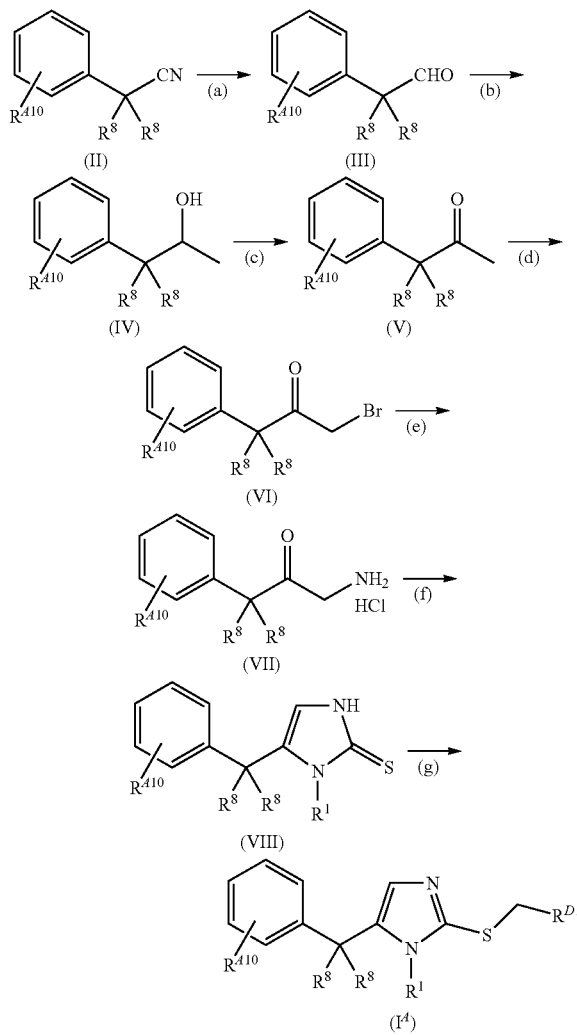

Compounds of formula (II) are commercially available or may be prepared from known compounds using standard methodologies as exemplified in the preparations below.

Step (a): An aldehyde of formula (III) may be prepared by reaction of nitrile (II) with diisobutylaluminum hydride in a suitable solvent, such as THF.

Step (b): Formation of carbinol (IV) may be achieved by treatment of aldehyde (III) with methylmagnesium bromide in a suitable solvent, such as diethyl ether or THF.

Step (c): Conversion of carbinol (IV) to ketone (V) may occur under standard conditions, such as the Swern oxidation-known to one trained in the art of chemistry.

Step (d): Bromoketone (VI) may be prepared by bromination of ketone (V) under typical conditions, such as with tetrabutylammonium tribromide in 1:2 mixture of MeOH-DCM.

Step (e): Reaction of bromoketone (VI) with sodium azide in a suitable solvent, such as DMF, followed by reduction of the resulting azido-ketone under standard conditions, such as with zinc dust and hydrochloric acid in THF, may afford amino-ketone hydrochloride (VII).

Step (f): Isothiocyanate R$^1$NCS may react with amino-ketone hydrochloride (VII) in a suitable solvent, such as DCM or toluene, and in the presence of a base, such as triethylamine, at elevated temperature to yield the corresponding thiourea, which may condense upon treatment with HOAc at elevated temperature to give a compound of formula (VIII).

Step (g): Alkylation of imidazol-2-thione (VIII) with an electrophile R$^{D1}$CH$_2$Br in a suitable solvent, such as acetone or MeCN, and in the presence of a base, such as potassium carbonate, may afford a compound of formula (I$^4$).

Compounds of formula (I$^B$) may be prepared as shown in Scheme 2.

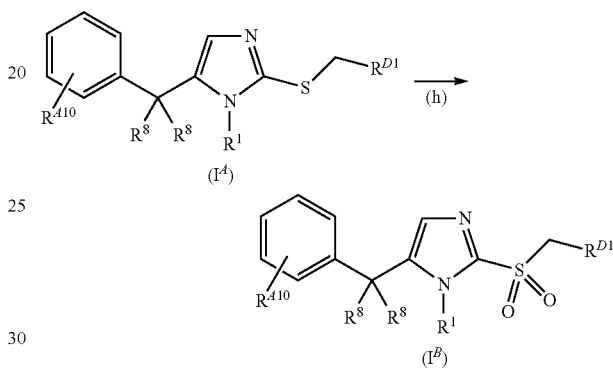

Step (h): Reaction of thioether (I$^4$) with a suitable oxidant, such as mCPBA (2.5-3.0 eq), in a suitable solvent such as DCM may yield a compound of formula (I$^B$).

Compounds of formula (I$^C$) may be synthesized as shown in Scheme 3.

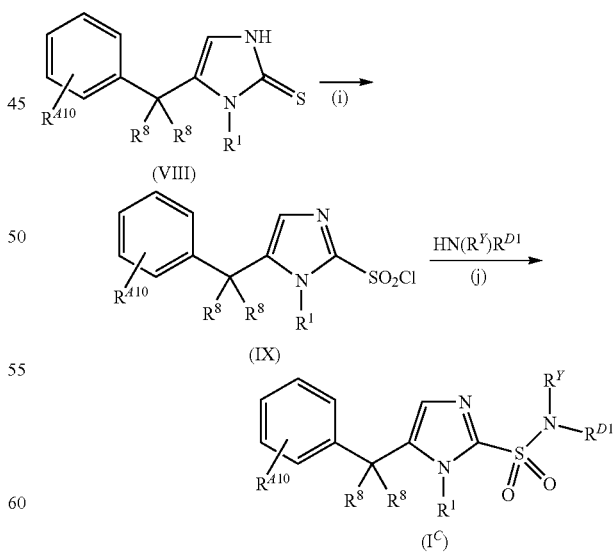

Step (i): Thione (I$^4$) may be converted to the corresponding sulfonyl chloride (IX) under standard conditions, such as adding NaOCl (3 eq) to thione (I$^4$) in a 1:1 mixture of DCM and 1N HCl at reduced temperature, preferably below 0° C.

Step (j): Compounds of formula (I$^c$) may be prepared by reaction of amine HN(R$^Y$)R$^{D1}$ with sulfonyl chloride (IX) in a suitable solvent, such as DCM, and in the presence of a base, such as triethylamine.

Compounds of formula (I$^D$) may be synthesized as depicted in Scheme 4.

Scheme 4

(VIII)

(X)

(I$^D$)

Step (k): Thione (VIII) may undergo desulfurization under standard conditions, such as with H$_2$O$_2$ in a mixture of HOAc-DCM, to afford imidazole (X).

Step (l): Reaction of imidazole (X) with butyllithium in a suitable solvent (e.g. THF) at reduced temperature, preferably at −78° C. for 30-40 minutes, may yield the corresponding organolithium, which may react with a suitable electrophile (e.g. isocyanate or carbamoyl chloride) at the same temperature to afford a compound of formula (I$^D$).

Compounds of formulae (I$^E$) and (I$^F$) may be prepared as shown in Scheme 5.

Scheme 5

(X)

(XI)

(I$^E$)

(I$^F$)

Step (m): Imidazole (X) may be converted to the corresponding organolithium, as described previously, and then treated with DMF, preferably at −78° C. for 30-40 minutes, to yield aldehyde (XI).

Step (n): Compounds of formula (I$^E$) may be prepared by reaction of aldehyde (XI) with a phosphorus ylide under Wittig or Horner-Emmons conditions-both known to one skilled in the art of chemistry.

Step (o): Compounds of formula (I$^F$) may be prepared by catalytic hydrogenolysis of alkene (I$^E$) under standard conditions, such as in MeOH under 50-60 psi of hydrogen and over PtO$_2$ (10-20 mole %).

Compounds of formula (I$^G$), wherein Y is chosen from NR$^Y$, O or S, may be prepared as depicted in Scheme 6.

Scheme 6

(XI)

(XII)

(I$^G$)

Step (p): Reduction of aldehyde (XI) using standard conditions, such as NaBH$_4$ in EtOH at ambient temperature, may afford the corresponding carbinol (XII).

Step (q): Compounds of formula (I$^G$) may be prepared from carbinol (XII) and a suitable nucleophile HYR$^{D1}$, such as a phenol or thiophenol wherein Y represents O or S, respectively, and R$^{D1}$ is aryl, under Mitsunobu conditions-known to one skilled in the art. Alternatively carbinol (XII) may be converted to the corresponding chloride, for example, by treatment with thionyl chloride (2 eq) in chloroform, followed by reaction with a suitable nucleophile HYR$^{D1}$ in MeCN (or acetone) and in the presence of a base (e.g. $K_2CO_3$) to yield compounds of formula ($I^G$).

Compounds of formula ($I^H$), wherein $R^4$ is chosen from Br, Cl or F, may be prepared as shown in Scheme 7.

Scheme 7

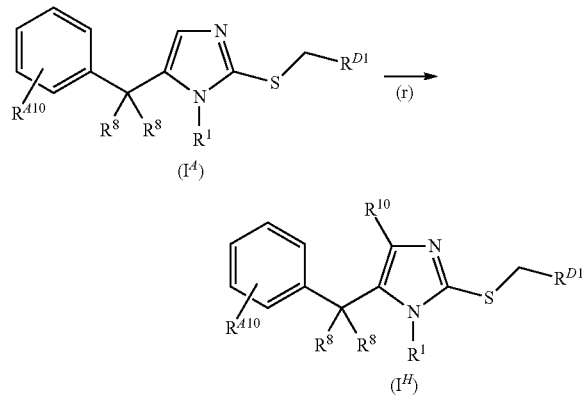

Step (r): Compounds of the formula ($I^H$) may be prepared from imidazole ($I^A$) by treatment with a suitable halogen source such as, for example, N-bromosuccinimide in DCM. N-chlorosuccinimide and Selectfluor™ in a suitable solvent, such as DCM or MeCN, may be used to generate the corresponding chloro- and fluoro-substituted compounds (1H), respectively.

When $L^D$ represents —$SCH_2$— and X is N, then compounds of formula ($I^J$) may be synthesized as depicted in Scheme 8.

Scheme 8

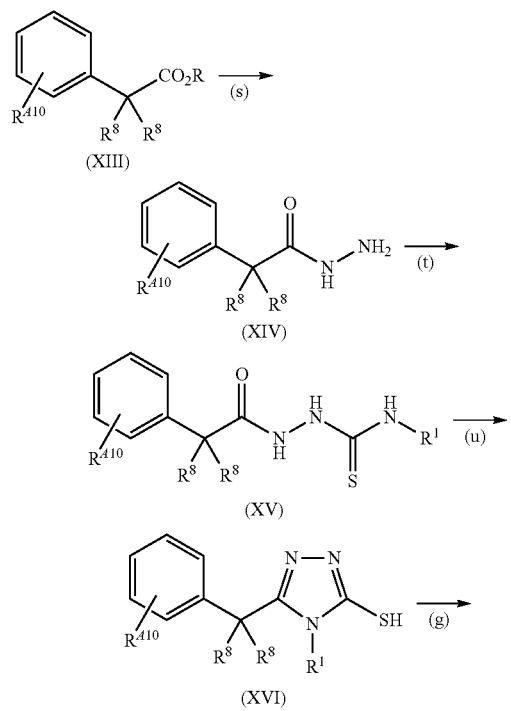

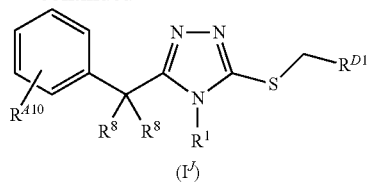

(I$^J$)

Compounds of formula (XIII) are commercially available or may be prepared from known compounds using standard methodologies.

Step (s): Ester (XIII), wherein R represents alkyl (e.g. methyl), may react with hydrazine in a suitable solvent, such as MeOH, at elevated temperature and in a sealed vessel to yield hydrazide (XIV). Alternatively acid (XIII), wherein R is H, may be converted to its hydrazide (XIV) under standard conditions-known to one skilled in the art.

Step (t): Hydrazide (XIV) may react with isothiocyanate $R^1NCS$ in a suitable solvent, such as EtOH, at elevated temperature, preferably at reflux, to generate thiourea (XV).

Step (u): Reaction of thiourea (XV) under basic conditions, such as in 5-10% aqueous NaOH at elevated temperature, preferably at reflux, may condense to yield thiol (XVI).

Next compounds of formula ($I^J$) may be prepared from thiol (XVI) under conditions previously described in step (g).

Compounds of formula ($I^K$) may be prepared as depicted in Scheme 9.

Scheme 9

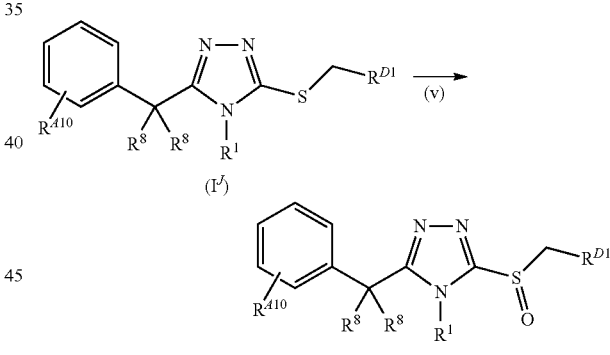

Step (v): Reaction of thioether ($I^J$) with a suitable oxidant, such as mCPBA (1-1.1 equiv) in DCM, may yield compounds of formula ($I^K$).

Compounds of formula ($I^L$), wherein $R^S$ is H, may be prepared as depicted in Scheme 10.

Scheme 10

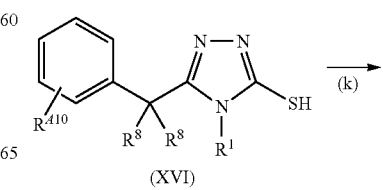

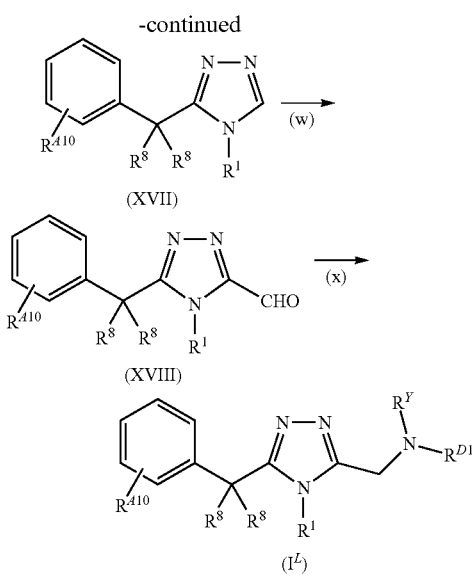

Under conditions previously described in step (k), thiol (XVI) may undergo desulfurization to afford triazole (XVII).

Step (w): Hydroxymethylation of triazole (XVII) may proceed under standard conditions, such as with paraformaldehyde in toluene heated at reflux, to afford the corresponding hydroxymethyltriazole, which may undergo oxidation upon treatment with a suitable oxidant, such as $MnO_2$, in THF to yield the corresponding aldehyde (XVIII).

Step (x): Reaction of aldehyde (XVIII) with amine $HN(R^Y)R^{D1}$ under typical reductive amination conditions, such as with $NaB(OAc)_3H$ in a suitable solvent, may give compounds of formula ($I^L$).

Scheme 11

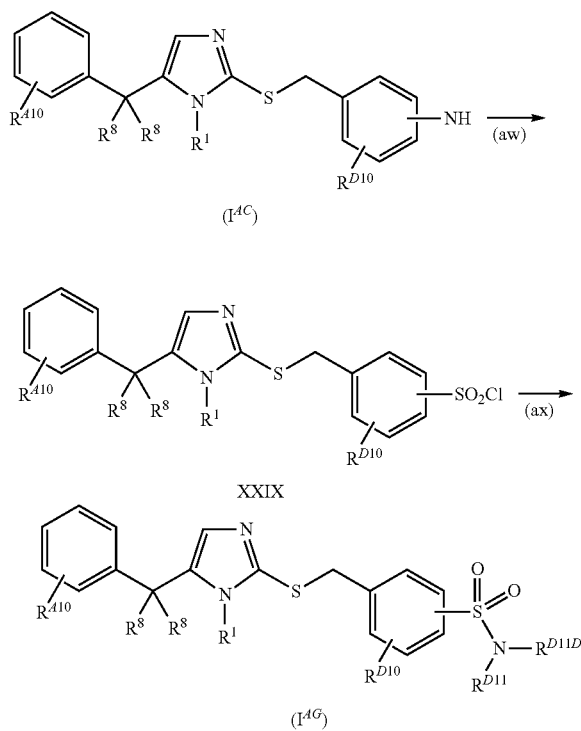

Step (aw): Amine ($I^{AC}$) may undergo diazotization under typical conditions, such as with aqueous sodium nitrite, and then may be converted to the corresponding sulfonyl chloride (XXIX) upon reaction with a mixture of copper (II) chloride, sulfur dioxide, HCl and HOAc.

Step (ax): Sulfonyl chloride (XXIX) may react with an amine $HN(R^{D11})R^{D11D}$ in the presence of a base, such as $K_2CO_3$, to afford compounds of formula ($I^{AG}$). In addition, ammonia may react with sulfonyl chloride (XXIX) to yield a sulfonamide ($IA^G$), wherein both $R^{D11}$ are H.

Compounds of formula ($I^P$) may be prepared as shown in Scheme 12.

Scheme 12

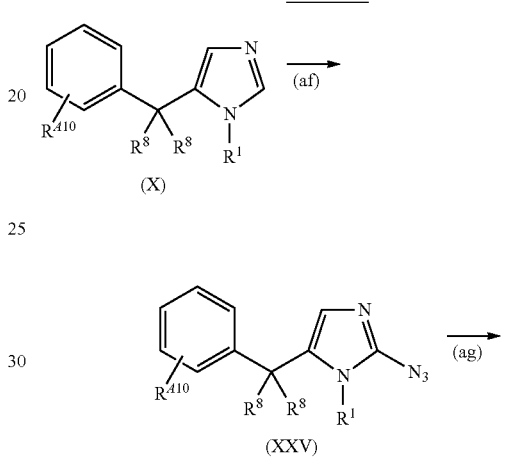

Step (af): Imidazole (X) may be converted to the corresponding organolithium, as described previously, and then treated with tosyl azide in a suitable solvent (e.g. THF), preferably at −78° C. for 30 minutes, to yield azide (XXV).

Step (ag): Azide (XXV) may undergo catalytic hydrogenation under standard conditions, such as with a suitable palladium catalyst, preferably Lindlar catalyst, under hydrogen at ambient pressure, to give amine (XXVI).

Step (ah): Reaction of amine (XXVI) with an acid chloride in a suitable solvent (e.g. DCM) and with a base (e.g. pyridine) may afford compounds of formula ($I^P$).

Compounds of formula ($I^Q$), for example, wherein $R^4$ is chosen from aryl or heteroaryl, may be prepared as shown in Scheme 13.

Scheme 13

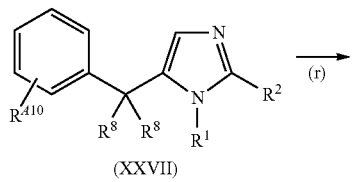

(XXVII)

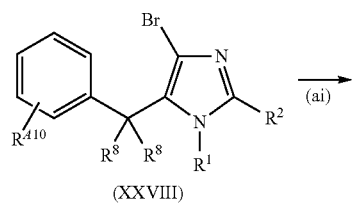

(XXVIII)

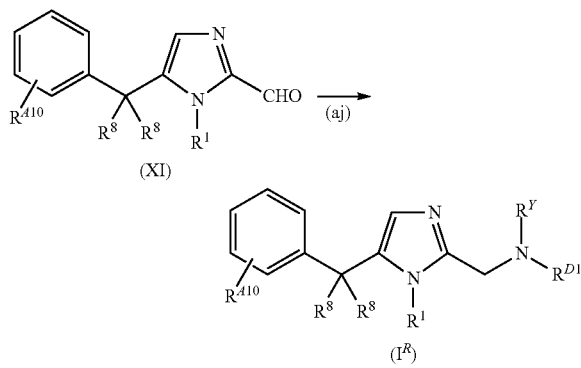

($I^Q$)

Step (r): Under conditions previously described in step (r), imidazole (XXVII) may be brominated to give bromoimidazole (XXVIII).

Step (ai): Compounds of the formula ($I^Q$) may be prepared from bromoimidazole (XXVIII) using standard cross-coupling conditions, such as with suitable boronic acids under Suzuki conditions known to one skilled in the art of chemistry.

Compounds of formula ($I^R$) may be prepared as depicted in Scheme 14.

Scheme 14

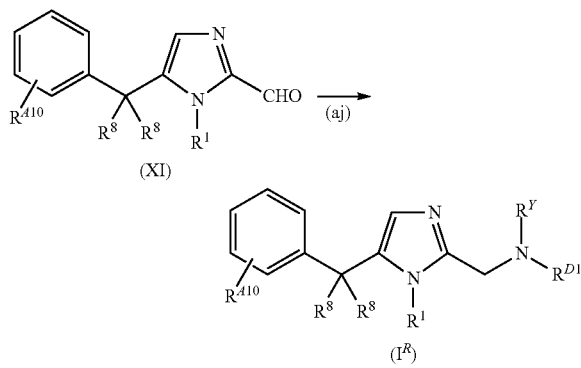

Step (aj): Reaction of aldehyde (XI) and a suitable amine $HN(R^Y)R^{D1}$ under standard reductive amination conditions, such as with toluene sulfonic acid followed by sodium borohydride in EtOH at ambient temperature, may afford compounds of formula ($I^R$).

Compounds of formula ($I^S$) may be prepared as depicted in Scheme 15.

Scheme 15

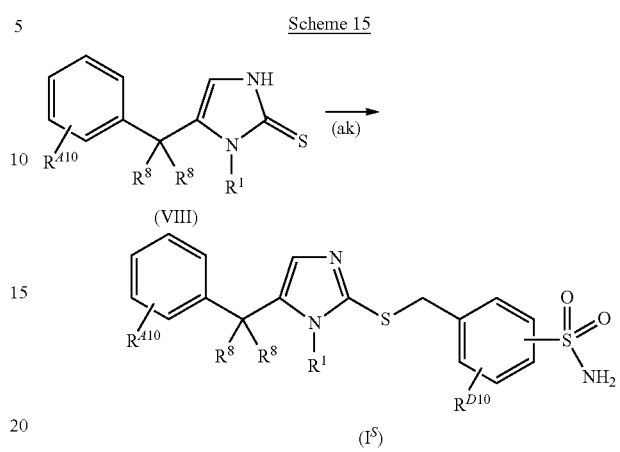

Step (ak): Alkylation of imidazol-2-thione (VIII) with an electrophile $R^{D1}CH_2Br$, wherein $R^{D1}$ is a benzenesulfonamide, in a suitable solvent (e.g. acetone) and with a base (e.g. potassium carbonate) may afford compounds of formula ($I^S$).

Compounds of formula ($I^T$) may be prepared as depicted in Scheme 16.

Scheme 16

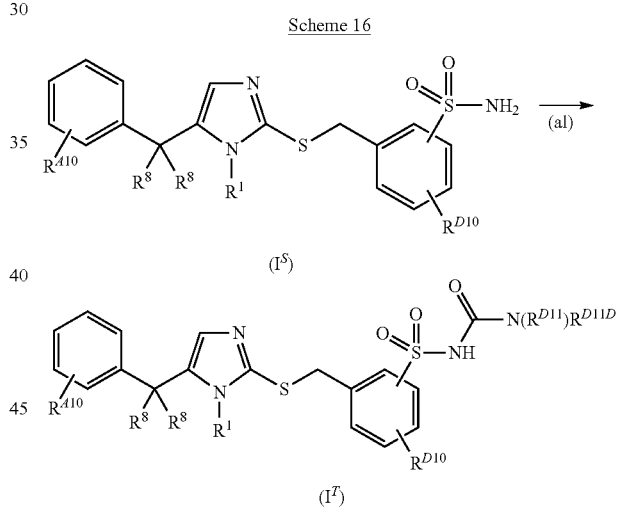

Step (al): Reaction of sulfonamide ($I^s$) with a suitable isocyanate and Lewis acid (e.g. aluminum trichloride) in a solvent such as toluene, preferably at 80° C. for over 12 hours, may yield compounds of formula ($I^T$).

Compounds of formula ($I^U$-$I^W$) may be prepared as depicted in Scheme 17

Scheme 17

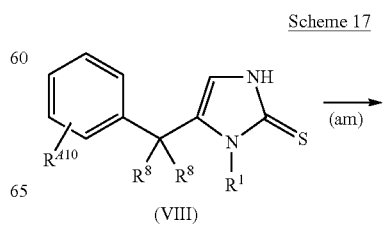

(VIII)

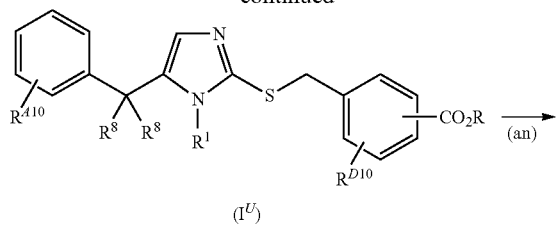

(I$^U$)

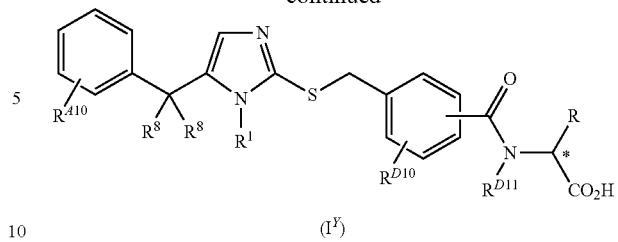

(I$^Y$)

Under conditions previously described in step (ao), acid (I$^V$) may be treated with a suitably protected amino ester (e.g. Alanine methyl ester) and HATU in DCM to afford compounds of formula (I$^Y$).

Step (ap): Hydrolysis of ester (I$^X$) may proceed under standard conditions, e.g. LiOH in a THF-water mixture, to afford compounds of formula (I$^Y$).

Compounds of formula (I$^Z$-I$^{AA}$) may be synthesized as shown in Scheme 19.

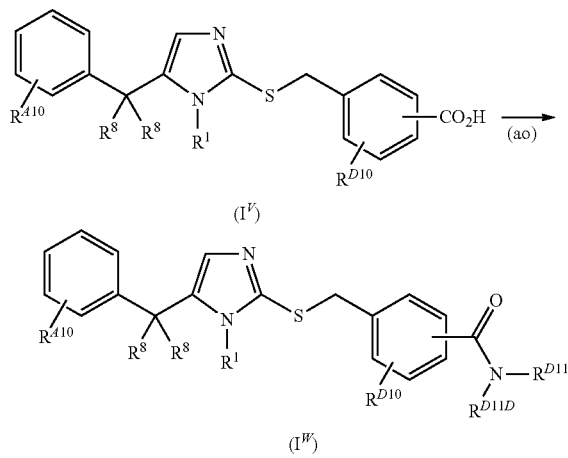

(I$^V$)

(I$^W$)

Step (am): Alkylation of imidazol-2-thione (VIII) with an electrophile R$^{D1}$CH$_2$Br, wherein R$^{D1}$ is a benzoate ester, in a suitable solvent (e.g. acetone) and with a base (e.g. potassium carbonate) may afford compounds of formula (I$^U$).

Step (an): Hydrolysis of ester (I$^U$) may proceed under standard conditions, e.g. NaOH in aqueous methanol, to afford compounds of formula (IV).

Step (ao): Conversion of acid (I$^V$) to compounds of formula (IW) may occur under standard peptide coupling conditions, e.g. upon addition of an amine HN(R$^{D11}$)R$^{D11D}$ and coupling agent HATU in a suitable solvent, such as DCM or DMF.

Compounds of formula (I$^X$-I$^Y$) may be prepared as depicted in scheme 18.

Scheme 18

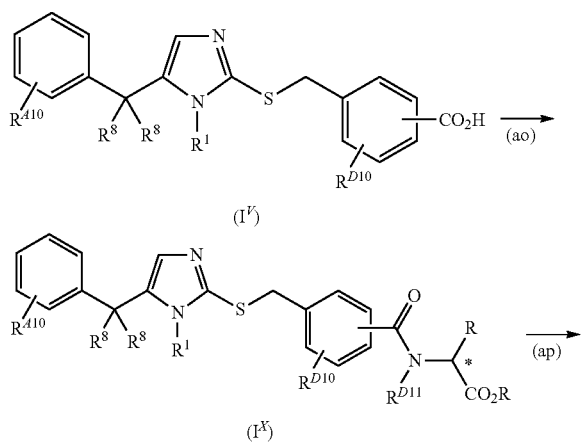

(I$^V$)

(I$^X$)

Scheme 19

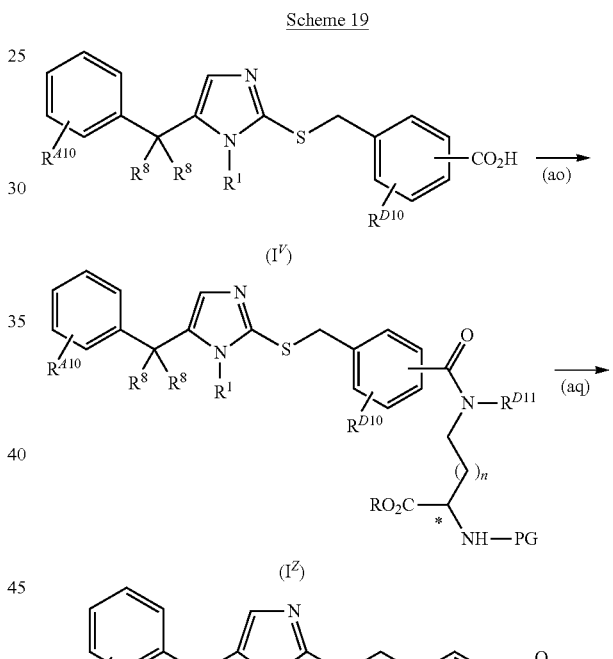

(I$^V$)

(I$^Z$)

(I$^{AA}$)

Under conditions previously described in step (ao), acid (I$^V$) may be treated with a suitably protected amino ester, such as one derived from Ornithine (wherein n=2), and HATU in DCM to afford compounds of formula (I$^Z$).

Step (aq): Hydrolysis of ester (I$^X$) and deprotection of the amine moiety may proceed under standard conditions, e.g. HCl in dioxane (wherein R=tert-butyl and PG=BOC), to afford compounds of formula (I$^{AA}$).

Compounds of formula (I$^{AB}$) may be synthesized as shown in Scheme 20.

Scheme 20

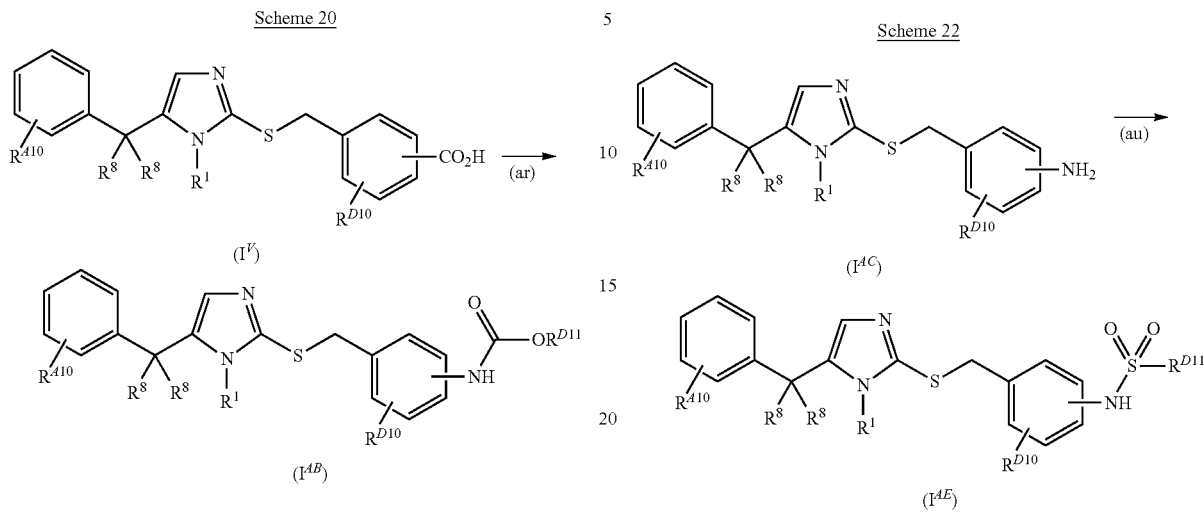

Step (ar): Under typical Curtius rearrangement conditions, acid (I$^V$) may react with diphenylphosphoryl azide, a suitable alcohol (e.g. tert-butanol), an organic base (e.g. Et$_3$N) and toluene at elevated temperature, preferably 80 to 100° C., to yield compounds of formula (I$^{AB}$).

Compounds of formula (I$^{AC}$-I$^{AD}$) may be synthesized as shown in Scheme 21.

Scheme 21

Step (as): Deprotection of carbamate (I$^{AB}$), may occur under standard conditions, such as with 1:1 TFA-DCM, to give compounds of formula (I$^{AC}$).

Step (at): Amine (I$^{AC}$) may react with acid chlorides in the presence of a base, such as Et$_3$N, to afford compounds of formula (I$^{AD}$).

Compounds of formula (I$^{AE}$-I$^{AF}$) may be synthesized as shown in Scheme 22.

Scheme 22

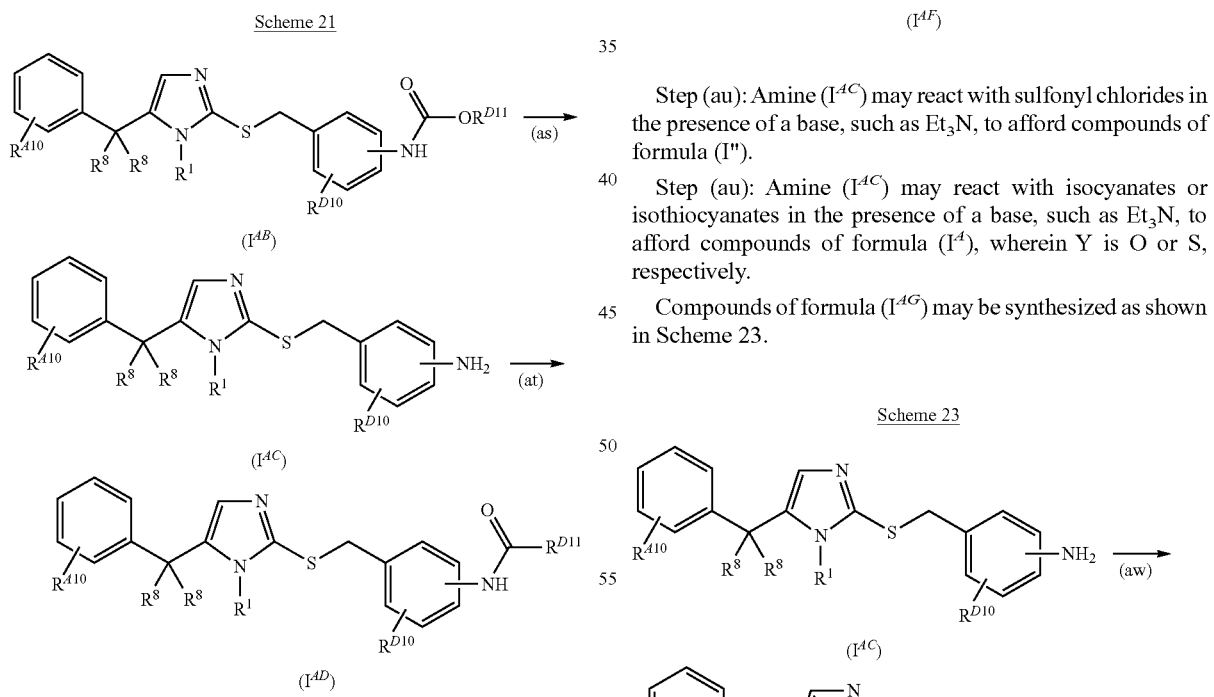

Step (au): Amine (I$^{AC}$) may react with sulfonyl chlorides in the presence of a base, such as Et$_3$N, to afford compounds of formula (I").

Step (au): Amine (I$^{AC}$) may react with isocyanates or isothiocyanates in the presence of a base, such as Et$_3$N, to afford compounds of formula (I$^A$), wherein Y is O or S, respectively.

Compounds of formula (I$^{AG}$) may be synthesized as shown in Scheme 23.

Scheme 23

-continued

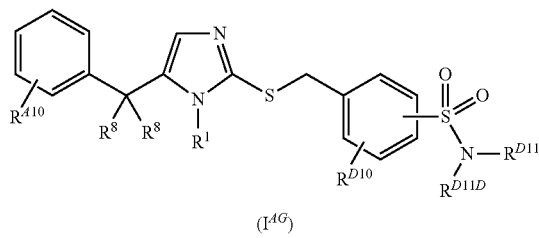

(I$^{AG}$)

Step (k): Thione (VIII) may undergo desulfurization under standard conditions, such as with H$_2$O$_2$ in a mixture of HOAc-DCM, to afford imidazole (X).

Step (l): Reaction of imidazole (X) with butyllithium in a suitable solvent (e.g. THF) at reduced temperature, preferably at –78° C. for 30-40 minutes, may yield the corresponding organolithium, which may react with a suitable electrophile (e.g. isocyanate or carbamoyl chloride) at the same temperature to afford a compound of formula (I$^D$).

Compounds of formula (I$^{AH}$) may be synthesized as shown in Scheme 24.

Scheme 24

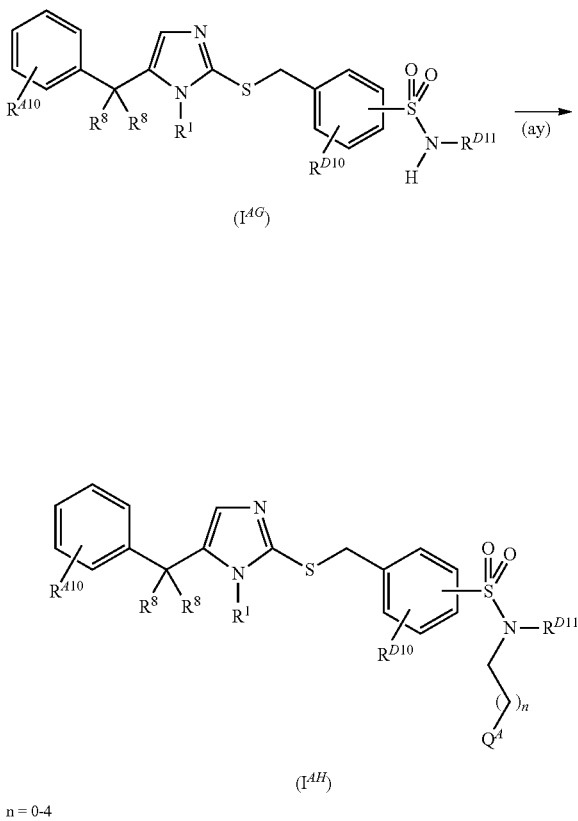

n = 0-4

Step (ay): Sulfonamide (I$^{AG}$), wherein one to two R$^D$1 are H, may react with electrophiles, such as an alkyl bromide functionalized with substituent Q, under suitable conditions, such as with K$_2$CO$_3$ in MeCN, to give compounds of formula (I$^{AH}$), wherein Q may be selected, for example, from a quaternary alkylammonium salt or heterocyclic salt.

Compounds of formula (I$^{AI}$) may be synthesized as shown in Scheme 28.

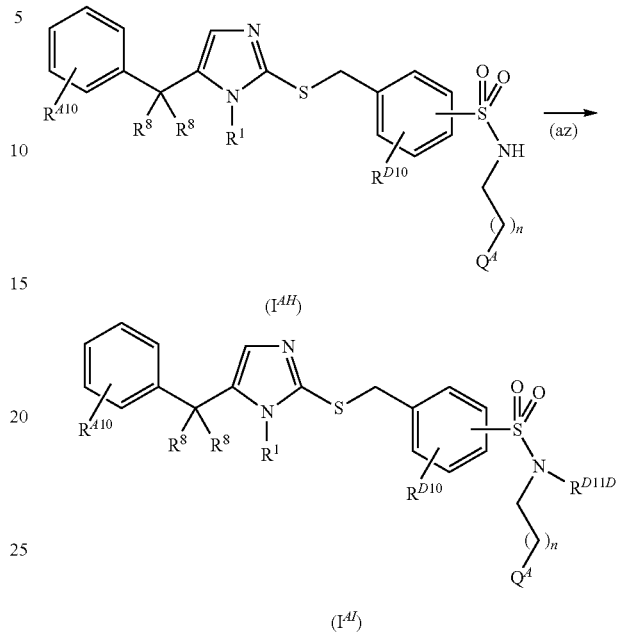

(n = 0-4)

Compounds of formula (I$^{AI}$) may be synthesized as shown in Scheme 25.

Scheme 25

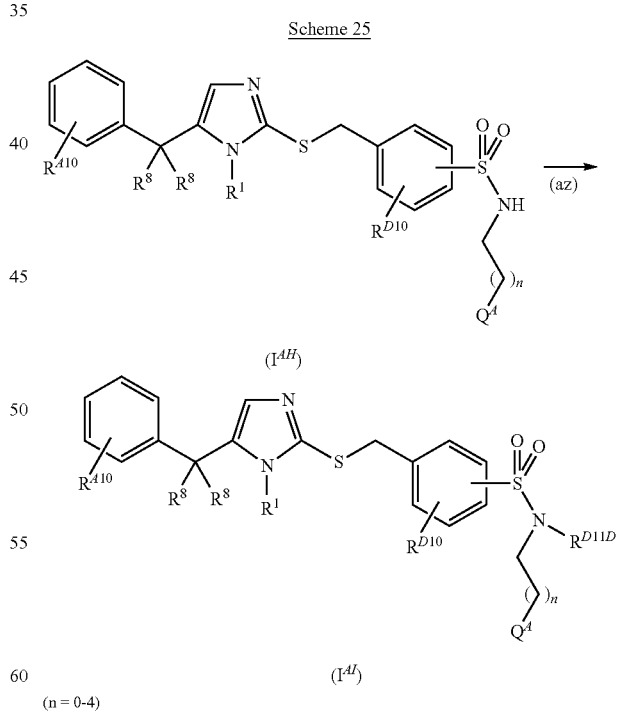

(n = 0-4)

Step (az): Sulfonamide (I$^{AH}$) may react with electrophiles, such as an alkyl bromide BrCH$_2$R$^{D12}$, under suitable conditions, such as with Cs$_2$CO$_3$ in DMF, to afford compounds of formula (I$^A$). R$^{D11D}$ stands for an H or an alkyl group.

Compounds of formula ($I^{AH}$-$I^{AJ}$) may be synthesized as shown in Scheme 26.

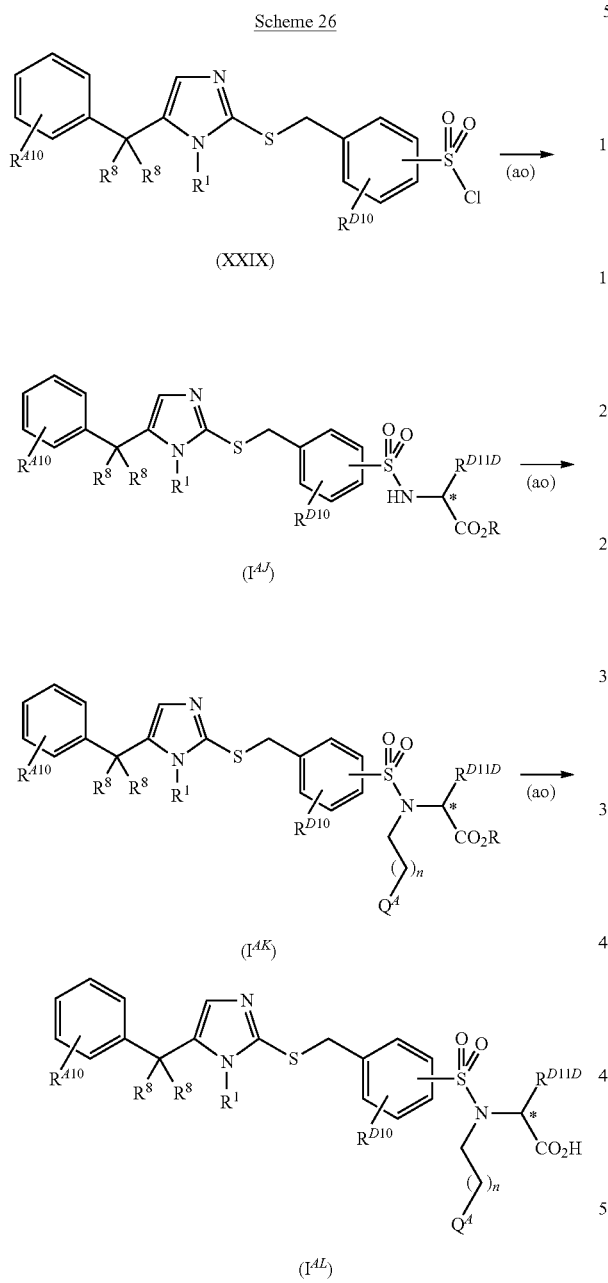

wherein R is alkyl and n is 0-4

Under conditions previously described in step (ax), sulfonyl chloride (XXIX) may react with an amino ester, such as alanine methyl ester, to yield compounds of formula ($I^{AJ}$).

Under conditions previously described in step (ay), sulfonamide ($I^{AJ}$) may be alkylated to give compounds of formula ($I^{AK}$).

Under conditions previously described in step (ap), ester ($I^{AK}$) may be hydrolyzed to afford compounds of formula ($I^{AL}$).

Compounds of formula ($I^{AM}$-$I^{AO}$) may be synthesized as shown in Scheme 27, wherein R stands for alkyl groups.

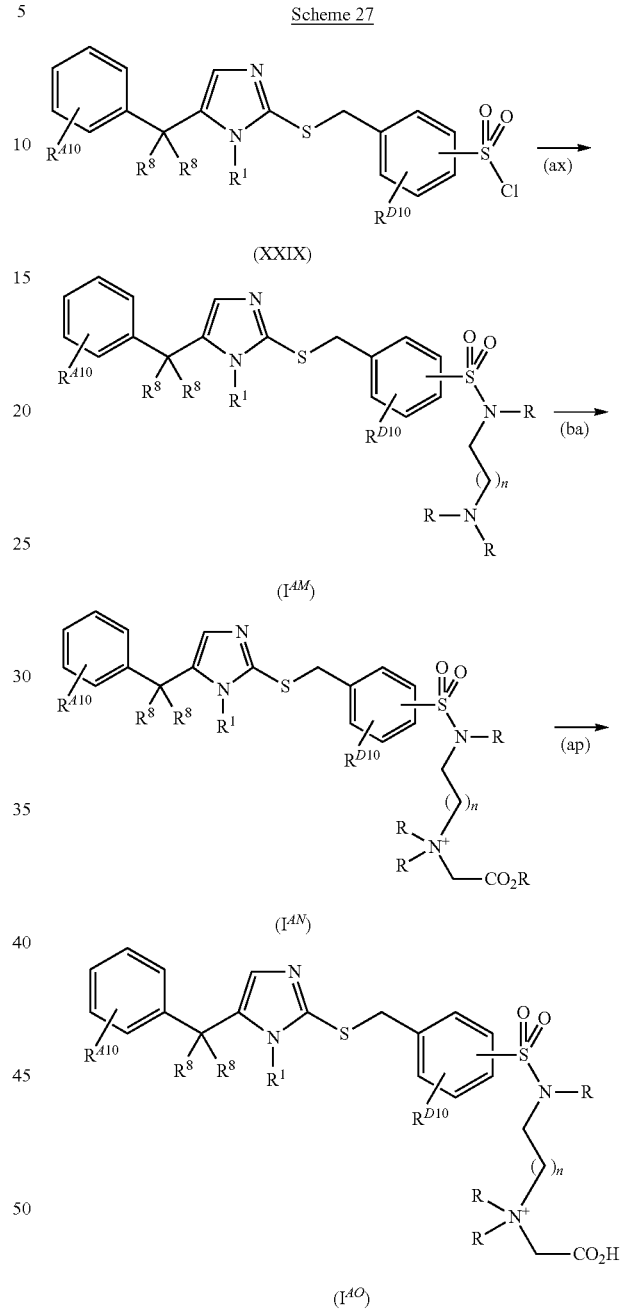

n is 0-4

Under conditions described in step (ax), sulfonyl chloride (XXIX) may react with a diamine, such as N,N,N'-trimethyl-1,3-propanediamine, to give compounds of formula ($I^{AM}$), wherein R is selected, for example, from $C_1$-$C_3$alkyl.

Step (ba): Sulfonamide ($I^{AM}$) may react with an alkyl bromoacetate under suitable conditions, such as in THF at 50° C., to yield compounds of formula ($I^{AN}$).

Under conditions described in step (ap), ester ($I^{AN}$) may be hydrolyzed to provide compounds of formula ($I^{AO}$).

Compounds of formula (I^{AQ}) may be prepared as depicted in Scheme 28.

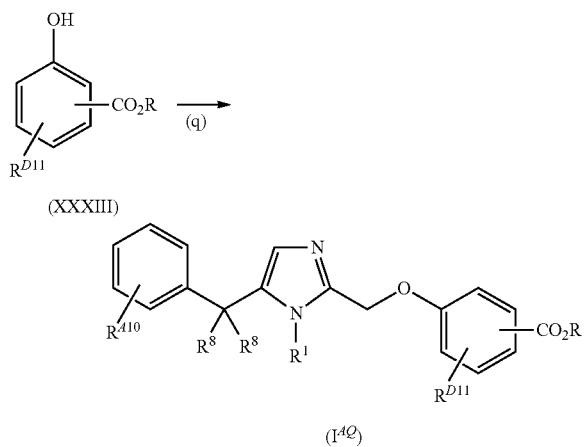

Under conditions previously described in step (q), phenol (XXXIII) may react with carbinol (XII) to afford compounds of formula (I^{AQ}).

Compounds of formula (I^{AR}) may be prepared as depicted in Scheme 29.

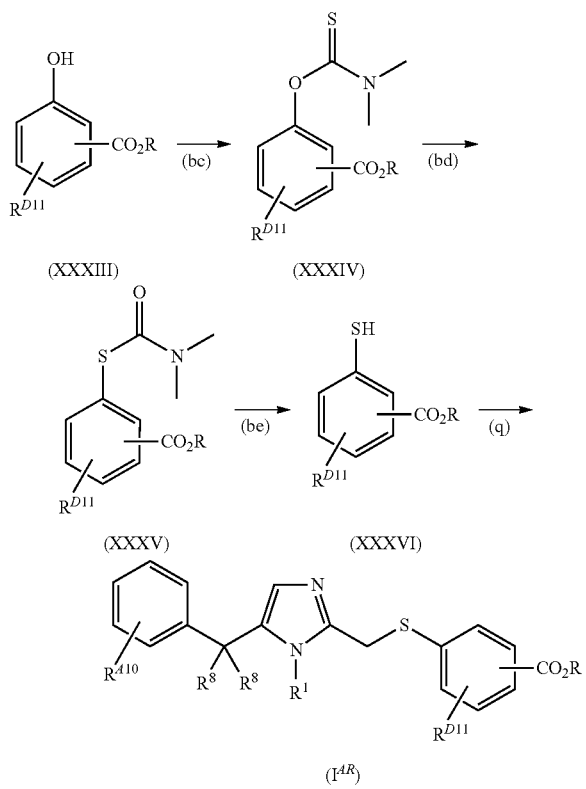

Step (bc): Phenol (XXXIII) may react under standard conditions, for example, with dimethylthiocarbamoyl chloride (1 eq) and DABCO (1.25 eq) in NMP at 50° C., to yield the respective O-aryl-thiocarbamate (XXXIV).

Step (bd): Upon heating, such as at 240° C. for 20 min in a microwave apparatus, thiocarbamate (XXXIV) may undergo a Newmann-Kwart rearrangement to give S-aryl-thiocarbamate (XXXV).

Step (be): Hydrolysis of thiocarbamate (XXXV), for example, with sodium hydroxide in methanol, may afford the corresponding thiophenol (XXXVI).

Under conditions previously described in step (q), thiophenol (XXXVI) may react with carbinol (XII) to afford compounds of formula (I^{AR}).

Compounds of formula (I^{AS}-I^{AT}) may be prepared as depicted in Scheme 30.

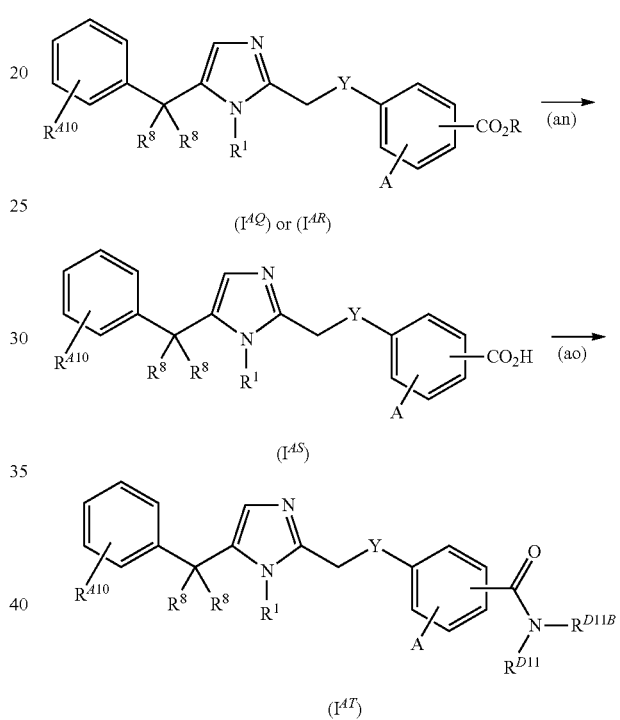

Under conditions previously described in step (an), ester (I^{AA} or I^{AR}) may be hydrolyzed to yield compounds of formula (I^{AS}), wherein Y is O or S, respectively.

Under conditions previously described in step (ao), acid (I^{AS}) may react with an amine to afford compounds of formula (I^{AT}), wherein Y is O or S.

Compounds of formula (I^{AU}-I^{AV}) may be prepared as depicted in Scheme 31.

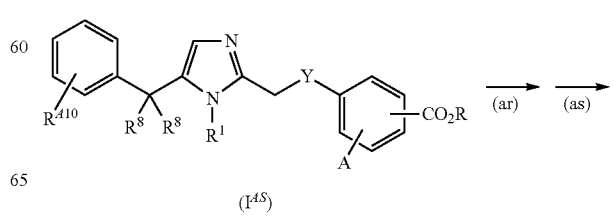

-continued

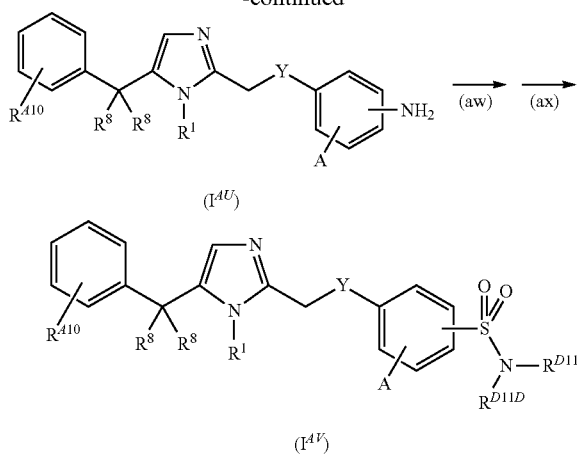

Under conditions previously described in steps (ar) to (as), acid ($I^{AS}$) may be converted to compounds of formula ($I^{AU}$), wherein Y is O or S.

Under conditions previously described in steps (aw) to (ax), amine ($I^{AU}$) may be converted to compounds of formula ($I^{AV}$), wherein Y is O or S.

Compounds of formula ($I^{AY}$-$I^{AZ}$) may be prepared as depicted in Scheme 32.

Scheme 32

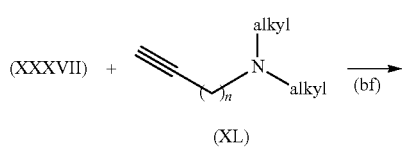

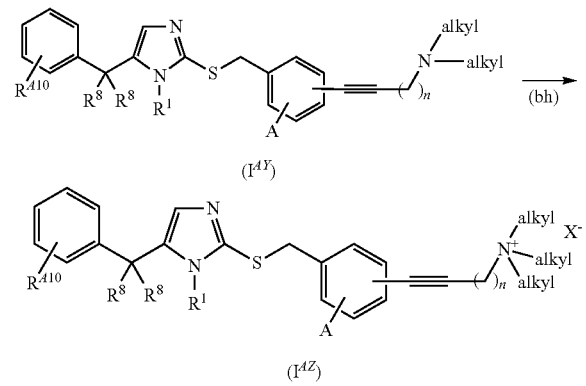

wherein X⁻ is a counter ion

Under conditions described for step (bf), aryl bromide (XXXVII) and an alkynyl-amine (XL) may react to give compounds of formula ($I^{AY}$).

Step (bh): Amine ($I^{AY}$) may react with an electrophile $R^{D11}X$, such as iodomethane or methyl tosylate, in a suitable solvent, such as MeCN, to afford compounds of formula ($I^{AZ}$), wherein X is iodide or tosylate, respectively.

Compounds of formula ($I^{BA}$-$I^{BB}$) may be prepared as depicted in Scheme 34.

Scheme 34

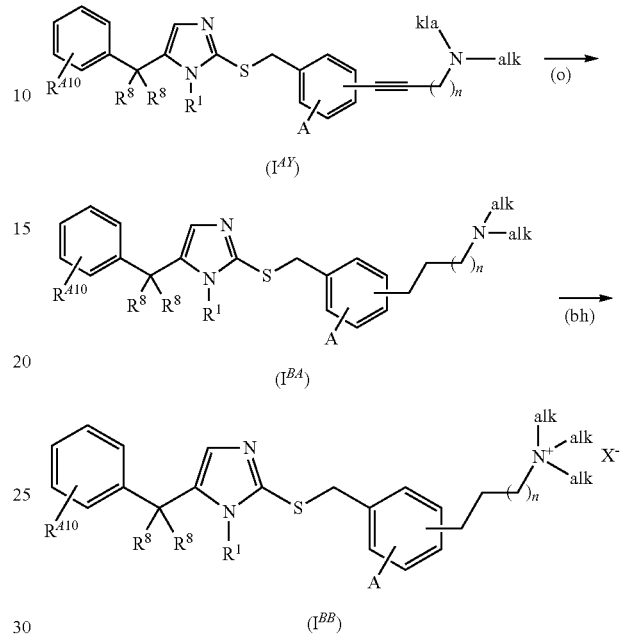

Under conditions previously described for step (o), alkyne ($I^{AY}$) may be hydrogenated to yield compounds of formula ($I^{BA}$).

Under conditions described for step (bh), amine ($I^{BA}$) may be converted to compounds of formula ($I_{BB}$).

Compounds of formula ($I^{BE}$-$I^{BF}$) may be prepared as depicted in Scheme 36.

Scheme 35

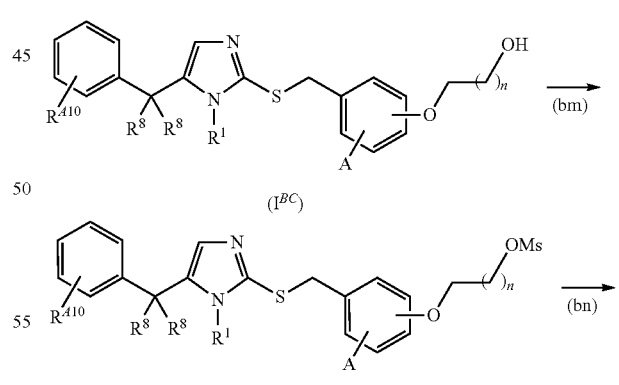

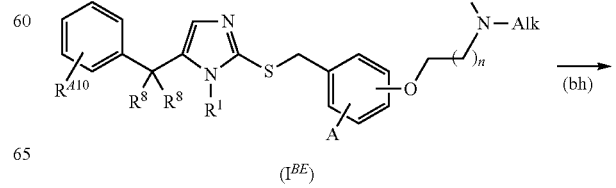

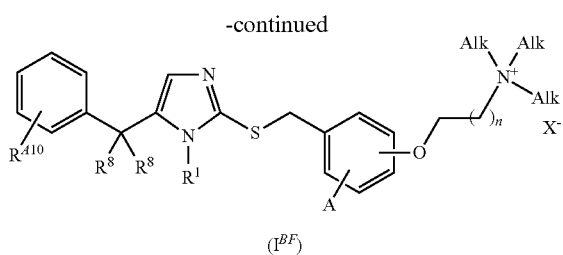

(I$^{BF}$)

Step (bm): Alcohol (I$^{BC}$) may be converted to its mesylate (XLV) under standard conditions, such as with methanesulfonyl chloride and Et$_3$N in DCM.

Step (bn): Treatment of mesylate (XLV) with an amine HN(alk)$_2$ at elevated temperature may provide compounds of formula (I$^{BE}$), wherein alk, for example, is C$_1$-C$_3$alkyl or two alk together form a C$_4$-C$_6$cycloalkylamine.

Under conditions described for step (bh), amine (I$^{BE}$) may be converted to compounds of formula (I$^{BF}$).

Compounds of formula (I$^{AH}$-I$^{AJ}$) may be synthesized as shown in Scheme 37.

Scheme 36

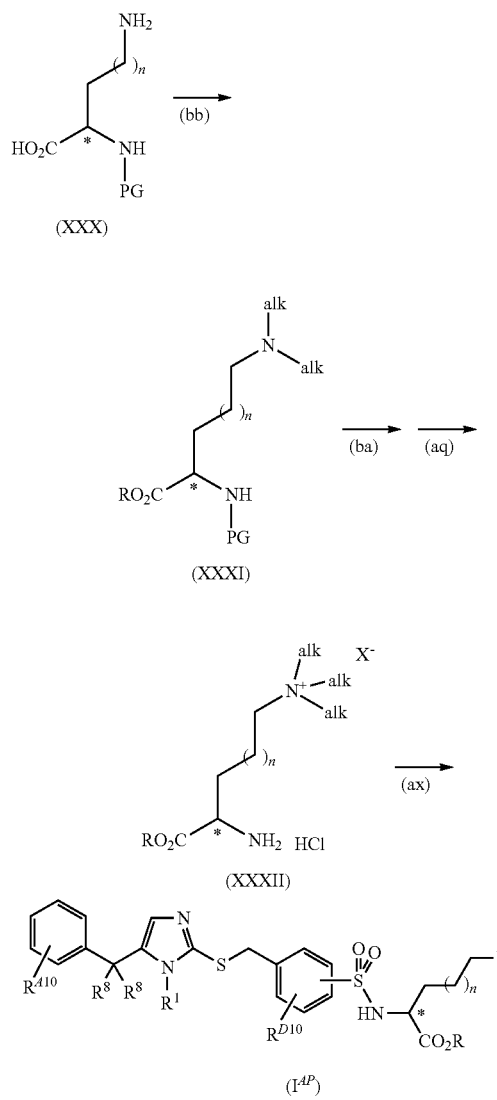

Step (bb): A suitably protected diamino acid, such as BOC-Lysine methyl ester (XXX), may undergo reductive amination under standard conditions, for example, with 37% formaldehyde in water and sodium triacetoxyborohydride, to yield the respective amine (XXXI).

Under conditions described for steps (ba) and (aq), amine (XXXI) may be alkylated, for example, with C$_1$-C$_3$alkyl bromide, and then may be deprotected to afford the corresponding diamine salt (XXXII).

Under conditions previously described for step (ax), diamine (XXXII) may react with sulfonyl chloride (XXIX) to give compounds of formula (I$^{AP}$).

EXAMPLES

Example 1

2-(3-chloro-4-((S-(2-(4-chloro-3-methoxyphenyl)propan-2-yl)-1-(4-fluorophenyl)-1H-imidazol-2-ylthio)methyl)-S-fluorobenzamido)-N,N,N-trimethylethanaminium chloride

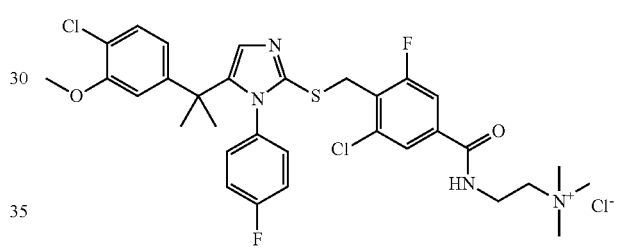

To a solution of 3-chloro-4-((5-(2-(4-chloro-3-methoxyphenyl)propan-2-yl)-1-(4-fluorophenyl)-1H-imidazol-2-ylthio)methyl)-5-fluorobenzoic acid (0.56 g, 1.0 mmol) in DCM (5 mL) was added oxalyl chloride (0.26 mL, 3.0 mmol). The reaction was stirred for 3 h at room temperature and concentrated. The resulting acid chloride was dissolved in DCM (5 mL) and then treated with (2-amino-ethyl)trimethylammonium chloride hydrochloride (0.25 g, 1.43 mmol) followed by DIPEA (0.50 mL, 2.9 mmol). The suspension was sonicated for 5 min and stirred at room temperature for 2 h. The reaction mixture was concentrated, dissolved in DMSO and purified by HPLC (MeCN/H$_2$O, 10-99%, 0.05% TFA modifier). The product fractions were concentrated in vacuo and then concentrated from a solution in 2N HCl (2×5 mL) to afford the title compound (432 mg). $^1$H-NMR (DMSO-d$_6$, 400 MHz) δ 9.82 (s, 1H), 7.96 (s, 1H), 7.89-7.84 (m, 2H), 7.27 (d, J=8.2 Hz, 1H), 7.0-6.96 (m, 2H), 6.49-6.41 (m, 4H), 4.26 (s, 2H), 3.75-3.71 (m, 2H), 3.67 (s, 3H), 3.61-3.58 (m, 2H), 3.18 (s, 9H), 1.49 (s, 6H); MS (EI) m/z 647 [M]$^+$.

The following compounds [1(a)-1(e)] were made by using procedures described in the above example by making any necessary substitutions of known materials that one skilled in the art would ordinarily understand how to do. The following compounds are represented as cations, wherein chloride was used as the counter ion as in the above Example. The counter ion can also be any pharmaceutically acceptable counter ion known to one skilled in the art. It is also understood that the source of the counter ions can be from either intermolecular sources, or, when possible, intramolecular sources.

Compound 1(a)

2-(3-Chloro-4-((5-(2-(3-chloro-4-sulfamoylphenyl)propan-2-yl)-1-(4-fluoro-3-methoxyphenyl)-1H-imidazol-2-ylthio)methyl)-5-fluorobenzamido)-N,N,N-trimethylethanaminium chloride MS (EI) m/z 726 [M]$^+$.

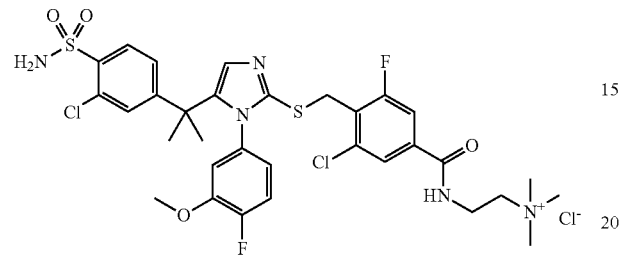

Compound 1(b)

2-(4-((5-(2-(3-aminobenzo[d]isoxazol-5-yl)propan-2-yl)-1-(4-fluoro-3-methoxyphenyl)-1H-imidazol-2-ylthio)methyl)-3-chloro-5-fluorobenzamido)-N,N,N-trimethylethanaminium chloride MS (EI) m/z 669 [M]$^+$.

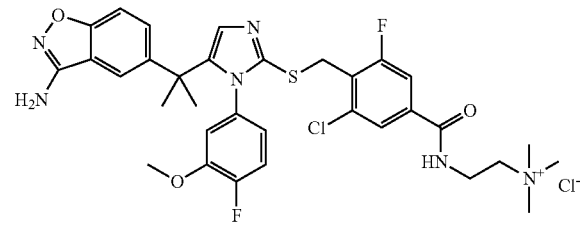 [SMILES: COc1cc(-n2c(C(C)(C)c3ccc4onc(N)c4c3)cnc2SCc2c(F)cc(C(=O)NCC[N+](C)(C)C)cc2Cl)ccc1F ; [Cl-]]

Compound 1(c)

2-(4-((5-(2-(3-aminobenzo[d]isoxazol-1-yl)propan-2-yl)-1-(4-fluorophenyl)-1H-imidazol-2-ylthio)methyl)-3-chloro-5-fluorobenzamido)-N,N,N-trimethylethanaminium chloride MS (EI) m/z 639 [M]$^+$.

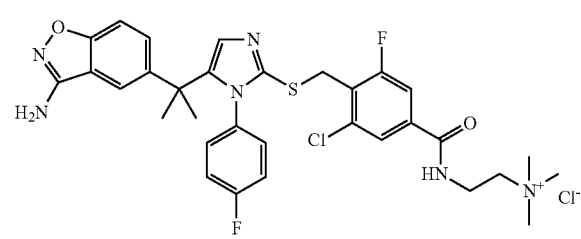 [SMILES: CC(C)(c1ccc2onc(N)c2c1)c1cnc(SCc2c(F)cc(C(=O)NCC[N+](C)(C)C)cc2Cl)n1-c1ccc(F)cc1 ; [Cl-]]

Compound 1(d)

2-(3-chloro-5-fluoro-4-((5-(2-(4-fluoro-3-methoxyphenyl)propan-2-yl)-1-(4-fluorophenyl)-1H-imidazol-2-ylthio)methyl)benzamido)-N,N,N-trimethylethanaminium bromide MS (EI) m/z 726 [M]$^+$.

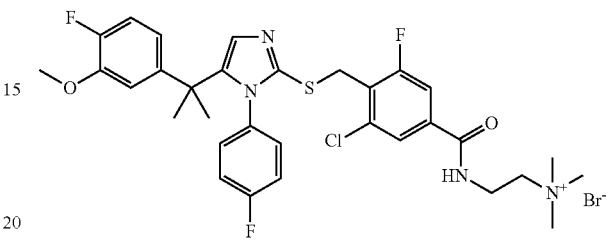

Compound 1(e)

2-(3-Chloro-4-((5-(2-(4-chloro-3-methoxyphenyl)propan-2-yl)-1-(4-fluorophenyl)-1H-imidazol-2-yl)methoxy)-5-fluorobenzamido)-N,N,N-trimethylethanaminium 2,2,2-trifluoroacetate

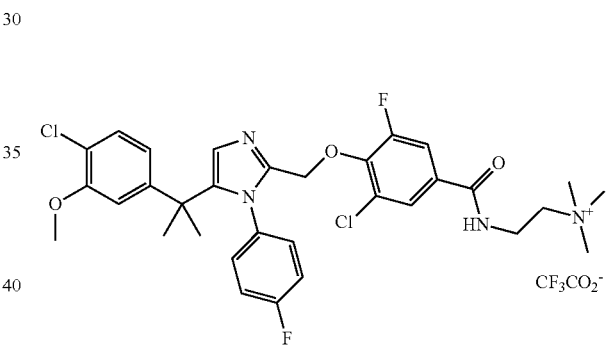

$^1$H NMR (400 MHz, MeOD) δ 7.87 (s, 1H), 7.79 (s, 1H), 7.63 (dd, J=11.1, 2.1 Hz, 1H), 7.25-7.20 (m, 1H), 7.06-6.99 (m, 2H), 6.90-6.86 (m, 2H), 6.61-6.59 (m, 2H), 5.04 (s, 2H), 3.84 (t, J=6.6 Hz, 2H), 3.74 (s, 3H), 3.57 (t, J=6.7 Hz, 2H), 3.23 (s, 9H), 1.66 (s, 6H); MS (ESI) m/z 631.5 [M]$^+$.

Compound 1(f)

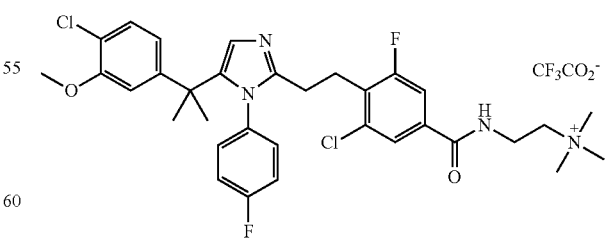

$^1$H NMR (400 MHz, MeOD) δ 8.82 (d, J=5.6 Hz, 1H), 7.77 (s, 1H), 7.72 (s, 1H), 7.54 (dd, J=9.9, 1.5 Hz, 1H), 7.23 (d, J=8.1 Hz, 1H), 7.01 (t, J=8.6 Hz, 2H), 6.73-6.39 (m, 4H), 3.88 (t, J=6.1 Hz, 2H), 3.76 (s, 3H), 3.58 (dd, J=27.1, 20.4 Hz, 2H), 3.26 (s, 9H), 3.19-3.03 (m, 2H), 3.03-2.77 (m, 2H), 1.62 (s, 6H); MS (EI) m/z 629.5 [M]+.

Example 2

1-(2-(3-chloro-4-((5-(2-(4-chloro-3-methoxyphenyl)propan-2-yl)-1-(4-fluorophenyl)-1H-imidazol-2-ylthio)methyl)-5-fluorobenzamido)ethyl)-4-aza-1-azoniabicyclo-[2.2.2]octane chloride hydrochloride

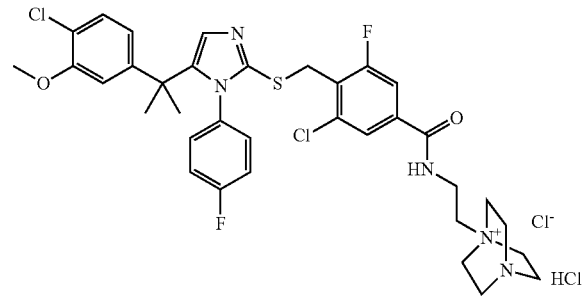 [SMILES: COc1cc(C(C)(C)c2cnc(SCc3c(F)cc(C(=O)NCC[N+]45CCN(CC4)CC5)cc3Cl)n2-c2ccc(F)cc2)ccc1Cl ; [Cl-] ; Cl]

To a solution of 1,4-diazabicyclo[2.2.2]octane (0.40 g, 3.57 mmol) in ether (5 mL) was added tert-butyl 2-bromoethylcarbamate (0.80 g, 3.57 mmol). The reaction was stirred overnight and the solvent was removed in vacuo. EtOAc (10 mL) was added and the reaction was stirred vigorously overnight. The precipitates were collected by filtration to give 1-(2-(tert-butoxycarbonylamino)ethyl)-4-aza-1-azonia-bicyclo[2.2.2]octane bromide (0.84 g) as a white solid. The solids were dissolved in MeOH (3 mL) and 4 M HCl in dioxane (3.5 mL, 14 mmol). The reaction was stirred at room temperature until it was determined to be complete by LCMS. The mixture was filtered to afford 1-(2-aminoethyl)-4-aza-1-azoniabicyclo[2.2.2]octane chloride hydrochloride (0.74 g) as a white solid. $^1$H-NMR (D$_2$O, 400 MHz) δ 3.98-3.72 (m, 8H), 3.79-3.69 (m, 6H), 3.66-3.61 (m, 2H).

To a suspension of 3-chloro-4-((5-(2-(4-chloro-3-methoxyphenyl)propan-2-yl)-1-(4-fluorophenyl)-1H-imidazol-2-ylthio)methyl)-5-fluorobenzoic acid (0.11 g, 0.19 mmol), 1-(2-aminoethyl)-4-aza-1-azoniabicyclo[2.2.2]octane chloride hydrochloride (0.066 g, 2.5 mmol), and HATU (0.088 g, 0.23 mmol) in DMF (0.7 mL) was added DIPEA (0.2 mL, 1.16 mmol). The reaction was stirred for 2 h and purified by HPLC (MeCN/H$_2$O, 10-99%, 0.05% TFA modifier). The product fractions were concentrated and then dissolved in THF (2 mL) and 2N solution of HCl in ether (2 mL). The mixture was filtered to afford the title compound (59 mg) as a white solid. $^1$H-NMR (DMSO-d$_6$, 400 MHz) δ 9.67 (s, 1H), 7.84 (s, 1H), 7.84-7.76 (m, 2H), 7.27 (d, J=8.2 Hz, 1H), 7.01-6.97 (m, 2H), 6.50-6.43 (m, 4H), 4.22 (s, 2H), 3.86-3.71 (m, 10H), 3.67 (s, 3H), 3.53-3.49 (m, 6H), 1.49 (s, 6H); MS (ES): 700 [M]+.

The following compounds [2(a)-2(b)] were made by using procedures described in the above example by making any necessary substitutions of known materials that one skilled in the art would ordinarily understand how to do. The following compounds are represented as cations, wherein chloride was used as the counter ion as in the above Example. The counter ion can also be any pharmaceutically acceptable counter ion known to one skilled in the art. It is also understood that the source of the counter ions can be from either intermolecular sources, or, when possible, intramolecular sources.

| Compound 2(a) | 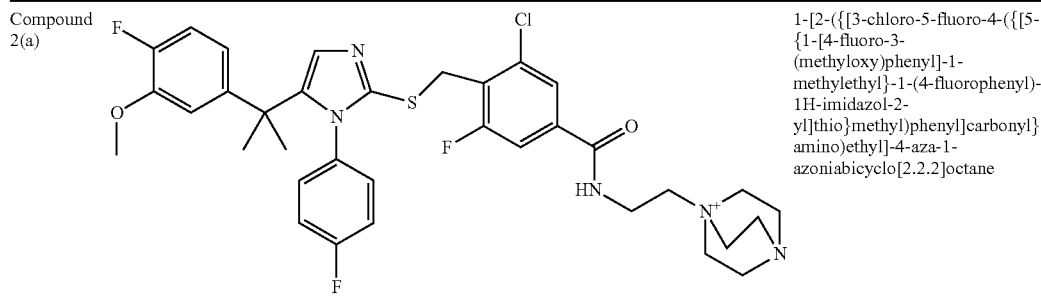 | 1-[2-({[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]carbonyl}amino)ethyl]-4-aza-1-azoniabicyclo[2.2.2]octane |
|---|---|---|
| Compound 2(b) | 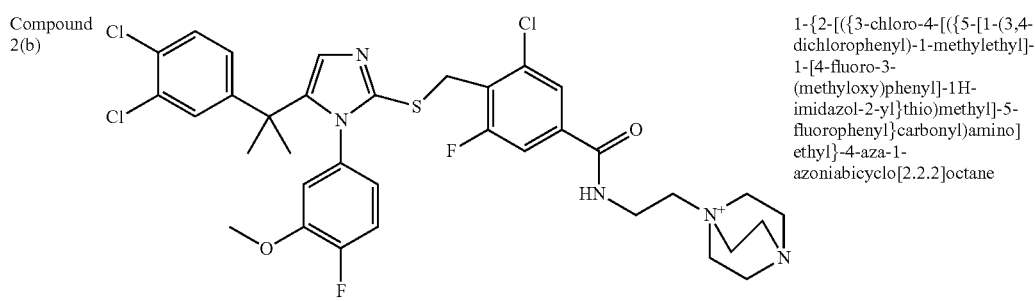 | 1-{2-[({3-chloro-4-[({5-[1-(3,4-dichlorophenyl)-1-methylethyl]-1-[4-fluoro-3-(methyloxy)phenyl]-1H-imidazol-2-yl}thio)methyl]-5-fluorophenyl}carbonyl)amino]ethyl}-4-aza-1-azoniabicyclo[2.2.2]octane |

Compound 2(c)

4-(3-Chloro-4-((5-(2-(4-chloro-3-methoxyphenyl)propan-2-yl)-1-(4-fluorophenyl)-1H-imidazol-2-ylthio)methyl)-5-fluorobenzamido)-1,1-dimethylpiperidinium 2,2,2-trifluoroacetate

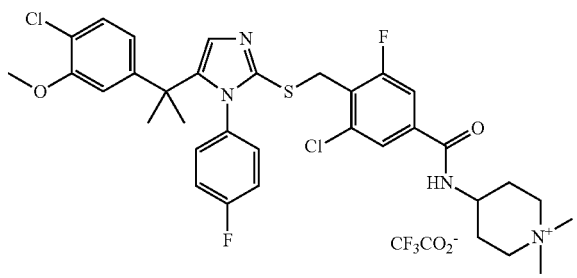

$^{1}$H-NMR (DMSO-d$_{6}$, 400 MHz) δ 8.63-8.53 (m, 1H), 7.77 (s, 1H), 7.64-7.60 (m, 1H), 7.52-7.35 (m, 1H), 7.22 (d, J=7.2Hz, 1H), 6.96 (m, 2H), 6.52-6.47 (m, 4H), 4.13-4.05 (m, 4H), 3.67 (m, 3H), 3.52-3.45 (m, 4H), 3.12-3.09 (m, 2H), 2.08-1.92 (m, 3H) 1.78 (s, 6H); MS (EI) m/z 673 [M]$^{+}$.

Compound 2(d)

(S)-3-(3-chloro-4-((5-(2-(4-chloro-3-methoxyphenyl)propan-2-yl)-1-(4-fluorophenyl)-1H-imidazol-2-ylthio)methyl)-5-fluorobenzamido)-1,1-dimethylpiperidinium 2,2,2-trifluoroacetate

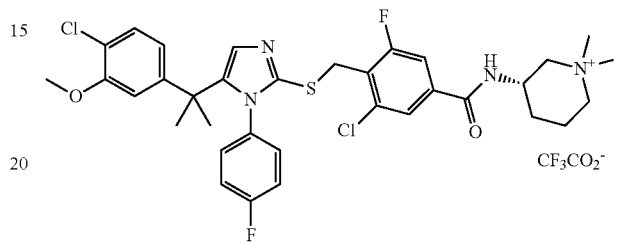

$^{1}$H NMR (400 MHz, DMSO) δ 8.72 (d, J=7.0 Hz, 1H), 7.79 (s, 1H), 7.63 (dd, J=10.0, 1.4 Hz, 1H), 7.45 (s, 1H), 7.23 (d, J=8.3 Hz, 1H), 7.08-6.90 (m, 2H), 6.64-6.43 (m, 4H), 5.77 (s, 1H), 4.54-4.30 (m, 1H), 4.13 (s, 2H), 3.69 (s, 3H), 3.66-3.57 (m, 1H), 3.54-3.41 (m, 1H), 3.39-3.24 (m, 1H), 3.19 (s, 6H), 3.03 (t, J=11.8 Hz, 1H), 2.07-1.88 (m, 2H), 1.64-1.52 (m, 1H), 1.49 (s, 6H). MS (EI) m/z 673.3 (M ).

Compound 2(e)

(3S)-3-(3-chloro-4-((5-(2-(4-chloro-3-methoxyphenyl)propan-2-yl)-1-(4-fluorophenyl)-1H-imidazol-2-ylthio)methy)-5-fluorobenzamido)-1-(4-fluorobenzyl)-1-methylpyrrolidinium 2,2,2-trifluoroacetate

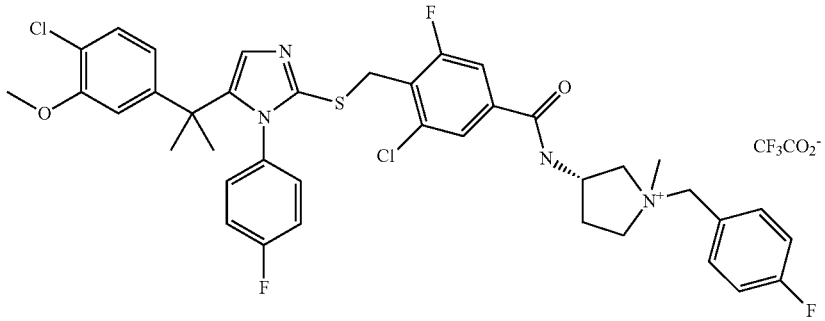 [SMILES: COc1cc(C(C)(C)c2cnc(SCc3c(F)cc(C(=O)N[C@H]4CC[N+](C)(Cc5ccc(F)cc5)C4)cc3Cl)n2-c2ccc(F)cc2)ccc1Cl ; "CF3CO2-"]

¹H NMR (400 MHz, DMSO) δ 8.81 (d, J=6.2 Hz, 1H), 7.66 (s, 1H), 7.62-7.44 (m, 3H), 7.37-7.20 (m, 3H), 7.21-7.06 (m, 1H), 6.96-6.79 (m, 2H), 6.58-6.25 (m, 4H), 4.67 (s, 1H), 4.60-4.47 (m, 2H), 4.01 (s, 2H), 3.84-3.62 (m, 2H), 3.62-3.55 (m, 3H), 3.55-3.38 (m, 2H), 3.00-2.84 (m, 3H), 2.69-2.46 (m, 1H), 2.19 (s, 1H), 1.49-1.29 (m, 6H); MS (EI) m/z 753.3 (M ).

The following compounds [2(f)-2(r)] were made by using procedures described in the above example by making any necessary substitutions of known materials that one skilled in the art would ordinarily understand how to do. The following compounds are represented as cations, wherein 2,2,2-trifluoroacetate was used as the counter ion as in the above Example. The counter ion can also be any pharmaceutically acceptable counter ion known to one skilled in the art. It is also understood that the source of the counter ions can be from either intermolecular sources, or, when possible, intramolecular sources.

Compound 2(f)

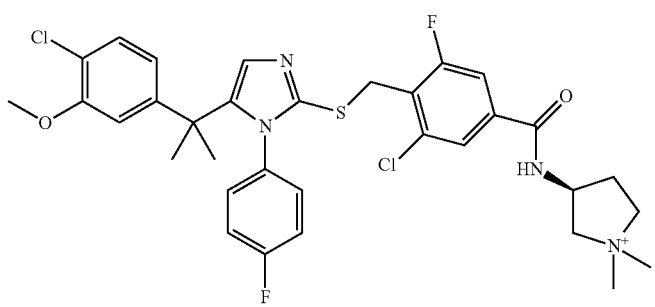

(3S)-3-({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]carbonyl}amino)-1,1-dimethylpyrrolidinium Compound 2(g)

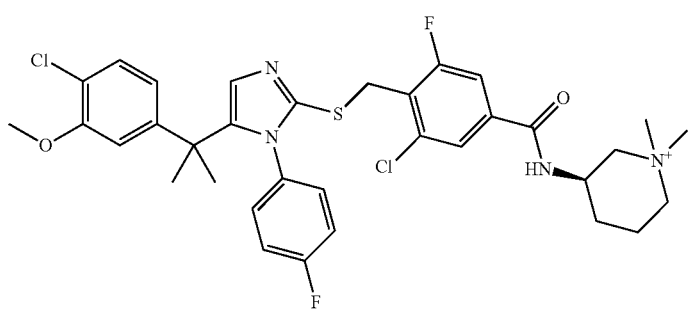

(3R)-3-({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]carbonyl}amino)-1,1-dimethylpiperidinium Compound 2(h)

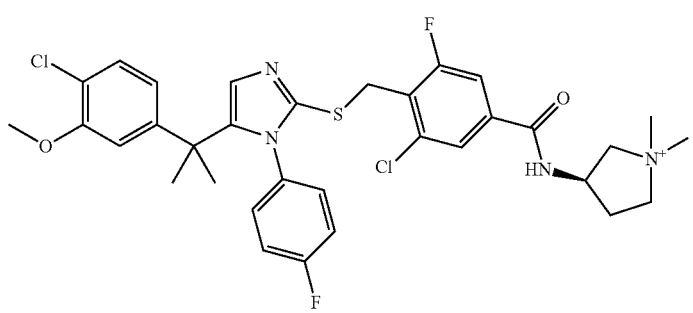

(3R)-3-({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]carbonyl}amino)-1,1-dimethylpyrrolidinium Compound 2(i)

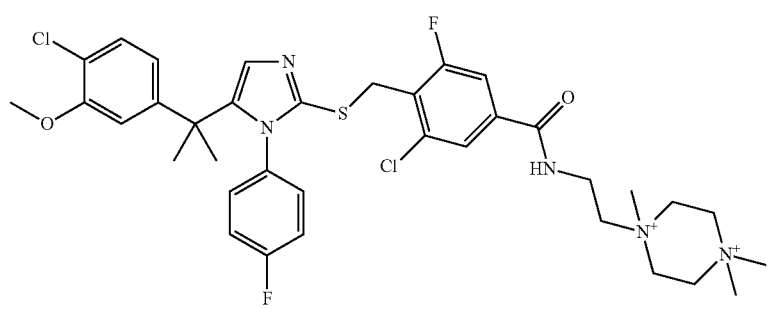

1-[2-({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]carbonyl}amino)ethyl]-1,4,4-trimethylpiperazinediium -continued

| | | |
|---|---|---|
| Compound 2(j) | 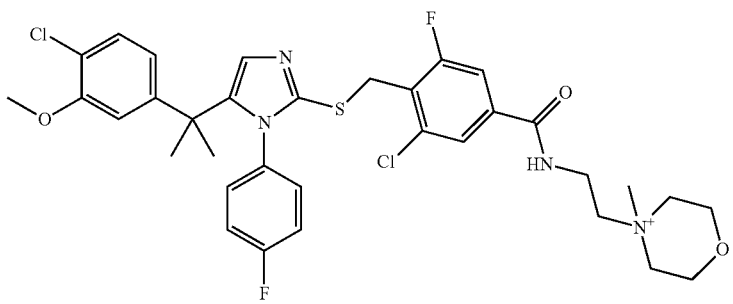 [SMILES: COc1cc(C(C)(C)c2cnc(SCc3c(F)cc(C(=O)NCC[N+]4(C)CCOCC4)cc3Cl)n2-c2ccc(F)cc2)ccc1Cl] | 4-[2-({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]carbonyl}amino)ethyl]-4-methylmorpholin-4-ium |
| Compound 2(k) | 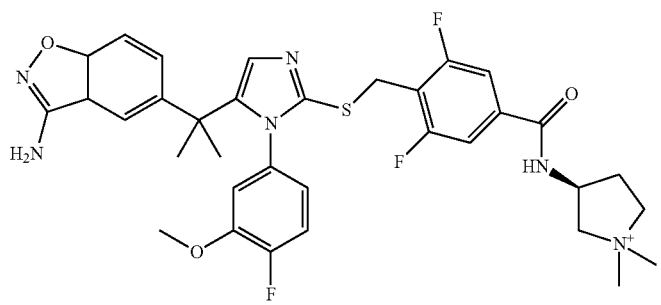 [SMILES: COc1cc(-n2c(C(C)(C)C3=CC4C(N)=NOC4C=C3)cnc2SCc2c(F)cc(C(=O)N[C@H]3CC[N+](C)(C)C3)cc2F)ccc1F] | (3S)-3-[({4-[({5-[1-(3-amino-1,2-benzisoxazol-5-yl)-1-methylethyl]-1-[4-fluoro-3-(methyloxy)phenyl]-1H-imidazol-2-yl}thio)methyl]-3,5-difluorophenyl}carbonyl)amino]-1,1-dimethylpyrrolidinium |
| Compound 2(l) | 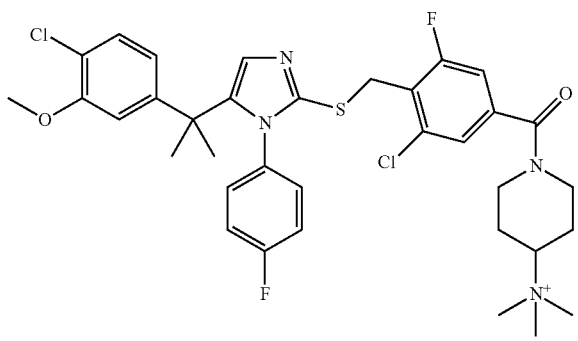 | 1-{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]carbonyl}-N,N,N-trimethylpiperidin-4-aminium |
| Compound 2(m) | 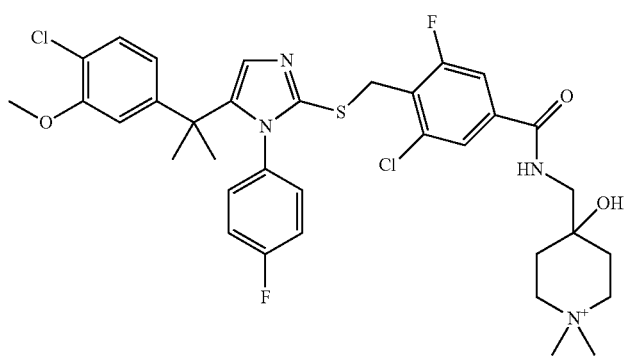 [SMILES: COc1cc(C(C)(C)c2cnc(SCc3c(F)cc(C(=O)NCC4(O)CC[N+](C)(C)CC4)cc3Cl)n2-c2ccc(F)cc2)ccc1Cl] | 4-[({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]carbonyl}amino)methyl]-4-hydroxy-1,1-dimethylpiperidinium |
| Compound 2(n) | 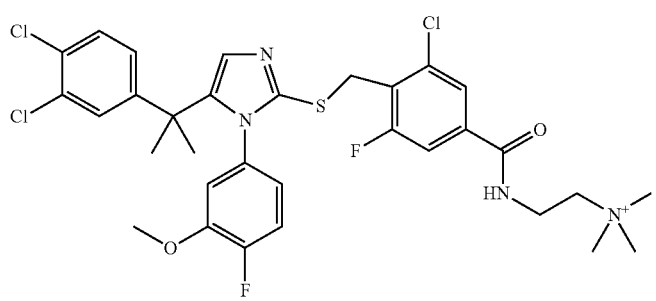 [SMILES: COc1cc(-n2c(C(C)(C)c3ccc(Cl)c(Cl)c3)cnc2SCc2c(F)cc(C(=O)NCC[N+](C)(C)C)cc2Cl)ccc1F] | 2-[({3-chloro-4-[({5-[1-(3,4-dichlorophenyl)-1-methylethyl]-1-[4-fluoro-3-(methyloxy)phenyl]-1H-imidazol-2-yl}thio)methyl]-5-fluorophenyl}carbonyl)amino]-N,N,N-trimethylethanaminium |

| | | |
|---|---|---|
| Compound 2(o) | 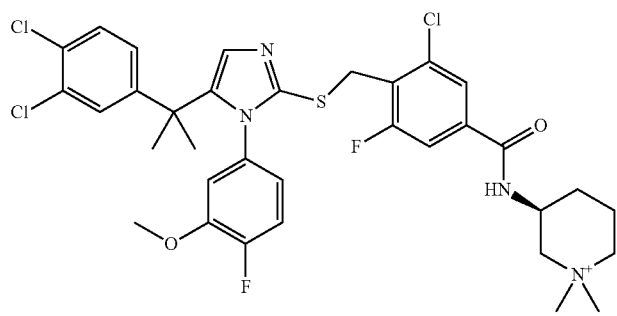 [SMILES: COc1cc(-n2c(C(C)(C)c3ccc(Cl)c(Cl)c3)cnc2SCc2c(F)cc(C(=O)N[C@H]3CCC[N+](C)(C)C3)cc2Cl)ccc1F] | (3S)-3-[({3-chloro-4-[({5-[1-(3,4-dichlorophenyl)-1-methylethyl]-1-[4-fluoro-3-(methyloxy)phenyl]-1H-imidazol-2-yl}thio)methyl]-5-fluorophenyl}carbonyl)amino]-1,1-dimethylpiperidinium |
| Compound 2(p) | 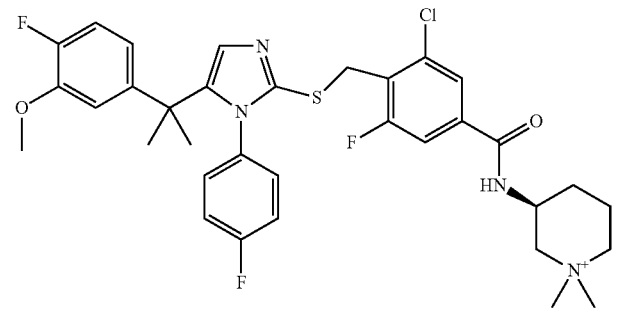 [SMILES: COc1cc(C(C)(C)c2cnc(SCc3c(F)cc(C(=O)N[C@H]4CCC[N+](C)(C)C4)cc3Cl)n2-c2ccc(F)cc2)ccc1F] | (3S)-3-({[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]carbonyl}amino)-1,1-dimethylpiperidinium |
| Compound 2(q) | 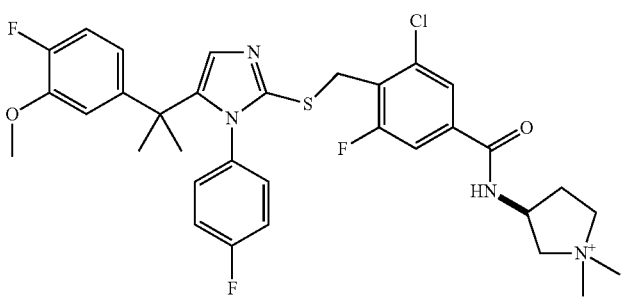 | (3S)-3-({[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]carbonyl}amino)-1,1-dimethylpyrrolidinium |
| Compound 2(r) | 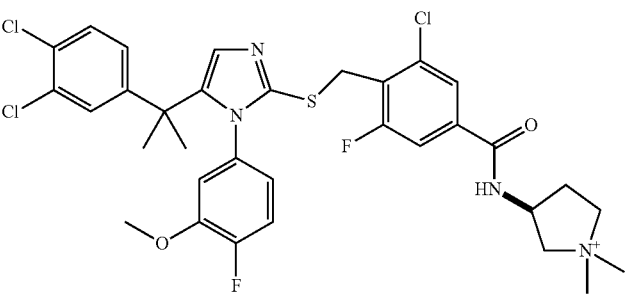 | (3S)-3-[({3-chloro-4-[({5-[1-(3,4-dichlorophenyl)-1-methylethyl]-1-[4-fluoro-3-(methyloxy)phenyl]-1H-imidazol-2-yl}thio)methyl]-5-fluorophenyl}carbonyl)amino]-1,1-dimethylpyrrolidinium |

Example 3

1-(Carboxymethyl)-4-(3-chloro-4-((5-(2-(4-chloro-3-methoxyphenyl)propan-2-yl)-1-(4-fluorophenyl)-1H-imidazol-2-ylthio)methyl)-5-fluorobenzamido)-1-methyl-piperidinium 2,2,2-trifluoroacetate

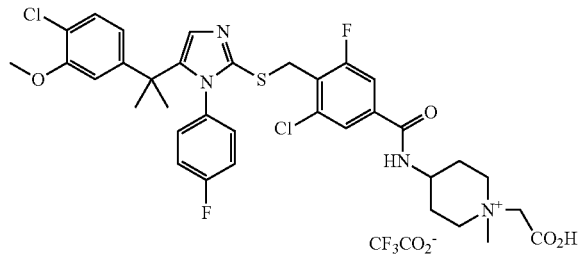 [SMILES: COc1cc(C(C)(C)c2cnc(SCc3c(F)cc(C(=O)NC4CC[N+](C)(CC(=O)O)CC4)cc3Cl)n2-c2ccc(F)cc2)ccc1Cl ; "CF3CO2-"]

$^1$H-NMR (DMSO-d$_6$, 400 MHz) δ 8.70-8.50 (m, 1H), 7.79-7.78 (m, 1H), 7.65-7.62 (m, 1H), 7.51-7.38 (m, 1H), 7.22 (d, J=8.4 Hz, 1H), 6.99-6.95 (m, 2H), 6.52-6.47 (m, 4H), 4.39 (s, 2H), 4.14-4.03 (m, 3H), 3.88-3.83 (m, 1H), 3.78-3.72 (m, 1H), 3.67 (m, 3H), 3.65-3.54 (m, 2H), 3.28-3.26 (m, 3H), 2.11-2.02 (m, 4H), 1.48 (m, 6H); MS (ES): 717 [M]$^+$.

Example 4

3-((2-(3-Chloro-4-((5-(2-(4-chloro-3-methoxyphenyl)propan-2-yl)-1-(4-fluorophenyl)-1H-imidazol-2-ylthio)methyl)-5-fluorobenzamido)ethyl)dimethylammonio)-propane-1-sulfonate

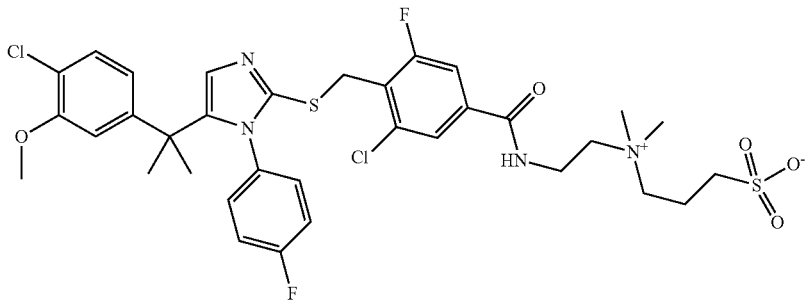 [SMILES: COc1cc(C(C)(C)c2cnc(SCc3c(F)cc(C(=O)NCC[N+](C)(C)CCCS(=O)(=O)[O-])cc3Cl)n2-c2ccc(F)cc2)ccc1Cl]

A solution of tert-butyl 2-(dimethylamino)ethylcarbamate (1.8 g, 7.98 mmol) and 1,3-sultone (1.07 g, 8.77 mmol) in toluene was heated 4 h at 60° C. to form a white solid. After cooling to room temperature, the solids were collected by filtration and rinsed with hexanes (2×30 mL). The solids were dissolved in DCM (5 mL) and charged dropwise with TFA (5 mL). After 30 min, the reaction mixture was concentrated under reduced pressure to yield 3-((2-aminoethyl)-dimethylammonio)propane-1-sulfonate as a white solid (2.15 g). This quartarnary amine (82 mg, 0.266 mmol) was added to a solution of 3-chloro-4-((5-(2-(4-chloro-3-methoxyphenyl)-propan-2-yl)-1-(4-fluorophenyl)-1H-imidazol-2-ylthio)methyl)-5-fluorobenzoic acid (100 mg, 0.1776 mmol) in DMF (1 mL) followed by DIPEA (137 mg, 1.06 mmol) and HATU (74.2 mg, 0.195 mmol). After 20 min, the reaction was determined to be complete by LC-MS. The product mixture was concentrated and purified by HPLC (MeCN/H$_2$O, 10-99%) to yield the title compound as a white solid (85 mg). $^1$H NMR (400 MHz, MeOD) δ 8.96 (t, J=5.3 Hz, 1H), 7.88 (s, 1H), 7.79 (s, 1H), 7.60 (dd, J=10.0, 1.6 Hz, 1H), 7.28-7.18 (m, 1H), 6.98 (d, J=8.6 Hz, 1H), 6.95 (d, J=8.6 Hz, 1H) 6.57-6.52 (m, 2H), 6.51-6.45 (m, 2H), 4.18 (s, 2H), 3.89 (t, J=5.5 Hz, 2H), 3.75 (s, 3H), 3.68-3.56 (m, 4H), 3.23 (s, 6H), 2.87 (t, J=6.7 Hz, 2H), 2.25 (dt, J=14.2, 7.1 Hz, 2H), 1.60 (s, 6H). LC-MS: 655.3 [M]$^+$.

Example 5

2-(3-(3-chloro-4-((5-(2-(4-chloro-3-methoxyphenyl)propan-2-yl)-1-(4-fluorophenyl)-1H-imidazol-2-ylthio)methyl)-5-fluorophenylureido)-N,N,N-trimethylethanaminium 2,2,2-trifluoroacetate

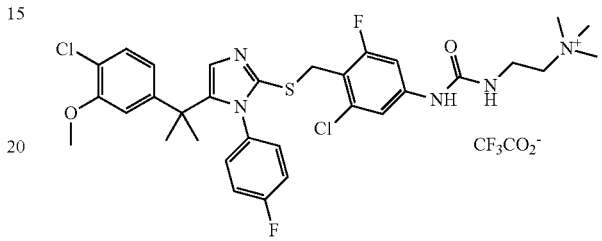

To a solution of 3-chloro-4-((5-(2-(4-chloro-3-methoxyphenyl)propan-2-yl)-1-(4-fluorophenyl)-1H-imidazol-2-ylthio)methyl)-5-fluoroaniline (50 mg, 0.0936 mmol) in CHCl$_3$ (0.5 mL) at 0° C. was added triphosgene (30.5 mg, 0.103 mmol) followed by Et$_3$N (79.3 mg, 0.78 mmol). After stirring the reaction mixture 20 min, a solution of 2-amino-N,N,N-trimethylethanaminium in NMP (1 mL) was added. After stirring 1 h, the reaction mixture was purified by HPLC (MeCN/H$_2$O with 0.05% TFA, 10-99%) to yield the title compound. $^1$H NMR (400 MHz, MeOD) δ 7.94 (s, 1H), 7.42-7.20 (m, 3H), 6.92 (d, J=8.4 Hz, H), 6.89 (d, J=8.4 Hz, 1H), 6.53 (d, J=7.8 Hz, H), 6.50 (s, 1H), 6.25-6.20 (m, 2H), 4.20 (s, 2H), 3.74 (t, J=6.3 Hz, 2H), 3.69 (s, 3H), 3.54 (t, J=6.6 Hz, 2H), 3.24 (s, 9H), 1.60 (s, 6H); MS (EI) m/z 662 [M]$^+$.

Example 6

3-(4-((5-(2-(4-Chloro-3-methoxyphenyl)propan-2-yl)—(4-fluorophenyl)-1H-imidazol-2-ylthio)methyl)-3,5-difluorophenylsulfonamido)-N,N,N-trimethylpropan-1-aminium 2,2,2-trifluoroacetate

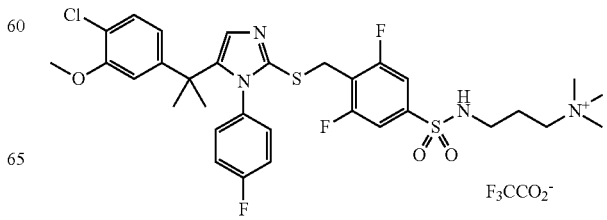

To a solution of 4-((5-(2-(4-chloro-3-methoxyphenyl)propan-2-yl)-1-(4-fluorophenyl)-1H-imidazol-2-ylthio)methyl)-3,5-difluombenzenesulfonamide (650 mg, 1.12 mmol) in DMF (6 mL) was added K$_2$CO$_3$ (464 mg, 3.36 mmol) and 3-bromopropyl trimethyl ammonium bromide (364 mg, 1.39 mmol) at 25° C. and the resulting suspension was stirred for 2 h. The reaction mixture was filtered to remove the solids and purified by preparatory HPLC (MeCN/H$_2$O with 0.1% TFA, 10-99%) to give the title product (482 mg, 54%) as a white foam. $^1$H NMR (400 MHz, MeOD) δ 7.81 (s, 1H), 7.46 (d, J=6.7 Hz, 2H), 7.25 (d, J=8.9 Hz, 1H), 6.94 (t, J=8.6 Hz, 2H), 6.59-6.49 (m, 4H), 4.09 (s, 2H), 3.72 (s, 3H), 3.48-3.40 (m, 2H), 3.14 (s, 9H), 3.00 (t, J=6.3 Hz, 2H), 2.07-1.97 (m, 2H), 1.59 (s, 6H); MS (EI) m/z 681 (M ).

Under similar conditions as the procedure described in the above example, the following compounds [Compounds 6(a)-6(d)] were prepared from appropriate reagents:

Compound 6(a)

3-(3-Chloro-5-fluoro-4-((5-(2-(4-fluoro-3-methoxyphenyl)propan-2-yl)-1-(4-fluorophenyl)-1H-imidazol-2-ylthio)methyl)phenylsulfonamido)-N,N,N-trimethylpropan-1-aminium 2,2,2-trifluoroacetate

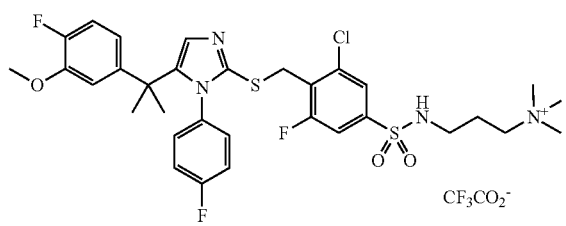

$^1$H NMR (400 MHz, CD$_3$OD) δ 7.67 (s, 1H), 7.49 (d, 1H), 7.25 (s, 1H), 6.95 (dd, 1H), 6.86 (t, 2H), 6.62 (d, 2H), 6.54-6.50 (m, 1H), 6.37-6.34 (m, 2H), 4.02 (s, 2H), 3.73 (s, 3H), 3.51-3.46 (m, 2H), 3.19 (s, 9H), 3.03 (t, 2H), 2.05 (p, 2H), 1.52 (s, 6H); MS (EI) m/z 681 (M$^+$).

Compound 6(b)

3-(4-((5-(2-(3-Chloro-4-sulfamoylphenyl)propan-2-yl)-1-(4-fluoro-3-methoxyphenyl)-H-imidazol-2-ylthio)methyl)-3,5-difluorophenylsulfonamido)-N,N,N-trimethylpropan-1-aminium chloride

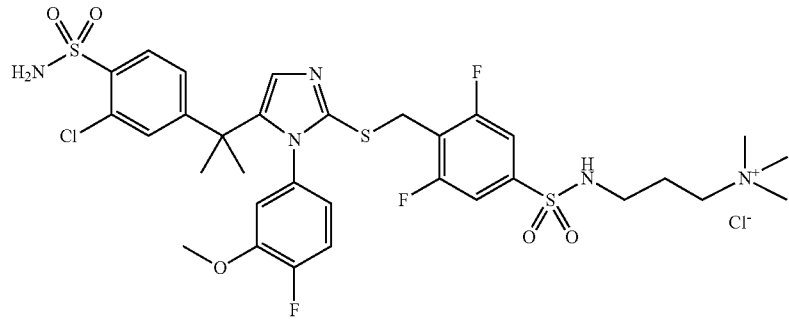 [SMILES: COc1cc(-n2c(C(C)(C)c3ccc(S(N)(=O)=O)c(Cl)c3)cnc2SCc2c(F)cc(S(=O)(=O)NCCC[N+](C)(C)C)cc2F)ccc1F ; [Cl-]]

$^1$H NMR (400 MHz, CDCl$_3$) δ 8.05 (s, 1H), 7.95 (d, J=8.2 Hz, 1H), 7.50 (d, J=6.6 Hz, 2H), 7.19 (d, J=1.29 Hz, 2H), 7.04-6.92 (m, 1H), 6.51-6.40 (m, 1H), 6.22-6.08 (m, 1H), 4.18 (d, J=4.8 Hz, 2H), 3.56 (s, 3H), 3.49-3.38 (m, 2H), 3.30-3.25 (m, 6H), 3.12 (d, J=9.8 Hz, 9H), 3.01 (t, J=5.6 Hz, 3H), 2.01 (dd, J=8.6, 7.82 Hz, 2H), 1.62 (d, J=2.2 Hz, 6H); MS (EI) m/z 760 (M ).

Compound 6(c)

3-(3-Chloro-4-((5-(2-(4-chloro-3-methoxyphenyl)propan-2-yl)-1-(4-fluorophenyl)-1H-imidazol-2-ylthio)methyl)-5-fluorophenylsulfonamido)-N,N,N-triethylpropan-1-aminium 2,2,2-trifluoroacetate

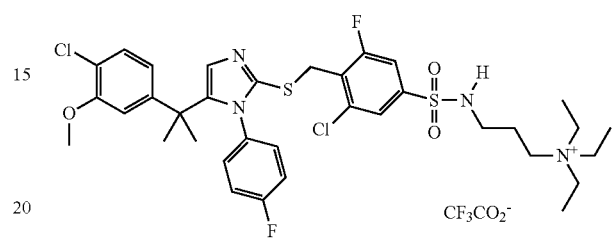

$^1$H NMR (400 MHz, MeOD) δ 8.03 (s, 1H), 7.78 (s, 1H), 7.60 (dd, J=8.7, 1.6 Hz, 1H), 7.28 (d, J=8.1 Hz, 1H), 6.94 (d, J=8.6 Hz, 1H), 6.90 (d, J=8.6 Hz, 1H), 6.59-6.51 (m, 4H), 4.26 (s, 2H), 3.74 (s, 3H), 3.67 (t, J=6.0 Hz, 2H), 3.35 (q, J=7.3 Hz, 6H), 3.03 (t, J=6.0 Hz, 2H), 2.01-1.88 (m, 2H), 1.63 (s, 6H), 1.33 (t, J=7.2 Hz, 9H); MS (EI) m/z 639.4 [M]$^+$.

Compound 6(d)

3-(4-((5-(2-(4-Chloro-3-methoxyphenyl)propan-2-yl)-4-(4-fluorophenyl)-4H-1,2,4-triazol-3-ylthio)methyl)-3,5-difluorophenylsulfonamido)-N,N,N-trimethylpropan-1-aminium 2,2,2-trifluoroacetate

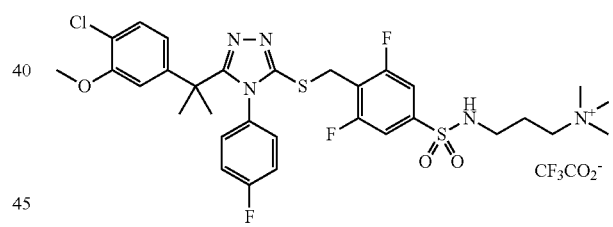

A mixture of 4-((5-(2-(4-chloro-3-methoxyphenyl)propan-2-yl)-4-(4-fluorophenyl)-4H-1,2,4-triazol-3-ylthio)methyl)-3,5-difluorobenzenesulfonamide (109 mg, 0.19 mmol), K$_2$CO$_3$ (100 mg, 0.72 mmol), 3-bromopropyl-trimethylammonium bromide (70 mg, 0.27 mmol) and DMF (2 mL) was stirred for 2 h. The reaction mixture was filtered, concentrated and purified by preparatory HPLC (MeCN/H$_2$O with 0.1% TFA, 10-99%) to give the title product (79 mg, 53%) as a white foam. $^1$H NMR (400 MHz, DMSO) δ 8.10 (t, J=5.9 Hz, 1H), 7.49 (d, J=6.5 Hz, 2H), 7.27 (d, J=8.3 Hz, 1H), 7.09 (t, J=8.7 Hz, 2H), 6.73 (dd, J=8.8, 4.8 Hz, 2H), 6.57 (d, J=1.7 Hz, 1H), 6.48 (dd, J$^{=8.3, 1.9}$ Hz, 1H), 4.11 (s, 2H), 3.71 (s, 3H), 3.42-3.22 (m, 2H), 3.05 (s, 9H), 2.88 (q, J=6.2 Hz, 2H), 2.08-1.66 (m, 2H), 1.57 (s, 6H); MS (EI) m/z 682 (M$^+$).

The following compounds [Compounds 6(e)-6(r)] were made by using procedures described in the above example by making any necessary substitutions of known materials that one skilled in the art would ordinarily understand how to do. The following compounds are represented as cations, wherein 2,2,2-trifluoroacetate was used as the counter ion as in the above Example. The counter ion can also be any pharmaceutically acceptable counter ion known to one skilled in the art. It is also understood that the source of the counter ions can be from either intermolecular sources, or, when possible, intramolecular sources.

| Compound 6(e) | 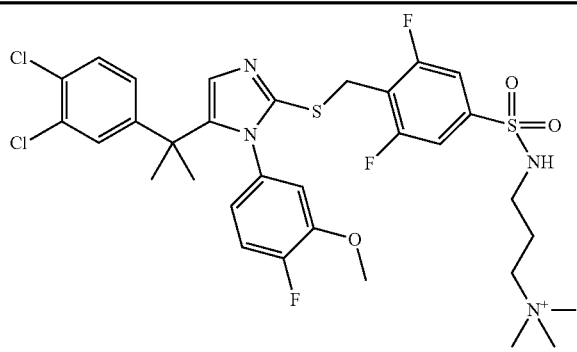 | 3-[({4-[({5-[1-(3,4-dichlorophenyl)-1-methylethyl]-1-[4-fluoro-3-(methyloxy)phenyl]-1H-imidazol-2-yl}thio)methyl]-3,5-difluorophenyl}sulfonyl)amino]-N,N,N-trimethylpropan-1-aminium |
| Compound 6(f) | 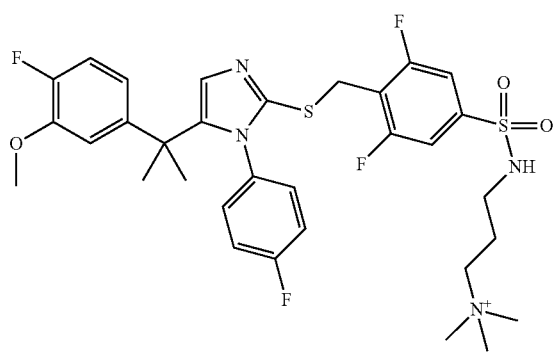 | 3-({[3,5-difluoro-4-({[5-{1-[4-fluoro-3-(methyloxy)phenyl]-1-methylethyl}-1-(4-fluorophenyl)-1H-imidazol-2-yl]thio}methyl)phenyl]sulfonyl}amino)-N,N,N-trimethylpropan-1-aminium |
| Compound 6(g) | 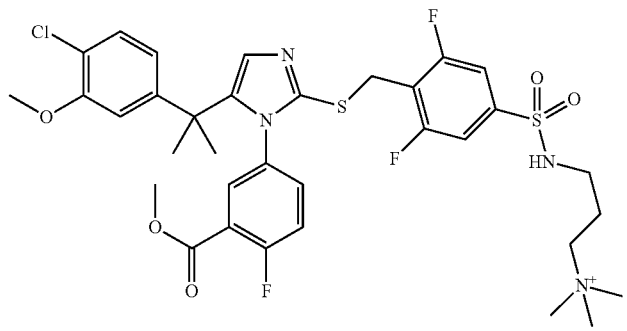 | 3-{[(4-{[(5-{1-[4-chloro-3-(methyloxy)phenyl]-1-methylethyl}-1-{4-fluoro-3-[(methyloxy)carbonyl]phenyl}-1H-imidazol-2-yl)thio]methyl}-3,5-difluorophenyl)sulfonyl]amino}-N,N,N-trimethylpropan-1-aminium |

| | | |
|---|---|---|
| Compound 6(h) | 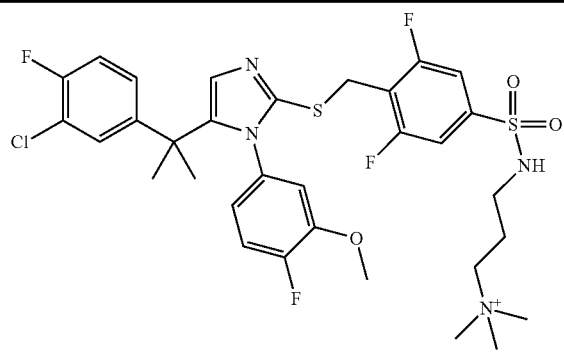 | 3-[({4-[({5-[1-(3-chloro-4-fluorophenyl)-1-methylethyl]-1-[4-fluoro-3-(methyloxy)phenyl]-1H-imidazol-2-yl}thio)methyl]-3,5-difluorophenyl}sulfonyl)amino]-N,N,N-trimethylpropan-1-aminium |
| Compound 6(i) | 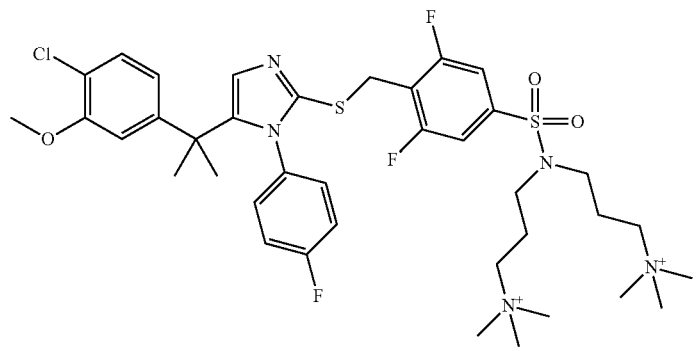 | 3,3'-({[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}imino)bis(N,N,N-trimethylpropan-1-aminium) |
| Compound 6(j) | 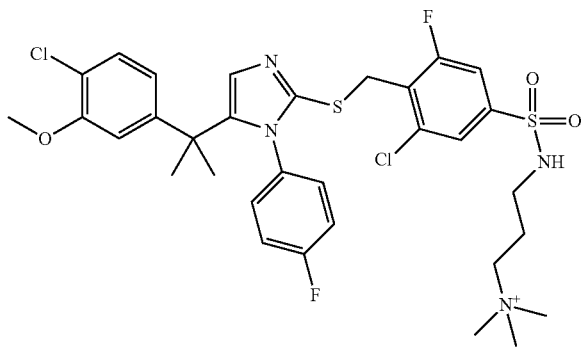 | 3-({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl)sulfonyl}amino)-N,N,N-trimethylpropan-1-aminium |
| Compound 6(k) | 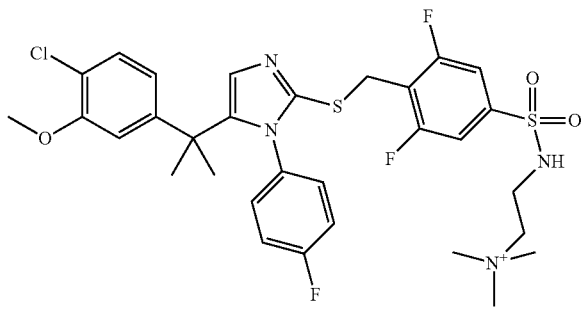 [SMILES: COc1cc(C(C)(C)c2cnc(SCc3c(F)cc(S(=O)(=O)NCC[N+](C)(C)C)cc3F)n2-c2ccc(F)cc2)ccc1Cl] | 2-({[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}amino)-N,N,N-trimethylethanaminium |
| Compound 6(l) | 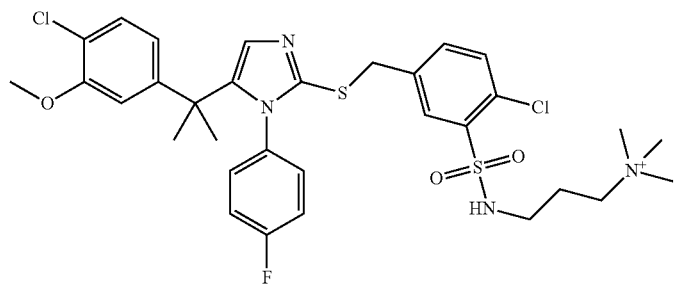 | 3-({[2-chloro-5-({[5-{1-[4-chloro-3-(methyloxy)phenyl]-1-methylethyl}-1-(4-fluorophenyl)-1H-imidazol-2-yl]thio}methyl)phenyl]sulfonyl}amino)-N,N,N-trimethylpropan-1-aminium |

| | | |
|---|---|---|
| Compound 6(m) | 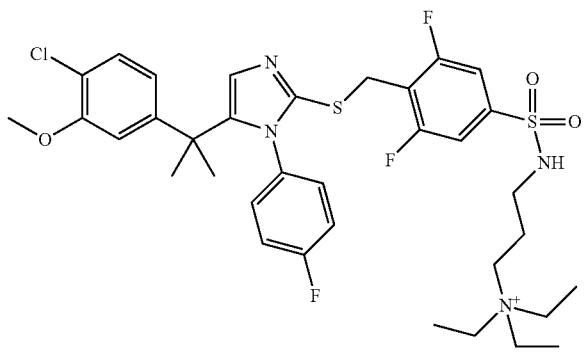 | 3-({[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}amino)-N,N,N-triethylpropan-1-aminium |
| Compound 6(n) | 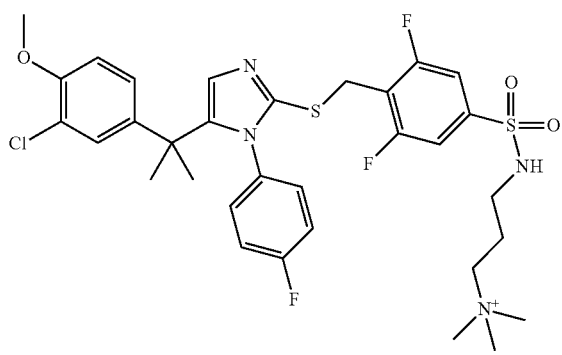 | 3-({[4-({[5-{1-[3-chloro-4-(methyloxy)phenyl]-1-methylethyl}-1-(4-fluorophenyl)-1H-imidazol-2-yl]thio}methyl)-3,5-difluorophenyl]sulfonyl}amino)-N,N,N-trimethylpropan-1-aminium |
| Compound 6(o) | 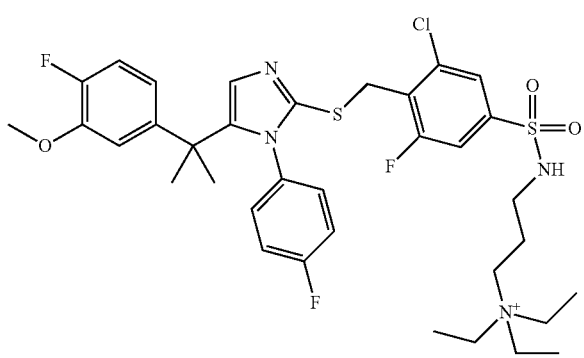 | 3-({[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]sulfonyl}amino)-N,N,N-triethylpropan-1-aminium |
| Compound 6(p) | 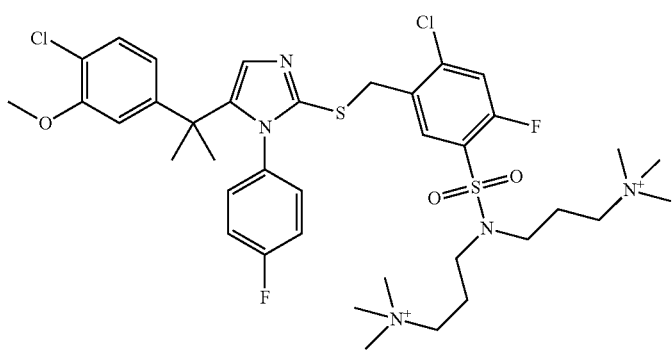 | 3,3'-({[4-chloro-5-({[5-{1-[4-chloro-3-(methyloxy)phenyl]-1-methylethyl}-1-(4-fluorophenyl)-1H-imidazol-2-yl]thio}methyl)-2-fluorophenyl]sulfonyl}imino)bis(N,N,N-trimethylpropan-1-aminium) |

| | | |
|---|---|---|
| Compound 6(q) | 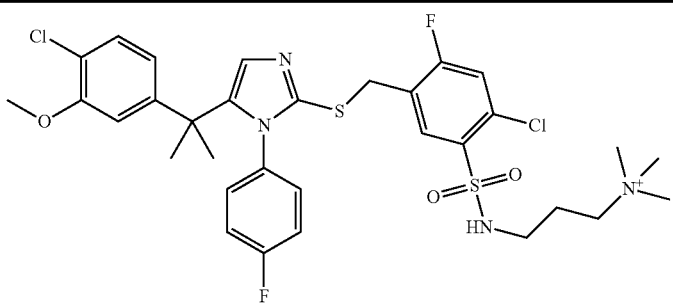 | 3-({[2-chloro-5-({[5-{1-[4-chloro-3-(methyloxy)phenyl]-1-methylethyl}-1-(4-fluorophenyl)-1H-imidazol-2-yl]thio}methyl)-4-fluorophenyl]sulfonyl}amino)-N,N,N-trimethylpropan-1-aminium |
| Compound 6(r) | 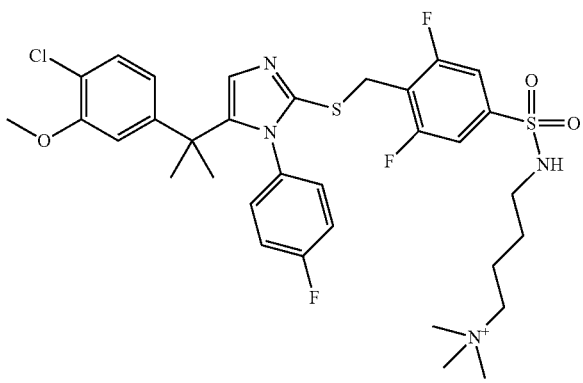 | 4-({[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}amino)-N,N,N-trimethylbutan-1-aminium |

Example 7

3-(4-Chloro-5-((5-(2-(4-chloro-3-methoxyphenyl)propan-2-yl)-1-(4-fluorophenyl)-1H-imidazol-2-ylthio)methyl)-2-fluorophenylsulfonamido)-N,N,N-trimethylpropan-1-aminium 2,2,2-trifluoroacetate

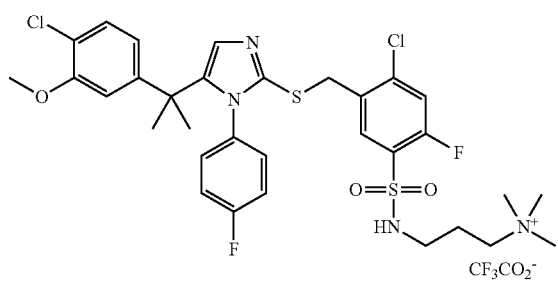

To a suspension of 4-chloro-5-((5-(2-(4-chloro-3-methoxyphenyl)propan-2-yl)-1-(4-fluorophenyl)-1H-imidazol-2-ylthio)methyl)-2-fluorobenzenesulfonamide (0.305 g, 0.51 mmol) and K$_2$CO$_3$ (0.084 g, 0.612 mmol) in 1 mL CH$_3$CN was added 3-bromo-N,N,N-trimethylpropan-1-aminium bromide (0.15 g, 0.56 mmol). The reaction was stirred at room temperature for 12 h. The reaction mixture was diluted with DMSO, neutralized with 2N HCl, and then purified by preparatory HPLC (MeCN/H$_2$O with 0.1% TFA, 10-99%) to afford the title product (115 mg) as a white solid. $^1$H-NMR (DMSO-d$_6$, 400 MHz) δ 8.21 (t, J=5.9 Hz, 1H), 7.78-7.75 (m, 2H), 7.36 (s, 1H), 7.23-7.21 (m, 1H), 7.02-6.98 (m, 2H), 6.55-6.47 (m, 4H), 4.25 (s, 2H), 3.65 (s, 3H), 3.33-3.29 (m, 2H), 3.04 (s, 9H), 2.93-2.89 (m, 2H), 1.90-1.84 (m, 2H), 1.47 (s, 6H); MS (EI) m/z 697 [M]$^+$.

Compound 7(a)

3-(3-((5-(2-(4-chloro-3-methoxyphenyl)propan-2-yl)-1-(4-fluorophenyl)-1H-imidazol-2-ylthio)methyl)-2,4-difluorophenylsulfonamido)-N,N,N-trimethylpropan-1-aminium 2,2,2-trifluoroacetate

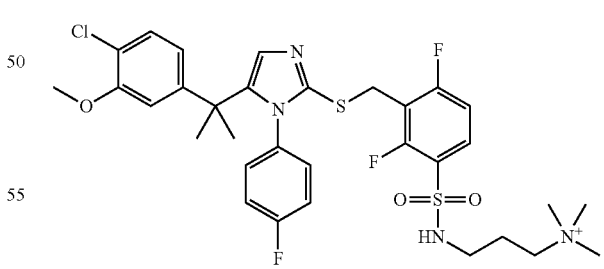

$^1$H NMR (400 MHz, DMSO) δ 8.21-8.07 (m, 1H), 7.78 (dd, J=14.8, 8.4 Hz, 1H), 7.46-7.35 (m, 1H), 7.32-7.20 (m, 2H), 7.05-6.95 (m, 2H), 6.59-6.46 (m, 4H), 4.09 (s, 2H), 3.67 (s, 3H), 3.37-3.24 (m, 2H), 3.04 (s, 9H), 2.94-2.84 (m, 2H), 1.94-1.77 (m, 2H), 1.48 (s, 6H); MS (EI): 681 [M]$^+$.

Example 8

3-(3-(4-((5-(2-(4-Chloro-3-methoxyphenyl)propan-2-yl)-1-(4-fluorophenyl)-1H-imidazol-2-ylthio)methyl)-3,5-difluorophenylsulfonyl)ureido)-N,N,N-triethylpropan-1-aminium 2,2,2-trifluoroacetate

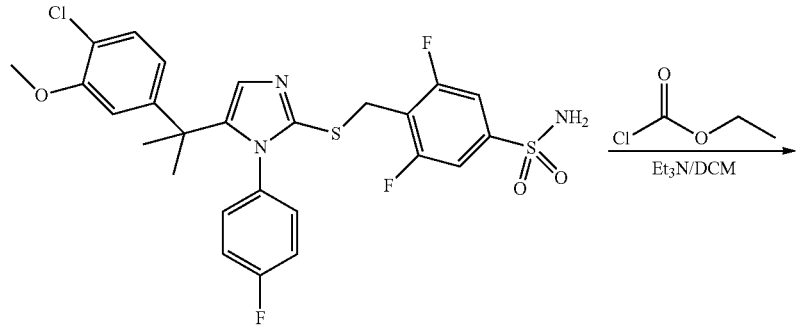

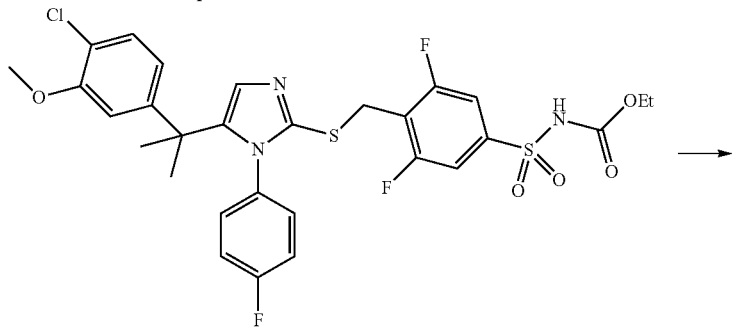

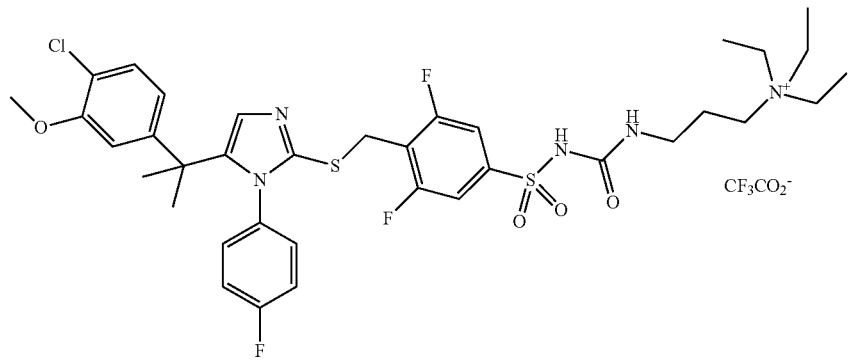

To a mixture of 4-((5-(2-(4-chloro-3-methoxyphenyl)propan-2-yl)-1-(4-fluorophenyl)-1H-imidazol-2-ylthio)methyl)-3,5-difluorobenzenesulfonamide (100 mg, 0.17 mmol) and ethyl chloroformate (0.022 mL, 0.21 mmol, 1.2 eq) in DCM was added Et$_3$N (0.05 mL, 0.34 mmol, 2.0 eq). After stirring 3 h, the reaction mixture was diluted with EtOAc, washed with water and brine, and purified by chromatography (0 to 80% EtOAc/Hex, then 10% MeOH/DCM) to give 76 mg (68%) of ethyl 4-((5-(2-(4-chloro-3-methoxyphenyl)propan-2-yl)-1-(4-fluorophenyl)-1H-imidazol-2-ylthio)methyl)-3,5-difluorophenylsulfonylcarbamate. MS (EI): 655 (MH$^+$).

To ethyl 4-((5-(2-(4-chloro-3-methoxyphenyl)propan-2-yl)-1-(4-fluorophenyl)-1H-imidazol-2-ylthio)methyl)-3,5-difluorophenylsulfonylcarbamate (203 mg, 0.31 mmol, 1.0 eq) in dry toluene (1.3 mL) and acetonitrile (0.2 mL) was added 3-amino-N,N,N-triethylpropan-1-aminium chloride hydrochloride (360 mg, 1.54 mmol, 5.0 eq) followed by DIPEA (0.54 mL, 3.1 mmol, 10 eq) and the mixture was heated 120° C. for 3 h. The crude product solidified and the supernatant was decanted. The residue was purified by preparative HPLC (30 to 100% MeCN/water, 0.1% TFA modifier) to afford 140 mg (51%) of the title product. $^1$H NMR (400 MHz, DMSO) δ 11.36 (s, 1H), 7.56 (d, J=6.6 Hz, 2H), 7.40 (s, 1H), 7.24 (d, J=8.3 Hz, 1H), 7.15 (t, J=5.7 Hz, 1H), 6.99 (t, J=8.7 Hz, 2H), 6.60-6.52 (m, 3H), 6.48 (dd, J=8.3, 2.0 Hz, 1H), 4.05 (s, 2H), 3.69 (s, 3H), 3.19 (q, J=7.2 Hz, 6H), 3.09-2.99 (m, 4H), 1.78-1.66 (m, 2H), 1.47 (s, 6H), 1.12 (t, J=7.1 Hz, 9H); MS (EI) m/z 766.6 (M$^+$).

Example 9

1-(3-(3-chloro-5-fluoro-4-((5-(2-(4-fluoro-3-methoxyphenyl)propan-2-yl)-1-(4-fluorophenyl)-1H-imidazol-2-ylthio)methyl)phenylsulfonamido)propyl)pyridinium methanesulfonate sulfonamide (1.04 g, 1.35 mmol) and (3-bromopropoxyXtert-butyl)dimethylsilane (497 mg, 1.96 mmol) in CH₃CN was heated at reflux overnight. The resulting mixture was filtered and evaporated in vacuo. The residue was purified by column chromatography (Hex/EtOAc=2:1) to give N-(3-(tert-butyldimethylsilyloxy)propyl)-3-chloro-5-fluoro-4-((5-(2-(4-fluoro-3-methoxyphenyl)propan-2-yl)-1-

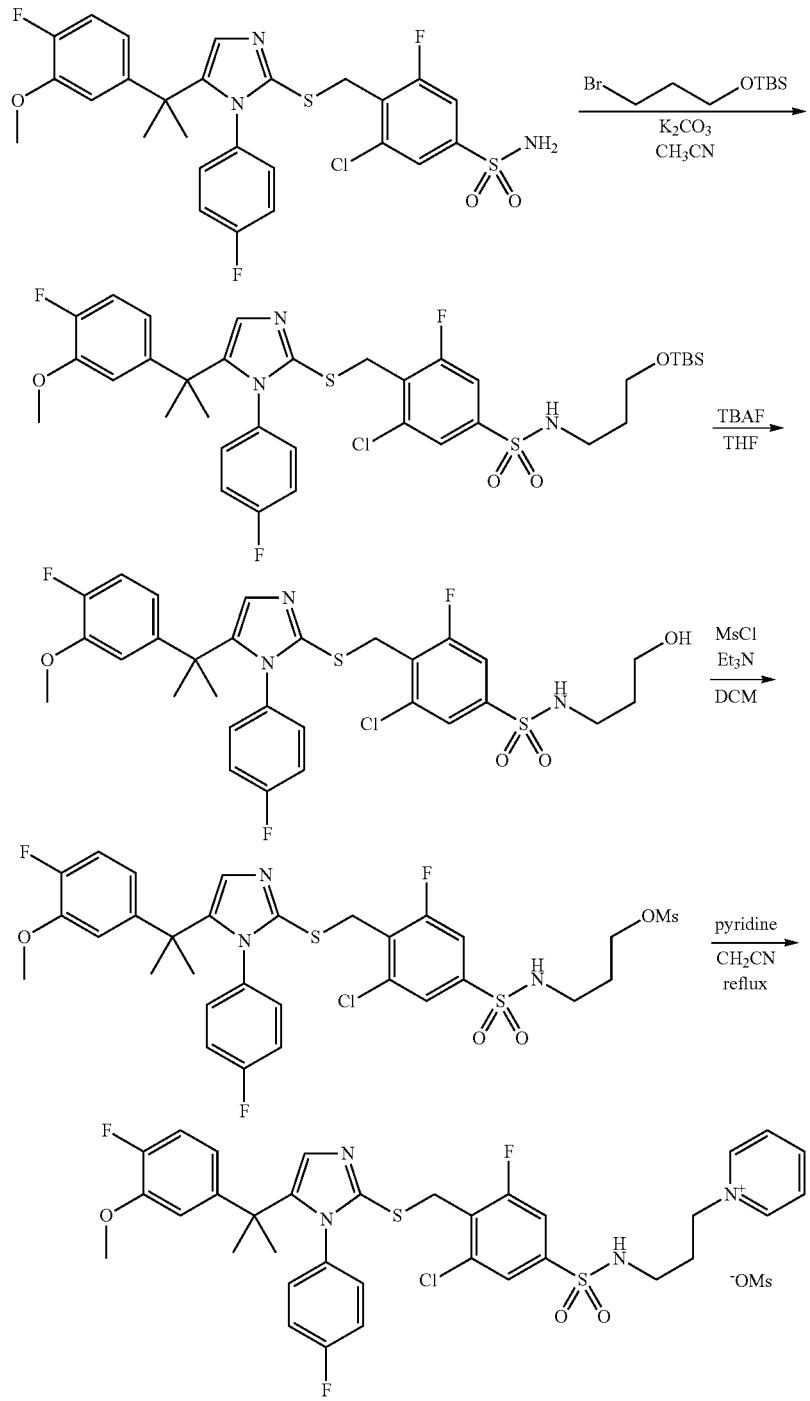

A mixture of K₂CO₃(296 mg, 2.14 mmol), 3-chloro-5-fluoro-4-((5-(2-(4-fluoro-3-methoxyphenyl)propan-2-yl)-1-(4-fluorophenyl)-1H-imidazol-2-ylthio)methyl)benzene- (4-fluorophenyl)-1H-imidazol-2-ylthio)methyl)benzenesulfonamide (1.08 g, 80%). ¹H NMR (400 MHz, CDCl₃) δ 7.56 (s, 1H), 7.32 (dd, J=8.29, 1.62 Hz, 1H), 7.21 (s, 1H), 7.15

(s, 1H), 6.83 (dd, J=10.95, 8.48 Hz, 1H), 6.78-6.72 (m, 3H), 6.50 (dd, J=8.06, 2.21 Hz, 1H), 6.44 (ddd, J=8.41, 4.09, 2.27 Hz, 1H), 6.36-6.30 (m, 3H), 5.55 (t, J=5.42 Hz, 1H), 4.18 (d, J=1.14 Hz, 1H), 3.71 (s, 4H), 3.68-3.64 (m, 3H), 3.08 (dd, J=11.71, 5.69 Hz, 3H), 1.67 (td, J=10.98, 5.68 Hz, 3H), 1.44 (s, 9H), 0.83 (td, J=5.41, 4.73 Hz, 13H).

To a solution of N-(3-(tert-butyldimethylsilyloxy)propyl)-3-chloro-5-fluoro-4-((5-(2-(4-fluoro-3-methoxyphenyl)propan-2-yl)-1-(4-fluorophenyl)-1H-imidazol-2-ylthio)methyl)benzenesulfonamide (1.08 g, 1.44 mmol) in THF (10 mL) was added TBAF (1.0M in THF, 0.7 mL, 1.39 mmol). After stirring 2 h, the reaction was quenched with AcOH (1 mL) and then evaporated in vacuo. The residue was purified by column chromatography (Hex/EtOAc=1:2) to give 3-chloro-5-fluoro-4-((5-(2-(4-fluoro-3-methoxyphenyl)propan-2-yl)-1-(4-fluorophenyl)-1H-imidazol-2-ylthio)methyl)-N-(3-hydroxypropyl)benzenesulfonamide (0.91 g, 99%). $^1$H NMR (400 MHz, CDCl$_3$) δ 7.69 (d, J=1.11 Hz, 1H), 7.43 (dd, J=8.41, 1.71 Hz, 1H), 7.15 (s, 1H), 6.56 (dd, J=8.17, 2.21 Hz, 1H), 6.48 (ddd, J=4.63, 3.53, 1.95 Hz, 3H), 3.93 (d, J=1.24 Hz, 2H), 3.78 (s, 3H), 3.64 (t, J=5.63 Hz, 2H), 3.29-3.19 (m, 2H), 1.77-1.69 (m, 2H), 1.51 (s, 7H), 1.30-1.23 (m, 1H), 5.41-5.23 (m, 1H), 6.87 (ddd, J=10.85, 9.87, 5.32 Hz, 3H).

To a solution of 3-chloro-5-fluoro-4-((5-(2-(4-fluoro-3-methoxyphenyl)propan-2-yl)-1-(4-fluorophenyl)-1H-imidazol-2-ylthio)methyl)-N-(3-hydroxypropyl)benzenesulfonamide (910 mg, 1.42 mmol) and diisopropylethylamine (0.74 mL, 0.74 mmol) in DCM (6 mL) was added methanesulfonyl chloride (0.13 mL, 1.706 mmol) at −10° C. After the reaction was slowly warmed to ambient temperature over 30 min, it was extracted with DCM (10 mL). The combined extracts were washed with water (10 mL), dried over MgSO$_4$ and evaporated in vacuo. The residue was purified by column chromatography (Hex:EA=1:2) to give 3-(3-chloro-5-fluoro-4-((5-(2-(4-fluoro-3-methoxyphenyl)propan-2-yl)-1-(4-fluorophenyl)-1H-imidazol-2-ylthio)methyl)phenylsulfonamido)propyl methanesulfonate (0.80 g, 78% yield) as a white solid. $^1$H NMR (400 MHz, CDCl$_3$): δ 7.63 (s, 1H), 7.39 (dd, J=8.27, 1.73 Hz, 1H), 7.27 (d, J=2.32 Hz, 2H), 6.89 (dd, J=10.97, 8.54 Hz, 1H), 6.84-6.74 (m, 2H), 6.58 (dd, J=8.09, 2.16 Hz, 1H), 6.53-6.45 (m, 1H), 6.41-6.33 (m, 2H), 5.26 (s, 1H), 4.42-4.29 (m, 2H), 4.23-4.08 (m, 3H), 3.78 (d, J=2.18 Hz, 4H), 3.21-3.10 (m, 2H), 3.10-2.99 (m, 4H), 2.00 (dd, J=11.78, 6.04 Hz, 2H), 1.65 (s, 7H).

A mixture of 3-(3-chloro-5-fluoro-4-((5-(2-(4-fluoro-3-methoxyphenyl)propan-2-yl)-1-(4-fluorophenyl)-1H-imidazol-2-ylthio)methyl)phenylsulfonamido)propyl methanesulfonate (50 mg, 0.064 mmol) and pyridine (0.1 mL, 12.8 mmol) in CH$_3$CN was refluxed in sealed tube 3 h. After cooling and evaporation of volatiles, the residue was purified by column chromatography (DCM/MeOH=5:1) to give the title compound (36 mg, 80% yield). $^1$H NMR (400 MHz, CD$_3$OD) δ 9.21 (d, J=5.71 Hz, 2H), 8.40 (t, J=7.79 Hz, 1H), 8.07-7.98 (m, 2H), 7.49 (s, 1H), 7.29 (dd, J=8.90, 1.32 Hz, 1H), 7.17 (s, 1H), 6.86 (dd, J=11.02, 8.48 Hz, 1H), 6.80 (dd, J=11.65, 5.39 Hz, 2H), 6.55 (dd, J=8.10, 2.16 Hz, 1H), 6.47 (ddd, J=8.34, 4.11, 2.22 Hz, 1H), 6.44-6.38 (m, 2H), 4.99 (t, J=6.27 Hz, 2H), 4.07 (s, 2H), 2.92-2.82 (m, 2H), 2.63 (s, 3H), 2.25-2.12 (m, 2H), 3.75 (s, 3H), 1.49 (s, 7H); MS (EI) m/z 701 (M$^+$).

Example 10

Preparation of 3-(3-(3-chloro-5-fluoro-4-((5-(2-(4-fluoro-3-methoxyphenyl)propan-2-yl)-1-(4-fluorophenyl)-1H-imidazol-2-ylthio)methyl)phenylsulfonamido)propyl)-1-methyl-1H-imidazol-3-ium methanesulfonate

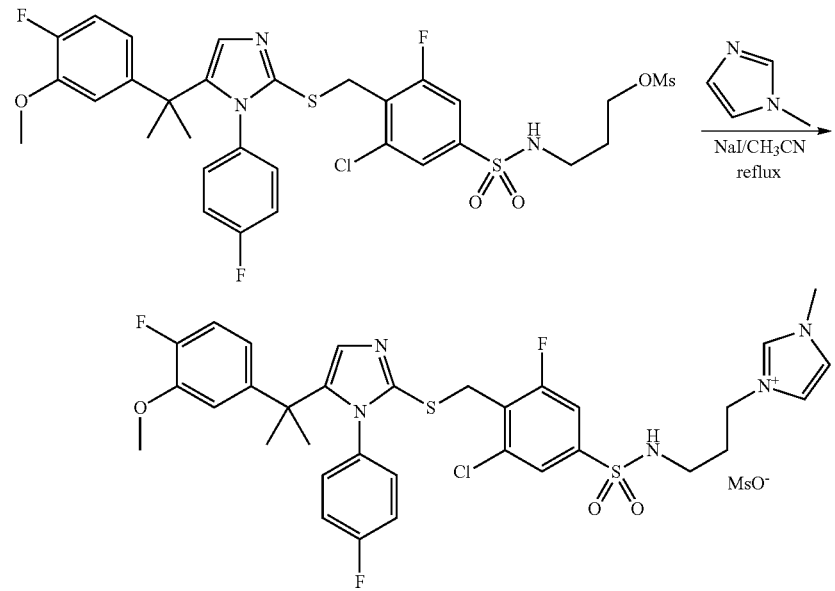

A mixture of 3-(3-chloro-5-fluoro-4-((5-(2-(4-fluoro-3-methoxyphenyl)propan-2-yl)-1-(4-fluorophenyl)-1H-imidazol-2-ylthio)methyl)phenylsulfonamido)propyl methanesulfonate (50 mg, 0.064 mmol) and 1-methylimidazole (0.1 mL) in CH$_3$CN was refluxed in sealed tube for 3 h. After cooling and evaporation of volatiles, the residue was purified by column chromatography (DCM/MeOH=5:1) to give the title compound (8 mg, 16% yield). $^1$H NMR (400 MHz, CD$_3$OD) δ 8.98-8.94 (m, 1H), 7.66 (d, J=1.95 Hz, 1H), 7.61 (t, J=1.73 Hz, 2H), 7.47-7.39 (m, 1H), 7.24 (s, 1H), 6.99-6.89 (m, 1H), 6.83 (t, J=8.63 Hz, 2H), 6.65-6.56 (m, 1H), 6.56-6.48 (m, 1H), 6.32 (dd, J=8.88, 4.80 Hz, 2H), 4.37 (t, J=6.77 Hz, 3H), 4.02 (d, J=1.33 Hz, 3H), 3.95 (s, 4H), 3.73 (d, J=3.60 Hz, 4H), 2.99-2.88 (m, 3H), 2.69 (d, J=3.79 Hz, 14H), 2.15-2.05 (m, 3H), 1.51 (s, 9H); MS (EI) m/z 704 (M$^+$).

Example 11

3-(2-(3-chloro-5-fluoro-4-((5-(2-(4-fluoro-3-methoxyphenyl)propan-2-yl)-1-(4-fluorophenyl)-1H-imidazol-2-ylthio)methyl)phenylsulfonamido)ethyl)-1-methylpyridinium chloride

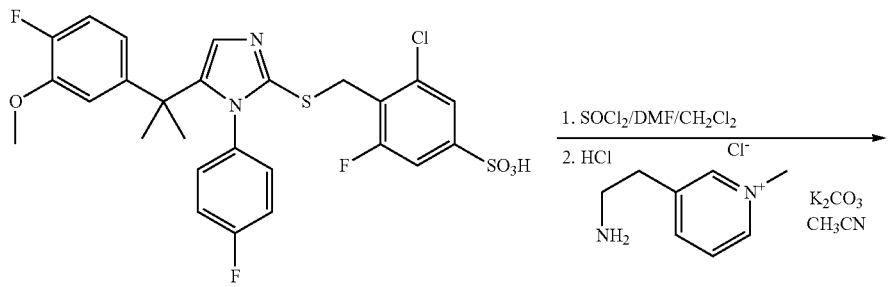

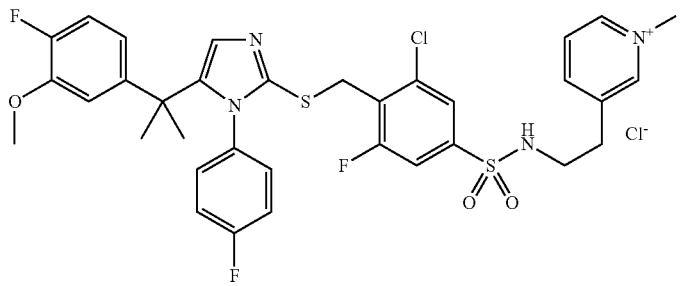

To a suspension of 3-chloro-5-fluoro-4-((5-(2-(4-fluoro-3-methoxyphenyl)propan-2-yl)-1-(4-fluorophenyl)-1H-imidazol-2-ylthio)methyl)benzenesulfonic acid (250 mg, 0.43 mmol) in DCM (5 mL) was added thionyl chloride (1 mL) and DMF (10 uL, anhyd). The reaction mixture was heated 2 h at 50° C., concentrated, diluted with DCM, and concentrated to dryness. The sulfonyl chloride intermediate was diluted with DCM (3 mL) and added slowly to a well-stirred mixture of 3-(2-aminoethyl)-1-methylpyridinium chloride hydrochloride (100 mg, 0.58 mmol) and K$_2$CO$_3$(178 mg, 1.29 mmol) in CH$_3$CN (10 mL). After stirring 2 h, the reaction mixture was filtered and concentrated. The residue was purified by chromatography (10-20% MeOH/DCM) to afford the title compound as a solid (18 mg, 6%). $^1$H NMR (400 MHz, CDCl$_3$) δ 9.13 (s, 1H), 8.77 (s, 1H), 8.40-8.32 (m, 1H), 8.03 (s, 1H), 7.71 (s, 1H), 7.51 (d, J=8.29 Hz, 1H), 7.15 (s, 1H), 6.96-6.78 (m, 3H), 6.62-6.38 (m, 5H), 4.54 (s, 3H), 4.03 (s, 2H), 3.77 (s, 4H), 3.52-3.41 (m, 4H), 3.22-3.12 (m, 2H), 1.82-1.58 (m, 6H), 1.50 (s, 7H), 1.21 (t, J=7.02 Hz, 4H); MS (EI) m/z 701 [M]$^+$.

The following compounds [Compounds 11(a)-11(w)] were made by using procedures described above by making any necessary substitutions of known materials that one skilled in the art would ordinarily understand how to do. The following compounds are represented as cations, wherein chloride was used as the counter ion as in the above Example. The counter ion can also be any pharmaceutically acceptable counter ion known to one skilled in the art. It is also understood that the source of the counter ions can be from either intermolecular sources, or, when possible, intramolecular sources.

| Compound | | |
|---|---|---|
| 11 | 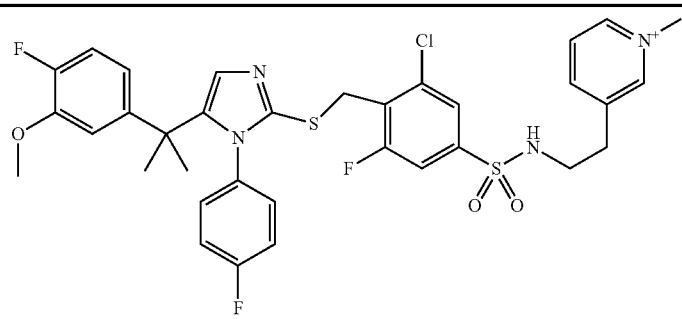 | 3-(2-(3-chloro-5-fluoro-4-((5-(2-(4-fluoro-3-methoxyphenyl)propan-2-yl)-1-(4-fluorophenyl)-1H-imidazol-2-ylthio)methyl)phenylsulfonamido)ethyl)-1-methylpyridinium |

| | | |
|---|---|---|
| Compound 11(a) | 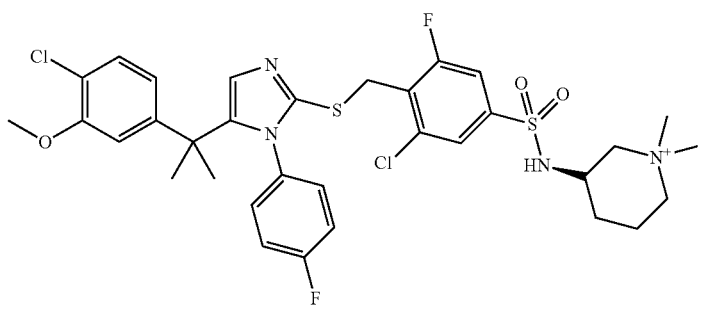 | (3S)-3-({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}amino)-1,1-dimethylpiperidinium |
| Compound 11(b) | 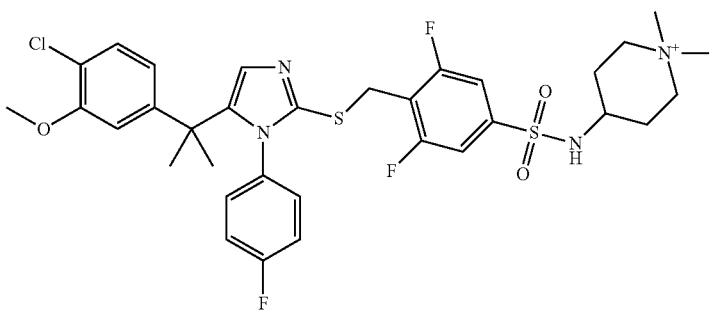 | 4-({[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}amino)-1,1-dimethylpiperidinium |
| Compound 11(c) | 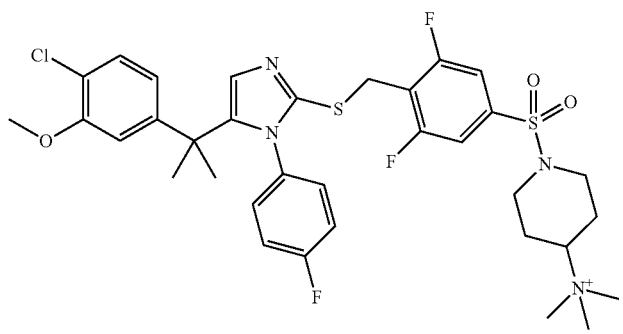 | 1-{[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}-N,N,N-trimethylpiperidin-4-aminium |
| Compound 11(d) | 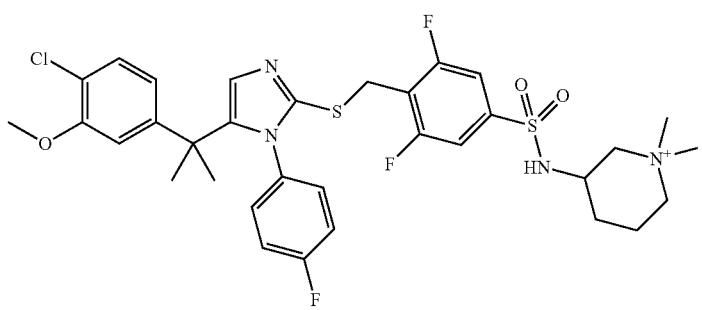 | (3R)-3-({[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}amino)-1,1-dimethylpiperidinium |
| Compound 11(e) | 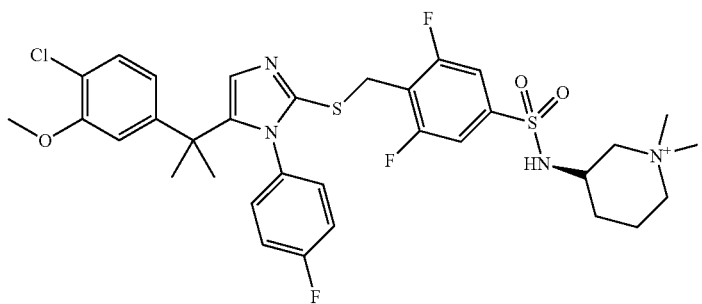 | (3S)-3-({[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}amino)-1,1-dimethylpiperidinium |

-continued

| | | |
|---|---|---|
| Compound 11(f) | 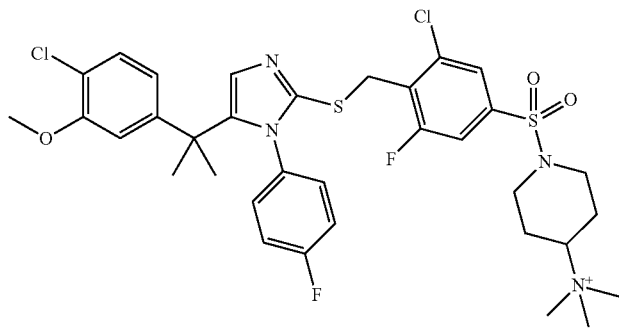 | 1-{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}-N,N,N-trimethylpiperidin-4-aminium |
| Compound 11(g) | 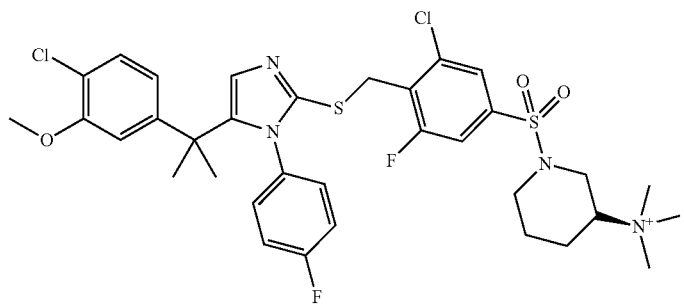 | (3R)-1-{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}-N,N,N-trimethylpiperidin-3-aminium |
| Compound 11(h) | 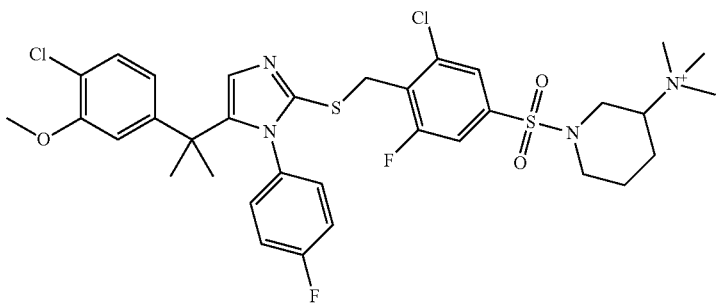 | (3S)-1-{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}-N,N,N-trimethylpiperidin-3-aminium |
| Compound 11(i) | 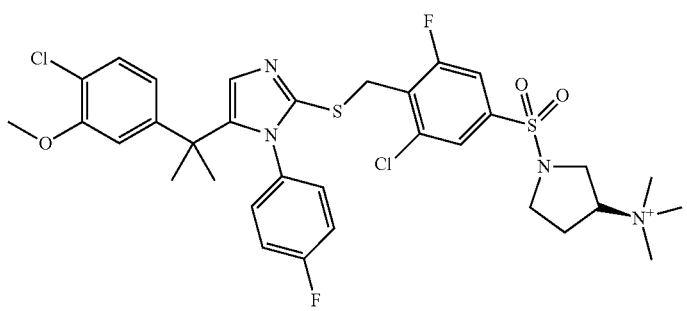 | (3R)-1-{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}-N,N,N-trimethylpyrrolidin-3-aminium |
| Compound 11(j) | 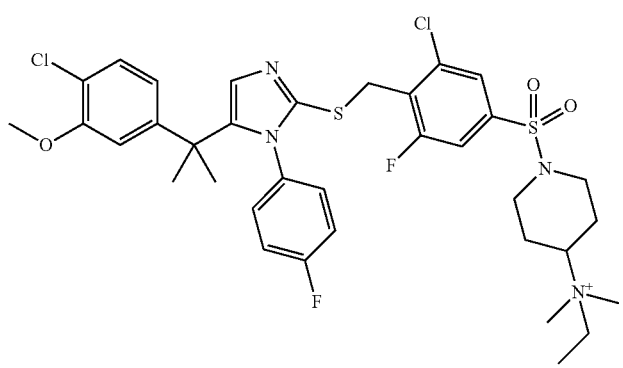 | 1-{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl)sulfonyl}-N-ethyl-N,N-dimethylpiperidin-4-aminium |

| | | |
|---|---|---|
| Compound 11(k) | 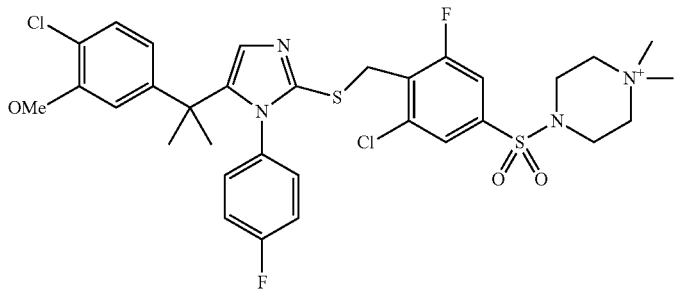 [SMILES: COc1cc(C(C)(C)c2cnc(SCc3c(F)cc(S(=O)(=O)N4CC[N+](C)(C)CC4)cc3Cl)n2-c2ccc(F)cc2)ccc1Cl] | 4-{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}-1,1-dimethylpiperazin-1-ium |
| Compound 11(l) | 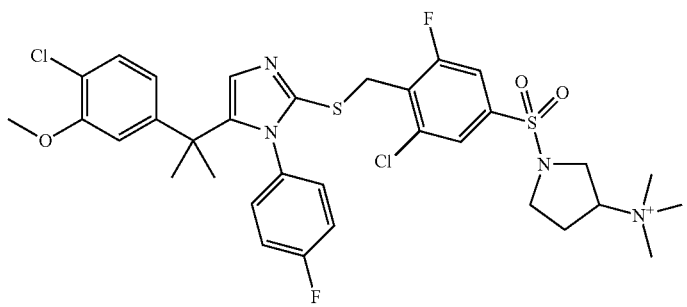 | (3S)-1-{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}-N,N,N-trimethylpyrrolidin-3-aminium |
| Compound 11(m) | 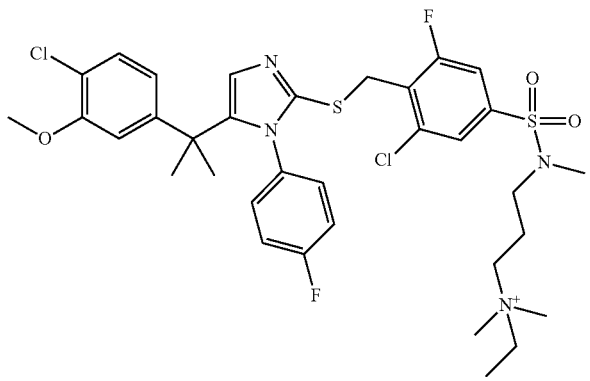 | 3-[{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl)sulfonyl}(methyl)amino]-N-ethyl-N,N-dimethylpropan-1-aminium |
| Compound 11(n) | 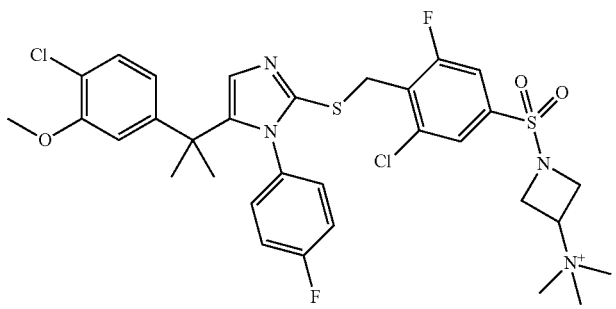 | 1-{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}-N,N,N-trimethylazetidin-3-aminium |
| Compound 11(o) | 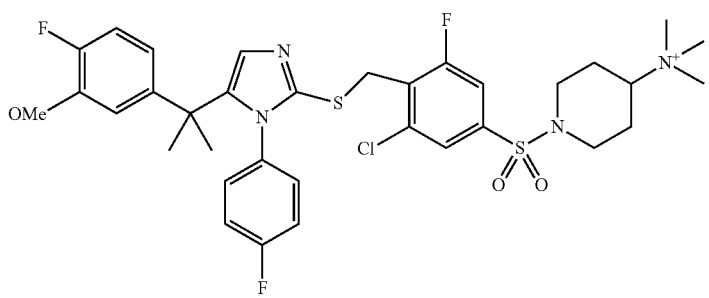 [SMILES: COc1cc(C(C)(C)c2cnc(SCc3c(F)cc(S(=O)(=O)N4CCC([N+](C)(C)C)CC4)cc3Cl)n2-c2ccc(F)cc2)ccc1F] | 1-{[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]sulfonyl}-N,N,N-trimethylpiperidin-4-aminium |

| | | |
|---|---|---|
| Compound 11(p) | 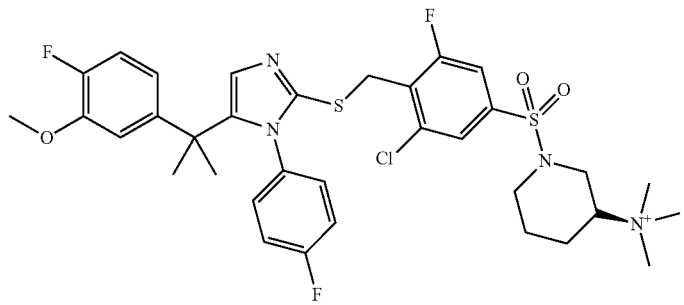 | (3R)-1-{[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]sulfonyl}-N,N,N-trimethylpiperidin-3-aminium |
| Compound 11(q) | 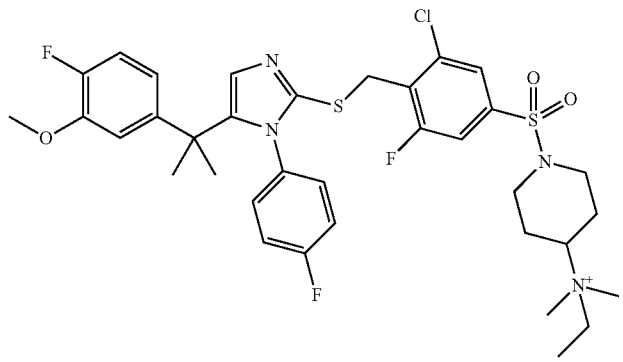 | 1-{[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]sulfonyl}-N-ethyl-N,N-dimethylpiperidin-4-aminium |
| Compound 11(r) | 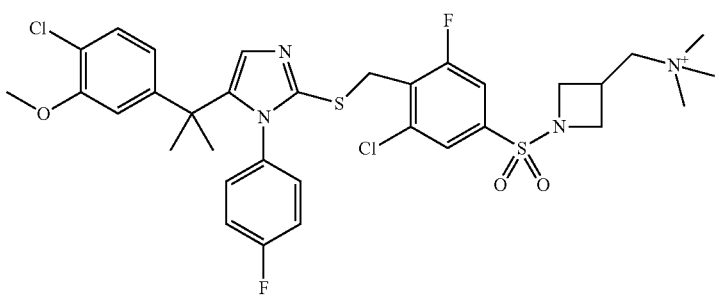 | (1-{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}azetidin-3-yl)-N,N,N-trimethylmethanaminium |
| Compound 11(s) | 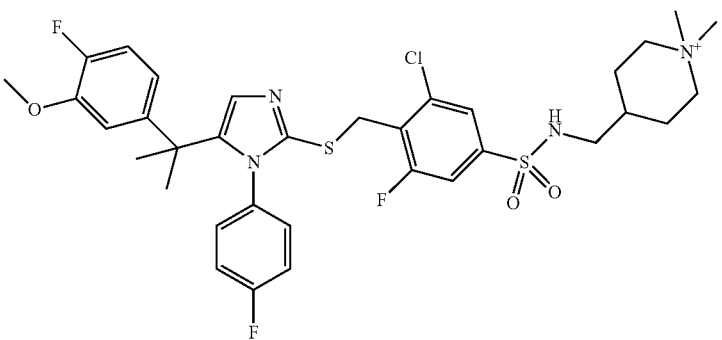 | 4-[({[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]sulfonyl}amino)methyl]-1,1-dimethylpiperidinium |

| | | |
|---|---|---|
| Compound 11(t) | 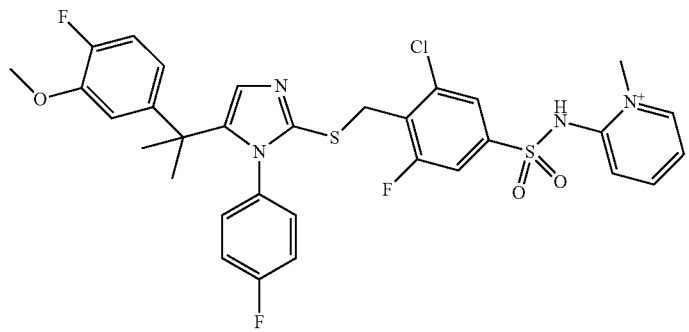 | 2-({[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]sulfonyl}amino)-1-methylpyridinium |
| Compound 11(u) | 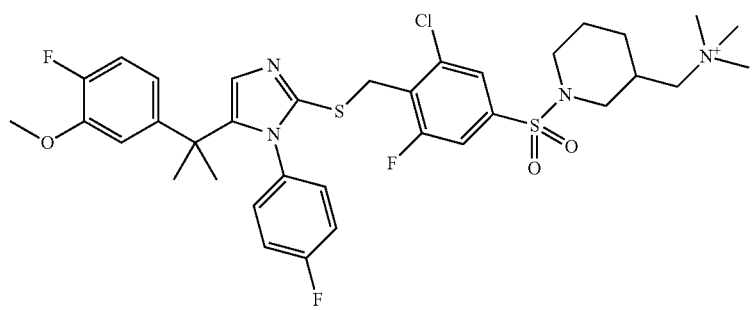 | [(3S)-1-{[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]sulfonyl}piperidin-3-yl]-N,N,N-trimethylmethanaminium |
| Compound 11(v) | 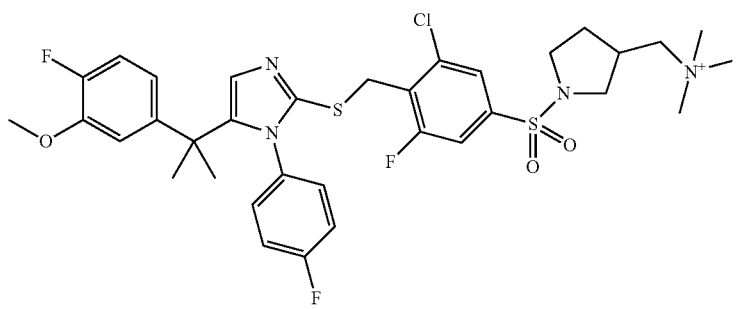 | [(3S)-1-{[3-chloro-5-fluoro-4-({[5-(1-[4-fluoro-3-(methyloxy)phenyl]-1-methylethyl}-1-(4-fluorophenyl)-1H-imidazol-2-yl]thio}methyl)phenyl]sulfonyl}pyrrolidin-3-yl]-N,N,N-trimethylmethanaminium |
| Compound 11(w) | 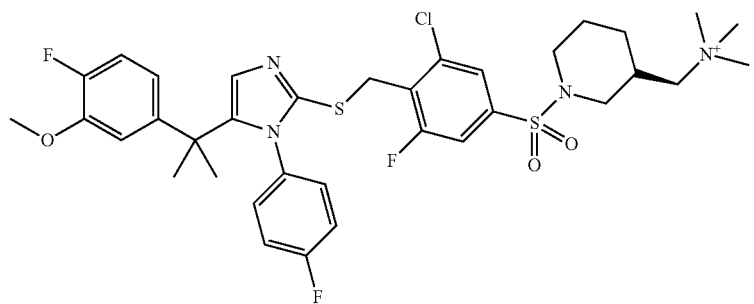 | [(3R)-1-{[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]sulfonyl}piperidin-3-yl]-N,N,N-trimethylmethanaminium |

The following compound [Compound 11 (x)] were made by using procedures described above by making any necessary substitutions of known materials that one skilled in the art would ordinarily understand how to do. The following compound is represented as a cation, wherein chloride was used as the counter ion as in the above Example. The counter ion can also be any pharmaceutically acceptable counter ion known to one skilled in the art. It is also understood that the source of the counter ions can be from either intermolecular sources, or, when possible, intramolecular sources.

Compound 11(x)

(4-carboxy-1-{[4-({[5-{1-[4-chloro-3-(methyloxy) phenyl]-1-methylethyl}-1-(4-fluorophenyl)-1H-imidazol-2-yl]thio}methyl)-3,5-difluorophenyl] sulfonyl}piperidin-4-yl)-N,N,N-trimethylmethanaminium

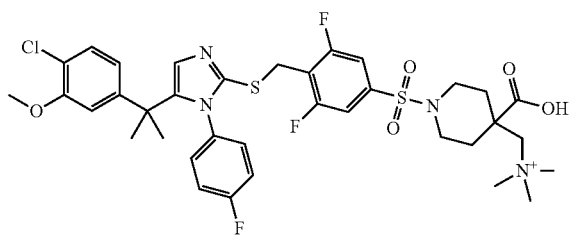

Example 12

3-(N-(carboxymethyl)-4-((5-(2-(4-chloro-3-methoxyphenyl)propan-2-yl)-1-(4-fluorophenyl)-1H-imidazol-2-ylthio)methyl)-3, -difluorophenylsulfonamido)-N,N,N-trimethylpropan-1-aminium 2,2,2-trifluoroacetate

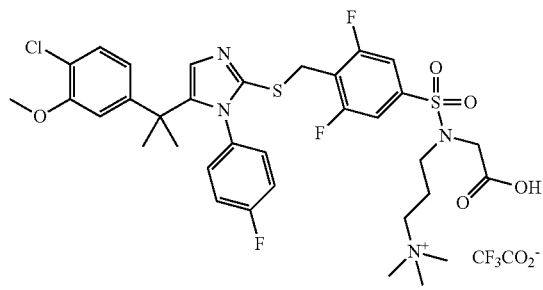

To a solution of 3-(4-((5-(2-(4-chloro-3-methoxyphenyl) propan-2-yl)-1-(4-fluorophenyl)-1H-imidazol-2-ylthio)methyl)-3,5-difluorphenylsulfonamido)-N,N,N-trimethylpropan-1-aminium chloride (500 mg, 0.7 mmol) in DMF (2.5 mL) was added potassium carbonate (290 mg, 2.1 mmol) followed by tert-butyl bromoacetate. The mixture was heated at 80° C. for 2 h. After cooling, the reaction mixture was partitioned between DCM (50 mL) and 50% satd brine (50 mL). The organic layer was dried ($Na_2SO_4$), filtered and concentrated in vacuo. The residue was purified by flash chromatography (silica, 0-20% MeOH/DCM). The combined pure fractions were concentrated in vacuo and dissolved in DCM (5 mL). TFA (5 mL) was added and, after stirring at room temperature for 1 h, the volatiles were removed. The residue was purified by preparative HPLC (MeCN/$H_2O$ with 0.1% TFA, 10-99%) to afford the title compound as a white foam (160 mg, 27%). $^1$H NMR (400 MHz, DMSO-$d_6$) δ 7.58 (d, J=6.7 Hz, 2H), 7.40 (s, 1H), 7.26 (d, J=8.3 Hz, 1H), 7.02 (t, J=8.7 Hz, 2H), 6.69-6.59 (m, 2H), 6.55 (d, J=2.0 Hz, 1H), 6.50 (dd, J=8.3, 2.0 Hz, 1H), 4.12 (s, 2H), 4.06 (s, 2H), 3.69 (s, 3H), 3.39-3.23 (m, 4H), 3.06 (s, 9H), 2.06-1.88 (m, 2H), 1.49 (s, 6H). MS (EI) m/z 739.5 ($M^+$).

3-(4-((5-(2-(4-chloro-3-methoxyphenyl)propan-2-yl)-1-(4-fluorophenyl)-1H-imidazol-2-ylthio)methyl)-3,5-difluoro-N-methylphenylsulfonamido)-N, N,N-trimethylpropan-1-aminium 2,2,2-trifluoroacetate The following compounds [12(a)-12(g)] were made by using procedures described in the above example by making any necessary substitutions of known materials that one skilled in the art would ordinarily understand how to do. The following compounds are represented as cations, wherein 2,2,2-trifluoroacetate was used as the counter ion as in the above Example. The counter ion can also be any pharmaceutically acceptable counter ion known to one skilled in the art. It is also understood that the source of the counter ions can be from either intermolecular sources, or, when possible, intramolecular sources.

Compound 12(a)

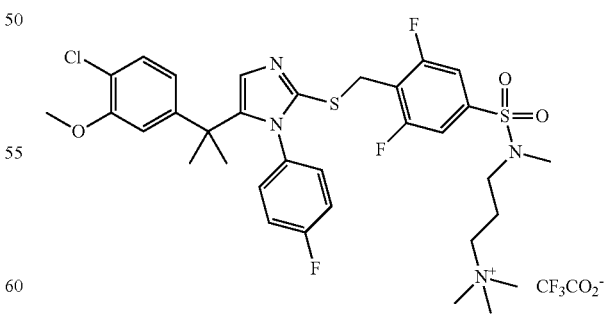

Under similar conditions as the procedure described in the above example, the above title compound was prepared using iodomethane and purified by preparative HPLC (MeCN/$H_2O$ with 0.1% TFA, 10-99%). MS (EI) m/z 695.4 ($M^+$).

Compound 12(b)

3-(4-((5-(2-(4-chloro-3-methoxyphenyl)propan-2-yl)-1-(4-fluorophenyl)-1H-imidazol-2-ylthio)methyl)-N-ethyl-3,5-difluorophenylsulfonamido)-N,N,N-trimethylpropan-1-aminium 2,2,2-trifluoroacetate

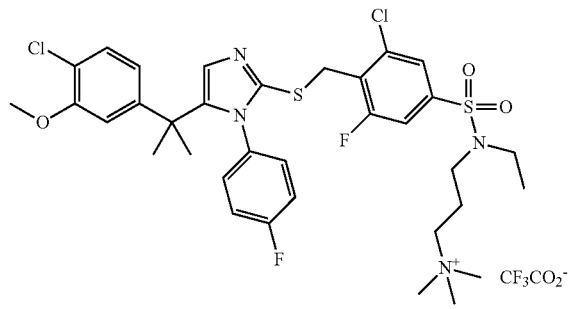

MS (EI) m/z 709 (M⁺).

Compound 12(c)

3-(3-chloro-4-((5-(2-(4-chloro-3-methoxyphenyl)propan-2-yl)-1-(4-fluorophenyl)-1H-imidazol-2-ylthio)methyl)-5-fluoro-N-methylphenylsulfonamido)-N,N,N-trimethylpropan-1-aminium 2,2,2-trifluoroacetate

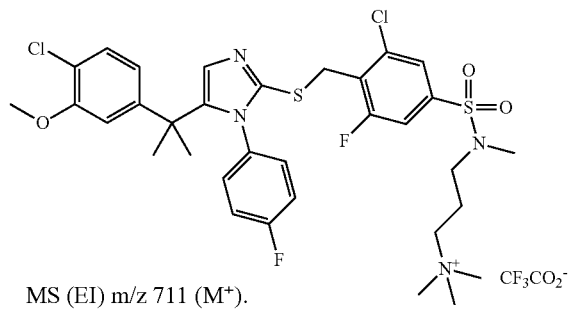

MS (EI) m/z 711 (M⁺).

Compound 12(d)

3-(3-chloro-5-fluoro-4-((5-(2-(4-fluoro-3-methoxyphenyl)propan-2-yl)-1-(4-fluorophenyl)-1H-imidazol-2-ylthio)methyl)-N-methylphenylsulfonamido)-N,N,N-trimethylpropan-1-aminium 2,2,2-trifluoroacetate

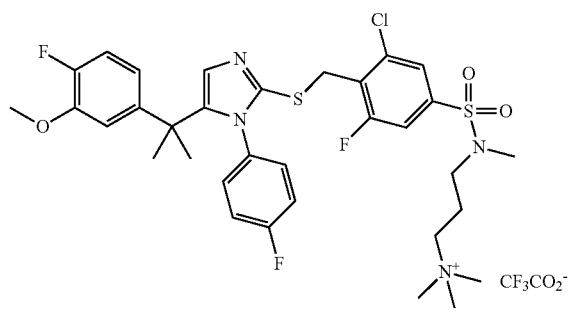

MS (EI) m/z 695 (M⁺).

Compound 12(e)

3-(3-Chloro-4-((5-(2-(4-chloro-3-methoxyphenyl)propan-2-yl)-1-(4-fluorophenyl)-1H-imidazol-2-yl)methoxy)-5-fluoro-N-methylphenylsulfonamido)-N,N,N-trimethylpropan-1-aminium 2,2,2-trifluoroacetate

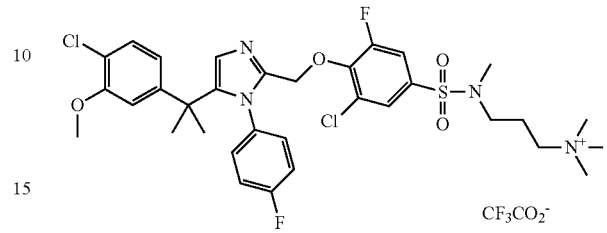

¹H NMR (400 MHz, MeOD) δ 7.70 (s, 1H), 7.66-7.57 (m, 2H), 7.25-7.19 (m, 1H), 7.04-6.97 (m, 2H), 6.90-6.84 (m, 2H), 6.62-6.55 (m, 2H), 4.98 (s, 2H), 3.73 (s, 3H), 3.50-3.41 (m, 2H), 3.23-3.15 (t, J=6.8, 2H), 3.16 (s, 9H), 2.81 (s, 3H), 2.16-2.01 (m, 2H), 1.64 (s, 6H); MS (ESI2) m/z 695.4 [M]⁺.

Compound 12(f)

3-(4-((5-(2-(4-Chloro-3-methoxyphenyl)propan-2-yl)-1-(4-fluorophenyl)-1H-imidazol-2-ylthio)methyl)-3,5-difluoro-N-(2-hydroxyethyl)phenylsulfonamido)-N,N,N-trimethylpropan-1-aminium 2,2,2-trifluoroacetate

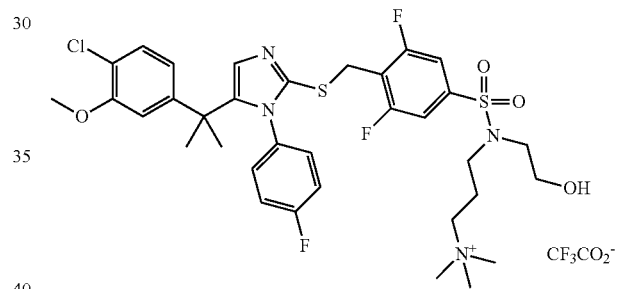

¹H NMR (400 MHz, DMSO-d₆) δ 7.56 (d, J=6.6 Hz, 2H), 7.36 (s, 1H), 7.25 (d, J=10.0 Hz, 1H), 7.01 (t, J=8.7 Hz, 2H), 6.72-6.58 (m, 2H), 6.55 (d, J=2.0 Hz, 1H), 6.50 (dd, J=8.3, 2.0 Hz, 1H), 4.06 (s, 2H), 3.69 (s, 3H), 3.55 (t, J=5.7 Hz, 2H), 3.39-3.28 (m, 2H), 3.24 (m, 4H), 3.07 (s, 9H), 2.08-1.92 (m, 2H), 1.48 (s, 6H). MS (EI) m/z 725.5 (M ).

Compound 12(g)

3-(4-((5-(2-(4-chloro-3-methoxyphenyl)propan-2-yl)-1-(4-fluorophenyl)-1H-imidazol-2-ylthio)methyl)-3,5-difluoro-N-(3-hydroxypropyl)phenylsulfonamido)-N,N,N-trimethylpropan-1-aminium 2,2,2-trifluoroacetate

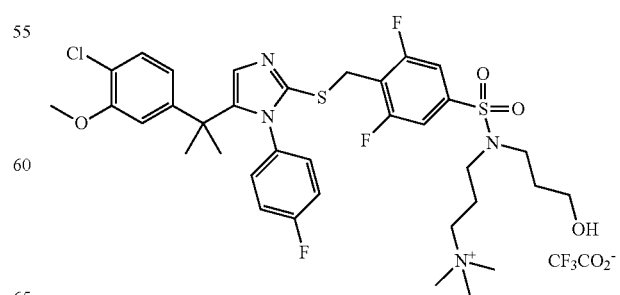

MS (EI) m/z 739.5 (M⁺).

Compound 12(h)

3-(N-(2-amino-2-oxoethyl)-4-((5-(2-(4-chloro-3-methoxyphenyl)propan-2-yl)-1-(4-fluorophenyl)-1H-imidazol-2-ylthio)methyl)-3,5-difluorophenylsulfonamido)-N,N,N-trimethylpropan-1-aminium 2,2,2-trifluoroacetate

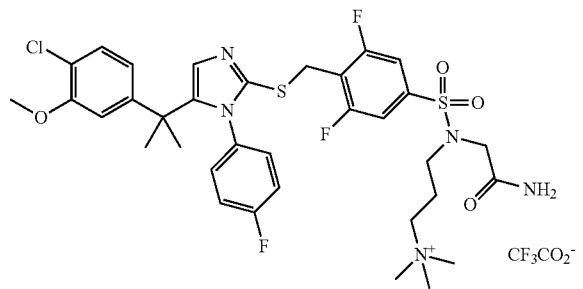

$^1$H NMR (400 MHz, DMSO-d$_6$) δ 7.58-7.52 (m, 2H), 7.49 (s, 1H), 7.35 (s, 1H), 7.25 (d, J=8.3 Hz, 1H), 7.18 (s, 1H), 7.05-6.97 (m, 2H), 6.61 (dd, J=8.9, 4.9 Hz, 2H), 6.55 (d, J=2.0 Hz, 1H), 6.50 (dd, J=8.3, 2.0 Hz, 1H), 4.07 (s, 2H), 3.89 (s, 2H), 3.69 (s, 3H), 3.43-3.33 (m, 2H), 3.28 (t, J=6.3 Hz, 2H), 3.06 (s, 9H), 2.00-1.89 (m, 2H), 1.48 (s, 6H); MS (EI) m/z 738 (M).

Example 13

3-(N-(4-carboxybenzyl)-4-((5-(2-(4-chloro-3-methoxyphenyl)propan-2-yl)-1-(4-fluorophenyl)-1H-imidazol-2-ylthio)methyl)-3,5-difluorophenylsulfonamido)-N,N,N-trimethylpropan-1-aminium chloride To a solution of 3-(4-((5-(2-(4-chloro-3-methoxyphenyl)propan-2-yl)-1-(4-fluorophenyl)-1H-imidazol-2-ylthio)methyl)-3,5-difluorphenylsulfonamido)-N,N,N-trimethylpropan-1-aminium chloride (96 mg, 0.13 mmol) in DMF (2 mL) was added K$_2$CO$_3$ (80 mg, 0.58 mmol) and methyl-(4-bromomethyl)-benzoate (40 mg, 0.18 mmol) at 25° C. and the resulting suspension was stirred for 24 h. The reaction mixture was quenched into water (20 mL) and extracted with EtOAc (3×20 mL). The combined organic layers were washed with brine (20 mL), dried over MgSO$_4$ and concentrated to a colorless oil. The oil was reconstituted in THF (6 mL) and added to a solution of LiOH.H$_2$O (420 mg) in water (10 mL) at 25° C. After 30 min the reaction was concentrated and adjusted to pH 1 with conc HCl. The aqueous layer was extracted with DCM, and combined extracts were dried (MgSO$_4$) and concentrated to furnish the title product (104 mg, 95%) as a white solid. $^1$H NMR (400 MHz, DMSO-d$_6$) δ 7.94 (d, J=8.2 Hz, 2H), 7.62 (d, J=6.4 Hz, 2H), 7.48 (d, J=8.2 Hz, 2H), 7.25 (d, J=8.3 Hz, 1H), 7.18 (s, 1H), 7.01 (t, J=8.7 Hz, 2H), 6.61 (dd, J=8.8, 4.9 Hz, 2H), 6.55 (d, J=1.8 Hz, 1H), 6.50 (dd, J=8.3, 1.9 Hz, 1H), 4.51 (s, 2H), 4.02 (s, 2H), 3.68 (s, 3H), 3.28-3.14 (m, 2H), 3.14-3.04 (m, 2H), 2.92 (s, 9H), 1.67 (d, J=8.3 Hz, 2H), 1.47 (s, 6H); MS (EI) m/z 815 (MH$^+$).

The following compound [Compound 13(a)], was made by using procedures described in the above example by making any necessary substitutions of known materials that one skilled in the art would ordinarily understand how to do, and wherein 2,2,2-trifluoroacetate was used as the counter ion as in the above Example. The counter ion can also be any pharmaceutically acceptable counter ion known to one skilled in the art. It is also understood that the source of the counter ions can be from either intermolecular sources, or, when possible, intramolecular sources.

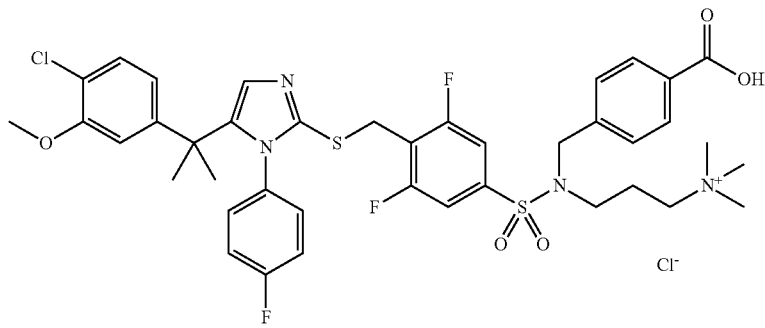 [SMILES: COc1cc(C(C)(C)c2cnc(SCc3c(F)cc(S(=O)(=O)N(CCC[N+](C)(C)C)Cc4ccc(C(=O)O)cc4)cc3F)n2-c2ccc(F)cc2)ccc1Cl ; [Cl-]]

Compound 13(a)

3-(4-((5-(2-(4-chloro-3-hydroxyphenyl)propan-2-yl)-1-(4-fluorophenyl)-1H-imidazol-2-ylthio)methyl)-3,5-difluorophenylsulfonamido)-N,N,N-trimethylpropan-1-aminium 2,2,2-trifluoroacetate

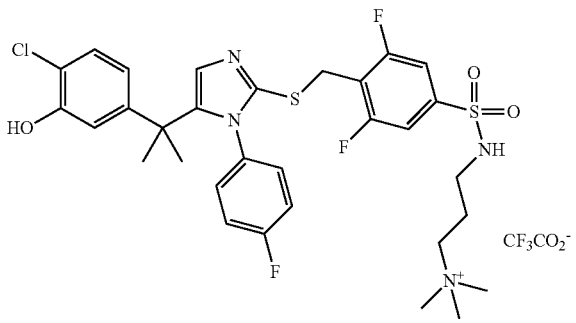

The title compound was prepared by treating 3-(4-((5-(2-(4-chloro-3-methoxyphenyl)propan-2-yl)-1-(4-fluorophenyl)-1H-imidazol-2-ylthio)methyl)-3,5-difluorophenylsulfonamido)-N,N,N-trimethylpropan-1-aminium 2,2,2-trifluoroacetate with boron tribromide in DCM, followed by standard workup and then purified by preparative HPLC. MS (EI) m/z 667.4 (M$^+$).

Example 14

(R)-3-(4-((5-(2-(4-chloro-3-methoxyphenyl)propan-2-yl)-1-(4-fluorophenyl)-1H-imidazol-2-ylthio)methyl)-3,5-difluoro-N-(1-methoxy-1-oxopropan-2-yl)phenylsulfonamido)-N,N,N-trimethylpropan-1-aminium 2,2,2-trifluoroacetate

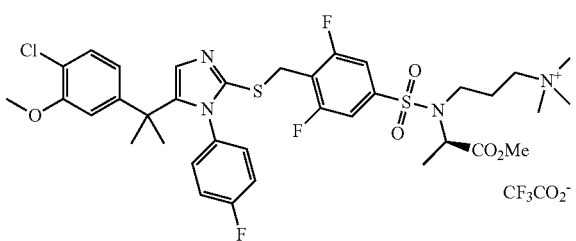

To a solution of (R)-methyl 2-(4-((5-(2-(4-chloro-3-methoxyphenyl)propan-2-yl)-1-(4-fluorophenyl)-1H-imidazol-2-ylthio)methyl)-3,5-difluomphenylsulfonamido)prpanoate (1.0 g, 1.5 mmol) in MeCN (6 mL) was added potassium carbonate (0.6 g, 4.6 mmol) and (3-bromopropyl)trimethylammonium bromide (0.6 g, 2.3 mmol). The mixture was heated at 65° C. with stirring in a sealed tube for 30 min. After cooling, the mixture was partitioned between DCM (100 mL) and water (100 mL). The organic layer was dried over Na$_2$SO$_4$, filtered and concentrated in vacuo. A sample (100 mg) was purified by preparative HPLC (MeCN/H$_2$O with 0.1% TFA, 10-99%) to afford (R)-3-(4-((5-(2-(4-chloro-3-methoxyphenyl)propan-2-yl)-1-(4-fluorophenyl)-1H-imidazol-2-ylthio)methyl)-3,5-difluoro-N-(1-methoxy-1-oxopropan-2-yl)phenylsulfonamido)-N,N,N-trimethylpropan-1-aminium 2,2,2-trifluoroacetate as a white foam (31 mg). $^1$H NMR (400 MHz, DMSO-d$_6$) δ 7.60 (d, J=6.7 Hz, 2H), 7.42 (s, 1H), 7.26 (d, J=8.3 Hz, 1H), 7.09-6.94 (m, 2H), 6.71-6.58 (m, 2H), 6.55 (d, J=1.9 Hz, 1H), 6.50 (dd, J=8.3, 2.0 Hz, 1H), 4.73 (q, J=7.2 Hz, 1H), 4.07 (s, 2H), 3.69 (s, 3H), 3.52 (s, 3H), 3.39-3.26 (m, 3H), 3.25-3.10 (m, 1H), 3.07 (s, 9H), 2.12-1.91 (m, 2H), 1.45 (s, 6H), 1.39 (d, J=7.3 Hz, 3H). MS (EI) m/z 767.5 (M$^+$).

The following compounds [14(a)-14(d)] were made by using procedures described in the above example by making any necessary substitutions of known materials that one skilled in the art would ordinarily understand how to do. The following compounds are represented as cations, wherein 2,2,2-trifluoroacetate was used as the counter ion as in the above Example. The counter ion can also be any pharmaceutically acceptable counter ion known to one skilled in the art. It is also understood that the source of the counter ions can be from either intermolecular sources, or, when possible, intramolecular sources.

Compound 14(a)

(R)-3-(N-(1-carboxyethyl)-4-((5-(2-(4-chloro-3-methoxyphenyl)propan-2-yl)-1-(4-fluorophenyl)-1H-imidazol-2-ylthio)methyl)-3,5-difluorophenylsulfonamido)-N,N,N-trimethylpropan-1-aminium 2,2,2-trifluoroacetate

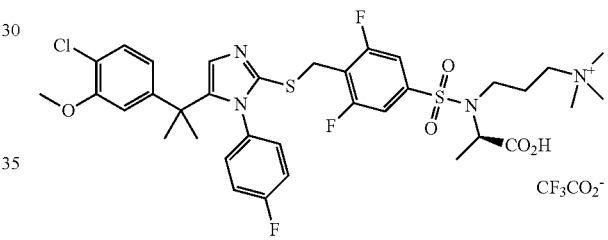

$^1$H NMR (400 MHz, DMSO-d$_6$) δ 7.58 (d, J=6.7 Hz, 2H), 7.35 (s, 1H), 7.26 (d, J=8.3 Hz, 1H), 7.08-6.95 (m, 2H), 6.70-6.59 (m, 2H), 6.56 (d, J=2.0 Hz, 1H), 6.50 (dd, J=8.3, 2.0 Hz, 1H), 4.61 (q, J=7.3 Hz, 1H), 4.15-3.99 (m, 2H), 3.69 (s, 3H), 3.34 (m, 3H), 3.28-3.12 (m, 1H), 3.06 (s, 9H), 2.10-1.93 (m, 2H), 1.54-1.42 (s, 6H), 1.37 (d, J=7.3 Hz, 3H); MS (EI) m/z 753.4 (M$^+$).

Compound 14(b)

(S)-3-(N-(1-carboxyethyl)-4-((5-(2-(4-chloro-3-methoxyphenyl)propan-2-yl)-1-(4-fluorophenyl)-1H-imidazol-2-ylthio)methyl)-3,5-difluorophenylsulfonamido)-N,N,N-trimethylpropan-1-aminium 2,2,2-trifluoroacetate

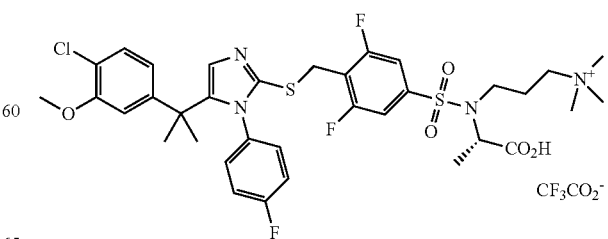

MS (EI) m/z 753 (M$^+$).

Compound 14(c)

(R)-3-(N-(1-carboxyethyl)-3-chloro-4-((5-(2-(3,4-difluoro-5-methoxyphenyl)propan-2-yl)-1-(4-fluorophenyl)-1H-imidazol-2-ylthio)methyl)-5-fluorophenylsulfonamido)-N,N,N-trimethylpropan-1-aminium 2,2,2-trifluoroacetate

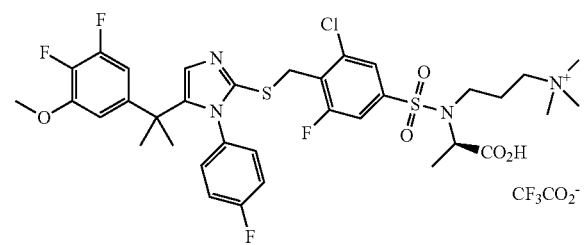

MS (EI) m/z 771 (M+).

Compound 14(d)

(R)-4-(N-(1-carboxyethyl)-4-((5-(2-(4-chloro-3-methoxyphenyl)propan-2-yl)-1-(4-fluorophenyl)-1H-imidazol-2-ylthio)methyl)-3,5-difluorophenylsulfonamido)-N,N,N-trimethylbutan-1-aminium 2,2,2-trifluoroacetate

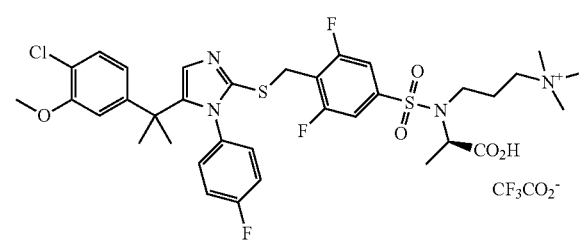

$^1$H NMR (400 MHz, DMSO-d$_6$) δ 7.63 (d, J=6.7 Hz, 2H), 7.41-7.28 (m, 2H), 7.15-7.01 (m, 2H), 6.75-6.64 (m, 2H), 6.64-6.60 (m, 1H), 6.56 (dd, J=8.3, 2.0 Hz, 1H), 4.66 (q, J=7.3 Hz, 1H), 4.09 (s, 2H), 3.75 (s, 3H), 3.41-3.13 (m, 4H), 3.09 (s, 9H), 1.80-1.57 (m, 4H), 1.53 (s, 6H), 1.41 (d, J=7.3 Hz, 3H). MS (EI) m/z 767.6 (M+).

Compound 14(e)

(S)-4-carboxy-4-(3,5-difluoro-4-((5-(2-(4-luoro-3-methoxyphenyl)propan-2-yl)-1-(4-fluorophenyl)-1H-imidazol-2-ylthio)methyl)-N-methylphenylsulfonamido)-N,N,N-trimethylbutan-1-aminium chloride

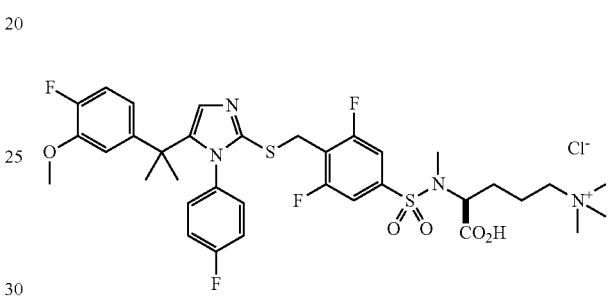

$^1$H NMR (CD$_3$OD, 400 MHz) δ 7.44 (d, 2H), 7.32 (s, 1H), 6.99 (dd, 1H), 6.89 (t, 1H), 6.85 (t, 1H), 6.64 (d, 1H), 6.52 (m, 1H), 6.43 (m, 1H), 6.25 (m, 1H), 4.69 (m, 1H), 3.94 (q, 2H), 3.76 (s, 3H), 3.55 (m, 1H), 3.45 (m, 1H), 3.35 (s, 3H), 2.88 (s, 3H), 2.00 (m, 4H), 1.53 (d, 6H);

MS (EI) m/z 737.2 (M+).

Compound 14(f)

(S)-4-carboxy-4-(4-((5-(2-(3,4-difluoro-5-methoxyphenyl)propan-2-yl)-1-(4-fluorophenyl)-1H-imidazol-2-ylthio)methyl)-3,5-difluoro-N-methylphenylsulfonamido)-N,N,N-trimethylbutan-1-aminium chloride

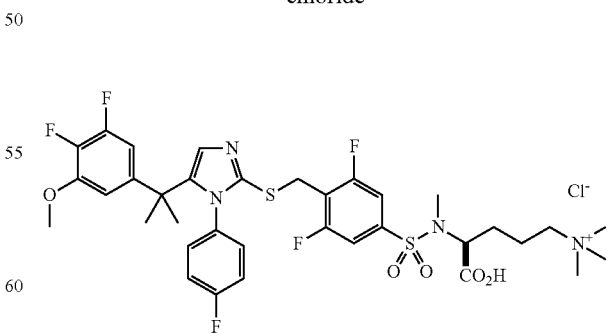

$^1$H NMR (400 MHz, CD$_3$OD) δ 7.98 (s, 1H), 7.48 (d, 2H), 6.96-7.04 (m, 2H), 6.68 (s, 1H), 6.44-6.48 (m, 3H), 4.74 (m,

1H), 4.15 (s, 2H), 3.78 (s, 3H), 3.43-3.50 (m, 2H) 3.17 (s, 9H), 2.83 (s, 3H) 1.93-1.99 (m, 4H), 1.54-1.57 (d, 6H).

Compound 14(g)

(S)-4-carboxy-4-(4-((5-(2-(3-chloro-4-methoxyphenyl)propan-2-yl)-1-(4-fluorophenyl)-1H-imidazol-2-ylthio)methyl)-3,5-difluoro-N-methylphenylsulfonamido)-N,N,N-trimethylbutan-1-aminium chloride

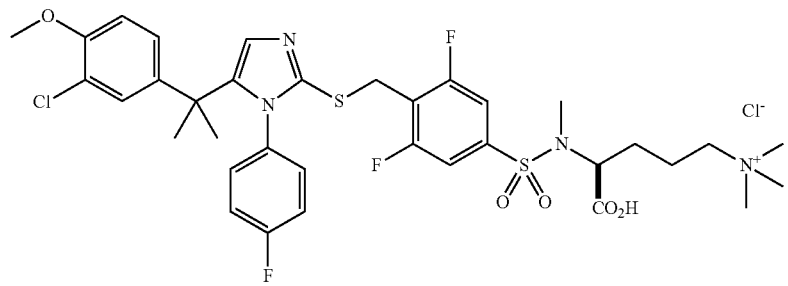

$^1$H NMR (400 MHz, CD$_3$OD) δ 7.91 (s, 1H), 7.55 (d, J=6.78 Hz, 2H), 7.03-6.84 (m, 5H), 6.52-6.40 (m, 2H), 4.78 (m, 1H), 4.15 (s, 2H), 3.91 (s, 3H), 3.52 (m, 2H), 3.19 (s, 9H), 2.87 (s, 3H), 2.10-1.86 (m, 4H), 1.55 (d, J=2.13 Hz, 6H).

Compound 14(h)

(S)-4-carboxy-4-(4-((5-(2-(3-chloro-4-fluorophenyl)propan-2-yl)-1-(4-fluorophenyl)-1H-imidazol-2-ylthio)methyl)-3,5-difluoro-N-methylphenylsulfonamido)-N,N,N-trimethylbutan-1-aminium chloride

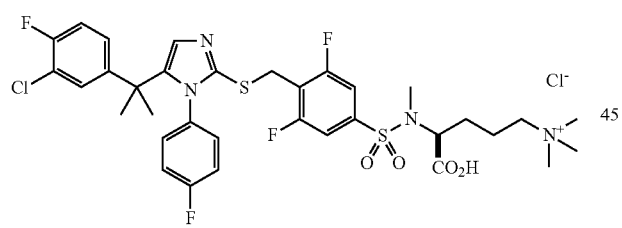

$^1$H NMR (400 MHz, CDCl$_3$) δ 7.84 (s, 1H), 7.59 (d, 2H), 7.30 (t, 1H), 7.08-6.92 (m, 4H), 6.64-6.63 (m, 1H), 6.55-6.54 (m, 1H), 4.55-4.53 (m, 1H), 4.14 (s, 2H), 3.39-3.32 (m, 2H), 3.05 (s, 9H), 2.79 (s, 3H), 1.75-1.68 (m, 4H), 1.48 (d, 6H).

Compound 14(i)

(S)-4-carboxy-4-(4-(2-(5-(2-(4-chloro-3-methoxyphenyl)propan-2-yl)-1-(4-fluorophenyl)-1H-imidazol-2-yl)ethyl)-3,5-difluoro-N-methylphenylsulfonamido)-N,N,N-trimethylbutan-1-aminium chloride

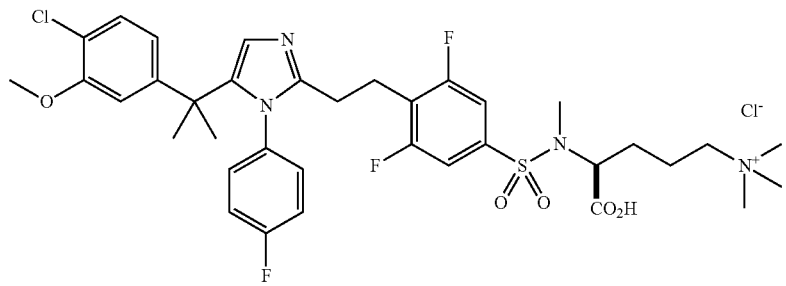

¹H NMR (400 MHz, DMSO) δ 7.80 (brs, 1H), 7.51 (d, J=6.6 Hz, 2H), 7.25 (d, J=8.3 Hz, 1H), 7.18-7.07 (m, 2H), 6.98-6.75 (m, 2H), 6.55 (d, J=2.0 Hz, 1H), 6.51 (dd, J=8.3, 2.1 Hz, 1H), 4.54-4.48 (m, 1H), 3.71 (s, 3H), 3.41-3.21 (m, 2H), 3.10 (s, 9H), 2.89 (t, J=7.6 Hz, 2H), 2.76 (s, 3H), 2.74-2.65 (m, 2H), 1.87-1.61 (m, 4H), 1.51 (s, 6H).

The following compounds [Compounds 14(i)-14(af)] were made by using procedures described in the above example by making any necessary substitutions of known materials that one skilled in the art would ordinarily understand how to do. The following compounds are represented as cations, wherein 2,2,2-trifluoroacetate was used as the counter ion as in the above Example. The counter ion can also be any pharmaceutically acceptable counter ion known to one skilled in the art. It is also understood that the source of the counter ions can be from either intermolecular sources, or, when possible, intramolecular sources.

| Compound 14(j) | 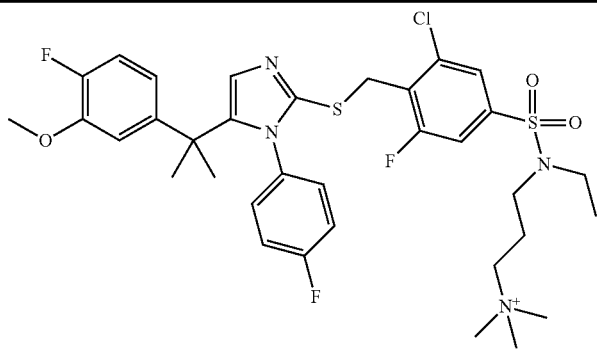 | 3-[{[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]sulfonyl}(ethyl)amino]-N,N,N-trimethylpropan-1-aminium |
| Compound 14(k) | 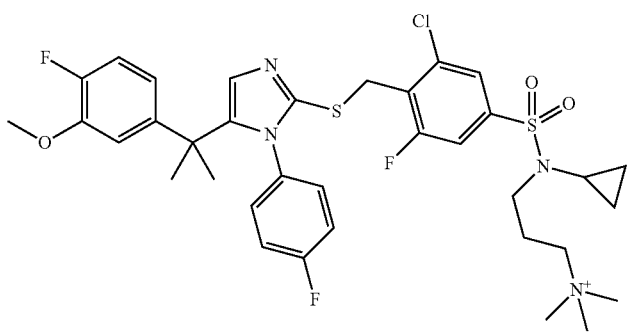 [SMILES: COc1cc(C(C)(C)c2cnc(SCc3c(F)cc(S(=O)(=O)N(CCC[N+](C)(C)C)C4CC4)cc3Cl)n2-c2ccc(F)cc2)ccc1F] | 3-[{[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]sulfonyl}(cyclopropyl)amino]-N,N,N-trimethylpropan-1-aminium |
| Compound 14(l) | 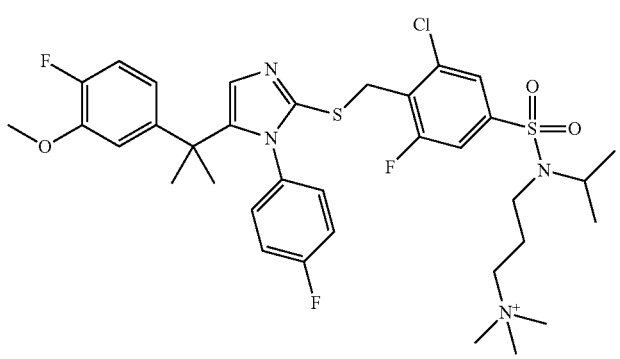 | 3-[{[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]sulfonyl}(1-methylethyl)amino]-N,N,N-trimethylpropan-1-aminium |
| Compound 14(m) | 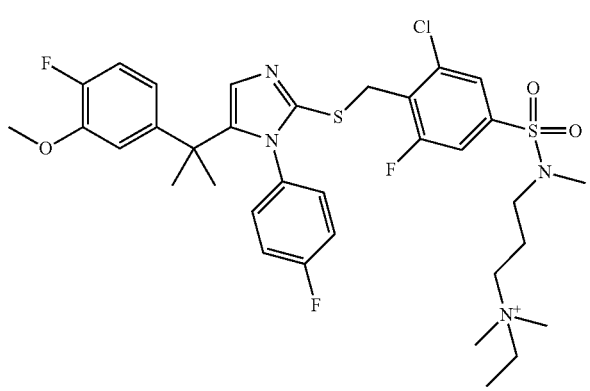 | 3-[{[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]sulfonyl}(methyl)amino]-N-ethyl-N,N-dimethylpropan-1-aminium |

| | | |
|---|---|---|
| Compound 14(n) | 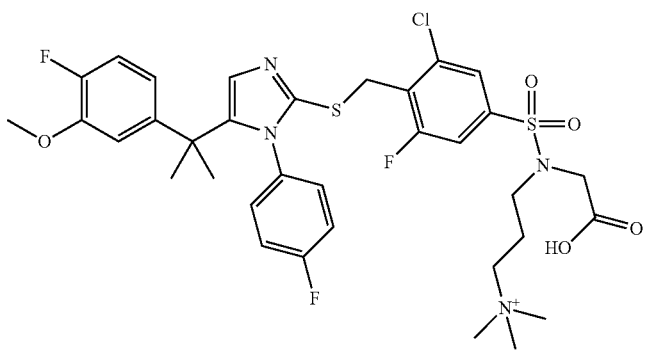 | 3-[(carboxymethyl){[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]sulfonyl}amino]-N,N,N-trimethylpropan-1-aminium |
| Compound 14(o) | 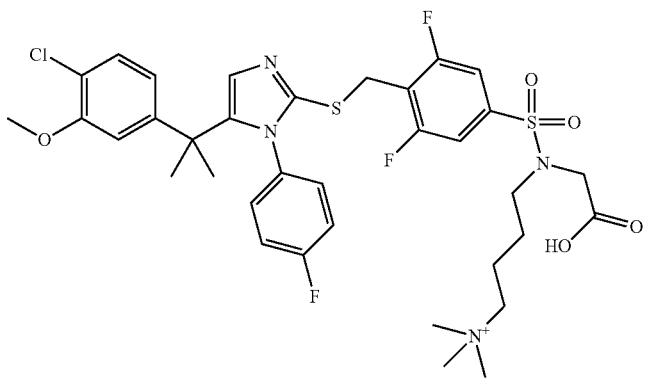 | 4-[(carboxymethyl){[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}amino]-N,N,N-trimethylbutan-1-aminium |
| Compound 14(p) | 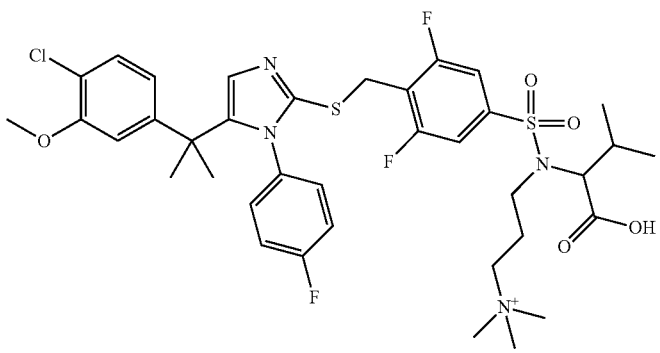 | 3-({[(1S)-1-carboxy-2-methylpropyl]{[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}amino)-N,N,N-trimethylpropan-1-aminium |
| Compound 14(q) | 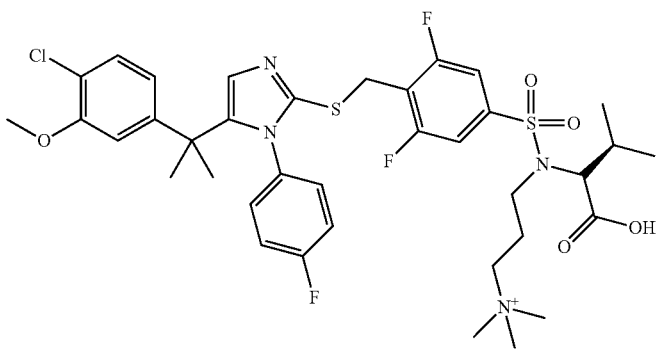 | 3-({[(1R)-1-carboxy-2-methylpropyl]{[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}amino)-N,N,N-trimethylpropan-1-aminium |

| | | |
|---|---|---|
| Compound 14(r) | 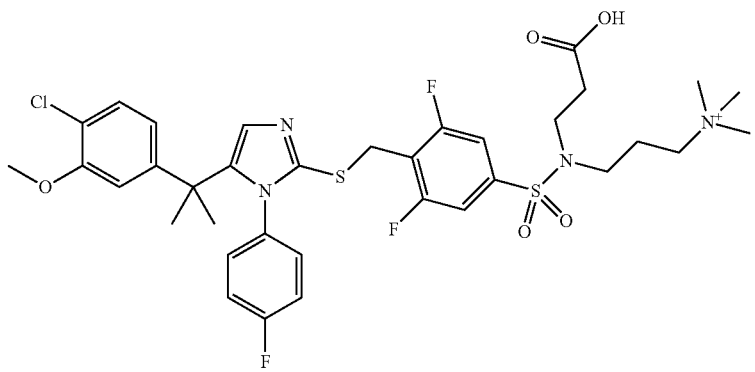 | 3-[(2-carboxyethyl){[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}amino]-N,N,N-trimethylpropan-1-aminium |
| Compound 14(s) | 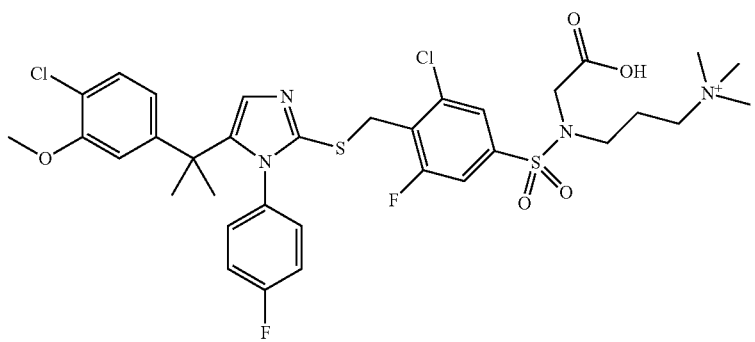 | 3-[(carboxymethyl){[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}amino]-N,N,N-trimethylpropan-1-aminium |
| Compound 14(t) | 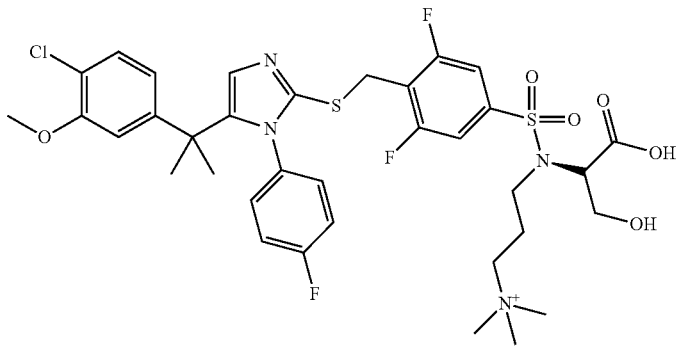 | 3-({[(1S)-1-carboxy-2-hydroxyethyl]{[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}amino)-N,N,N-trimethylpropan-1-aminium |
| Compound 14(u) | 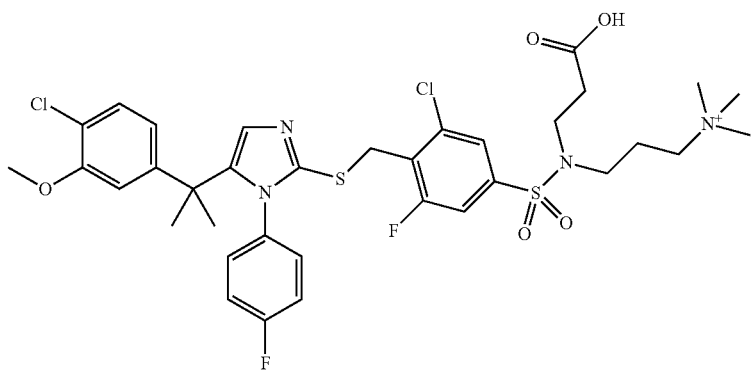 | 3-[(2-carboxyethyl){[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl)sulfonyl}amino]-N,N,N-trimethylpropan-1-aminium |

| | | |
|---|---|---|
| Compound 14(v) | 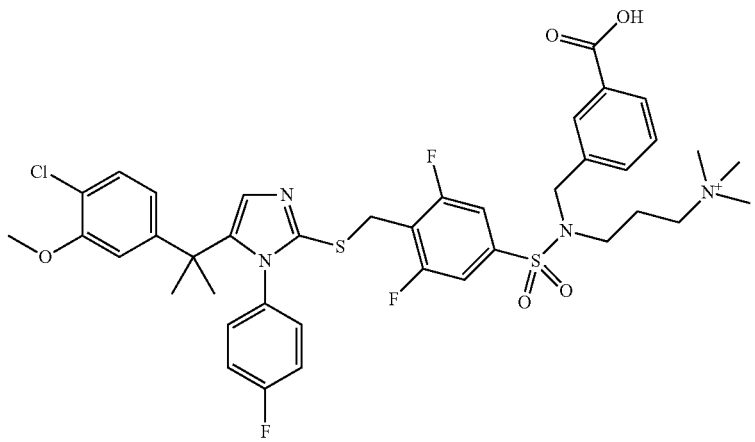 | 3-([(3-carboxyphenyl)methyl]{[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}amino)-N,N,N-trimethylpropan-1-aminium |
| Compound 14(w) | 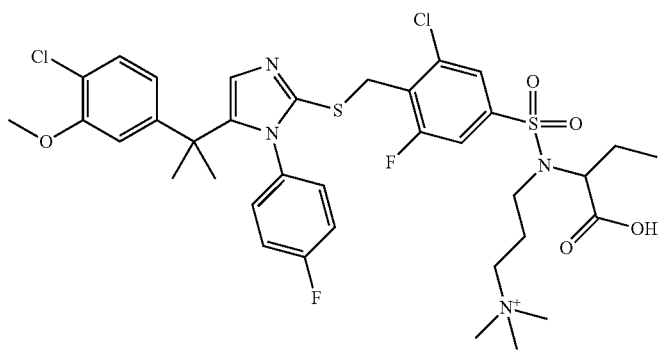 | 3-([[(1S)-1-carboxypropyl]{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}amino)-N,N,N-trimethylpropan-1-aminium |
| Compound 14(x) | 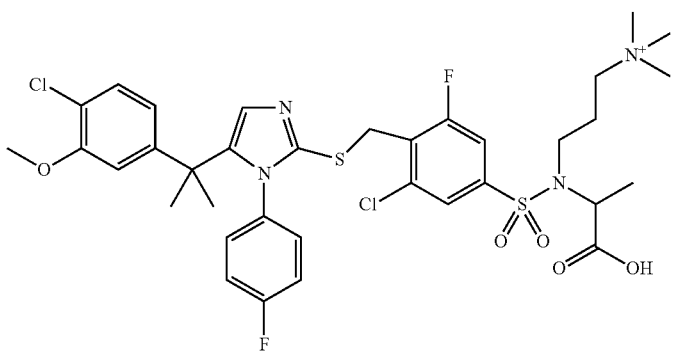 | 3-([[(1S)-1-carboxyethyl]{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}amino)-N,N,N-trimethylpropan-1-aminium |
| Compound 14(y) | 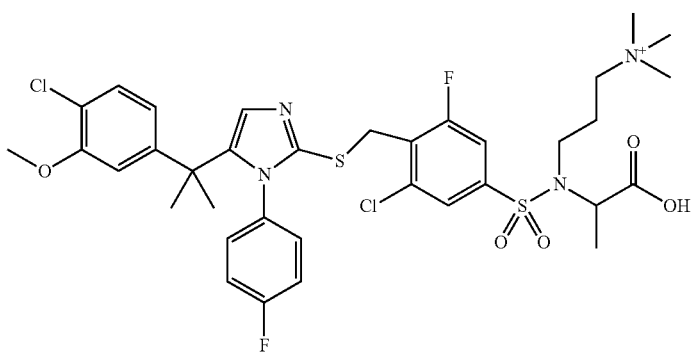 [SMILES: COc1cc(C(C)(C)c2cnc(SCc3c(F)cc(S(=O)(=O)N(CCC[N+](C)(C)C)C(C)C(=O)O)cc3Cl)n2-c2ccc(F)cc2)ccc1Cl] | 3-([[(1R)-1-carboxyethyl]{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}amino)-N,N,N-trimethylpropan-1-aminium |

-continued

| | | |
|---|---|---|
| Compound 14(z) | 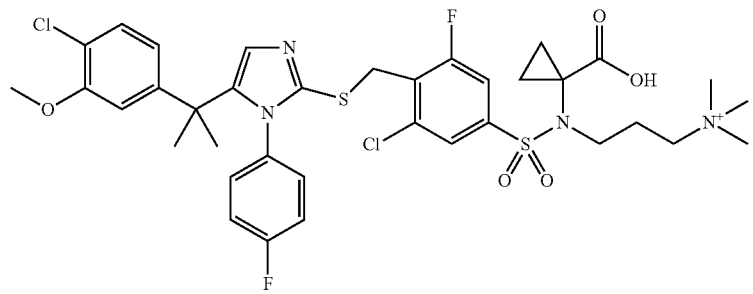 | 3-[(1-carboxycyclopropyl){[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}amino]-N,N,N-trimethylpropan-1-aminium |
| Compound 14(aa) | 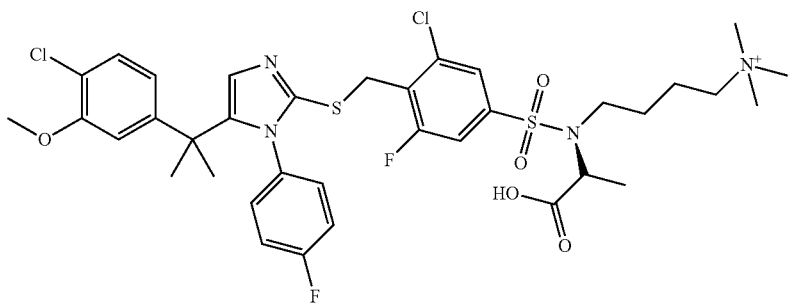 | 4-([(1R)-1-carboxyethyl]{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}amino)-N,N,N-trimethylbutan-1-aminium |
| Compound 14(ab) | 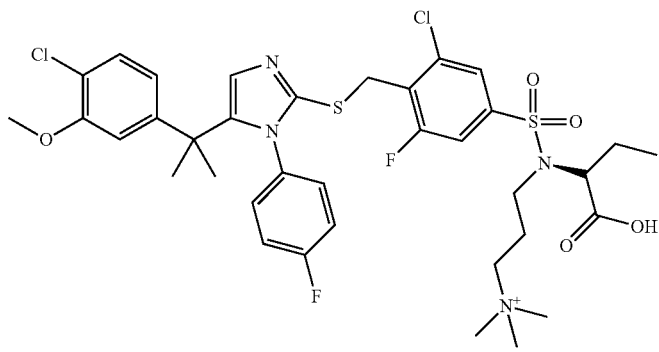 | 3-([(1R)-1-carboxypropyl]{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}amino)-N,N,N-trimethylpropan-1-aminium |
| Compound 14(ac) | 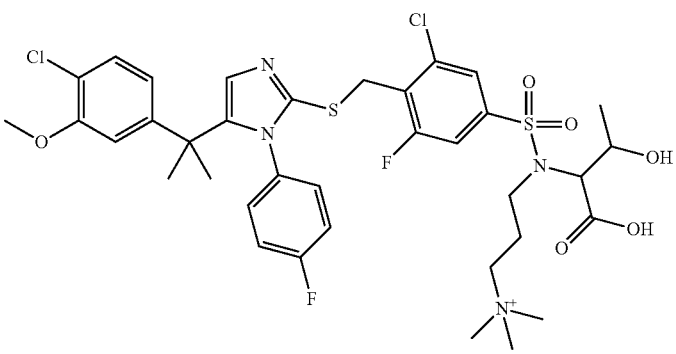 [SMILES: COc1cc(C(C)(C)c2cnc(SCc3c(F)cc(S(=O)(=O)N(CCC[N+](C)(C)C)C(C(=O)O)C(C)O)cc3Cl)n2-c2ccc(F)cc2)ccc1Cl] | 3-([(1S,2R)-1-carboxy-2-hydroxypropyl]{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}amino)-N,N,N-trimethylpropan-1-aminium |
| Compound 14(ad) | 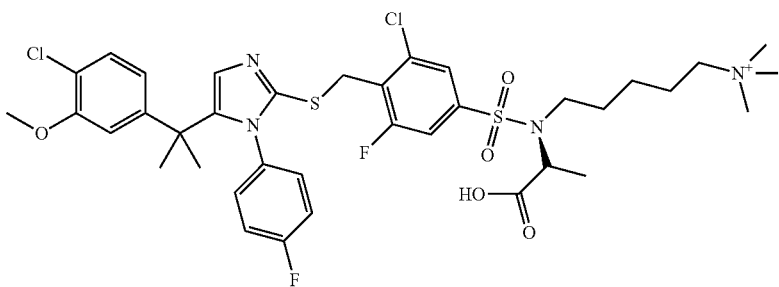 | 5-([(1R)-1-carboxyethyl]{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}amino)-N,N,N-trimethylpentan-1-aminium |

| | | |
|---|---|---|
| Compound 14(ae) | 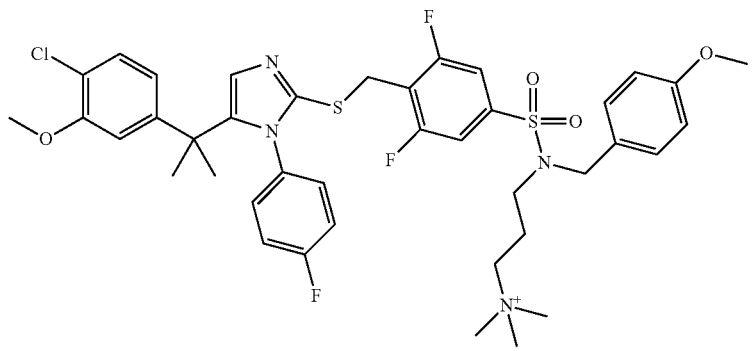 | 3-({[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}{[4-(methyloxy)phenyl]methyl}amino)-N,N,N-trimethylpropan-1-aminium<br>MS (EI) m/z 801 (M⁺). |
| Compound 14(af) | 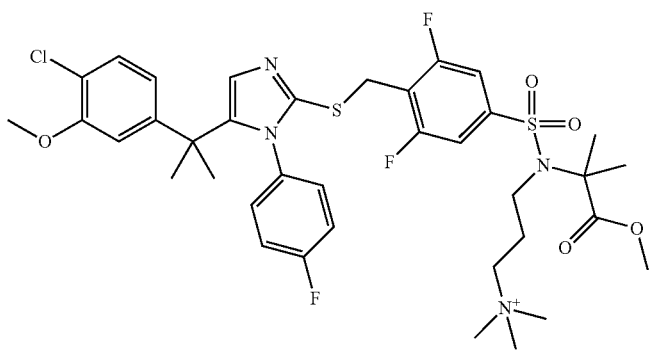 | 3-({[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}[1,1-dlmethyl-2-(methyloxy)-2-oxoethyl]amino)-N,N,N-trimethylpropan-1-aminium |
| Compound 14(ag) | 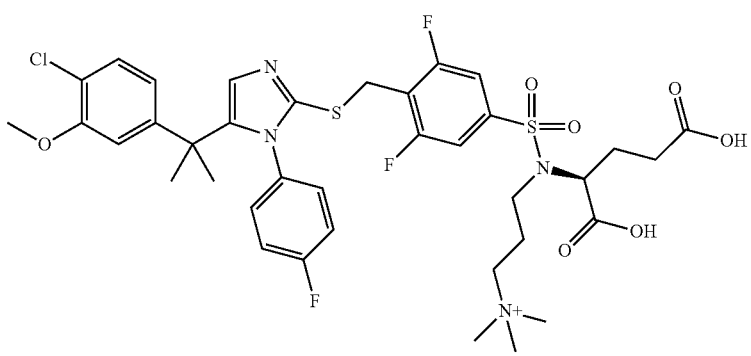 [SMILES: COc1cc(C(C)(C)c2cnc(SCc3c(F)cc(S(=O)(=O)N(CCC[N+](C)(C)C)[C@@H](CCC(=O)O)C(=O)O)cc3F)n2-c2ccc(F)cc2)ccc1Cl] | (S)-3-(4-((5-(2-(4-chloro-3-methoxyphenyl)propan-2-yl)-1-(4-fluorophenyl)-1H-imidazol-2-ylthio)methyl)-N-(1,3-dicarboxypropyl)-3,5-difluorophenylsulfonamido)-N,N,N-trimethylpropan-1-aminium |

The following compounds [Compounds 14(ah)-14(aj)] were made by using procedures described in the above example by making any necessary substitutions of known materials that one skilled in the art would ordinarily understand how to do. The counter ion used in these examples was 2,2,2-trifluoroacetate, but it can also be any pharmaceutically acceptable counter ion known to one skilled in the art. It is also understood that the source of the counter ions can be from either intermolecular sources, or, when possible, intramolecular sources.

Compound 14(ah)

3-(N-(2-carboxypropan-2-yl)-4-((5-(2-(4-chloro-3-methoxyphenyl)propan-2-yl)-1-(4-fluorophenyl)-1H-imidazol-2-ylthio)methyl)-3, -difluorophenylsulfonamido)-N,N,N-trimethylpropan-1-aminium 2,2,2-trifluoroacetate

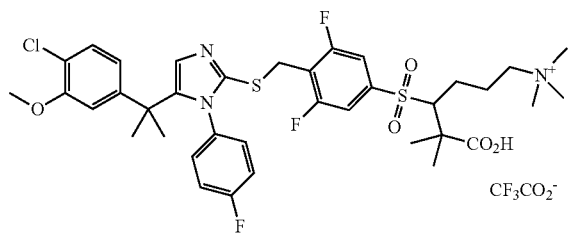

$^1$H NMR (400 MHz, DMSO-d$_6$) δ 7.62 (d, J=6.9 Hz, 2H), 7.36 (s, 1H), 7.25 (d, J=8.3 Hz, 1H), 7.02 (t, J=8.7 Hz, 2H), 6.70-6.59 (m, 2H), 6.55 (d, J=2.0 Hz, 1H), 6.50 (dd, J=8.3, 2.0 Hz, 1H), 4.05 (s, 2H), 3.70 (s, 3H), 3.37-3.20 (m, 4H), 3.05 (s, 9H), 2.10-1.95 (m, 2H), 1.55 (s, 6H), 1.49 (s, 6H); MS (EI) m/z 767.6 (M$^+$).

Compound 14(ai)

4-(N-(2-carboxypropan-2-yl)-4-((5-(2-(4-chloro-3-methoxyphenyl)propan-2-yl)-1-(4-fluorophenyl)-1H-imidazol-2-ylthio)methyl)-3,5-difluorophenylsulfonamido)-N,N,N-trimethylbutan-1-aminium 2,2,2-trifluoroacetate

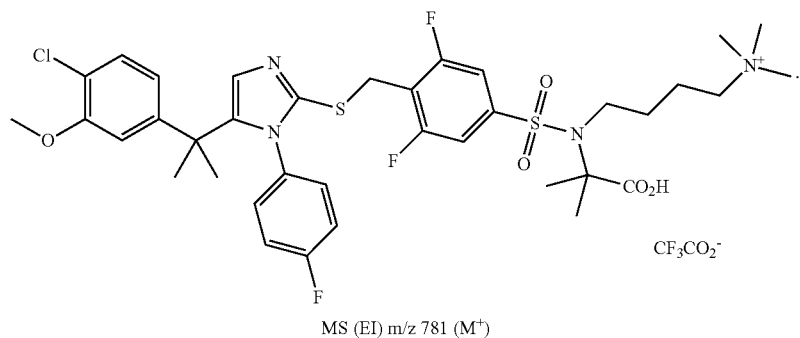

MS (EI) m/z 781 (M$^+$)

Compound 14(aj)

(R)-3-(N-(1-carboxypropan-2-yl)-3-chloro-4-((5-(2-(4-chloro-3-methoxyphenyl)-propan-2-yl)-1-(4-fluorophenyl)-1H-imidazol-2-ythio)methyl)-5-fluorophenyl-sulfonamido)-N,N,N-trimethylpropan-1-aminium 2,2,2-trifluoroacetate

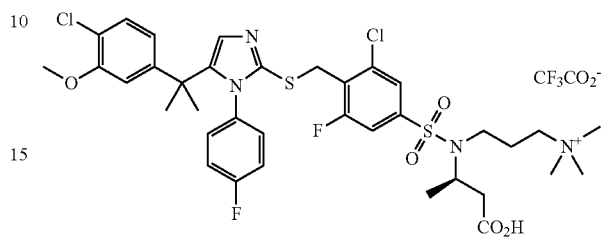

$^1$H NMR (400 MHz, DMSO-d$_6$) δ 7.71 (s, 1H), 7.66 (dd, J=8.7, 1.6 Hz, 1H), 7.36 (s, 1H), 7.28-7.22 (m, 1H), 7.06-6.96 (m, 2H), 6.68-6.60 (m, 2H), 6.56-6.47 (m, 2H), 4.18 (dd, J=14.0, 6.9 Hz, 1H), 4.04 (s, 2H), 3.69 (s, 3H), 3.37-3.22 (m, 4H), 3.08 (s, 9H), 2.56-2.52 (m, 1H), 2.47-2.37 (m, 1H), 2.04 (dd, J=18.9, 10.6 Hz, 2H), 1.48 (s, 6H), 1.11 (d, J=6.7 Hz, 3H); MS (EI) m/z 783 [M]$^+$.

Example 15

(R)-4-((4-((5-(2-(4-chloro-3-methoxyphenyl)propan-2-yl)-1-(4-fluorophenyl)-1H-imidazol-2-ylthio)methyl)-3,5-difluoro-N-(1-methoxy-1-oxopropan-2-yl)phenyl-sulfonamido)methyl)-1,1-dimethylpiperidinium 2,2,2-trifluoroacetate

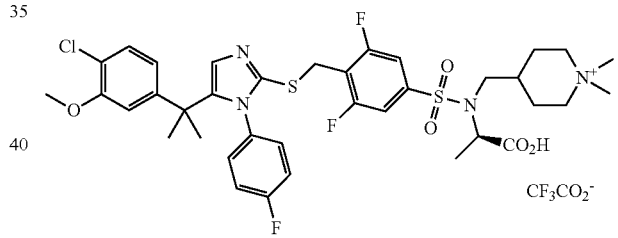

Diisopropyl azodicarboxylate (0.185 mL, 0.94 mmol) was added to a solution of (R)-methyl 2-(4-((5-(2-(4-chloro-3-methoxyphenyl)propan-2-yl)-1-(4-fluorophenyl)-1H-imidazol-2-ylthio)-methyl)-3,5-difluorophenylsulfonamido)propanoate (0.314 g, 0.47 mmol), 4-(hydroxymethyl)-1,1-dimethylpiperidinium iodide (0.24 g, 0.89 mmol) and triphenyl phosphine (0.25 g, 0.94 mmol) in THF (1.5 mL). The reaction was stirred 1 h at 65° C. and then concentrated in vacuo. To the material dissolved in $H_2O$ (0.5 mL) and THF (0.5 mL) was added $LiOH.H_2O$ (50 mg). After stirring 2 h, the reaction mixture was filtered and purified by HPLC using ($CH_3CN$, $H_2O$ with 0.1% TFA, 10-99%) to afford the title compound (63 mg) as a white solid. $^1H$ NMR (400 MHz, DMSO-$d_6$) δ 7.62-7.51 (m, 2H), 7.37 (s, 1H), 7.26 (d, J=82.1 Hz, 1H), 4.56 (q, J=7.2 Hz, 1H), 4.04 (s, 2H), 3.68 (s, 3H), 3.50-3.38 (m, 2H), 3.35-3.17 (m, 3H), 3.18-2.93 (m, 7H), 1.87 (d, J=10.4 Hz, 3H), 1.70-1.52 (m, 2H), 1.48 (s, 6H), 1.33 (d, J=7.3 Hz, 3H); MS (ES) m/z 779 $[M]^+$.

Compound 15(a)

(R)-1-(3-(N-(1-carboxyethyl)-3-chloro-4-((5-(2-(4-chloro-3-methoxyphenyl)propan-2-yl)-1-(4-fluorophenyl)-1H-imidazol-2-ylthio)methyl)-5-fluorophenylsulfonamido)propyl)pyridinium chloride

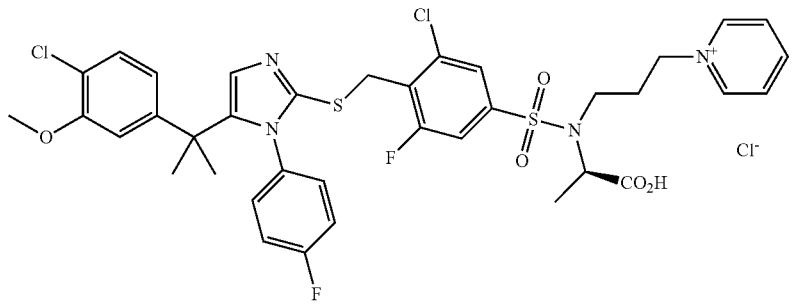 [SMILES: COc1cc(C(C)(C)c2cnc(SCc3c(F)cc(S(=O)(=O)N(CCC[n+]4ccccc4)[C@H](C)C(=O)O)cc3Cl)n2-c2ccc(F)cc2)ccc1Cl ; [Cl-]]

$^1H$ NMR (400 MHz, $CDCl_3$) δ 9.06 (d, J=5.4 Hz, 2H), 8.66-8.51 (m, 1H), 8.17-8.03 (m, 2H), 7.69-7.57 (m, 1H), 7.51-7.40 (m, 1H), 7.21 (s, 2H), 6.80 (s, 2H), 6.53 (s, 2H), 6.45-6.26 (m, 2H), 4.85 (s, 3H), 4.48-4.30 (m, 1H), 4.01 (s, 2H), 3.69 (s, 4H), 3.61-3.45 (m, 1H), 2.45-2.23 (m, 2H), 1.33-1.19 (m, 5H), 1.50 (s, 6H); MS (EI) m/z 789 ($M^+$).

The following compounds can be made by using procedures described in the above example by making any necessary substitutions of known materials that one skilled in the art would ordinarily understand how to do. The following compounds are represented as cations, and these cations are understood, to those skilled in the art, to be in the presence of a counter ion. These counter ions can be any pharmaceutically acceptable counter ion known to one skilled in the art, including, but not limited to, the counter ions described in the example(s) described herein. It is also understood that the source of the counter ions can be from either intermolecular sources, or, when possible, intramolecular sources.

(R)-3-(3-(N-(1-carboxyethyl)-3-chloro-4-((5-(2-(4-chloro-3-methoxyphenyl)propan-2-yl)-1-(4-fluorophenyl)-1H-imidazol-2-ylthio)methyl)-5-fluorophenylsulfonamido)propyl)-1-methyl-1H-imidazol-3-ium chloride Compound 15(b)

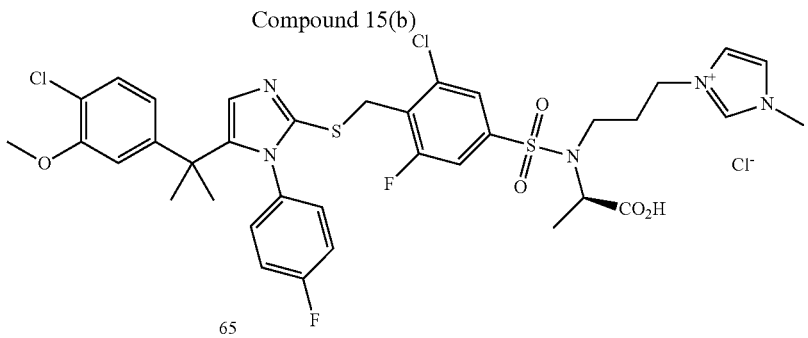

MS (EI) m/z 792 ($M^+$).

(R)-3-(2-(N-(1-carboxyethyl)-3-chloro-4-((5-(2-(4-chloro-3-methoxyphenyl)propan-2-yl)-1-(4-fluorophenyl)-1H-imidazol-2-ylthio)methyl)-5-fluorophenylsulfonamido)ethyl)-1-methylpyridinium chloride Compound 15(c)

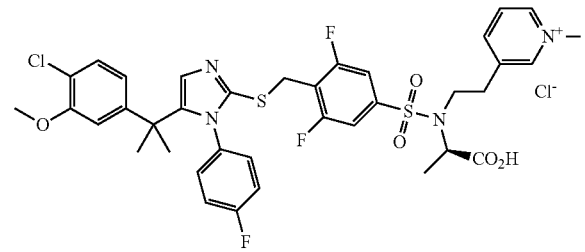

MS (EI) m/z 789 (M$^+$).

Example 16

(S)-4-carboxy-4-(4-((5-(2-(4-chloro-3-methoxyphenyl)propan-2-yl)-1-(4-fluorophenyl)-1H-imidazol-2-ylthio)methyl)-3,5-difluoro-N-methylphenylsulfonamido)-N,N,N-trimethylbutan-1-aminium 2,2,2-trifluoroacetate

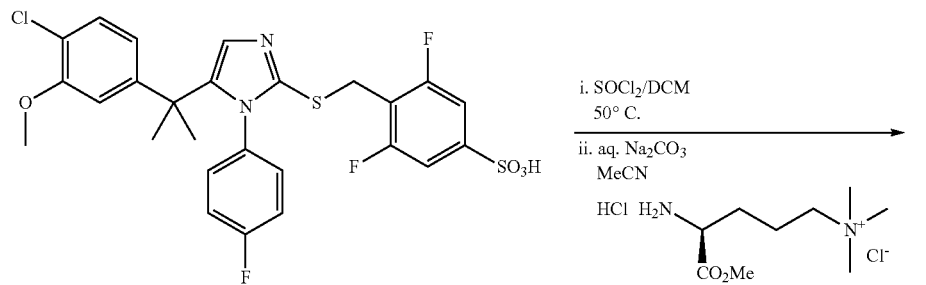

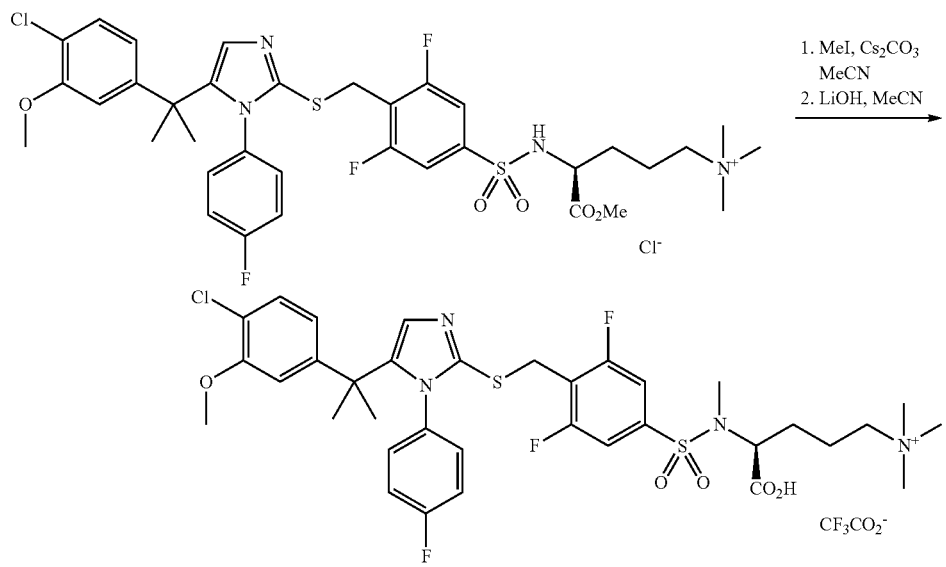

To 4-((5-(2-(4-chloro-3-methoxyphenyl)propan-2-yl)-1-(4-fluorophenyl)-1H-imidazol-2-ylthio)methyl)-3,5-difluorobenzenesulfonic acid (1.2 g, 2.1 mmol, 1.1 eq) in DCM (6 mL) was added thionyl chloride (3 mL) followed by catalytic DMF (30 drops). After heating at 40° C. for 1 h, the reaction mixture was concentrated under reduced pressure and the resulting sulfonyl chloride was further dried on a high-vacuum pump for several hours. A solution of this sulfonyl chloride in MeCN (12 mL) was added to another flask containing (S)-4-amino-5-methoxy-N,N,N-trimethyl-5-oxopentan-1-aminium chloride hydrochloride (2.0 g, 7.5 mmol, 4.0 eq) and aq. Na$_2$CO$_3$ (2.0 g, 18.7 mmol, 10 eq, in 12 mL of water). The reaction mixture was stirred vigorously for 10 min. The organic layer was removed by pipette and concentrated to yield (S)-4-(4-((5-(2-(4-chloro-3-methoxyphenyl)propan-2-yl)-1-(4-fluorophenyl)-1H-imidazol-2-ylthio)methyl)-3,5-difluorophenylsulfonamido)-5-methoxy-N,N,N-trimethyl-5-oxopentan-1-aminium chloride (1.56 g, over theoretical), which was used in the next step without purification. MS (EI) m/z 601 (M$^+$).

To a solution of (S)-4-(4-((5-(2-(4-chloro-3-methoxyphenyl)propan-2-yl)-1-(4-fluorophenyl)-1H-imidazol-2-ylthio)methyl)-3,5-difluorophenylsulfonamido)-5-methoxy-N,N,N-trimethyl-5-oxopentan-1-aminium chloride (1.87 mmol, 1.0 eq) in MeCN (2 mL) was added cesium carbonate (1.8 g, 5.6 mmol, 3.0 eq), followed by iodomethane (0.18 mL, 2.8 mmol, 1.5 eq). After 1 h at room temperature, the mixture was diluted with MeCN (2 mL) and 2N LiOH (4 mL) was added. After 25 min, the hydrolysis was complete as observed by LCMS and the reaction mixture was acidified to pH 6 with 6N HCl followed by 1N HCl. The mixture was directly purified by preparative HPLC (20-100% MeCN/water, 0.1% TFA, 17 min.) to provide the title compound (1.0 g, 63% over 3 steps). $^1$H NMR (400 MHz, DMSO-d$_6$) δ 7.56 (d, J=6.7 Hz, 2H), 7.42 (s, 1H), 7.26 (d, J=8.3 Hz, 1H), 7.07-6.96 (m, 2H), 6.69-6.54 (m, 3H), 6.50 (dd, J=8.3, 2.0 Hz, 1H), 4.58-4.48 (m, 1H), 4.06 (s, 2H), 3.69 (s, 3H), 3.38-3.30 (m, 2H), 3.04 (s, 9H), 2.80 (s, 3H), 1.90-1.63 (m, 4H), 1.49 (s, 3H), 1.48 (s, 3H); $^{19}$F NMR (376 MHz, DMSO) δ −74.53 (s, 3F), −111.48-111.56 (m, 2F), −111.73 (s, 1F); MS (EI) m/z 753 (M$^+$).

Example 17

(S)-2-(4-((5-(2-(4-chloro-3-methoxyphenyl)propan-2-yl)-1-(4-fluorophenyl)-1H-imidazol-2-ylthio)methyl)-3,5-difluoro-N-methylphenylsulonamido)-5-trimethylammonio)pentanoate

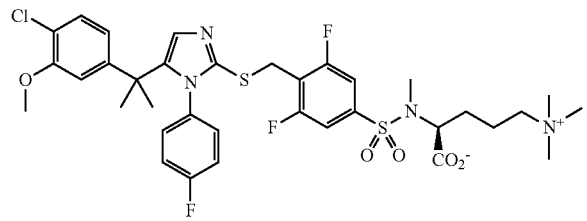

The title compound can be obtained upon HPLC purification of the previous product without a modifier (e.g. 0 to 100% MeCN/water, no TFA). $^1$H NMR (400 MHz, DMSO-d$_6$) δ 7.81 (d, J=7.1 Hz, 2H), 7.25 (d, J=8.3 Hz, 1H), 7.20 (s, 1H), 7.05-6.92 (m, 2H), 6.62-6.52 (m, 2H), 6.51-6.44 (m, 2H), 4.02 (s, 2H), 4.02-3.96 (m, 1H), 3.68 (s, 3H), 3.37-3.30 (m, 2H), 3.05 (s, 9H), 2.70 (s, 3H), 1.96-1.83 (m, 1H), 1.79-1.62 (m, 2H), 1.57-1.49 (m, 1H), 1.46 (s, 6H); $^{19}$F NMR (376 MHz, DMSO) δ −111.95-112.03 (m, 2F), −112.35-112.45 (m, 1F); MS (EI) m/z 753 (M$^+$).

(S)-4-carboxy-4-(4-((5-(2-(4-chloro-3-methoxyphenyl)propan-2-yl)-1-(4-fluorophenyl)-1H-imidazol-2-ylthio)methyl)-3,5-difluoro-N-methylphenylsulfonamido)-N,N,N-trimethylbutan-1-aminium chloride A solution of (S)-2-(4-((5-(2-(4-chloro-3-methoxyphenyl)propan-2-yl)-1-(4-fluorophenyl)-1H-imidazol-2-ylthio)methyl)-3,5-difluoro-N-methylphenylsulfonamido)-5-(trimethylammonio)-pentanoate in water was treated with 1N HCl (1.0 eq) and lyophilized to yield the title compound in quantitative yield. $^1$H NMR (400 MHz, DMSO-d$_6$) δ 13.14 (s, 1H), 7.55 (d, J=6.7 Hz, 2H), 7.29 (s, 1H), 7.26 (d, J=8.3 Hz, 1H), 7.05-6.96 (m, 2H), 6.68-6.60 (m, 1H), 6.60-6.53 (m, 2H), 6.50 (dd, J=8.3, 2.0 Hz, 1H), 4.53 (dd, J=9.5, 4.7 Hz, 1H), 4.05 (s, 2H), 3.69 (s, 3H), 3.39-3.27 (m, 2H), 3.04 (s, 9H), 2.80 (s, 3H), 1.91-1.60 (m, 4H), 1.48 (s, 3H), 1.47 (s, 3H); $^{19}$F NMR (376 MHz, DMSO) δ −111.37-111.46 (m, 2F), −112.02-112.11 (m, 1F); MS (EI) m/z 753 (M$^+$).

The following compounds [Compounds 17(a)-17(o)] were made by using procedures described in the above example by making any necessary substitutions of known materials that one skilled in the art would ordinarily understand how to do. The counter ion used in these examples was 2,2,2-trifluoroacetate, but it can also be any pharmaceutically acceptable counter ion known to one skilled in the art. It is also understood that the source of the counter ions can be from either intermolecular sources, or, when possible, intramolecular sources.

Compound 17(a)

(S)-4-carboxy-4-(4-((5-(2-(4-chloro-3-methoxyphenyl)propan-2-yl)-1-(4-fluorophenyl)-1H-imidazol-2-ylthio)methyl)-N-ethyl-3,5-difluorophenylsulfonamido)-N,N,N-trimethylbutan-1-aminium 2,2,2-trifluoroacetate

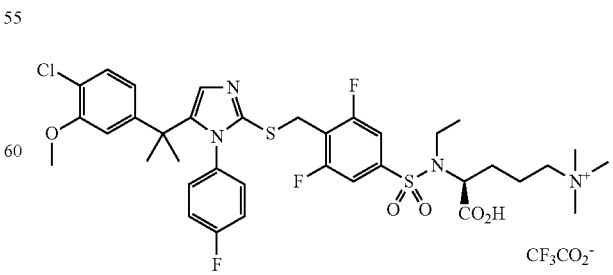

MS (EI) m/z 767 (M$^+$).

Compound 17(b)

(S)-4-carboxy-4-(3-chloro-4-((5-(2-(4-chloro-3-methoxyphenyl)propan-2-yl)-1-(4-fluorophenyl)-1H-imidazol-2-ylthio)methyl)-5-fluoro-N-methylphenylsulfonamido)-N,N,N-trimethylbutan-1-aminium 2,2,2-trifluoroacetate

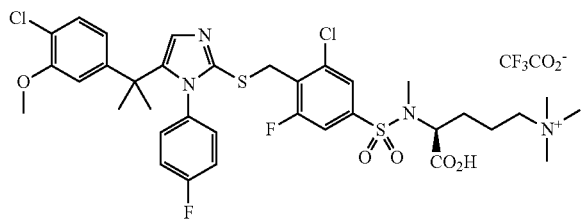 [SMILES: COc1cc(C(C)(C)c2cnc(SCc3c(F)cc(S(=O)(=O)N(C)[C@@H](CCC[N+](C)(C)C)C(=O)O)cc3Cl)n2-c2ccc(F)cc2)ccc1Cl ; "CF3CO2-"]

$^1$H NMR (400 MHz, MeOD) δ 7.88 (s, 1H), 7.80 (s, 1H), 7.63 (dd, J=8.8, 1.6 Hz, 1H), 7.29 (d, J=8.2 Hz, 1H), 7.00-6.89 (m, 2H), 6.62-6.50 (m, 3H), 6.46-6.38 (m, 1H), 4.79 (dd, J=10.3, 4.1 Hz, 1H), 4.29-4.19 (m, 2H), 3.75 (s, 3H), 3.60-3.39 (m, 2H), 3.21 (s, 9H), 2.88 (s, 3H), 2.10-1.90 (m, 4H), 1.62 (s, 3H), 1.61 (s, 3H); MS (EI): 769.4 (M$^+$).

Compound 17(c)

(R)-4-carboxy-4-(4-((5-(2-(4-chloro-3-methoxyphenyl)propan-2-yl)-1-(4-fluorophenyl)-1H-imidazol-2-ylthio)methyl)-3,5-difluoro-N-methylphenylsulfonamido)-N,N,N-trimethylbutan-1-aminium 2,2,2-trifluoroacetate

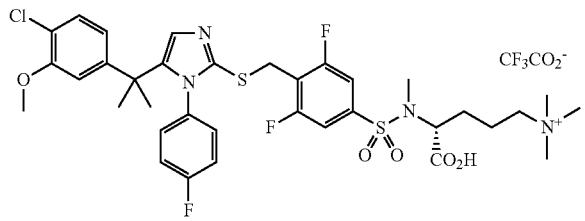 [SMILES: COc1cc(C(C)(C)c2cnc(SCc3c(F)cc(S(=O)(=O)N(C)[C@H](CCC[N+](C)(C)C)C(=O)O)cc3F)n2-c2ccc(F)cc2)ccc1Cl ; "CF3CO2-"]

$^1$H NMR (400 MHz, DMSO) δ 7.55 (d, J=6.7 Hz, 2H), 7.32 (s, 1H), 7.26 (d, J=8.3 Hz, 1H), 7.06-6.93 (m, 2H), 6.68-6.52 (m, 3H), 6.50 (dd, J=8.3, 2.0 Hz, 1H), 4.52 (dd, J=9.5, 4.7 Hz, 1H), 4.03 (s, 2H), 3.68 (s, 3H), 3.41-3.24 (m, 2H), 3.03 (s, 9H), 2.79 (s, 3H), 1.88-1.58 (m, 4H), 1.48 (s, 3H), 1.47 (s, 3H); MS (EI): 753.5 (M$^+$).

Compound 17(d)

(R)-4-carboxy-4-(3-chloro-4-((5-(2-(4-chloro-3-methoxyphenyl)propan-2-yl)-1-(4-fluorophenyl)-1H-imidazol-2-ylthio)methyl)-5-fluoro-N-methylphenylsulfonamido)-N,N,N-trimethylbutan-1-aminium 2,2,2-trifluoroacetate

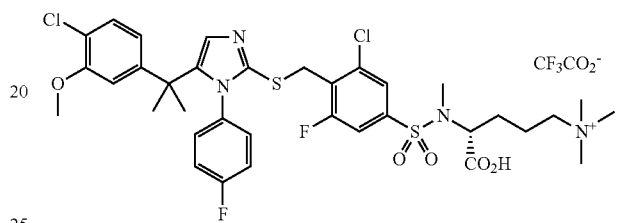

$^1$H NMR (400 MHz, MeOD) δ 7.87 (s, 1H), 7.79 (s, 1H), 7.62 (dd, J=8.8, 1.6 Hz, 1H), 7.28 (d, J=8.1 Hz, 1H), 6.98-6.88 (m, 2H), 6.59-6.49 (m, 3H), 6.44-6.37 (m, 1H), 4.78 (dd, J=10.4, 4.2 Hz, 1H), 4.27-4.17 (m, 2H), 3.73 (s, 3H), 3.60-3.37 (m, 2H), 3.19 (s, 9H), 2.86 (s, 3H), 2.08-1.89 (m, 4H), 1.61 (s, 3H), 1.59 (s, 3H); MS (EI): 769.5 (M$^+$).

Compound 17(e)

(S)-5-carboxy-5-(3-chloro-4-((5-(2-(4-chloro-3-methoxyphenyl)propan-2-yl)-1-(4-fluorophenyl)-1H-imidazol-2-ylthio)methyl)-5-fluorophenylsulfonamido)-N,N,N-trimethylpentan-1-aminium 2,2,2-trifluoroacetate

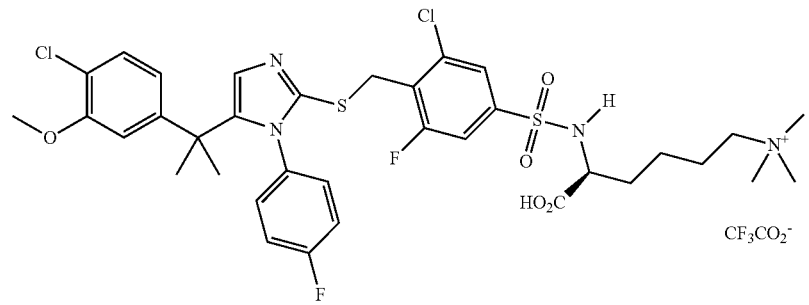

¹H NMR (400 MHz, MeOD) δ 7.72 (s, 1H), 7.69 (s, 1H), 7.53 (dd, J=8.8, 1.5 Hz, 1H), 7.27-7.21 (m, 1H), 6.95-6.91 (m, 2H), 6.59-6.51 (m, 3H), 6.46-6.38 (m, 1H), 4.17-4.06 (m, 2H), 4.01 (dd, J=9.4, 4.7 Hz, 1H), 3.73 (s, 3H), 3.44-3.33 (m, 2H), 3.15 (s, 9H), 2.03-1.72 (m, 4H), 1.59 (s, 3H), 1.58 (s, 3H); MS (ESI) m/z 769.5 [M]⁺.

Compound 17(f)

(S)-5-carboxy-5-(3-chloro-4-((5-(2-(4-chloro-3-methoxyphenyl)propan-2-yl)-1-(4-fluorophenyl)-1H-imidazol-2-ylthio)methyl)-5-fluoro-N-methylphenyl-sulfonamido)-N,N,N-trimethylpentan-1-aminium 2,2,2-trifluoroacetate

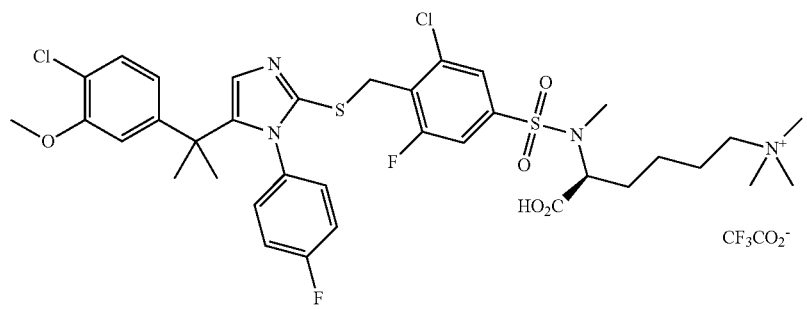

¹H NMR (400 MHz, MeOD) δ 7.72 (s, 1H), 7.62 (s, 1H), 7.54 (dd, J=8.8, 1.6 Hz, 1H), 7.27-7.23 (m, 1H), 6.95-6.84 (m, 2H), 6.59-6.48 (m, 3H), 6.41-6.33 (m, 1H), 4.72 (dd, J=11.2, 4.5 Hz, 1H), 4.17-4.07 (m, 2H), 3.73 (s, 3H), 3.47-3.33 (m, 2H), 3.16 (s, 9H), 2.85 (s, 3H), 2.13-1.76 (m, 4H), 1.58 (s, 3H), 1.56 (s, 3H), 1.50 (dd, J=10.1, 5.4 Hz, 2H); MS (ESI) m/z 783.5 [M]⁺.

Compound 17(g)

(S)-5-carboxy-5-(4-((5-(2-(4-chloro-3-methoxyphenyl)propan-2-yl)-1-(4-fluorophenyl)-1H-imidazol-2-ylthio)methyl)-3,5-difluoro-N-methylphenylsulfonamido)-N,N,N-trimethylpentan-1-aminium 2,2,2-trifluoroacetate

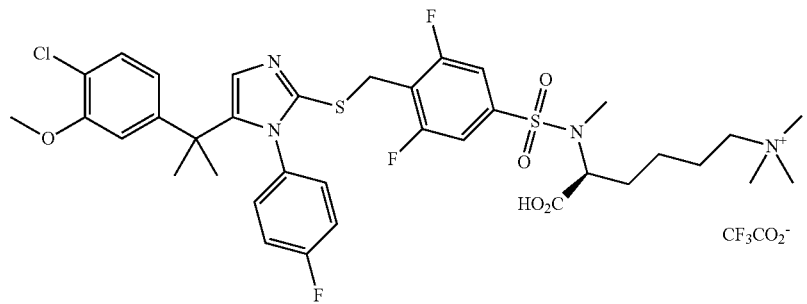

¹H NMR (400 MHz, MeOD) δ 7.79 (s, 1H), 7.53-7.45 (m, 2H), 7.27 (d, J=8.5 Hz, 1H), 6.99-6.88 (m, 2H), 6.62-6.52 (m, 3H), 6.47-6.39 (m, 1H), 4.73 (dd, J=11.2, 4.5 Hz, 1H), 4.14-4.05 (m, 2H), 3.74 (s, 3H), 3.47-3.33 (m, 2H), 3.16 (s, 9H), 2.85 (s, 3H), 2.13-1.77 (m, 4H), 1.60 (s, 3H), 1.58 (s, 3H), 1.56-1.43 (m, 2H); MS (ESI) m/z 767.5 [M]⁺.

Compound 17(h)

(S)-5-carboxy-5-(3-chloro-4-((5-(2-(3,4-dichlorophenyl)propan-2-yl)-1-(4-fluorophenyl)-1H-imidazol-2-ylthio)methyl)-5-fluoro-N-methylphenylsulfonamido)-N,N,N-trimethylpentan-1-aminium 2,2,2-trifluoroacetate

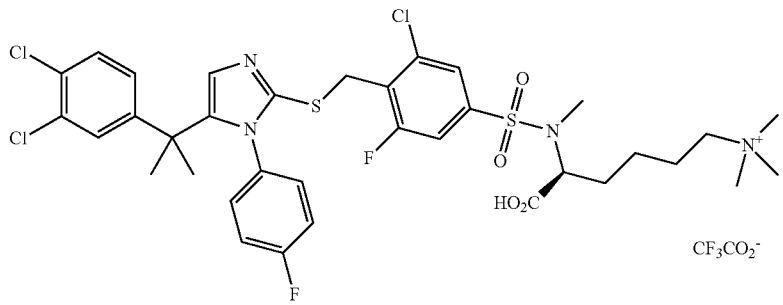

MS (ESI) m/z 787 [M]⁺.

Compound 17(i)

(R)-5-carboxy-5-(3-chloro-4-((5-(2-(4-chloro-3-methoxyphenyl)propan-2-yl)-1-(4-fluorophenyl)-1H-imidazol-2-ylthio)methyl)-5-fluorophenylsulfonamido)-N,N,N-trimethylpentan-1-aminium 2,2,2-trifluoroacetate

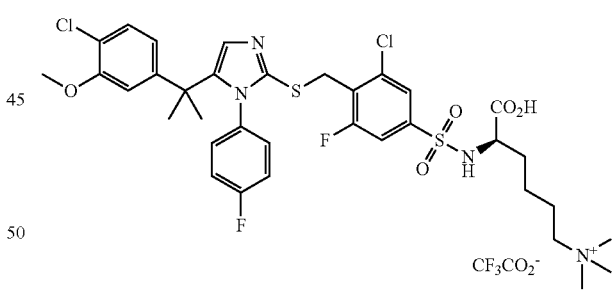

¹H NMR (400 MHz, DMSO-d₆) δ 8.53 (d, J=9.0 Hz, 1H), 7.64 (s, 1H), 7.54 (dd, J=8.7, 1.6 Hz, 1H), 7.39 (s, 1H), 7.24 (d, J=8.3 Hz, 1H), 7.05-6.94 (m, 2H), 6.63 (dd, J=8.6, 4.8 Hz, 1H), 6.60-6.53 (m, 2H), 6.50 (dd, J=8.3, 2.0 Hz, 1H), 4.08 (s, 2H), 3.92-3.80 (m, 1H), 3.69 (s, 3H), 3.36-3.10 (m, 2H), 3.02 (s, 9H), 1.83-1.54 (m, 4H), 1.53-1.39 (m, 6H), 1.37-1.18 (m, 2H); MS (EI): 769 [M]⁺.

Compound 17(j)

(R)-5-carboxy-5-(3-chloro-4-((5-(2-(4-chloro-3-methoxyphenyl)propan-2-yl)-1-(4-fluorophenyl)-1H-imidazol-2-ylthio)methyl)-5-fluoro-N-methylphenylsulfonamido)-N,N,N-trimethylpentan-1-aminium 2,2,2-trifluoroacetate

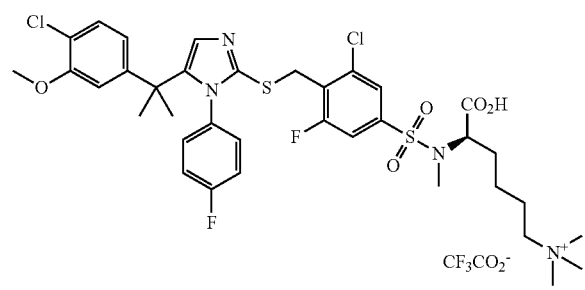

¹H NMR (400 MHz, DMSO-d₆) δ 7.69 (s, 1H), 7.64 (dd, J=8.7, 1.5 Hz, 1H), 7.42 (s, 1H), 7.28-7.22 (m, 1H), 7.04-6.93 (m, 2H), 6.67-6.59 (m, 1H), 6.58-6.47 (m, 3H), 4.52 (dd, J=10.8, 4.7 Hz, 1H), 4.12 (s, 2H), 3.69 (s, 3H), 3.38-3.16 (m, 2H), 3.04 (s, 9H), 2.77 (s, 3H), 1.96-1.58 (m, 4H), 1.57-1.39 (m, 6H), 1.39-1.17 (m, 2H); MS (EI) m/z 783 [M]⁺.

Compound 17(k)

(R)-5-carboxy-5-(4-((5-(2-(4-chloro-3-methoxyphenyl)propan-2-yl)-1-(4-fluoro-phenyl)-1H-imidazol-2-ylthio)methyl)-3,5-difluoro-N-methylphenylsulfonamido)-N,N,N-trimethylpentan-1-aminium 2,2,2-trifluoroacetate

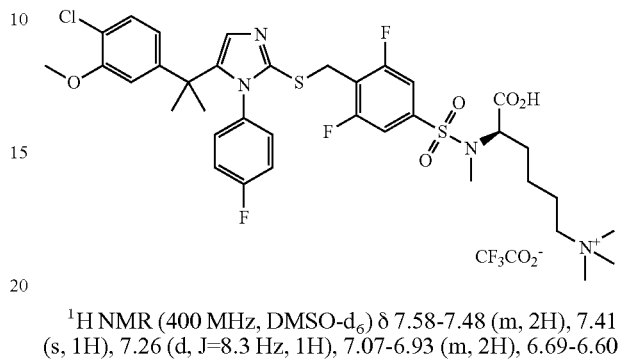

¹H NMR (400 MHz, DMSO-d₆) δ 7.58-7.48 (m, 2H), 7.41 (s, 1H), 7.26 (d, J=8.3 Hz, 1H), 7.07-6.93 (m, 2H), 6.69-6.60 (m, 1H), 6.59-6.52 (m, 2H), 6.52-6.46 (m, 1H), 4.51 (dd, J=10.8, 4.7 Hz, 1H), 4.05 (s, 2H), 3.69 (s, 3H), 3.29 (pd, J=12.4, 5.3 Hz, 2H), 3.04 (s, 9H), 2.77 (s, 3H), 1.95-1.61 (m, 4H), 1.57-1.34 (m, 6H), 1.35-1.20 (m, 2H); MS (EI) m/z 767 [M]⁺.

Compound 17(l)

(S)-6-carboxy-6-(3-chloro-4-((5-(2-(4-chloro-3-methoxyphenyl)propan-2-yl)-1-(4-fluorophenyl)-1H-imidazol-2-ylthio)methyl)-5-fluoro-N-methylphenylsulfonamido)-N,N,N-trimethylhexan-1-aminium 2,2,2-trifluoroacetate

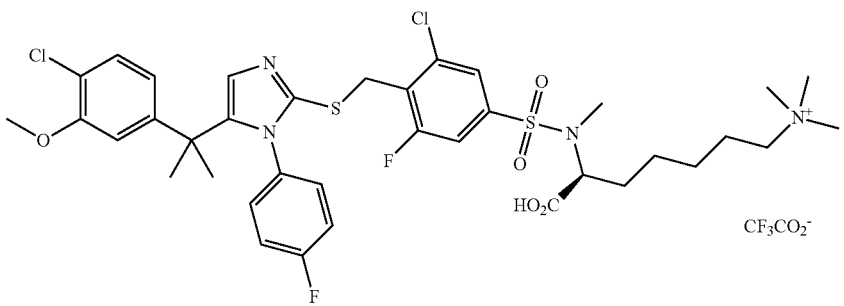

MS (ESI) m/z 797 [M]⁺.

Compound 17(m)

(R)-3-(N-(1-carboxyethyl)-3-chloro-4-(2-(5-(2-(4-chloro-3-methoxyphenyl)propan-2-yl)-1-(4-fluorophenyl)-1H-imidazol-2-yl)ethyl)-5-fluorophenyl-sulfonamido)-N,N,N-trimethylpropan-1-aminium 2,2,2-trifluoroacetate

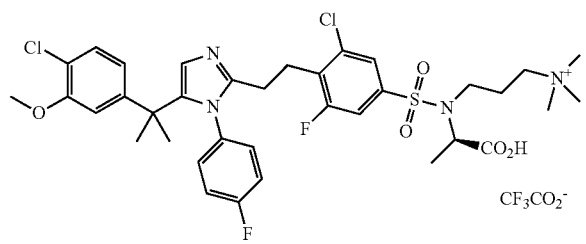

$^1$H-NMR (MeOH-d$_4$, 400 MHz) δ 7.79 (s, 1H), 7.72 (s, 1H), 7.58 (dd, J=8.8, 1.6, 1H), 7.25 (d, J=8.1, 1H), 7.10-6.90 (m, 2H), 6.75-6.59 (m, 2H), 6.59 (d, J=1.6, 1H), 6.56 (s, 1H), 4.67 (q, J=7.4, 1H), 3.73 (s, 3H), 3.61-3.33 (m, 4H), 3.18 (s, 9H), 3.13 (t, J=7.6, 2H), 2.92 (t, J=7.2, 2H), 2.24-2.09 (m, 2H), 1.61 (s, 6H), 1.45 (d, J=7.4, 3H); MS (ESI) m/z 751.5 [M]$^+$.

Compound 17(n)

(S)-5-carboxy-5-(3-chloro-4-(2-(5-(2-(4-chloro-3-methoxyphenyl)propan-2-yl)-1-(4-fluorophenyl)-1H-imidazol-2-yl)ethyl)-5-fluorophenylsulfonamido)-N,N,N-trimethylpentan-1-aminium 2,2,2-trifluoroacetate

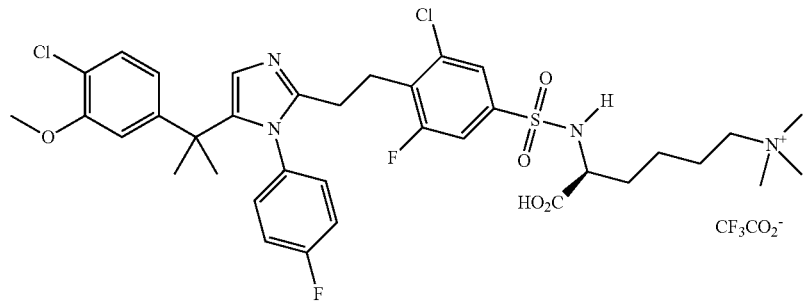

$^1$H-NMR (MeOH-d$_4$, 400 MHz) δ 7.78 (s, 1H), 7.68 (s, 1H), 7.51 (dd, J=8.8, 1.6, 1H), 7.25 (d, J=8.2, 1H), 7.10-6.95 (m, 2H), 6.78-6.66 (m, 1H), 6.65-6.50 (m, 3H), 4.00 (dd, J=9.4, 4.5, 1H), 3.73 (s, 3H), 3.42-3.30 (m, 2H), 3.14 (s, 9H), 3.09 (t, J=7.8, 2H), 2.92 (t, J=7.8, 2H), 2.03-1.67 (m, 4H), 1.61 (s, 3H), 1.59 (s, 3H), 1.60-1.45 (m, 2H); MS (ESI) m/z 751.5 [M]$^+$.

Compound 17(o)

(S)-5-carboxy-5-(3-chloro-4-(2-(5-(2-(4-chloro-3-methoxyphenyl)propan-2-yl)-1-(4-fluorophenyl)-1H-imidazol-2-yl)ethyl)-5-fluoro-N-methylphenylsulfonamido)-N,N,N-trimethylpentan-1-aminium 2,2,2-trifluoroacetate

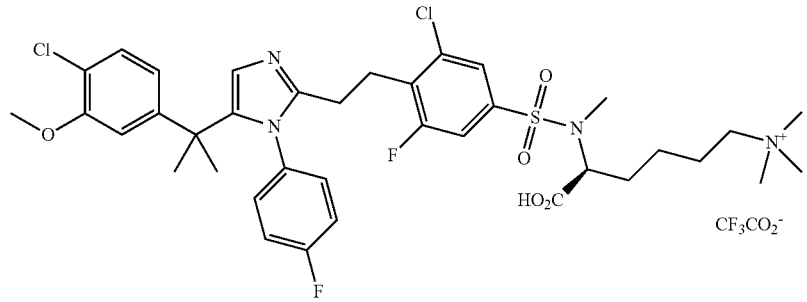

155
$^1$H-NMR (MeOH-d$_4$, 400 MHz) δ 7.77 (s, 1H), 7.69 (s, 1H), 7.54 (dd, J=8.8, 1.6, 1H), 7.25 (d, J=8.1, 1H), 7.10-6.95 (m, 2H), 6.75-6.63 (m, 1H), 6.62-6.52 (m, 3H), 4.72 (dd, J=11.2, 4.4, 1H), 3.73 (s, 3H), 3.51-3.30 (m, 2H), 3.16 (s, 9H), 3.13 (t, J=7.8, 2H), 2.92 (t, J=7.8, 2H), 2.84 (s, 3H), 1.98-1.80 (m, 4H), 1.62 (s, 3H), 1.61 (s, 3H), 1.61-1.50 (m, 2H); MS (ESI) m/z 765.5 [M]$^+$.
156
Example 18
3-(4-((5-(2-(4-Chloro-3-methoxyphenyl)propan-2-yl)-1-(4-fluorophenyl)-1H-imidazol-2-ylthio)methyl)-3,5-difluorophenyl)-N,N,N-trimethylprop-2-yn-1-aminium 4-methylbenzenesulfonate
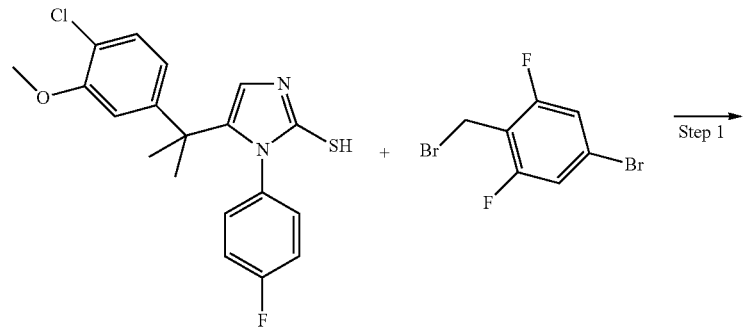
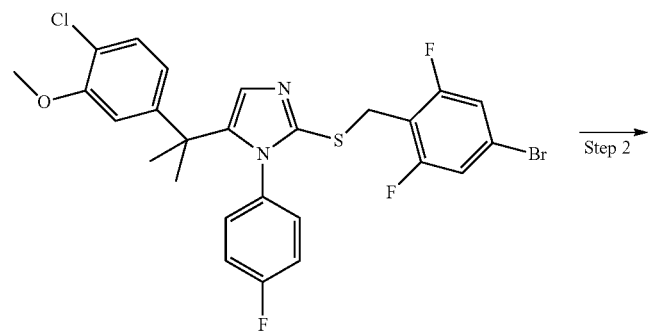
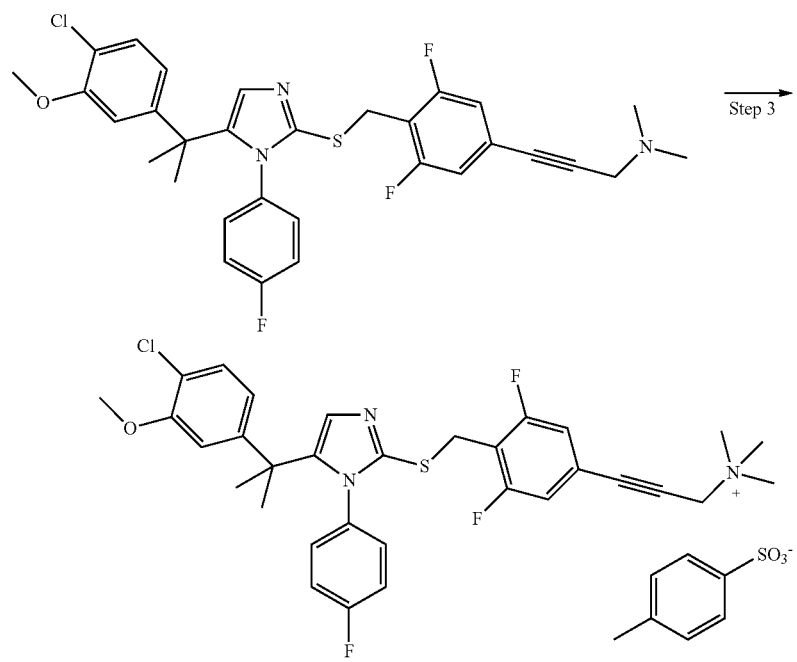

Step 1: A mixture of 5-(2-(4-chloro-3-methoxyphenyl)propan-2-yl)-1-(4-fluorophenyl)-1H-imidazole-2-thiol (1.5 g, 4.0 mmol, 1.0 eq), 5-bromo-2-(bromomethyl)-1,3-difluorobenzene (1.37 g, 4.8 mmol, 1.2 eq) and potassium carbonate (830 mg, 6.0 mmol, 1.5 eq) in acetone (20 mL) was stirred at room temperature overnight. The mixture was filtered and the filtrate was concentrated and purified by chromatography (silica, 0 to 60% EtOAc/Hex) to provide 2-(4-bromo-2,6-difluorobenzylthio)-5-(2-(4-chloro-3-methoxyphenyl)propan-2-yl)-1-(4-fluorophenyl)-1H-imidazole (1.96 g (85%) as a beige solid: $^1$H NMR (400 MHz, CDCl$_3$) δ 7.56 (s, 1H), 7.27-7.20 (m, 1H), 7.10-7.00 (m, 2H), 6.93-6.82 (m, 2H), 6.51-6.44 (m, 2H), 6.42-6.32 (m, 2H), 4.59 (s, 2H), 3.81-3.76 (m, 3H), 1.55 (d, J=10.3 Hz, 6H).

Step 2: To a solution of 2-(4-bromo-2,6-difluorobenzylthio)-5-(2-(4-chloro-3-methoxyphenyl)propan-2-yl)-1-(4-fluorophenyl)-1H-imidazole (250 mg, 0.43 mmol, 1.0 eq), N,N-dimethylprop-2-yn-1-amine (0.07 mL, 0.64 mmol, 1.5 eq) and pyrrolidine (0.05 mL, 0.64 mmol, 1.5 eq) in dry, degassed DMF (2 mL) were added PdCl$_2$(dppf)$_2$ (16 mg, 0.022 mmol, 5 mol %) and CuI (8 mg, 0.043 mmol, 10 mol %). The reaction mixture was heated at 80° C. for 16 h, at which time LCMS showed complete consumption of starting material. The mixture was diluted with EtOAc, washed with brine, dried and concentrated. Purification by column chromatography (0 to 15% MeOH/DCM) furnished 238 mg (95% yield) of 3-(4-((5-(2-(4-chloro-3-methoxyphenyl)propan-2-yl)-1-(4-fluorophenyl)-1H-imidazol-2-ylthio)methyl)-3,5-difluorophenyl)-N,N-dimethylprop-2-yn-1-amine as a brown oil: MS (EI): 584 (MH$^+$).

Step 3: To a solution of 3-(4-((5-(2-(4-chloro-3-methoxyphenyl)propan-2-yl)-1-(4-fluorophenyl)-1H-imidazol-2-ylthio)methyl)-3,5-difluorophenyl)-N,N-dimethylprop-2-yn-1-amine (50 mg, 0.09 mmol, 1.0 eq) in Et$_2$O (0.1 mL) was added methyl p-toluenesulfonate. After 1 h, an additional 1.0 eq methyl p-toluenesulfonate was added and the reaction mixture stirred 30 min. The mixture was filtered to provide 3-(4-((5-(2-(4-chloro-3-methoxyphenyl)propan-2-yl)-1-(4-fluorophenyl)-1H-imidazol-2-ylthio)methyl)-3,5-difluorophenyl)-N,N,N-trimethylprop-2-yn-1-aminium 4-methylbenzenesulfonate (20 mg) as a white crystalline solid: $^1$H NMR (400 MHz, DMSO) δ 7.52-7.44 (m, 2H), 7.40 (d, J=7.6 Hz, 2H), 7.26 (d, J=8.3 Hz, 1H), 7.19 (s, 1H), 7.12 (d, J=7.8 Hz, 2H), 7.03-6.92 (m, 2H), 6.55 (d, J=2.0 Hz, 1H), 6.51-6.40 (m, 3H), 4.64 (s, 2H), 3.98 (s, 2H), 3.69 (s, 3H), 3.20 (d, J=13.8 Hz, 9H), 2.29 (s, 3H), 1.46 (s, 6H); MS (EI) m/z 598.3 (M$^+$).

Compound 18(a)

3-(4-((-5-(2-(4-chloro-3-methoxyphenyl)propan-2-yl)-1-(4-fluorophenyl)-1H-imidazol-2-ylthio)methyl)-3,5-difluorophenyl)-N,N,N-triethylprop-2-yn-1-aminium chloride

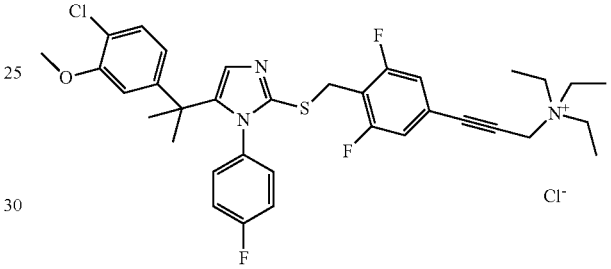

MS (EI) m/z 640 (M$^+$).

Example 19

1-(3-(4-((5-(2-(4-chloro-3-methoxyphenyl)propan-2-yl)-1-(4-fluorophenyl)-1H-imidazol-2-ylthio)methyl)-3,5-difluorophenyl)propyl)-4-aza-1-azoniabicyclo[2.2.2]octane 2,2,2-trifluoroacetate

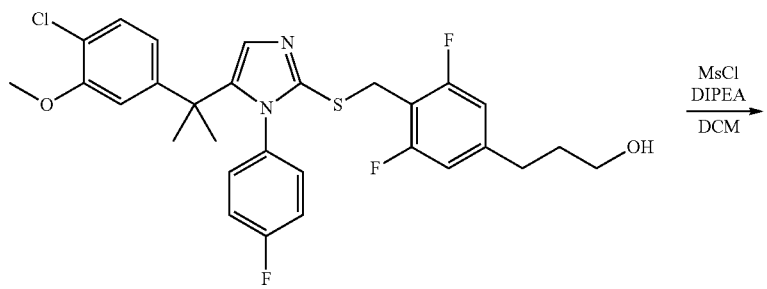

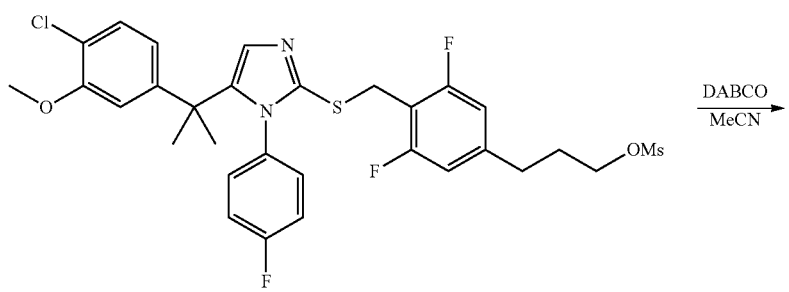

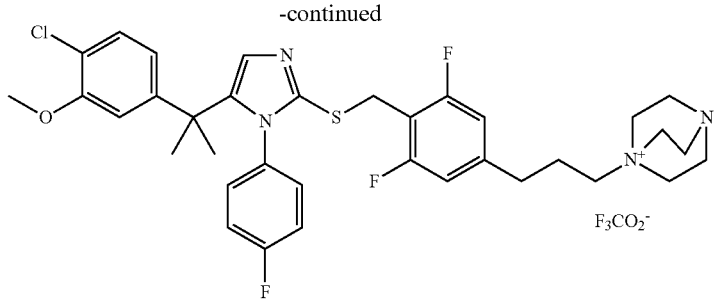

To a solution of 3-(4-((5-(2-(4-chloro-3-methoxyphenyl)propan-2-yl)-1-(4-fluorophenyl)-1H-imidazol-2-ylthio)methyl)-3,5-difluorophenyl)propan-1-ol (530 mg, 0.94 mmol) and DIPEA (740 μL, 4.25 mmol) in DCM (6 mL) was added methanesulfonyl chloride (220 μL, 2.83 mmol) at 25° C. and the resulting solution was stirred for 1 h. The reaction mixture was quenched with satd NaHCO$_3$ and was extracted with DCM (3×10 mL). The combined extracts were dried over Na$_2$SO$_4$ and concentrated to a black oil. Azeotropic drying of the oil with toluene (2×20 mL) afforded a black foam (600 mg, 99%), that was used directly in the next step without further purification. $^1$H NMR (400 MHz, CDCl$_3$) δ 7.30-7.08 (m, 2H), 6.75 (t, J=8.5 Hz, 2H), 6.64 (d, J=7.9 Hz, 2H), 6.57-6.46 (m, 2H), 6.38-6.29 (m, 2H), 4.23 (t, J=6.2 Hz, 2H), 4.07 (s, 2H), 3.78 (s, 3H), 3.02 (s, 3H), 2.75-2.64 (m, 2H), 2.09-1.93 (m, 2H), 1.49 (s, 6H). MS (EI) m/z 639 (MH$^+$).

A solution of 3-(4-((5-(2-(4-chloro-3-methoxyphenyl)propan-2-yl)-1-(4-fluorophenyl)-1H-imidazol-2-ylthio)methyl)-3,5-difluorophenyl)propyl methanesulfonate (200 mg, 0.45 mmol) and 1,4-diazabicyclo[2.2.2]octane (DABCO) (137 mg, 1.22 mmol) in MeCN (4 mL) was heated in a sealed microwave tube at 100° C. for 30 min. The reaction mixture was concentrated to an oil, reconstituted in DMF and purified by HPLC (MeCN/H$_2$O with 0.1% TFA, 10-99%) to give the title product (330 mg, 95%) as a white foam. $^1$H NMR (400 MHz, MeOD) δ 7.89 (s, 1H), 7.25 (d, J=8.2 Hz, 1H), 6.92 (m, 4H), 6.55 (dd, J=8.0, 5.1 Hz, 2H), 6.36 (dd, J=8.9, 4.7 Hz, 2H), 4.10 (s, 2H), 3.74 (s, 3H), 3.44-3.35 (m, 6H), 3.30 (m, 2H), 3.27-3.18 (m, 6H), 2.72 (t, J=7.8 Hz, 2H), 2.17-2.03 (m, 2H), 1.58 (s, 6H). MS (EI) m/z 655 (MH$^+$).

The following compounds [Compounds 19(a)-19(f)] were made by using procedures described in the above example by making any necessary substitutions of known materials that one skilled in the art would ordinarily understand how to do. The counter ion used in these examples was 2,2,2-trifluoroacetate, but it can also be any pharmaceutically acceptable counter ion known to one skilled in the art. It is also understood that the source of the counter ions can be from either intermolecular sources, or, when possible, intramolecular sources.

Compound 19(a)

3-(4-((5-(2-(4-chloro-3-methoxyphenyl)propan-2-yl)-1-(4-fluorophenyl)-1H-imidazol-2-ylthio)methyl)-3,5-difluorophenyl)-N,N,N-trimethylpropan-1-aminium 2,2,2-trifluoroacetate

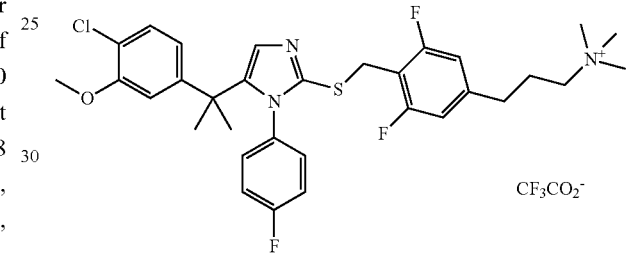

$^1$H NMR (400 MHz, DMSO-d$_6$) δ 7.56-7.42 (m, 1H), 7.28 (d, J=8.3 Hz, 1H), 7.08-6.93 (m, 4H), 6.53 (d, J=2.0 Hz, 1H), 6.49 (dd, J=8.3, 2.0 Hz, 1H), 6.46-6.37 (m, 2H), 4.05 (s, 2H), 3.70 (s, 3H), 3.34-3.23 (m, 2H), 3.07 (s, 9H), 2.62 (t, J=7.7 Hz, 2H), 2.10-1.92 (m, 2H), 1.48 (s, 6H). MS (EI) m/z 602.4 (M$^+$).

Compound 19(b)

3-(4-((5-(2-(3-chloro-4-fluorophenyl)propan-2-yl)-1-(4-fluoro-3-methoxyphenyl)-1H-imidazol-2-ylthio)methyl)-3,5-difluorophenyl)-N,N,N-trimethylpropan-1-aminium 2,2,2-trifluoroacetate

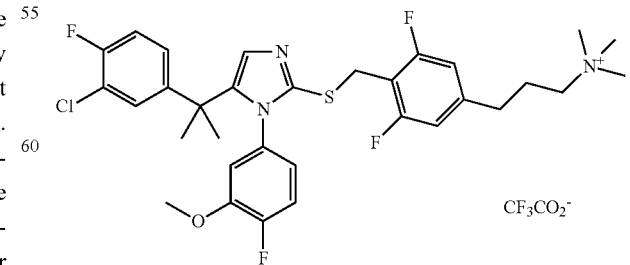

MS (EI) m/z 620 (M$^+$).

Compound 19(c)

3-(4-((5-(2-(3-chloro-4-methoxyphenyl)propan-2-yl)-1-(4-fluorophenyl)-1H-imidazol-2-ylthio)methyl)-3,5-difluorophenyl)-N,N,N-trimethylpropan-1-aminium 2,2,2-trifluoroacetate

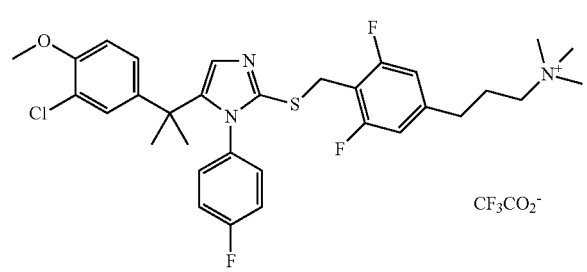

MS (EI) m/z 602 (M+).

Compound 19(d)

3-(3-chloro-4-((5-(2-(4-chloro-3-methoxyphenyl)propan-2-yl)-1-(4-fluorophenyl)-1H-imidazol-2-ylthio)methyl)-5-fluorophenyl)-N,N,N-trimethylpropan-1-aminium 2,2,2-trifluoroacetate

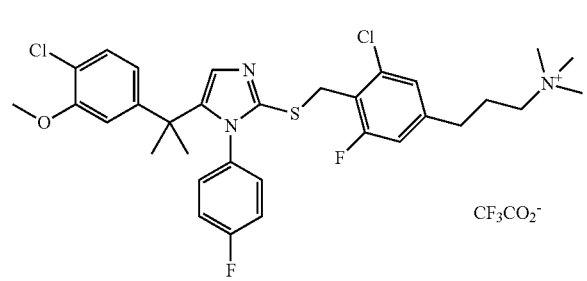

MS (EI) m/z 618 (M+).

Compound 19(e)

4-(4-((5-(2-(4-chloro-3-methoxyphenyl)propan-2-yl)-1-(4-fluorophenyl)-1H-imidazol-2-ylthio)methyl)-3,5-difluorophenyl)-N,N,N-trimethylbutan-1-aminium 2,2,2-trifluoroacetate

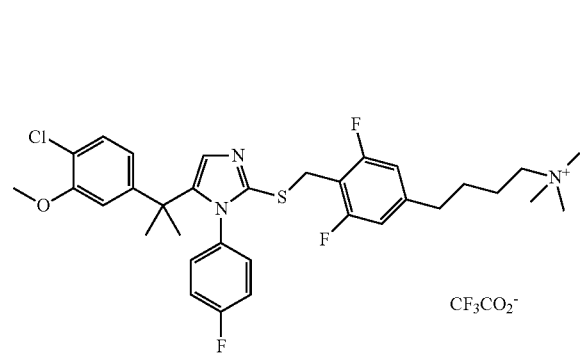

MS (EI) m/z 616 (M+).

Compound 19(f)

3-(4-((5-(2-(3-chloro-4-sulfamoylphenyl)propan-2-yl)-1-(4-fluoro-3-methoxyphenyl)-1H-imidazol-2-ylthio)methyl)-3,5-difluorophenyl)-N,N,N-trimethylpropan-1-aminium 2,2,2-trifluoroacetate

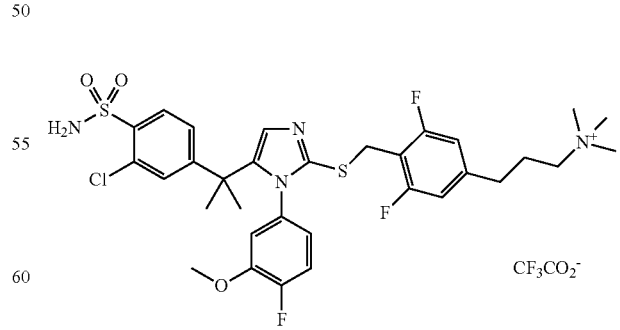

MS (EI) m/z 681 (M+).

Example 20
2-(4-((5-(2-(4-Chloro-3-methoxyphenyl)propan-2-yl)-1-(4-fluorophenyl)-1H-imidazol-2-ylthio)methyl)-3,5-difluorophenoxy)-N,N,N-trimethylethanaminium 2,2,2-trifluoroacetate
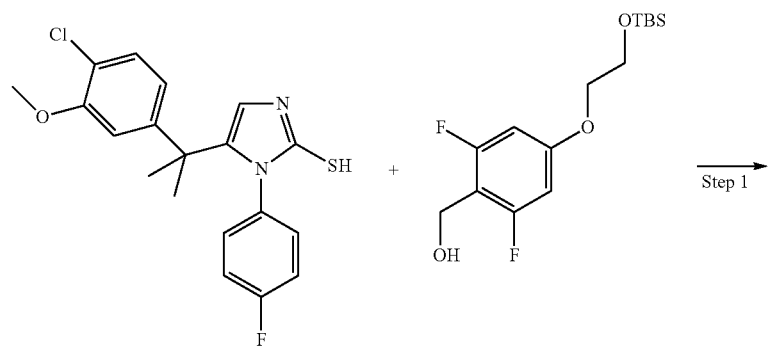
Step 1
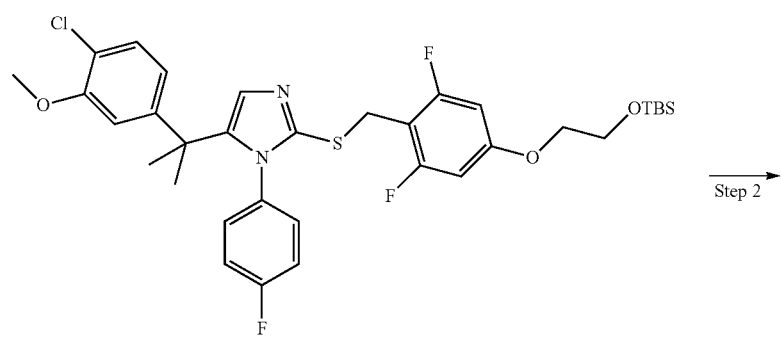
Step 2
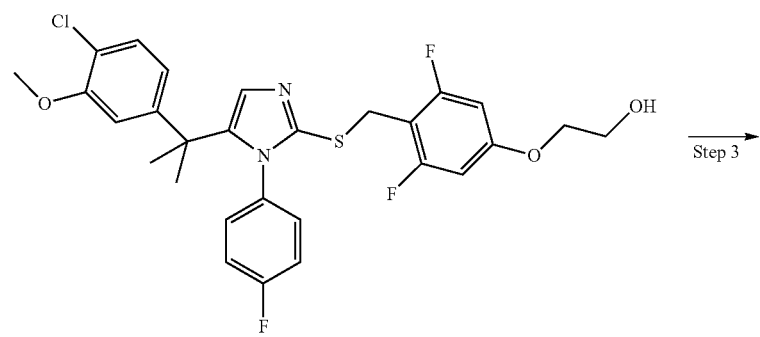
Step 3
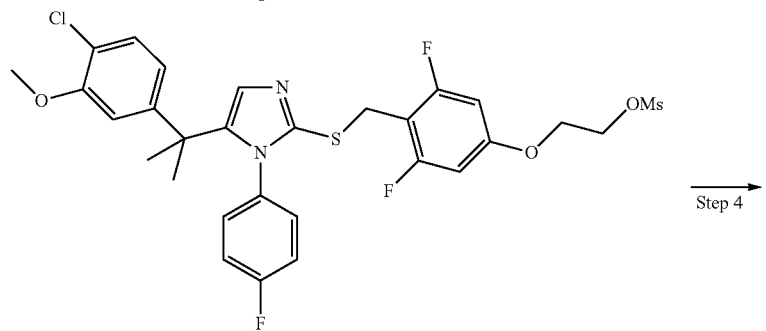
Step 4

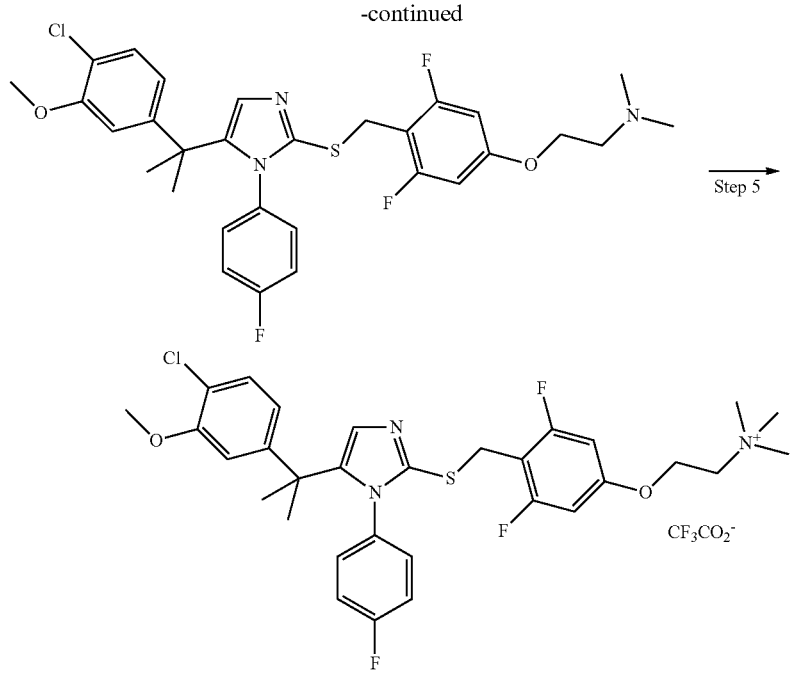

Step 1: To a mixture of 5-(2-(4-chloro-3-methoxyphenyl)propan-2-yl)-1-(4-fluorophenyl)-1H-imidazole-2-thiol (136 mg, 0.36 mmol, 1.0 eq), (4-(2-(tert-butyldimethylsilyloxy)ethoxy)-2,6-difluorophenyl)methanol (115 mg, 0.36 mmol, 1.0 eq) and triphenylphosphine (140 mg, 0.54 mmol, 1.5 eq) in dry THF (2 mL) was added diisopropylazodicarboxylate (0.1 mL). After stirring 16 h, the reaction mixture was concentrated and purified by chromatography (silica, 0-50% EtOAc/Hex) to afford 2-(4-(2-(tert-butyldimethylsilyloxy)ethoxy)-2,6-difluorobenzylthio)-5-(2-(4-chloro-3-methoxyphenyl)propan-2-yl)-1-(4-fluorophenyl)-1H-imidazole (161 mg, 66%). ¹H NMR (400 MHz, CDCl₃) δ 7.56 (s, 1H), 7.11 (d, J=7.9 Hz, 1H), 6.76 (dd, J=8.9, 7.8 Hz, 2H), 6.39-6.23 (m, 6H), 4.61 (s, 2H), 3.94-3.80 (m, 4H), 3.69 (s, 3H), 1.45 (s, 6H), 1.26-1.15 (m, 3H), 0.81 (s, 9H), 0.00 (s, 6H).

Step 2: To a solution of 2-(4-(2-(tert-butyldimethylsilyloxy)ethoxy)-2,6-difluorobenzylthio)-5-(2-(4-chloro-3-methoxyphenyl)propan-2-yl)-1-(4-fluorophenyl)-1H-imidazole (440 mg, 0.65 mmol, 1.0 eq) in anhyd DCM was added tetrabutylammonium fluoride (2.9 mL, 2.9 mmol, 4.4 eq, 1.0 M in THF). After stirring 16 h, the reaction was quenched with satd NaHCO₃ and extracted with DCM. The combined extracts were washed with water and brine, dried, concentrated and purified (silica, 0 to 80% EtOAc/Hex) to yield 2-(4-((5-(2-(4-chloro-3-methoxyphenyl)propan-2-yl)-1-(4-fluorophenyl)-1H-imidazol-2-ylthio)methyl)-3,5-difluorophenoxy)ethanol (290 mg, 79%) as a white foam: ¹H NMR (400 MHz, CDCl₃) δ 7.18 (d, J=7.8 Hz, 1H), 7.06 (d, J=8.2 Hz, 1H), 6.74-6.63 (m, 2H), 6.46-6.33 (m, 2H), 6.33-6.20 (m, 4H), 4.03 (s, H), 3.90 (dt, J=8.7, 4.1 Hz, 4H), 3.68 (s, 3H), 1.39 (s, 6H).

Step 3: To 2-(4-((5-(2-(4-chloro-3-methoxyphenyl)propan-2-yl)-1-(4-fluorophenyl)-1H-imidazol-2-ylthio)methyl)-3,5-difluorophenoxy)ethanol (270 mg, 0.48 mmol, 1.0 eq) in DCM (2.5 mL) was added methanesulfonyl chloride (0.1 mL, 1.44 mmol, 3.0 eq), followed by diisopropylamine (0.25 mL, 1.44 mmol, 3.0 eq). The reaction mixture was stirred at room temperature for 45 min at which time LCMS showed complete consumption of starting material. Aqueous work up (EtOAc and water) followed by purification (column chromatography, 0 to 80% EtOAc/Hex) provided 2-(4-((5-(2-(4-chloro-3-methoxyphenyl)propan-2-yl)-1-(4-fluorophenyl)-1H-imidazol-2-ylthio)methyl)-3,5-difluorophenoxy)ethyl methanesulfonate (230 mg, 75%) as a white foam. MS (EI) m/z 462 (MH⁺).

Step 4: A mixture of 2-(4-((5-(2-(4-Chloro-3-methoxyphenyl)propan-2-yl)-1-(4-fluorophenyl)-1H-imidazol-2-ylthio)methyl)-3,5-difluorophenoxy)ethyl methanesulfonate (230 mg, 0.36 mmol, 1.0 eq), dimethylamine (7.2 mL, 14.4 mmol, 40.0 eq, 2.0 M in THF) and diisopropylamine (0.2 mL, 1.1 mmol, 3.0 eq) in anhyd DMF (3.5 mL) was heated at 110° C. for 16 h. The mixture was diluted with EtOAc, washed sequentially with brine, satd NaHCO₃ and brine, dried over MgSO₄ and concentrated to provide 2-(4-((5-(2-(4-chloro-3-methoxyphenyl)propan-2-yl)-1-(4-fluorophenyl)-1H-imidazol-2-ylthio)methyl)-3,5-difluorophenoxy)-N,N-dimethylethanamine (187 mg). ¹H NMR (400 MHz, CDCl₃) δ 7.13 (s, 1H), 7.07 (d, J=8.2 Hz, 1H), 6.72-6.65 (m, 2H), 6.48-6.40 (m, 2H), 6.34-6.25 (m, 4H), 3.98-3.92 (m, 4H), 3.68 (s, 3H), 2.68 (t, J=5.5 Hz, 2H), 2.28 (s, 3H), 1.41 (s, 6H); MS (EI) m/z 590 (MH⁺).

Step 5: To a solution of 2-(4-((5-(2-(4-chloro-3-methoxyphenyl)propan-2-yl)-1-(4-fluorophenyl)-1H-imidazol-2-ylthio)methyl)-3,5-difluorophenoxy)-N,N-dimethylethanamine (187 mg, 0.32 mmol, 1.0 eq) in acetonitrile was added methyl tosylate (0.053 mL, 0.35 mmol, 1.1 eq). After stirring 1 h, complete conversion was observed by LCMS. The reaction was concentrated and then purified by preparative HPLC (30 to 70% acetonitrile/water, 0.1% TFA) to provide 2-(4-((5-(2-(4-chloro-3-methoxyphenyl)propan-2-yl)-1-(4-fluorophenyl)-1H-imidazol-2-ylthio)methyl)-3,5-difluorophenoxy)-N,N,N-trimethylethanaminium 2,2,2-trifluoroacetate (30 mg). ¹H NMR (400 MHz, MeOD) δ 7.94 (s, 1H), 7.27 (d, J=8.4 Hz, 1H), 7.01-6.93 (m, 2H), 6.81-6.70 (m, 2H), 6.62-6.47 (m, 4H), 4.60-4.52 (m, 2H), 4.08 (s, 2H), 3.96-3.86 (m, 2H), 3.77 (s, 3H), 3.30 (s, 9H), 1.63 (s, 6H); MS (EI): 604.4 (M⁺).

Compound 20(a)

2-(4-((5(2-(4-chloro-3-methoxyphenyl)propan-2-yl)-(4-fluorophenyl)-1H-imidazol-2-ylthio)methyl)-3,5-difluorophenoxy)-N,N,N-triethylethanaminium chloride

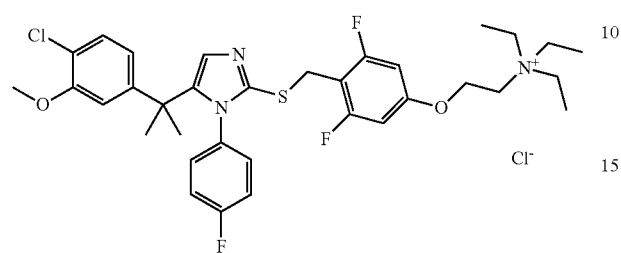

MS (EI) m/z 646 (M+).

Example 21

(4-carboxy-1-{[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}piperidin-4-yl)-N,N,N-trimethylmethanaminium, with the appropriate couter ion, can be made by the Examples described above by substituting materials one skilled in the art would understand how to do.

Example 22

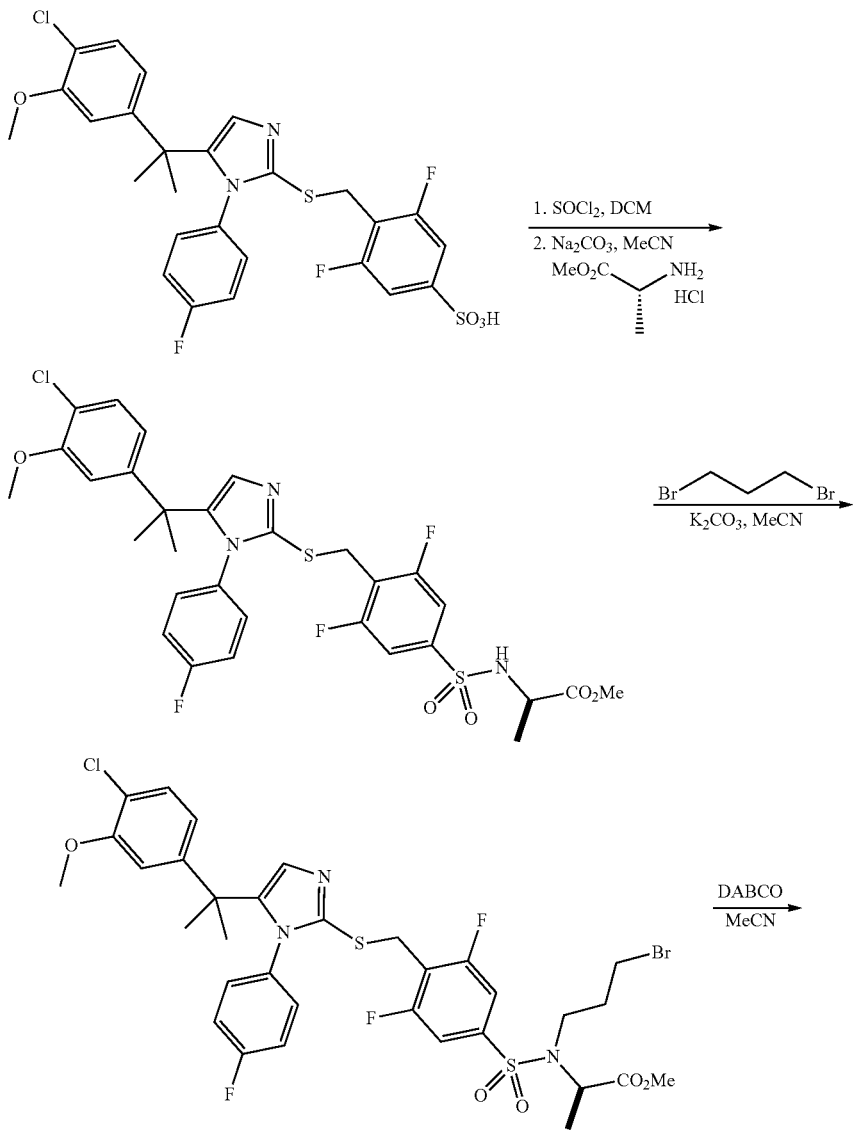

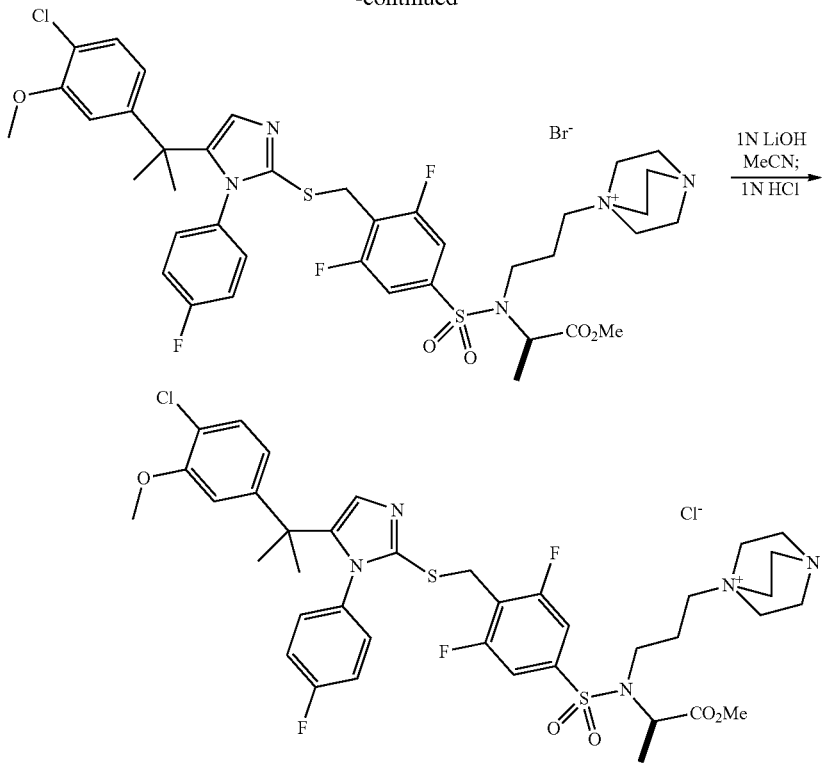

(R)-1-(3-(N-(1-carboxyethyl)-4-((5-(2-(4-chloro-3-methoxyphenyl)propan-2-yl)-1-(4-fluorophenyl)-1H-Imidazol-2-ylthio)methyl)-3,5-difluorophenylsulfonamido)propyl)-4-aza-1-azoniabicyclo[2.2.2]octane chloride

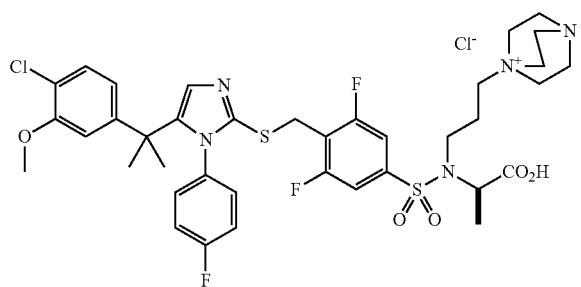 [SMILES: COc1cc(C(C)(C)c2cnc(SCc3c(F)cc(S(=O)(=O)N(CCC[N+]45CCN(CC4)CC5)[C@H](C)C(=O)O)cc3F)n2-c2ccc(F)cc2)ccc1Cl ; [Cl-]]

To a solution of 4-((5-(2-(4-chloro-3-methoxyphenyl)propan-2-yl)-1-(4-fluorophenyl)-1H-imidazol-2-ylthio)methyl)-3,5-difluorobenzenesulfonic acid (650 mg, 1.11 mol) in DCM (7 mL) and DMF (cat.) was added thionyl chloride (1.32 g, 11.1 mol, 10 eq.) and heated to reflux for 1.5 h with stirring. The reaction mixture was concentrated to dryness and the residue was diluted with 1,2-dichloroethane, co-evaporated (3×2 mL) and dried under high vacuum. Meanwhile a mixture of D-alanine methyl ester (622 mg, 4.44 mol, 4.0 eq.), MeCN (1.2 mL) and 2M $Na_2CO_3$ (6 mL) was stirred for 30 min and then cooled to 0° C. with an ice-water bath. A solution of the above sulfonyl chloride in MeCN (6 mL) then was added dropwise to the chilled aqueous mixture over 15 min with vigorously stirring. After complete addition, the ice-water bath was removed and the reaction slurry was stirred vigorously another 15 min. The reaction mixture was transferred into a separatory funnel with MeCN and the organic layer was collected. The aqueous layer was extracted with DCM (2×10 mL). The combined organic layers were washed with water/brine (1:1), dried over $MgSO_4$, filtered and concentrated under reduced pressure. The resulting product was purified by chromatography (silica, Hex/EtOAc, 1:1) to afford (R)-methyl 2-(4-((5-(2-(4-chloro-3-methoxyphenyl)propan-2-yl)-1-(4-fluorophenyl)-1H-imidazol-2-ylthio)methyl)-3,5-difluorophenylsulfonamido)propanoate (709 mg, 95%) as a white foam. $^1$H NMR (400 MHz, $CDCl_3$) δ 7.28 (d, 2H), 7.18 (s, 1H), 7.13-7.15 (d, 1H), 6.76-6.80 (t, 2H), 6.46-6.48 (m, 2H), 6.36-6.39 (m, 2H), 5.37 (d, 1H), 4.06 (s, 2H), 3.93-4.03 (m, 1H), 3.73 (s, 3H), 3.60 (s, 3H), 1.46 (s, 6H), 1.39-1.41 (d, 3H).

To a solution of (R)-methyl 2-(4-((5-(2-(4-chloro-3-methoxyphenyl)propan-2-yl)-1-(4-fluorophenyl)-1H-imidazol-2-ylthio)methyl)-3,5-difluorophenylsulfonamido)propanoate (200 mg, 0.30 mol) in MeCN (4 mL) were added $K_2CO_3$ (124 mg, 0.90 mol) and 1,3-dibromopropane (121 mg, 0.60 mol). The reaction flask was heated at 60° C. for 4 h. The reaction mixture was cooled to room temperature and concentrated under reduced pressure. The resulting product was purified by column chromatography (silica, Hex/EtOAc, 1:1) to afford (R)-methyl 2-(N-(3-bromopropyl)-4-((5-(2-(4-chloro-3-methoxyphenyl)propan-2-yl)-1-(4-fluorophenyl)-1H-imidazol-2-ylthio)methyl)-3,5-difluorophenylsulfonamido)propanoate (113 mg, 47%) as a white foam. $^1$H NMR (400 MHz, $CDCl_3$) δ 7.28 (d, 2H), 7.19 (s, 1H), 7.16-7.18 (d, 1H), 6.80-6.84 (t, 2H), 6.50-6.53 (m, 2H), 6.43-6.46 (m, 2H), 4.63-4.65 (q, 1H), 4.13 (s, 2H), 3.72 (s, 3H), 3.55 (s, 3H), 3.27-3.45 (m, 4H), 2.10-2.31 (m, 2H), 1.47 (s, 6H), 1.45 (s, 3H).

To a solution of (R)-methyl 2-(N-(3-bromopropyl)-4-((5-(2-(4-chloro-3-methoxyphenyl)propan-2-yl)-1-(4-fluorophenyl)-1H-imidazol-2-ylthio)methyl)-3,5-difluorophenylsulfonamido)propanoate (110 mg, 0.14 mol) in MeCN (3 mL) was added DABCO (20 mg, 0.18 mol.). The reaction flask was heated at 60° C. for 3 h. The reaction mixture was cooled to room temperature and concentrated under reduced pressure. Recrystallization of the residue from DCM/Et$_2$O (1:5) gave (R)-1-(3-(4-((5-(2-(4-chloro-3-methoxyphenyl)propan-2-yl)-1-(4-fluorophenyl)-1H-imidazol-2-ylthio)methyl)-3,5-difluoro-N-(1-methoxy-1-oxopropan-2-yl)phenylsulfonamido)propyl)-4-aza-1-azoniabicyclo[2.2.2]octane bromide (118 mg, 99%) as a white solid. $^1$H NMR (400 MHz, CDCl$_3$) δ 7.33 (d, 2H), 7.17-7.18 (d, 1H), 7.11 (s, 1H), 6.82-6.87 (m, 2H), 6.48-6.55 (m, 4H), 4.51-4.55 (q, 1H), 3.86-3.92 (q, 2H), 3.75 (s, 3H), 3.70 (s, 3H), 3.63-3.66 (t, 8H), 3.38-3.43 (m, 2H), 3.22-3.24 (t, 6H), 2.15-2.34 (m, 2H), 1.52 (s, 6H), 1.50 (s, 3H).

To a solution of (R)-1-(3-(4-((5-(2-(4-chloro-3-methoxyphenyl)propan-2-yl)-1-(4-fluorophenyl)-1H-imidazol-2-ylthio)methyl)-3,5-difluoro-N-(1-methoxy-1-oxopropan-2-yl)phenylsulfonamido)propyl)-4-aza-1-azoniabicyclo[2.2.2]octane bromide (118 mg, 0.14 mol) in MeCN (2 mL) was added 1N LiOH (0.3 mL). After stirring 1.5 h, the volatiles were removed under educed pressure. The resulting aqueous layer was acidified to pH 0 with 1N HCl and washed with EtOAc (2×10 mL). After extractions, the aqueous layer was neutralized to pH 7 with 1N NaOH and satd NaHCO$_3$, and extracted with DCM/IPA (2:1, v/v, 3×10 mL). The combined extracts were dried (MgSO$_4$), filtered and concentrated under reduced pressure. The residue was triturated in DCM, slurried with Celite and filtered over a pad of Celite to remove any inorganic salts. The DCM layer was concentrated and the residue recrystallized from DCM/Et$_2$O (1:3) to give the title compound (83 mg, 71%) as a white solid.

$^1$H NMR (400 MHz, CD$_3$OD) δ 7.41 (d, 2H), 7.22 (s, 1H), 7.19-7.20 (d, 1H), 6.82-6.86 (t, 2H), 6.51-6.55 (m, 2H), 6.38-6.42 (m, 2H), 4.39-4.40 (q, 1H), 3.91 (s, 2H), 3.71 (s, 3H), 3.42-3.59 (m, 2H), 3.32-3.37 (m, 7H), 3.16-3.20 (t, 7H), 2.10-2.14 (m, 2H), 1.52 (s, 6H), 1.25 (d, 3H); MS (EI) m/z 806.3 (M$^+$)

The following compound (Compound 22(a)) can be made by using procedures described in the above example by making any necessary substitutions of known materials that one skilled in the art would ordinarily understand how to do. The following compounds are represented as cations, and these cations are understood, to those skilled in the art, to be in the presence of a counter ion. These counter ions can be any pharmaceutically acceptable counter ion known to one skilled in the art, including, but not limited to, the counter ions described in the example(s) described herein. It is also understood that the source of the counter ions can be from either intermolecular sources, or, when possible, intramolecular sources.

Compound 22(a)

N-[4-(4-aza-1-azoniabicyclo[2.2.2]oct-1-yl)butyl]-N-{[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}-D-alanine

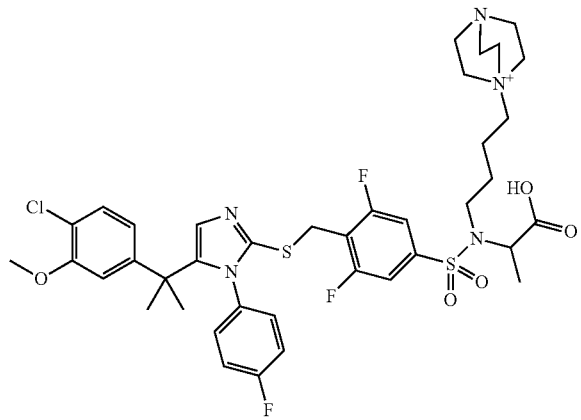 [SMILES: COc1cc(C(C)(C)c2cnc(SCc3c(F)cc(S(=O)(=O)N(CCCC[N+]45CCN(CC4)CC5)C(C)C(=O)O)cc3F)n2-c2ccc(F)cc2)ccc1Cl]

INTERMEDIATES

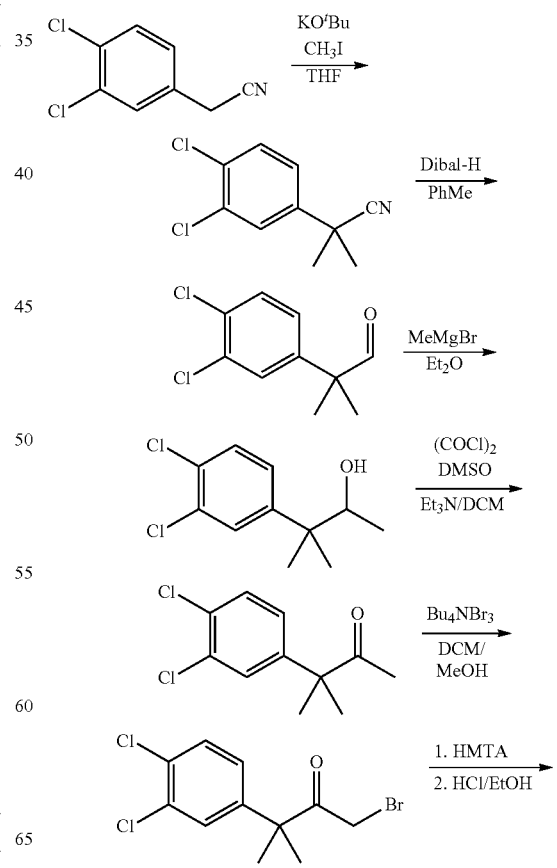

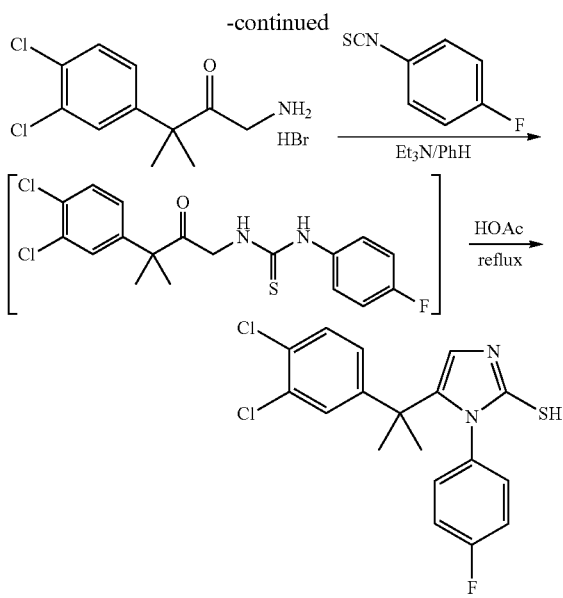

A solution of CH₃I (50 mL, 0.806 mol) and 3,4-dichlorophenylacetonitrile (50 g, 0.268 mol) in THF (200 mL) was added dropwise to a suspension of KOtBu (95 g, 0.806 mol) in THF (800 mL) at 0° C. under argon. After stirring 1.5 h, the reaction mixture was quenched with satd NH₄Cl solution (250 mL), diluted with H₂O (300 mL) and extracted with EtOAc (3×200 mL). The organic layers were washed with brine, dried over Na₂SO₄, filtered, and concentrated to give a residue, which was purified by column chromatography to afford 2-(3,4-dichlorophenyl)-2-methylpropanenitrile (56 g, 97%). $^1$H NMR (400 MHz, CDCl₃) δ 7.55 (d, 1H), 7.48 (d, 1H), 7.32 (dd, 1H), 1.72 (s, 6H).

A 1.0M solution of DIBAH (340 mL, 0.340 mol) in toluene was added dropwise to a solution of 2-(3,4-dichlorophenyl)-2-methylpropanenitrile (56 g, 0.261 mol) in toluene (650 mL) at −78° C. After stirring for 2 h, the mixture was quenched at −78° C. with 6N HCl solution (500 mL). The mixture was warmed to room temperature, stirred further for 1 h, and extracted with EtOAc (2×250 mL). To the combined extracts was added a satd solution of Rochelle's salt (300 mL) and the mixture was stirred until the organic layer was clear. The organic layer was separated, washed with brine, dried over Na₂SO₄, filtered, and concentrated. The crude product was purified by column chromatography to yield 2-(3,4-dichlorophenyl)-2-methylpropanal (47.1 g, 83%). $^1$H NMR (400 MHz, CDCl₃) δ 9.47 (s, 1H), 7.44 (d, 1H), 7.36 (m, 1H), 7.10 (d, 1H), 1.46 (s, 6H).

To a solution of 2-(3,4-dichlorophenyl)-2-methylpropanal (47.13 g, 0.217 mol) in Et₂O (223 mL) at 0° C. was added a 3.0M solution of MeMgBr (217 mL, 0.651 mol) in Et₂O. After stirring 2 h at 0° C., the reaction mixture was warmed to room temperature over 1 h. Then the reaction mixture was cooled to 0° C., quenched with H₂O (100 mL) and 3N HCl (200 mL), extracted with EtOAc and washed with brine. The organic layer was dried over Na₂SO₄ and concentrated to afford the crude product, which was purified by column chromatography to yield 3-(3,4-dichlorophenyl)-3-methylbutan-2-ol (45.9 g, 90%). $^1$H NMR (400 MHz, CDCl₃) δ 7.46 (d, 1H), 7.37 (d, 1H), 7.21 (dd, 1H), 3.83 (m, 1H), 1.31 (s, 3H), 1.29 (s, 3H), 1.05 (d, 3H).

DMSO (14.7 mL, 205 mmol) was added dropwise to a solution of oxalyl chloride (9.0 mL, 103 mmol) in CH₂Cl₂ (200 mL) at −78° C. The reaction mixture was stirred for 30 min and a solution of 3-(3,4-dichlorophenyl)-3-methylbutan-2-ol (12 g, 51.4 mmol) in CH₂Cl₂ (50 mL) was added by cannula over 15 min. After stirring 30 min, Et₃N (43 mL, 308 mmol) was added, and the reaction mixture was allowed to warm to room temperature over 1 h. Water (200 mL) was added, and the organic layer was separated. The aqueous layer was further extracted with CH₂Cl₂ (3×50 mL). The combined organic layers were washed with brine, dried over Na₂SO₄, filtered, and concentrated. The crude product was purified by column chromatography to give 3-(3,4-dichlorophenyl)-3-methylbutan-2-one (10.7 g, 89%). $^1$H NMR (400 MHz, CDCl₃) δ 7.41 (d, 1H), 7.37 (m, 1H), 7.08 (d, 1H), 1.95 (s, 3H), 1.59 (s, 6H).

Tetrabutylammonium tribromide (20.4 g, 41.5 mmol) was added to a solution of 3-(3,4-dichlorophenyl)-3-methylbutan-2-one (9.60 g, 41.5 mmol) in MeOH-DCM (160 mL, 1:2, v/v). After stirring 24 h, the reaction mixture was concentrated under reduced pressure and then combined with EtOAc (80 mL). The organic layer was washed with H₂O (50 mL), 1N HCl (50 mL), and H₂O (20 mL) successively. The organic layer was washed with brine, dried over Na₂SO₄, and concentrated. Purification by column chromatography afforded 1-bromo-3-(3,4-dichlorophenyl)-3-methylbutan-2-one (11.8 g, 91%). $^1$H NMR (400 MHz, CDCl₃) δ 7.45 (d, 1H), 7.38 (d, 1H), 7.08 (d, 1H), 3.86 (s, 2H), 1.56 (s, 6H).

A mixture of 1-bromo-3-(3,4-dichlorophenyl)-3-methylbutan-2-one (4.0 g, 13 mmol) and HMTA (hexamethylenetetramine, 2.0 g, 14 mmol) in DCM (25 mL) was stirred 48 h at room temperature. The volatiles were evaporated in vacuo. The crude material was dissolved in EtOH (80 mL) and combined with conc HCl (40 mL). The resulting mixture was heated at reflux 2 h, cooled to room temperature, and concentrated in vacuo to give 1-amino-3-(3,4-dichlorophenyl)-3-methylbutan-2-one hydrobromide (6.75 g), which was used in the next reaction without purification. $^1$H NMR (400 MHz, DMSO-d₆) δ 8.00 (bs, 3H), 7.61 (d, 1H), 7.52 (d, 1H), 7.29 (dd, 1H), 3.94 (m, 2H), 1.47 (s, 6H).

A mixture of 1-amino-3-(3,4-dichlorophenyl)-3-methylbutan-2-one hydrobromide (900 mg, 2.75 mmol), 4-fluorophenyl isothiocyanate (464 mg, 3.029 mmol), and Et₃N (570 uL, 4.13 mmol) in dry benzene (20 mL) was heated at reflux 6 h. The reaction mixture was concentrated under reduced pressure, diluted with acetic acid (9 mL) and then heated at reflux 5 h. After cooling to room temperature and concentrating, the crude product was purified by flash column chromatography to afford 5-(2-(3,4-dichlorophenyl)propan-2-yl)-1-(4-fluorophenyl)-1H-imidazole-2-thiol (370 mg). $^1$H NMR (400 MHz, CDCl₃) δ 7.15 (m, 2H), 6.91 (m, 2H), 6.80 (m, 2H), 6.62 (m, 2H), 1.61 (s, 6H).

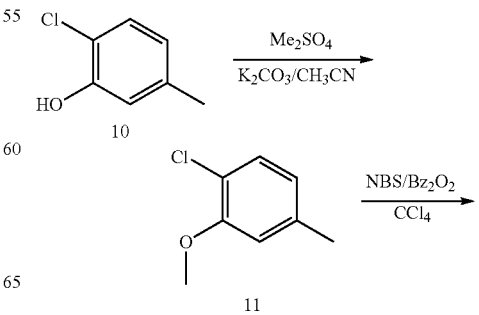

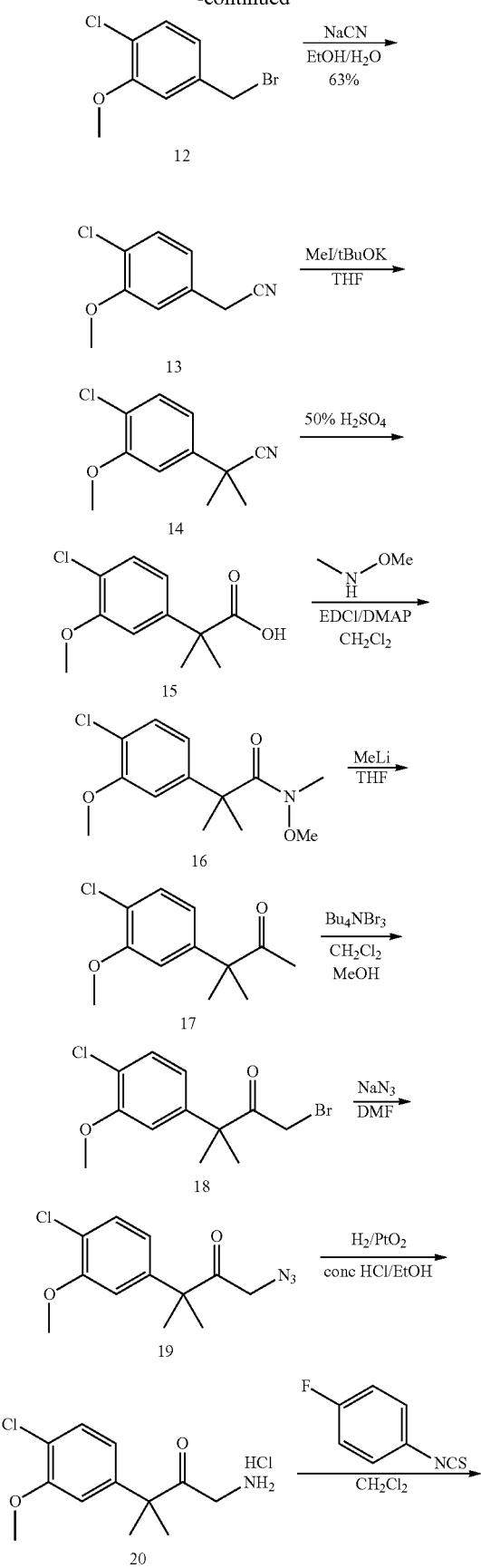

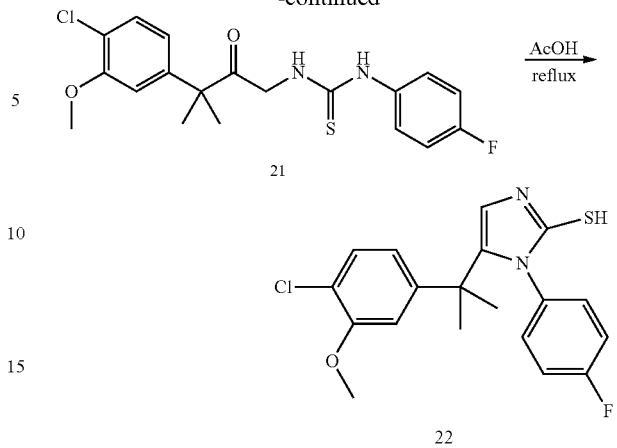

To a solution of 2-chloro-5-methylphenol (10) (250 g, 1.75 mol) in CH$_3$N (2.5 L) was added Me$_2$SO$_4$ (184 mL, 1.93 mol) and K$_2$CO$_3$ (314 g, 2.28 mol). The reaction mixture was heated to reflux for 6 h with mechanical stirring. The reaction mixture was cooled to ambient temperature and filtered through Celite. The filtrate was evaporated. The residue was diluted with EtOAc (1.5 L), washed with water (1.5 L*2) and brine (1.5 L) successively, dried over MgSO$_4$, filtered and concentrated under reduced pressure to give 2-chloro-5-methylanisole (11) as a light yellow oil (274 g, quantitative). $^1$H NMR (400 MHz, CDCl$_3$): δ 7.20-7.25 (d, 1H), 6.73 (s, 1H), 6.68-6.71 (d, 1H), 3.86 (s, 3H), 2.31 (s, 3H).

To a solution of 2-chloro-5-methylanisole (11) (274 g, 1.75 mol) in CCl$_4$ (2.5 L) was added benzoyl peroxide (4.23 g, 0.02 mol) and NBS (321 g, 1.80 mol). The reaction mixture was heated to reflux for 1 h with mechanical stirring. The reaction mixture was cooled, washed with 1N HCl (2 L), satd NaHCO$_3$ (2 L) and brine (2 L), dried over MgSO$_4$, filtered and concentrated under reduced pressure to give the 5-(bromomethyl)-3-chloroanisole (12) as a light yellow solid (412 g, quantitative). $^1$H NMR (400 MHz, CDCl$_3$): δ 7.30-7.34 (d, 1H), 6.95 (s, 1H), 6.91-6.93 (d, 1H), 4.45 (s, 2H), 3.92 (s, 3H).

To a solution of 5-(bromomethyl)-3-chloroanisole (12) (412 g, 1.75 mol) in EtOH (2 L) and H$_2$O (0.5 L) was added NaCN (129 g, 2.63 mol) and the reaction mixture was heated to reflux for 2 h with mechanical stirring. The reaction mixture was cooled and diluted with water (3.5 L). The mixture was extracted with diethyl ether (2 L×2) and the combined organic layers were washed with aq. 5% HCl (2.5 L), satd NaHCO$_3$ (2.5 L) and brine (2.5 L), dried over anhydrous MgSO$_4$, filtered and concentrated under reduced pressure. The resulting residue was purified by column chromatography (Hex/EtOAc=5:1) to afford 2-(4-chloro-3-methoxyphenyl)acetonitrile (13) (240 g, 75%) as yellow solid. $^1$H NMR (400 MHz, CDCl$_3$): δ 7.35-7.36 (d, 1H), 6.86 (s, 1H), 6.84-6.86 (d, 1H), 3.92 (s, 3H), 3.74 (s, 2H).

KOtBu (370 g, 3.3 mol) was dissolved in THF (1.7 L) and stirred at −20° C. After 30 min, to the reaction mixture was added 2-(4-chloro-3-methoxyphenyl)acetonitrile (13) (240 g, 1.32 mol) in THF (0.5 L) and then the resulting mixture was stirred for additional 30 min at the same temperature. CH$_3$I (563 g, 3.96 mol) was added and the mixture was slowly warm to room temperature over 2 h with mechanical stirring. The reaction mixture was quenched with water in ice-bath and extracted with EtOAc (1.5 L×2). The combined organic layers were washed with brine (3 L), dried over anhydrous MgSO$_4$, filtered and concentrated under reduced pressure to give 2-(4-chloro-3-methoxyphenyl)-2-methylpropanenitrile (14) as a amber liquid (269 g, 97%). $^1$H NMR (400 MHz, CDCl$_3$): δ 7.35-7.37 (d, 1H), 7.05 (s, 1H), 6.95-6.97 (d, 1H), 3.94 (s, 3H), 1.72 (s, 6H).

2-(4-Chloro-3-methoxyphenyl)-2-methylpropanenitrile (14) (269 g, 1.28 mol) was dissolved in 50% H$_2$SO$_4$ (2.7 L) and heated to reflux for 20 h with mechanical stirring. The reaction mixture was cooled to room temperature, diluted with water (5 L), and extracted with CH$_2$Cl$_2$ (1.5 L×3). The combined organic layers were washed with brine (5 L), dried over anhydrous MgSO$_4$, filtered and concentrated under reduced pressure to give 2-(4-chloro-3-methoxyphenyl)-2-methylpropanoic acid (15) as a brown solid (268 g, 92%). $^1$H NMR (400 MHz, CDCl$_3$): δ 7.30-7.32 (d, 1H), 6.92-6.96 (m, 3H), 3.89 (s, 3H), 1.59 (s, 6H).

To a solution of 2-(4-chloro-3-methoxyphenyl)-2-methylpropanoic acid (15) (268 g, 1.17 mol) in CH$_2$Cl$_2$ (1.7 L) was added N,O-dimethylhydroxylamine hydrochloride (137 g, 1.4 mol), EDCl (270 g, 1.4 mol), and DMAP (172 g, 1.4 mol). The resulting mixture was stirred for 3 h and washed with 10% citric acid solution (1.5 L), satd NaHCO$_3$ (1.5 L), and brine(1.5 L) successfully. The organic phase was dried over MgSO$_4$, filtered, and concentrated at reduced pressure to afford 2-(4-chloro-3-methoxyphenyl)-N-methoxy-N,2-dimethylpropanamide (16) as a brown solid (276 g, 96%). $^1$H NMR (400 MHz, CDCl$_3$): δ 7.30-7.32 (d, 1H), 6.81-6.84 (m, 3H), 3.89 (s, 3H), 3.12 (s, 3H), 2.78 (s, 3H), 1.53 (s, 6H).

To a solution of 2-(4-chloro-3-methoxyphenyl)-N-methoxy-N,2-dimethylpropanamide (16) (290 g, 1.06 mmol) in THF (1.5 L) was added MeLi (3M in THF, 462 mL, 1.38 mol) at −78° C. and the reaction mixture was warm to room temperature over 2 h. The reaction mixture was quenched with 2N HCl (1 L) in ice-bath, extracted with EtOAc (2 L). The separated organic layer was washed with brine (2 L), dried over anhydrous MgSO$_4$, filtered and concentrated under reduced pressure to give 3-(4-chloro-3-methoxyphenyl)-3-methyl-2-methylbutan-2-one (17) as a brown solid (241 g, quantitative).

$^1$H NMR (400 MHz, CDCl$_3$): δ 7.32-7.34 (d, 1H), 6.82-6.84 (d, 1H), 6.75 (s, 1H), 3.88 (s, 3H), 1.94 (s, 3H), 1.47 (s, 6H).

To a solution of 3-(4-chloro-3-methoxyphenyl)-3-methyl-2-methylbutan-2-one (17) (241 g, 1.06 mmol) in CH$_2$Cl$_2$ (2.2 L) and MeOH (1.1 L) was added Bu$_4$NBr$_3$ (514 g, 1.06 mol) at 0° C. and the reaction mixture was warm to room temperature over 3 h. The reaction mixture was quenched with 1N HCl (1 L) and evaporated. The residual diluted with EA (1.5 L) and EtOAc layer was washed with water (1.5 L), 1N HCl (1.5 L) and brine (1.5 L) successively. The organic layer was dried over MgSO$_4$, filtered and concentrated under reduced pressure to give 1-bromo-3-(4-chloro-3-methoxyphenyl)-3-methyl-2-methylbutan-2-one (18) as a brown solid (326 g, quantitative). $^1$H NMR (400 MHz, CDCl$_3$): δ 7.35-7.37 (d, 1H), 6.81-6.84 (d, 1H), 6.72 (s, 1H), 3.89 (s, 3H), 3.86 (s, 2H), 1.53 (s, 6H).

To a solution of 1-bromo-3-(4-chloro-3-methoxyphenyl)-3-methyl-2-methylbutan-2-one (18) (326 g, 1.06 mmol) in DMF (1 L) was added NaN$_3$ (90 g, 1.39 mol, 1.3 eq.) at 0° C. and the reaction mixture was warm to room temperature and stirred for 2 h. The reaction mixture was diluted with water (4 L) and extracted with diethyl ether (2 L×2). The combined organic layers were washed with brine (4 L×3), dried over anhydrous MgSO$_4$, filtered and concentrated under reduced pressure. Recrystallization of the residue from ethanol gave 1-azido-3-(4-Chloro-3-methoxyphenyl)-3-methyl-2-methylbutan-2-one (19) (146 g, 0.54 mol, 51%, white solid) along with impure product (120 g). $^1$H NMR (400 MHz, CD$_3$OD): δ 7.35-7.36 (d, 1H), 6.90 (s, 1H), 6.86-6.88 (d, 1H), 3.92 (s, 2H), 3.88 (s, 3H), 1.52 (s, 6H).

A pressure bottle was charged with a solution of 1-azido-3-(4-Chloro-3-methoxyphenyl)-3-methyl-2-methylbutan-2-one (19) (146 g, 0.54 mol) in MeOH (1.4 L), PtO$_2$ (2.5 g, 0.01 mol.) and conc HCl (10 mL, 1.1 mol). The bottle was purged with hydrogen gas (40 psi×2), pressurized with hydrogen (65 psi) and agitated for 5 h. The reaction mixture was filtered through Celite™ and the filtrate was evaporated to give a residue which was triturated with Et$_2$O to give 1-amido-3-(4-chloro-3-methoxyphenyl)-3-methyl-2-methylbutan-2-one hydrochloride (20) (131 g, 0.47 mol) as a white solid. $^1$H NMR (400 MHz, CD$_3$OD): δ 7.37-7.39 (d, 1H), 6.96 (s, 1H), 6.91-6.93 (d, 1H), 3.91 (s, 3H), 3.84 (s, 2H), 1.59 (s, 6H).

To a solution of 1-amido-3-(4-chloro-3-methoxyphenyl)-3-methyl-2-methylbutan-2-one HCl (20) (179 g, 0.643 mmol) and 4-fluorophenylisothiocyanate (93.6 g, 0.61 mol) in CH$_2$Cl$_2$ (1.5 L) were added TEA (179 mL, 1.29 mol) at 0° C. and the mixture was warm to room temperature and stirred for 1 h. The reaction mixture was washed with 10% citric acid (1.5 L), sat'd NaHCO$_3$ (1.5 L) and brine (1.5 L) successively, dried over MgSO$_4$, filtered and concentrated under reduced pressure to give a residue which was treated with Et$_2$O/Hex to afford 1-(3-(4-chloro-3-methoxyphenyl)-3-methyl-2-oxobutyl)-3-(4-fluorophenyl)thiourea (21) (230 g, 90%, white solid). $^1$H NMR (400 MHz, CDCl$_3$): δ 7.98 (s, 1H), 7.30-7.32 (d, 1H), 7.21-7.25 (m, 3H), 7.11-7.15 (t, 2H), 6.78-6.80 (d, 1H), 6.76 (s, 1H), 6.64 (s, 1H), 3.38 (d, 2H), 3.86 (s, 3H), 1.53 (s, 6H).

A solution of 1-(3-(4-chloro-3-methoxyphenyl)-3-methyl-2-oxobutyl)-3-(4-fluorophenyl)-thiourea (21) (230 g, 0.58 mmol) in HOAc (1 L) was heated to reflux for 4 h with mechanical stirring. The reaction mixture was cooled and evaporated to give a residue which was treated with diethyl ether to give 5-(2-(4-chloro-3-methoxyphenyl)propan-2-yl)-1-(4-fluorophenyl)-1H-imidazole-2-thiol (22) (207 g, 95%) as a white solid. $^1$H NMR (400 MHz, CDCl$_3$) δ 6.91-7.19 (d, 1H), 6.86-6.88 (t, 2H), 6.81 (s, 1H), 6.86-6.91 (t, 2H), 6.81 (s, 1H), 6.59-6.63 (m, 2H), 6.50-6.53 (d, 2H), 6.45 (s, 1H), 3.74 (s, 3H), 1.46 (s, 6H).

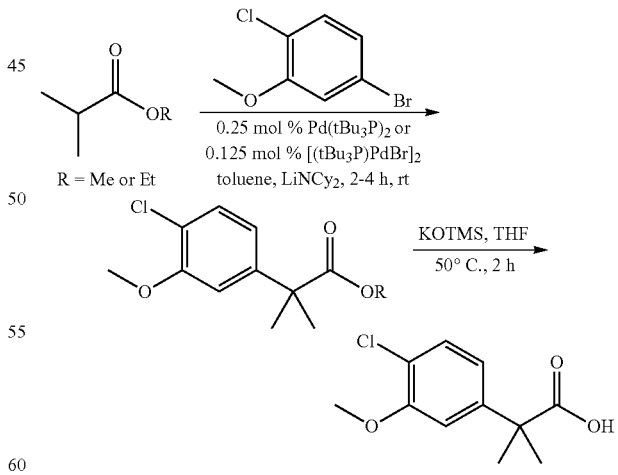

2-(4-chloro-3-methoxyphenyl)-2-methylpropanoic acid (alternative synthesis)

Dicyclohexylamine (2 mol) in 800 mL toluene under N$_2$ was cooled to 0-5° C. (jacket temperature at −10° C.). BuLi (2 mol, 800 mL, 2.5 M in hexanes) was added at a rate such that temperature does not exceed 15° C. After the end of the BuLi addition, the reaction mixture was allowed to cool to 0-5° C. Methyl isobutyrate (1.85 mol) was added neat at a rate such that the internal temperature did not exceed 10° C. The reaction mixture was then stirred at 10° C. for 20 min.

In a 1 L flask, 5-bromo-2-chloroanisole (1.54 mol) was dissolved in 340 mL toluene. [(tBu₃P)PdBr]₂ (0.125 mol %, 2.5 mol % Pd, 0.193 mmol, 1.5 g) added and stirred 5 min and added to ester enolate solution above rapidly in one portion. Flask rinsed with 100 mL toluene and added to the reaction.

The temperature was warmed to 25° C. and the reaction mixture was stirred under N₂ until consumption of bromochloroanisole was complete as determined by LC, typically 2-4 h. 1.7 L H₂O was added. The reaction mixture was stirred vigorously for 5 min and the organic and aqueous layers were allowed to separate. The lower aqueous layer was removed. The organic layer was washed twice with 1.7 L 25% aqueous AcOH, once with 1.7 L 10% NaHCO₃, and once with 1.7 L H₂O. The washed organic layer was line filtered (1 micron) and concentrated to give about 370 g (1.45 mol, 94%) of methyl 2-aryl-2-methylpropanoate as an a oil, which was solvent swapped to THF.

The methyl 2-aryl-2-methylpropanoate (~370 g, 1.45 mol) was dissolved in 3 L THF. 750 mL MTBE was added followed by powdered KOTMS (300 g, 90 wt %, 2.1 mol) and mixed under N₂ at 50° C. until the starting material was completely consumed as determined by LC, typically 2 h. The reaction mixture was cooled to 10° C. and 2 L H₂O was added and mixed vigorously for 5 min. The organic and aqueous layers were separated and lower aqueous phase was washed twice with 1 L heptane. 2 L IPAc were added to the aqueous layer and was acidified to pH 1 with conc HCl (~150 mL). The IPAc layer was washed with 1 L H₂O, line filtered (1 micron) and concentrated to give 320 g of 2-(4-chloro-3-methoxyphenyl)-2-methylpropanoic acid.

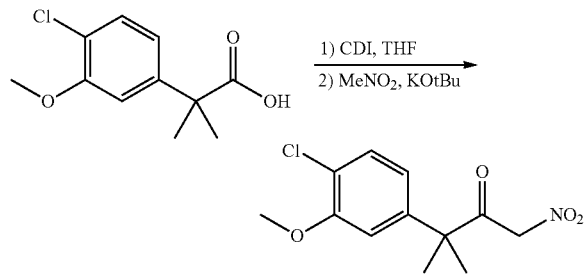

3-(4-chloro-3-methoxyphenyl)-3-methyl-1-nitrobutan-2-one (alternative synthesis)

A 500 mL 4-neck flask was charged with CDI (35.6 g; 0.22 mol) and 90 mL of THF. The suspension was heated to 35-40° C. and a solution of the 2-(4-chloro-3-methoxyphenyl)-2-methylpropanoic acid (45.7 g; 0.2 mol) in THF (90 mL) was added dropwise over ca. 30 min. At the end of the addition, the temperature was increased to 60° C. and stirred for an additional 1 hour.

In another 1000 mL 4-neck flask was charged a solution of potassium t-butoxide in THF (1 M; 250 mL; 0.25 mol) and cooled to below 5° C., under nitrogen Nitromethane (15.2 g; 0.25 mol) was added dropwise while keeping the temperature below 10° C. (ca. 10 min). The slurry was then aged at room temperature for 1 hour. The activated acid solution was added via cannula and heated at 60° C., for 4 hours. The reaction mixture was cooled to room temperature, and then treated with 200 mL of 2 M HCl. The organic layer was washed with water, 5% sodium carbonate solution and concentrated to half its volume. Isopropyl acetate (200 mL) was added to complete the precipitation of the 3-(4-chloro-3-methoxyphenyl)-3-methyl-1-nitrobutan-2-one, which was filtered, washed with isopropyl acetate and dried under vacuum to yield 47.5 g (87%).

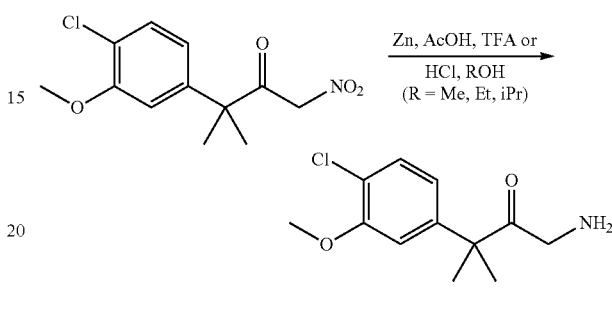

3-(4-chloro-3-methoxyphenyl)-3-methyl-1-nitrobutan-2-one (alternative synthesis)

3-(4-chloro-3-methoxyphenyl)-3-methyl-1-nitrobutan-2-one (1 g, 3.7 mmol) was dissolved in 5 mL isopropyl alcohol and AcOH (2.1 mL, 37 mmol, 10 equiv) was added and cooled to 0° C. Zn (8 equiv) was added slowly in small portions over 30 min with evolution of gas. The reaction mixture was stirred for an additional 10 minutes and filtered to remove residual Zn, washing with 15 mL IPAc (isopropyl alcohol). 10 mL saturated sodium bicarbonate solution was added and layers separated and organic layer was washed twice with 5 mL saturated sodium bicarbonate solution and once with water and concentrated to give a beige foam.

Under similar conditions the following intermediates were prepared from appropriate starting materials:

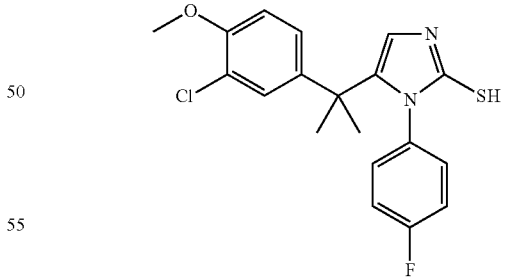

5-(2-(3-chloro-4-methoxyphenyl)propan-2-yl)-1-(4-fluorophenyl)-1H-imidazole-2-thiol $^1$H NMR (400 MHz, CDCl₃) δ 11.71 (s, 1H), 6.93 (t, J=3.10 Hz, 1H), 6.92-6.86 (m, 3H), 6.82-6.77 (m, 3H), 6.76-6.71 (m, 1H), 6.61 (ddd, J=6.83, 5.15, 2.70 Hz, 2H), 3.89 (s, 4H), 1.43 (s, 8H).

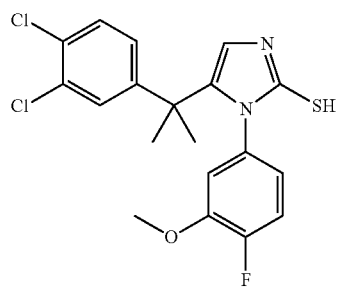 [SMILES: COc1cc(-n2c(C(C)(C)c3ccc(Cl)c(Cl)c3)cnc2S)ccc1F]

5-(2-(3,4-dichlorophenyl)propan-2-yl)-1-(4-fluoro-3-methoxyphenyl)-1H-imidazole-2-thiol $^1$H NMR (400 MHz, CDCl$_3$) δ 11.80 (dd, 1H), 7.31-7.24 (m, 2H), 7.07 (d, 1H), 7.00 (dd, 1H), 6.83 (s, 1H), 6.83-6.76 (m, 1H), 6.46 (ddd, 1H), 6.03 (dd, 1H), 3.55 (s, 3H), 2.11 (s, 1H), 1.48 (d, 7H).

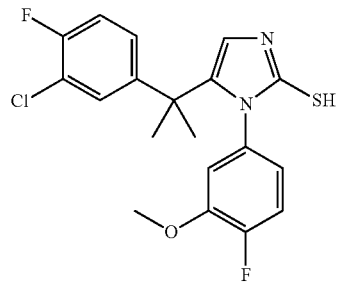 [SMILES: COc1cc(-n2c(C(C)(C)c3ccc(F)c(Cl)c3)cnc2S)ccc1F]

5-(2-(3-chloro-4-fluorophenyl)propan-2-yl)-1-(4-fluoro-3-methoxyphenyl)-1H-imidazole-2-thiol $^1$H NMR (400 MHz, CDCl$_3$) δ 10.99 (br s, 1H), 7.03-6.96 (m, 3H), 6.86-6.82 (m, 2H), 6.41-6.37 (m, 1H), 6.10 (d, 1H), 3.58 (s, 3H), 1.48 (d, 6H).

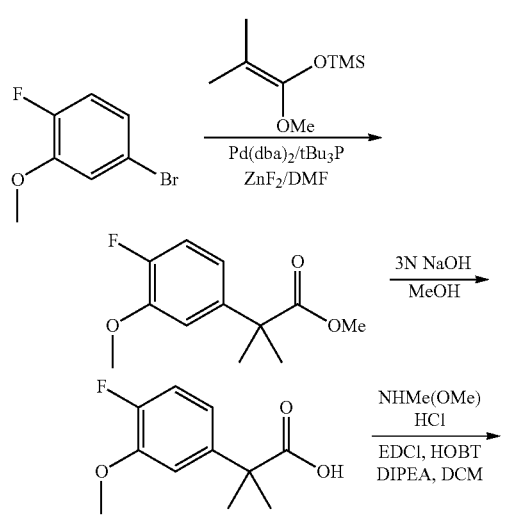

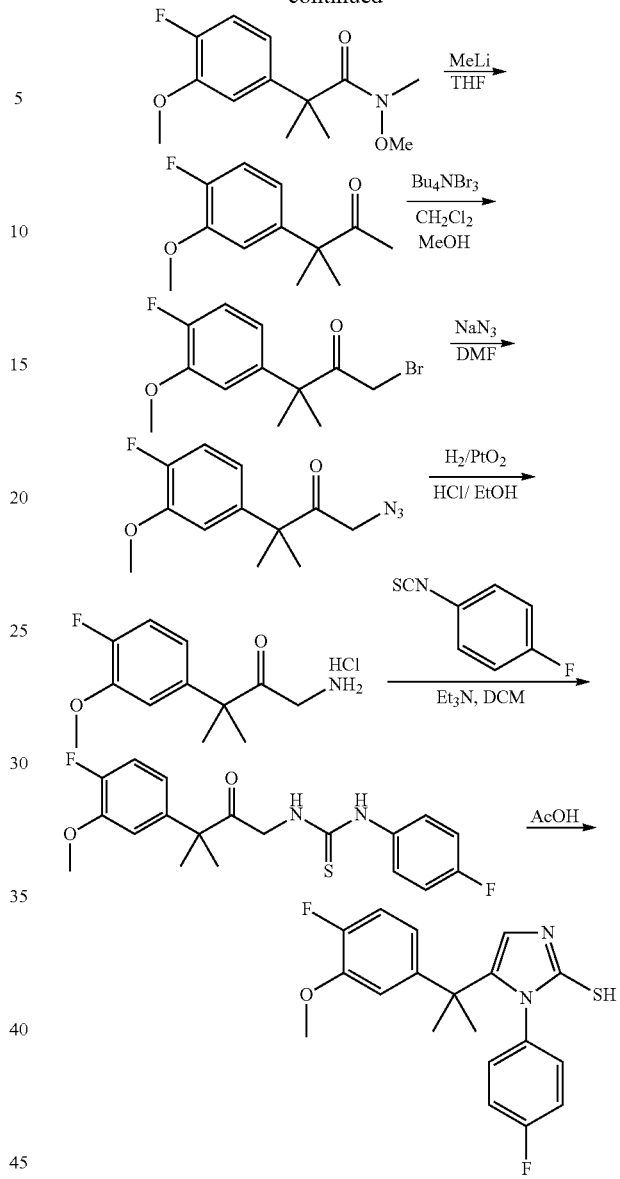

To a solution 5-bromo-2-fluoroanisole (109 g, 0.54 mol), ZnF$_2$ (2.52 g, 24.39 mmol), Pd(dba)$_2$ (3.08 g, 5.35 mmol), and P$^t$Bu$_3$ (5.2 mL of a 50% solution in toluene, 11 mmol) in DMF (1 L) was added trimethylsilyl methyl ketene acetal (121 g, 0.7 mol). The reaction mixture was stirred at 80-90° C. for 5 h under nitrogen atmosphere and then was allowed to cool to room temperature and diluted with EtOAc. The reaction mixture was filtered through Celite™. The filtrate was washed with H$_2$O (2 L) and the aqueous layer was extracted with EtOAc (2.5 L). The combined extracts were washed with brine (2 L×2), dried over MgSO$_4$, and concentrated at reduced pressure to give methyl 2-(4-fluoro-3-methoxyphenyl)-2-methylpropanoate (151 g), which was used for the next step without further purification. $^1$H NMR (400 MHz, CDCl$_3$): δ 7.04-6.98 (m, 1H), 6.95-6.92 (dd, 1H), 6.88-6.85 (m, 1H), 3.89 (s, 3H), 3.67 (s, 3H), 1.57 (s, 6H).

A solution of methyl 2-(4-fluoro-3-methoxyphenyl)-2-methylpropanoate (146 g) in MeOH (2 L) and 25% NaOH in H$_2$O (590 mL) was heated at reflux for 5 h. The reaction mixture was then allowed to cool to room temperature and concentrated at reduced pressure. The residue was dissolved in H$_2$O (2 L) and washed with ether (500 mL). The aqueous layer was acidified cautiously with conc HCl to pH 2. The resulting mixture was extracted with DCM (3 L), and combined extracts were dried over MgSO$_4$, and concentrated at reduced pressure to give 2-(4-fluoro-3-methoxyphenyl)-2-methylpropanoic acid (95 g, 84% over 2 steps). $^1$H NMR (400 MHz, CDCl$_3$): δ 7.06-7.00 (m, 2H), 6.93 (m, 1H), 3.90 (s, 3H), 3.86 (s, 2H), 1.60 (s, 6H).

To a solution of 2-(4-fluoro-3-methoxyphenyl)-2-methylpropanoic acid (114.75 g, 4.71 mmol) in DCM (2 L) was added N,O-dimethylhydroxylamine hydrochloride (79 g, 0.81 mol), EDCI (145 g, 0.72 mol), DMAP (33 g, 0.27 mol), and DIPEA (471 mL, 2.7 mol). The resulting mixture was stirred 5 h and quenched with H$_2$O (1 L). The organic layer was washed with 1N HCl (1 L×2), satd NaHCO$_3$ (1 L), and brine (1 L) successfully. The organic phase was dried over MgSO$_4$ and concentrated at reduced pressure to afford 2-(4-fluoro-3-methoxyphenyl)-N-methoxy-N,2-dimethylpropanamide as yellow color oil (123 g, 89%). $^1$H NMR (400 MHz, CDCl$_3$): δ 7.03 (t, 1H), 6.83 (d, 1H), 6.80 (m, 1H), 3.89 (s, 3H), 3.12 (s, 3H), 2.77 (s, 3H), 1.53 (s, 6H).

To a solution of 2-(4-fluoro-3-methoxyphenyl)-N-methoxy-N,2-dimethylpropanamide (123 g, 0.48 mol) in THF (1 L)-78° C. was added 3M ethereal solution of MeLi (210 mL, 0.627 mol). The resulting solution was warmed to ambient temperature and stirred 16 h. The reaction mixture was quenched with 3N HCl (400 mL) and extracted with EtOAc (600 mL×2). The combined extracts were washed with satd NaHCO$_3$ (1.0 L) and brine (1.0 L), then dried over MgSO$_4$ and concentrated at reduced pressure to give 3-(4-fluoro-3-methoxyphenyl)-3-methylbutan-2-one as yellow color oil (92.5 g, 91%). $^1$H NMR (400 MHz, CDCl$_3$): δ 7.05 (m, 1H), 6.83-6.78 (m, 2H), 3.88 (s, 3H), 1.95 (s, 3H), 1.47 (s, 6H).

To a solution of 3-(4-fluoro-3-methoxyphenyl)-3-methylbutan-2-one (92.52 g, 0.44 mmol) in DCM-MeOH (2:1, 1.2 L) was added Bu$_4$NBr$_3$ (222.8 g, 0.462 mol) at 0° C. The mixture was slowly warmed to room temperature and stirred 16 h. The reaction mixture was quenched with 0.5N Na$_2$S$_2$O$_3$ 5H$_2$O solution (2 L) and extracted with EtOAc (3 L). Combined extracts were washed 8 with 1N HCl (2 L), satd NaHCO$_3$ (1.0 L), and brine (1.0 L) successively, then dried over MgSO$_4$, filtered and concentrated under reduced pressure to give 1-bromo-3-(4-fluoro-3-methoxyphenyl)-3-methylbutan-2-one as brown solid (125.4 g, 98%). $^1$H NMR (400 MHz, CDCl$_3$): δ 7.10 (m, 1H), 6.82 (m, 1H), 6.76 (dd, 1H), 3.88 (s, 3H), 3.86 (s, 2H), 1.53 (s, 6H).

To a solution of 1-bromo-3-(4-fluoro-3-methoxyphenyl)-3-methylbutan-2-one (125.4 g, 0.44 mol) in DMF (500 mL) was added NaN$_3$ (37.2 g, 0.572 mol) at 0° C., and the mixture was warmed to room temperature over 3 h with stirring. The reaction mixture was diluted with water (2 L) and extracted with EtOAc (1 L×2). Combined extracts were washed with brine, dried over MgSO$_4$, and concentrated to give 1-azido-3-(4-fluoro-3-methoxyphenyl)-3-methylbutan-2-one (99.5 g), which was used in the next step without further purification. $^1$H NMR (400 MHz, CDCl$_3$): δ 7.07 (m, 1H), 6.79 (m, 2H), 3.92 (s, 3H), 3.78 (s, 2H), 1.53 (s, 6H).

A pressure bottle was charged with a solution of 1-azido-3-(4-fluoro-3-methoxyphenyl)-3-methylbutan-2-one (99.5 g, 0.396 mol) in MeOH (1.0 L), 50% wet 10% Pd/C (25 g, 25% w/w.) and conc HCl (105 mL, 1.19 mol). The bottle was purged with hydrogen gas (40 psi×2), pressurized with hydrogen (45 psi) and agitated overnight. The reaction mixture was filtered through a Celite™ pad. The filtrate was evaporated to give a residue, which was triturated with Et$_2$O to give 1-amino-3-(4-fluoro-3-methoxyphenyl)-3-methylbutan-2-one hydrochloride (57.4 g, 55%) as a white solid. $^1$H NMR (400 MHz, DMSO-d$_6$): δ 8.26 (b, 2H), 7.22 (m, 1H), 6.99 (dd, 1H), 6.89 (m, 1H), 3.87 (s, 3H), 3.81 (s, 2H), 1.50 (s, 6H).

To a mixture of 1-amino-3-(4-fluoro-3-methoxyphenyl)-3-methylbutan-2-one hydrochloride (35.4 g, 0.135 mol) and 4-fluorophenyl isothiocyanate (21.75 g, 0.142 mol) in DCM (500 mL) was added Et$_3$N (37.6 ml, 0.27 mol) at 0° C., and the reaction mixture was warm to room temperature over 1 h. The reaction mixture was washed with 1N HCl (500 mL), satd NaHCO$_3$ (500 mL) and brine (500 mL) successively, dried over MgSO$_4$, filtered and concentrated under reduced pressure give a residue, which was triturated with Hex-EtOAc to afford 1-(3-(4-fluoro-3-methoxyphenyl)-3-methyl-2-oxobutyl)-3-(4-fluorophenyl)thiourea (45 g, 88%) as a white solid. $^1$H NMR (400 MHz, CDCl$_3$) δ 7.85 (b, 1H), 7.25 (m, 2H), 7.15 (m, 2H), 7.05 (m, 1H), 6.79 (m, 2H), 6.67 (b, 1H), 3.88 (s, 3H), 1.54 (s, 6H).

A solution of 1-(3-(4-fluoro-3-methoxyphenyl)-3-methyl-2-oxobutyl)-3-(4-fluorophenyl)-thiourea (45 g, 0.119 mol) in AcOH (500 mL) was heated at reflux overnight. The cooled reaction mixture was concentrated and triturated with Et$_2$O to give 5-(2-(4-fluoro-3-methoxyphenyl)propan-2-yl)-1-(4-fluorophenyl)-1H-imidazole-2(3H)-thione (40.5 g, 94%) as a white solid. $^1$H NMR (400 MHz, CDCl$_3$) δ 6.90 (t, 3H), 6.81 (s, 1H), 6.61 (m, 2H), 6.50 (m, 2H), 3.76 (s, 3H), 1.46 (s, 6H); MS (ESI) m/z 361 (MH$^+$).

Preparation of 2-chloro-4-(2-(1-(4-fluoro-3-methoxyphenyl)-2-mercapto-1H-imidazol-5-yl)propan-2-yl)benzenesulfonamide

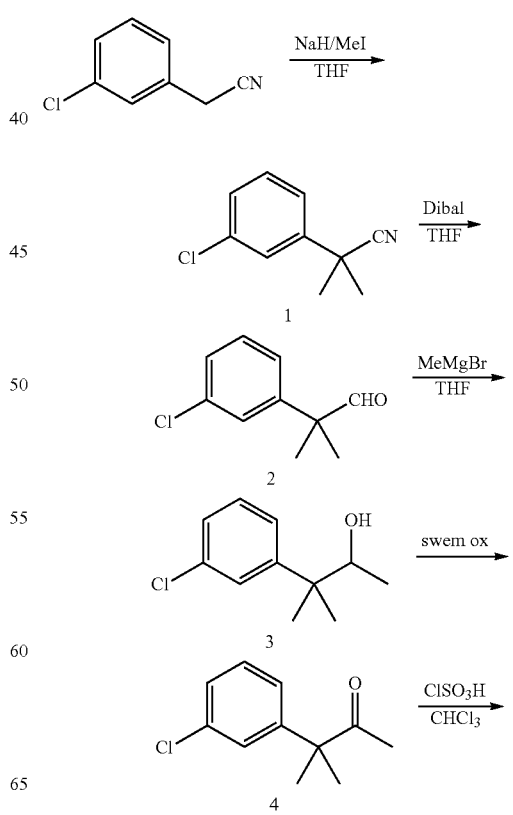

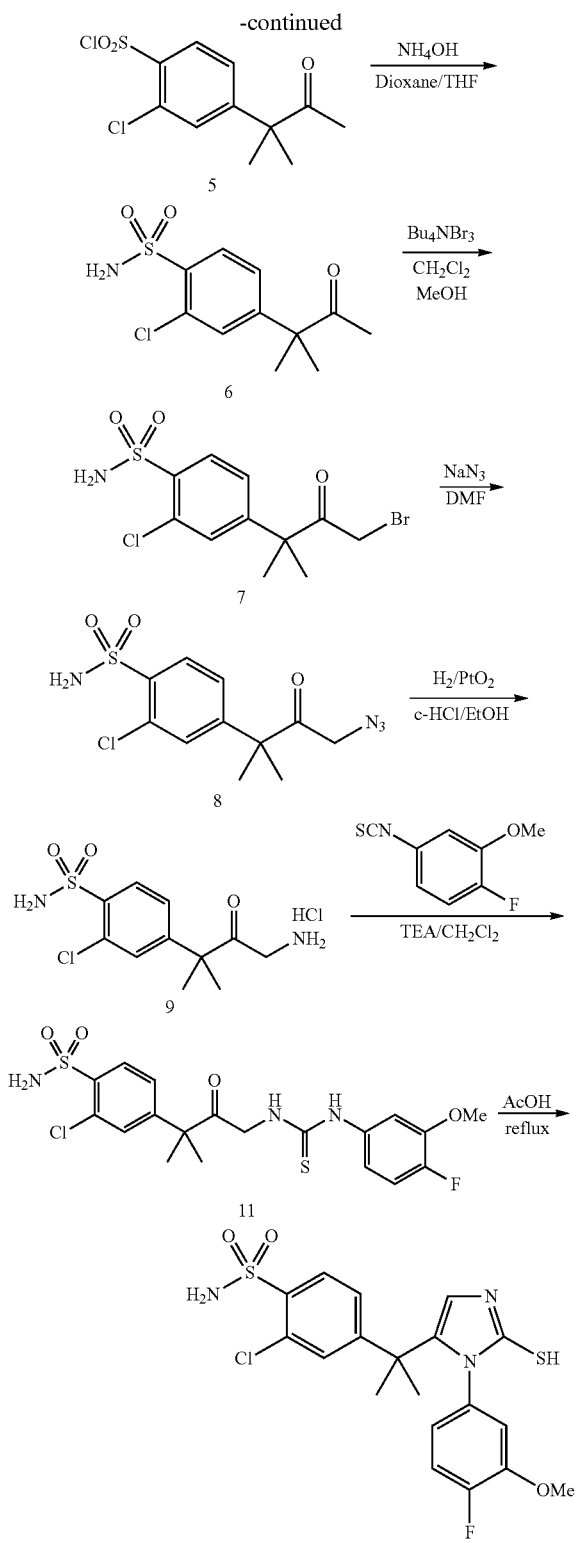

To a suspension of NaH (3.96 g, 99 mmol, 3 eq) in THF (100 mL) was added dropwise a solution of 3-chlorobenzyl-cyanide (5 g, 33 mmol) in THF (60 mL) at 0° C. After stirring 1 h, iodomethane (10.3 mL, 165 mmol, 5 eq) was added to the reaction mixture. After stirring for 2 h at 0° C., the reaction mixture was allowed to warm to room temperature, quenched carefully with the addition of water, and then extracted with EtOAc. The combined extracts were washed with brine, dried over $MgSO_4$ and evaporated in vacuo to give 2-(3-chlorophenyl)-2-methylpropanenitrile, which used in the next step without further purification (5.5 g, 92%). $^1$H NMR (400 MHz, $CDCl_3$) δ 7.44 (m, 1H), 7.37 (m, 2H), 7.29 (m, 1H), 1.72 (s, 6H).

To a solution of 2-(3-chlorophenyl)-2-methylpropanenitrile (5.3 g, 29.2 mmol) in THF (80 mL, anhyd) at −78° C. was added dropwise DIBAL-H (1M in toluene, 87 mL, 87 mmol, 3 eq) over 2 h. After stirring 30 min at −78° C., the reaction mixture was allowed to warm to room temperature, quenched with 2N HCl and extracted with EtOAc. The combined extracts were dried over $MgSO_4$ and evaporated in vacuo to give 2-(3-chlorophenyl)-2-methylpropanal (4.6 g, 88%). $^1$H NMR (400 MHz, $CDCl_3$) δ 9.48 (s, 1H), 7.32 (m, 3H), 7.14 (m, 1H), 1.51 (s, 6H).

To a stirred solution of 2-(3-chlorophenyl)-2-methylpropanal (4.6 g, 25.7 mmol) in THF (150 mL) at 0° C. was added MeMgBr (3M in ether, 17.1 mL, 51.3 mmol, 2 eq) dropwise over 2 h. After stirring 1 h at 0° C., the reaction was allowed to warm to room temperature, quenched with 1N HCl and then extracted with EtOAc. The extracts were dried over $MgSO_4$ and evaporated in vacuo. The residue was purified by chromatography (silica, Hex/EtOAc=20:1 to 10:1) to give 3-(3-chlorophenyl)-3-methylbutan-2-ol (3.9 g, 78%). $^1$H NMR (400 MHz, $CDCl_3$) δ 7.36 (s, 1H), 7.28 (m, 2H), 7.18 (m, 1H), 3.85 (q, 1H), 1.32 (d, J=6.4 Hz, 6H), 1.05 (d, J=6.8 Hz, 3H).

To a stirred solution of oxalyl chloride (3.4 mL, 40 mmol, 2 eq) in $CH_2Cl_2$ (100 mL) at −78° C. was added DMSO (4.9 mL, 70 mmol, 3.5 eq) dropwide. After stirring 1 h, the reaction mixture was treated dropwise with a solution of 3-(3-chlorophenyl)-3-methylbutan-2-ol (3.98 g, 20 mmol) in $CH_2Cl_2$ (100 mL). After stirring 1 h, $Et_3N$ (13.9 mL, 100 mmol, 5 eq) was added to the reaction mixture and the resulting mixture was slowly warmed to room temperature. The reaction mixture was partitioned in $CH_2Cl_2$ and water. The organic layer was separated, washed with 1N HCl and water, dried over $MgSO_4$ and evaporated in vacuo to give 3-(3-chlorophenyl)-3-methylbutan-2-one (3.9 g, 99%). $^1$H NMR (400 MHz, $CDCl_3$) δ 7.29 (m, 3H), 7.13 (m, 1H), 1.97 (s, 3H), 1.47 (s, 6H).

To a solution of 3-(3-chlorophenyl)-3-methylbutan-2-one (15 g, 76 mmol) in $CHCl_3$ (100 mL) was added chlorosulfuric acid (101 mL, 20 eq) at 0° C. over 2 h. Next $SOCl_2$ (20 mL) was added dropwise to the reaction mixture over 30 min under nitrogen. The reaction mixture was slowly warmed to room temperature and stirred overnight. The mixture was slowly added to ice-water and then extracted with EtOAc. The combined extracts were washed with brine, dried over $MgSO_4$ and evaporated. The residue was purified by chromatography (silica, Hex/EtOAc=9:1 to 4:1) to give 2-chloro-4-(2-methyl-3-oxobutan-2-yl)benzene-1-sulfonyl chloride as a yellow solid (9.8 g, 43%). $^1$H NMR (400 MHz, $CDCl_3$) δ 8.12 (d, J=8.4 Hz, 1H), 7.54 (s, 1H), 7.37 (d, J=2.2 Hz, 1H), 2.03 (s, 3H), 1.56 (s, 6H).

To a stirred solution of $NH_4OH$ (30 mL) was added a solution of 2-chloro-4-(2-methyl-3-oxobutan-2-yl)benzene-1-sulfonyl chloride (9.8 g, 33.2 mmol) in THF (150 mL) at 0° C. After stirring 2 h, volatiles were removed under reduced pressure. The residue was diluted with water and extracted with EtOAc (100 mL×2). The combined extracts were dried over $MgSO_4$, concentrated and purified by column chromatography (Hex/EtOAc=4:1 to 2:1) to give 2-chloro-4-(2-methyl-3-oxobutan-2-yl)benzenesulfonamide (8.9 g, 96% yield) as yellow oil. $^1$H NMR (400 MHz, $CDCl_3$) δ 8.09 (d, J=8.4 Hz, 1H), 7.43 (s, 1H), 7.27 (d, J=2.2 Hz, 1H), 5.09 (s, 2H), 2.04 (s, 3H), 1.52 (s, 6H).

To a solution of 2-chloro-4-(2-methyl-3-oxobutan-2-yl)benzenesulfonamide (8.9 g, 32.1 mmol) in CH$_2$Cl$_2$/MeOH (150 mL, 2:1, v/v) was added Bu$_4$NBr$_3$ (16.3 g, 33.7 mmol, 1.05 eq) in one portion. After 20 h, volatiles were removed and then the residue was partitioned in EtOAc and water. The organic layer was washed with 1M HCl solution and water sequentially, dried over MgSO$_4$, filtered and evaporated to give 4-(4-bromo-2-methyl-3-oxobutan-2-yl)-2-chlorobenzenesulfonamide (11.4 g, quant) as yellow oil, which was used for the next reaction without further purification. $^1$H NMR (400 MHz, CDCl$_3$) δ 8.11 (d, J=8.4 Hz, 1H), 7.44 (s, 1H), 7.30 (d, J=2.2 Hz, 1H), 5.16 (s, 2H), 3.88 (s, 2H), 1.61 (s, 6H).

To a solution of 4-(4-bromo-2-methyl-3-oxobutan-2-yl)-2-chlorobenzenesulfonamide (11.3 g, 31.8 mmol) in DMF (50 mL) was added NaN$_3$ (3.1 g, 47.8 mmol, 1.5 eq) at 0° C. After stirring 2 h, the residue was diluted with water and extracted with EtOAc. The combined extracts were washed with 1M HCl and water successively, dried over MgSO$_4$, filtered and evaporated. The residue was purified by chromatography (Hex/EtOAc=4:1 to 2:1) to give 4-(4-azido-2-methyl-3-oxobutan-2-yl)-2-chlorobenzenesulfonamide (8.0 g, 79% yield) as yellow sticky oil. $^1$H NMR (400 MHz, CDCl$_3$) δ 8.11 (d, J=8.4 Hz, 1H), 7.43 (s, 1H), 7.29 (d, J=2.2 Hz, 1H), 5.12 (s, 2H), 4.11 (s, 2H), 1.58 (s, 6H).

A pressure bottle was charged with a solution of 4-(4-azido-2-methyl-3-oxobutan-2-yl)-2-chlorobenzenesulfonamide (8 g, 25.2 mmol) in EtOH (100 mL), conc HCl (20 mL) and PtO$_2$ (114 mg, 0.5 mmol, 0.02 eq) and then was purged with hydrogen (2×45 psi). The bottle was pressurized with hydrogen (45 psi) and agitated 2 h. The reaction mixture was filtered through Celite™ and the filtrate was evaporated. The residue was triturated with Et$_2$O, filtered and dried to afford 4-(4-amino-2-methyl-3-oxobutan-2-yl)-2-chlorobenzenesulfonamide hydrochloride (7.8 g, 94% yield) as yellow solid. $^1$H NMR (400 MHz, DMSO) δ 8.22 (br s, 3H), 7.91 (d, J=8.4 Hz, 1H), 7.60 (s, 2H), 7.50 (s, 1H), 7.43 (d, J=8.4 Hz, 1H), 3.92 (m, 2H), 1.49 (s, 6H).

To a stirred mixture of 4-(4-amino-2-methyl-3-oxobutan-2-yl)-2-chlorobenzenesulfonamide hydrochloride (7.8 g, 23.7 mmol) in DCM (150 mL) was added Et$_3$N (9.9 mL, 71.1 mmol, 3 eq) and 1-fluoro-4-isothiocyanato-2-methoxybenzene (4.35 g, 23.7 mmol). After stirring 2 h, DCM and water were added to the reaction mixture. The organic layer was separated, dried over MgSO$_4$ and evaporated in vacuo. The residue was purified by flash column chromatography (Hex/EtOAc=1:1 to EtOAc/DCM=1:1) to give 2-chloro-4-(4-(3-(4-fluoro-3-methoxyphenyl)thioureido)-2-methyl-3-oxobutan-2-yl)benzenesulfonamide (8.6 g, 76%). $^1$H NMR (400 MHz, CDCl$_3$) δ 8.08 (d, J=8.4 Hz, 1H), 7.80 (s, 1H), 7.43 (d, J=2.0 Hz, 1H), 7.30 (d, J=8.8 Hz, 1H), 7.15 (m, 1H), 6.89 (d, J=7.6 Hz, 1H), 6.77 (m, 2H), 5.30 (s, 2H), 4.43 (d, J=4.4 Hz, 2H), 3.91 (s, 3H), 1.59 (s, 6H).

A solution of 2-chloro-4-(4-(3-(4-fluoro-3-methoxyphenyl)thioureido)-2-methyl-3-oxobutan-2-yl)benzenesulfonamide (8.6 g, 18.1 mmol) in AcOH (100 mL) was refluxed 3 h. After the reaction was complete, the solution was cooled to room temperature and azeotroped with toluene. The residue was triturated with Et$_2$O, filtered and dried to provide the title compound (6.8 g, 82% yield) as a light yellow solid. $^1$H NMR (400 MHz, CDCl$_3$+MeOD) δ 7.92 (d, J=8.4 Hz, 1H), 7.09 (s, 1H), 7.06 (d, J=8.4 Hz, 1H), 6.97 (t, J=8.4 Hz, 1H), 6.89 (s, 1H), 6.38 (m, 1H), 6.13 (d, J=7.2 Hz, 1H), 3.58 (s, 3H), 1.54 (s, 6H); MS (EI) m/z 456 (MH$^+$).

Preparation of 2-fluoro-5-(2-(1-(4-fluoro-3-methoxyphenyl)-2-mercapto-1H-imidazol-5-yl)propan-2-yl)benzonitrile

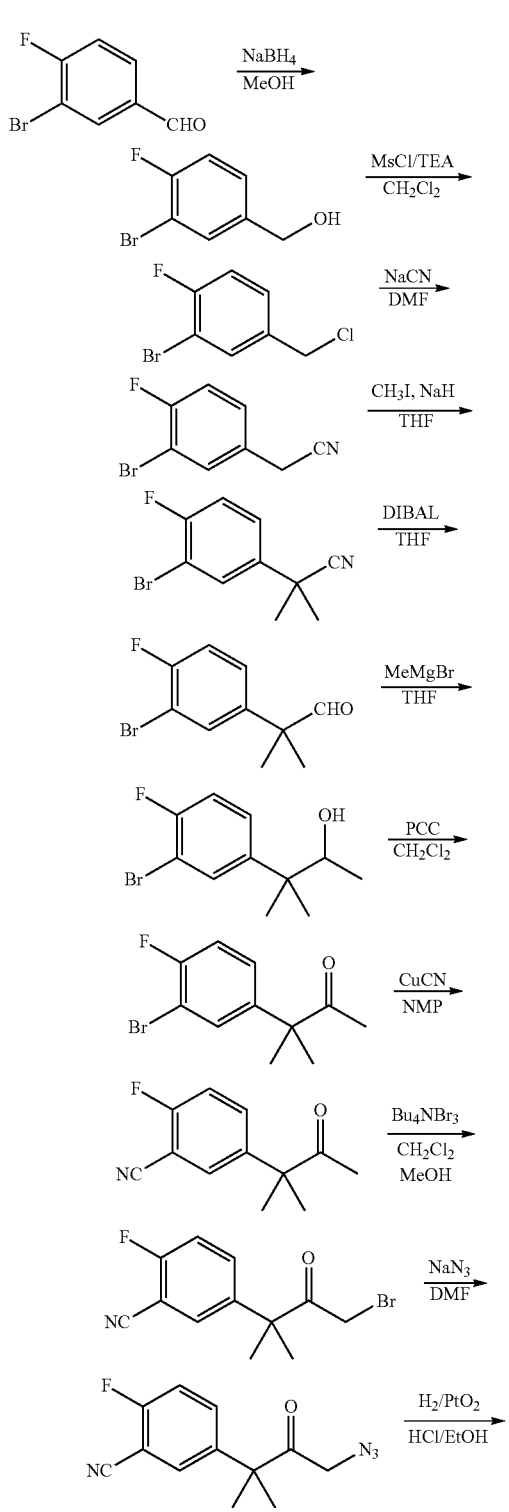

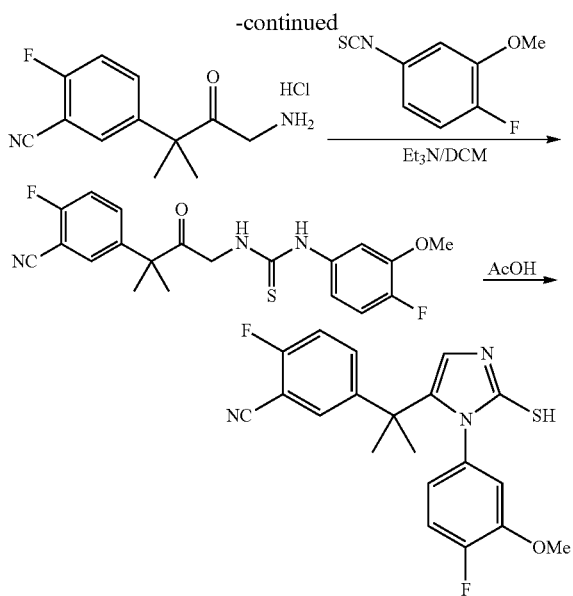

To a solution of 3-bromo-4-fluorobenzaldehyde (50 g, 0.246 mol) in MeOH (500 mL) at 0° C. was added NaBH₄ (9.3 g, 0.246 mol) portionwise. After 1 h, the reaction was concentrated in vacuo, diluted with water and extracted with DCM. The combined extracts were dried over MgSO₄ and concentrated in vacuo to give (3-bromo-4-fluorophenyl) methanol (53 g). $^1$H NMR (400 MHz, CDCl₃) δ 7.58-7.56 (m, 1H), 7.28-7.25 (m, 1H), 7.09 (t, J=4.4 Hz, 1H), 4.65 (d, J=5.2 Hz, 2H), 1.82 (t, J=5.6 Hz, 1H).

To a solution of (3-bromo-4-fluorophenyl)methanol (53 g, 0.258 mol) in DCM (500 mL) at 0° C. was added Et₃N (108 mL, 775 mmol, 3 eq) and methanesulfonyl chloride (24 mL, 310 mmol, 1.2 eq) successively. After stirring 30 min, the reaction mixture was partitioned in DCM and water. The organic layer was dried over MgSO₄ and evaporated in vacuo to give 3-bromo-4-fluorobenzyl methanesulfonate (60 g), which used to the next step without further purification. $^1$H NMR (400 MHz, CDCl₃) δ 7.65-7.62 (m, 1H), 7.37-7.33 (m, 1H), 7.16 (t, J=4.4 Hz, 1H), 5.17 (s, 2H), 2.99 (s, 3H).

To a stirred solution of 3-bromo-4-fluorobenzyl methanesulfonate (60 g, 0.212 mol) in DMF (300 mL) at 0° C. was added NaCN (31.1 g, 0.635 mol, 3 eq) portionwise. After stirring at room temperature 4 h, the reaction mixture was partitioned in EtOAc and water. The organic layer was dried over MgSO₄ and evaporated in vacuo. The residue was purified by column chromatography (Hex/EtOAc=4:1) to give 2-(3-bromo-4-fluorophenyl)acetonitrile (30 g, 3 step overall yield: 55%). $^1$H NMR (400 MHz, CDCl₃) δ 7.56-7.54 (m, 1H), 7.28-7.24 (m, 1H), 7.14 (t, J=4.4 Hz, 1H), 3.73 (s, 2H).

To a stirred suspension of NaH (16.3 g, 406 mmol, 3 eq) in anhyd THF (100 mL) at 0° C. was added dropwise a solution of 2-(3-bromo-4-fluorophenyl)acetonitrile (29 g, 135 mmol) in anhyd THF (200 mL). After stirring 1 h, MeI (42.1 mL, 675 mmol, 5 eq) was added to the reaction mixture. After stirring 2 h at 0° C., the reaction was allowed to warm to room temperature, quenched carefully with H₂O and extracted with EtOAc. The combined extracts were washed with brine, dried over MgSO₄ and evaporated in vacuo to give 2-(3-bromo-4-fluorophenyl)-2-methylpropanenitrile (29 g, 88%). $^1$H NMR (400 MHz, CDCl₃) δ 7.66-7.64 (m, 1H), 7.44-7.40 (m, 1H), 7.15 (t, J=8.4 Hz, 1H), 1.72 (s, 6H).

To a stirred solution of 2-(3-bromo-4-fluorophenyl)-2-methylpropanenitrile (29 g, 120 mmol) in THF (500 mL) at −78° C. was dropwise added DIBALH (1M in toluene, 360 mL, 3 eq) over 2 h. After the reaction mixture was stirred at same temperature for 30 minutes, it was allowed to warm to room temperature. After the reaction was complete, the mixture was quenched by 1N HCl and extracted with EA. The separated organic layer was dried over MgSO₄ and evaporated in vacuo to give 2-(3-bromo-4-fluorophenyl)-2-methylpropanal (27 g, 92%). $^1$H NMR (400 MHz, CDCl₃) δ 9.46 (s, 1H), 7.47-7.44 (m, 1H), 7.19-7.15 (m, 1H), 7.12 (t, J=8.4 Hz, 1H), 1.45 (s, 6H).

To a stirred solution of 2-(3-bromo-4-fluorophenyl)-2-methylpropanal (27 g, 110 mmol) in anhyd THF (300 mL) at 0° C. was added MeMgBr (3M in ether, 73 mL, 220 mmol, 2 eq) dropwise over 2 h. After stirring 1 h, the reaction was allowed to warm to room temperature, quenched carefully with 1N HCl and extracted with EtOAc. The combined extracts were washed with brine, dried over MgSO₄ and evaporated in vacuo. The residue was purified by column chromatography (Hex/EA=10:1) to give 3-(3-bromo-4-fluorophenyl)-3-methylbutan-2-ol (19 g, 66%). $^1$H NMR (400 MHz, CDCl₃) δ 7.56-7.54 (m, 1H), 7.32-7.28 (m, 1H), 7.07 (t, J=8.4 Hz, 1H), 3.84-3.79 (m, 1H), 1.31 (d, J=6.4 Hz, 6H), 1.04 (d, J=6.4 Hz, 3H).

To a stirred solution of 3-(3-bromo-4-fluorophenyl)-3-methylbutan-2-ol (18 g, 69 mmol) in DCM (300 mL) at 0° C. was added PCC (29.7 g, 2 eq) portionwise. After stirring 24 h at room temperature, the reaction mixture was combined with water and extracted with DCM. The combined extracts were dried over MgSO₄ and evaporated in vacuo. The residue was purified by flash column chromatography (Hex/EtOAc=10:1) to give 3-(3-bromo-4-fluorophenyl)-3-methylbutan-2-one (13 g, 73%). $^1$H NMR (400 MHz, CDCl₃) δ 7.47-7.45 (m, 1H), 7.17-7.14 (m, 1H), 7.09 (t, J=8.8 Hz, 1H), 1.98 (s, 3H), 1.45 (s, 6H).

To a solution of 3-(3-bromo-4-fluorophenyl)-3-methylbutan-2-one (13 g, 50 mmol) in NMP (100 mL) was added CuCN (17.9 g, 200 mmol, 4 eq). The mixture was heated 24 h at 160° C. After cooling, the reaction was diluted with EtOAc, washed with 2N HCl (200 mL), satd NaHCO₃ (200 mL) and brine (200 mL) successively, dried over MgSO₄ and evaporated in vacuo. The residue was purified by column chromatography (Hex/EtOAc=4:1) to give 2-fluoro-5-(2-methyl-3-oxobutan-2-yl)benzonitrile (7.1 g, 69%). $^1$H NMR (400 MHz, CDCl₃) δ 7.56-7.54 (m, 1H), 7.49-7.45 (m, 1H), 7.20 (t, J=8.4 Hz, 1H), 1.96 (s, 3H), 1.50 (s, 6H).

To a stirred solution of 2-fluoro-5-(2-methyl-3-oxobutan-2-yl)benzonitrile (7.1 g, 34.5 mmol) in CH₂Cl₂ and MeOH (2:1, 100 mL) was added Bu₄NBr₃ (17.5 g, 36.5 mmol, 1.05 eq) portionwise. The reaction mixture was stirred 48 h and evaporated in vacuo. The residue was diluted with 1N HCl (300 mL) and extracted with EtOAc (150 mL). The combined extracts were washed with satd NaHCO₃ solution (200 mL), dried over MgSO₄ and evaporated in vacuo to give 5-(4-bromo-2-methyl-3-oxobutan-2-yl)-2-fluorobenzonitrile (10 g), which used to the next step without further purification.

To a stirred solution of 5-(4-bromo-2-methyl-3-oxobutan-2-yl)-2-fluorobenzonitrile (10 g, 35.2 mmol) in DMF (100 mL) at 0° C. was added NaN₃ (2.52 g, 38.7 mmol, 1.1 eq) portionwise. After stirring 2 h, the residue was diluted with water and extracted with EtOAc. The combined extracts were washed with brine (100 mL), dried over MgSO₄ and evaporated in vacuo. The residue was purified by flash column chromatography (silica, Hex/EtOAc=4:1) to give 5-(4-azido-2-methyl-3-oxobutan-2-yl)-2-fluorobenzonitrile (6.6 g, 2 step overall yield 78%). $^1$H NMR (400 MHz, CDCl₃) δ 7.57-7.55 (m, 1H), 7.50-7.46 (m, 1H), 7.25 (t, J=7.2 Hz, 1H), 3.8 (s, 2H), 1.55 (s, 6H).

To a stirred solution of 5-(4-azido-2-methyl-3-oxobutan-2-yl)-2-fluorobenzonitrile (6.1 g, 24.7 mmol) in EtOH (100 mL) was added conc HCl (20 mL) and PtO₂ (112 mg, 0.49 mmol, 0.02 eq). The mixture was stirred at 1 atm of H₂ gas for 12 h, filtered through Celite™ and evaportated in vacuo. The residue was partitioned in DCM and water, and the aqueous layer was evaporated in vacuo. The resulting residue was triturated with Et₂O-Hex to give 5-(4-amino-2-methyl-3-oxobutan-2-yl)-2-fluorobenzonitrile hydrochloride as a yellow solid (6 g, 65%). ¹H NMR (400 MHz, CD₃OD) δ 7.74-7.68 (m, 2H), 7.37 (t, J=8.8 Hz, 1H), 3.89 (s, 2H), 1.58 (s, 6H).

To a suspension of 5-(4-amino-2-methyl-3-oxobutan-2-yl)-2-fluorobenzonitrile hydrochloride (2.8 g, 10.9 mmol) in DCM (50 mL) were added Et₃N (4.6 mL, 32.7 mmol, 3 eq) and 1-fluoro-4-isothiocyanato-2-methoxybenzene (2.2 g, 12 mmol, 1.1 eq). After stirring 2 h, the reation mixture was partitioned in DCM and water. The organic layer was separated, dried over MgSO₄ and evaporated in vacuo. The residue was purified by flash column chromatography (silica, Hex:EA=1:1) to give 1-(3-(3-cyano-4-fluorophenyl)-3-methyl-2-oxobutyl)-3-(4-fluoro-3-methoxyphenyl)thiourea (3.7 g, 84%). ¹H NMR (400 MHz, CDCl₃) δ 7.59 (bs, 1H), 7.53-7.49 (m, 2H), 7.26-7.18 (m, 2H), 6.89-6.79 (m, 2H), 6.70 (bs, 1H), 4.44 (d, J=4.4 Hz, 2H), 3.90 (s, 3H), 1.58 (s, 6H).

A solution of 1-(3-(3-cyano-4-fluorophenyl)-3-methyl-2-oxobutyl)-3-(4-fluoro-3-methoxyphenyl)thiourea (3.7 g, 9.17 mmol) in AcOH (50 mL) was refluxed 2 h at 110° C. After the reaction was complete, it was cooled to room temperature and co-evaporated with toluene in vacuo. The residue was purified by flash column chromatography (Hex:EA=1:3) to give 2-fluoro-5-(2-(1-(4-fluoro-3-methoxyphenyl)-2-mercapto-1H-imidazol-5-yl)propan-2-yl)benzonitrile (2.3 g, 65%) as a yellow solid. ¹H NMR (400 MHz, CDCl₃) δ 10.6 (bs, 1H), 7.26-7.23 (m, 1H), 7.08 (t, J=9.2 Hz, 1H), 6.96 (t, J=8.8 Hz, 1H), 6.84 (d, J=2.0 Hz, 1H), 6.25-6.25 (m, 1H), 6.17-6.15 (m, 1H), 3.59 (s, 3H), 1.51 (s, 6H).

Preparation of tert-butyl 3,5-difluoro-4-((methylsulfonyloxy)methyl)benzoate

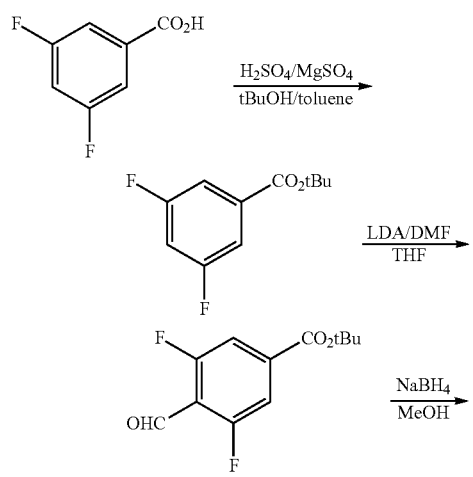

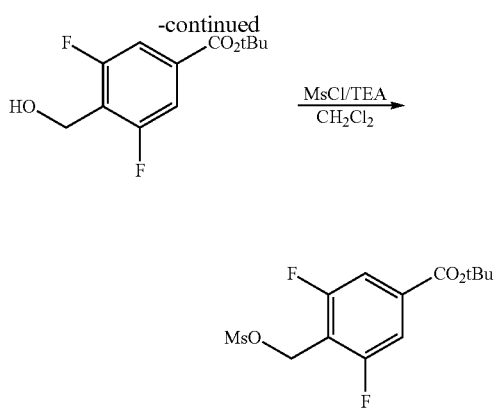

Concentrated H₂SO₄ (1.74 mL, 31.6 mmol) was added to a vigorously stirred suspension of MgSO₄ (15.2 g, 126.4 mmol, 4 eq) in toluene (100 mL). The mixture was stirred for 15 minutes, after which 3,5-difluorobenzoic acid (5 g, 31.6 mmol) and t-BuOH (14.9 mL, 158 mmol, 5 eq) were added successively. The mixture was stoppered tightly and stirred at room temperature until the reaction was complete by TLC analysis. The reaction mixture was then quenched with saturated NaHCO₃ solution and stirred until all MgSO₄ had dissolved. The organic layer was washed with brine, dried over MgSO₄ and concentrated to afford the crude product. The residue was purified by chromatography (silica, Hex) to give tert-butyl 3,5-difluorobenzoate (5.3 g, 78%) as a colorless oil.

To a stirred solution of diisopropylamine (5 mL, 35.5 mmol, 1.2 eq) in THF (100 mL, anhyd) was slowly added BuLi (1.6M in hexanes, 20 mL, 32.3 mmol, 1.1 eq) at below 0° C. After addition was completed, the solution was cooled to −78° C. and then charged dropwise with a solution of tert-butyl 3,5-difluorobenzoate (6.3 g, 29 mmol) in THF (50 mL, anhyd) over 1 h. The resulting solution was stirred for another 2 h at −78° C. Next anhyd DMF (2.5 mL, 32.3 mmol, 1.1 eq) was added dropwise and, after 30 min, AcOH (4 mL) and water were added successively to quench the reaction. The reaction mixture was warmed to room temperature and diluted with EtOAc (100 mL). The organic layer was washed with brine, dried over MgSO₄ and concentrated in vacuo. The residue was purified by flash column chromatography (Hex/EtOAc=4:1) to give tert-butyl 3,5-difluoro-4-formylbenzoate (5.8 g, 83%) as a white solid.

To a stirred solution of tert-butyl 3,5-difluoro-4-formylbenzoate (21 g, 86.7 mmol) in MeOH was portionwise added NaBH₄ (3.28 g, 86.7 mmol) at 0° C. After 20 min, the reaction mixture was evaporated in vacuo and the product was extracted with ethyl acetate. The organic layer was washed with brine, dried over MgSO₄ and evaporated in vacuo. The residue was purified by flash column chromatography (Hex/EtOAc=4:1) to give tert-butyl 3,5-difluoro-4-(hydroxymethyl)benzoate (20.7 g, 97%) as a white solid.

To a stirred solution of tert-butyl 3,5-difluoro-4-(hydroxymethyl)benzoate (1.9 g, 7.78 mmol) in DCM was added Et₃N (3.27 mL, 23.4 mmol, 3 eq) and methanesulfonylchloride (0.72 mL, 9.3 mmol, 1.2 eq) successively at 0° C. After the reaction was stirred for 30 min, it was extracted with CH₂Cl₂C and water. Organic layer was dried over MgSO₄ and evaporated in vacuo. The residue was purified by column chromatography (Hex/EtOAc=4:1) to give tert-butyl 3,5-difluoro-4-((methylsulfonyloxy)methyl)benzoate (2.25 g, 89% yield) as a ivory solid.

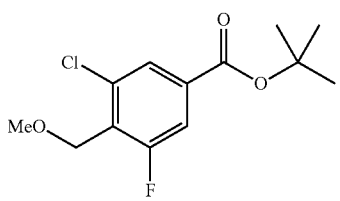 [SMILES: COCc1c(F)cc(C(=O)OC(C)(C)C)cc1Cl]

Under similar conditions, tert-butyl 3-chloro-5-fluoro-4-((methylsulfonyloxy)methyl)benzoate was prepared from 3-chloro-5-fluorobenzoic acid. $^1$H NMR (400 MHz, CDCl$_3$) δ 7.87-7.85 (m, 1H), 7.67-7.62 (m, 1H), 5.42 (d, 2H), 3.07 (s, 3H), 1.60 (s, 9H).

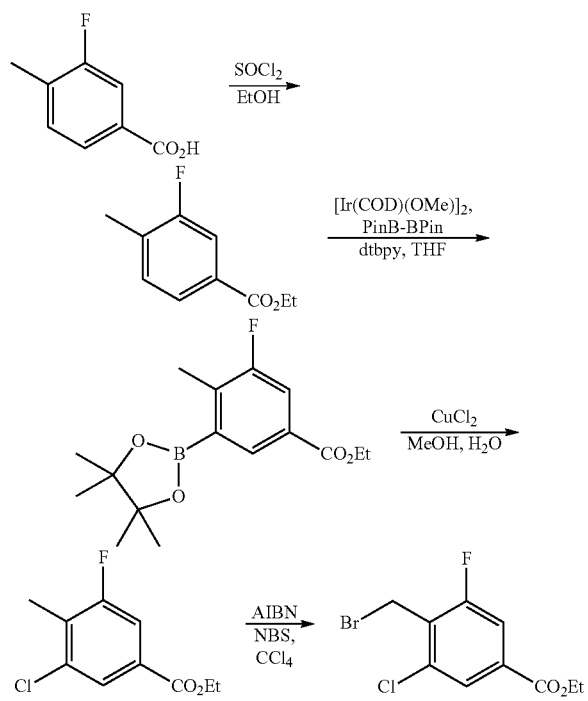

To a solution of 3-fluoro-4-methylbenzoic acid (13.23 g, 85.85 mmol) in EtOH (200 mL) at 0° C. was added SOCl$_2$ (3 mL) dropwise. The reaction mixture was heated at 60° C. overnight, then cooled to room temperature, concentrated under reduced pressure and diluted with DCM. The organic layer was washed with 1N NaOH (100 mL×2), dried (MgSO$_4$) and concentrated to give ethyl 3-fluoro-4-methylbenzoate (15.02 g, 96%).

To a solution of ethyl 3-fluoro-4-methylbenzoate (15.02 g, 82.42 mmol) and bispinacolotodiboron (20.93 g, 82.42 mmol) in THF (200 mL, anhyd) was added 4,4'-di-t-butylbipyridine (930 mg, 3.46 mmol) followed by 1-5-cyclooctadiene(methoxy)iridium (I) dimer (710 mg, 1.07 mmol) under nitrogen atmosphere. The reaction mixture was heated at 80° C. overnight. GC-MS showed conversion (>74%) of starting material to a mixture of two isomers (55:45). Ice was added slowly to the reaction mixture, which then was concentrated under reduced pressure, diluted with DCM and washed with H$_2$O (150 mL×2). The organic layer was dried (Na$_2$SO$_4$), concentrated and purified by flash chromatography (20-80% EtOAc/hexanes) to furnish ethyl 3-fluoro-4-methyl-5-(4,4,5,5-tetramethyl-1,3,2-dioxaborolan-2-yl)benzoate (8.664 g, 34%) as a white solid. $^1$H NMR (400 MHz, DMSO-d$_6$) δ 8.05 (d, J=1.7 Hz, 1H), 7.71 (dt, J=14.2, 7.1 Hz, 1H), 4.33 (q, J=7.1 Hz, 2H), 2.47 (d, J=2.5 Hz, 3H), 1.37-1.29 (m, 15H).

To a solution of ethyl 3-fluoro-4-methyl-5-(4,4,5,5-tetramethyl-1,3,2-dioxaborolan-2-yl)benzoate (8.664 g, 28.12 mmol) in MeOH (50 mL) was added CuCl$_2$ (11.34 g, 84.35 mmol) in H$_2$O (10 mL). The reaction mixture was heated at 90° C. overnight. GC-MS confirmed complete conversion to product. The volatiles were removed in vacuo. The resulting material was diluted with an additional 10 mL of H$_2$O, and extracted with DCM (50 mL×2). The combined extracts were dried (Na$_2$SO$_4$), concentrated and purified by flash chromatography to yield ethyl 3-chloro-5-fluoro-4-methylbenzoate (5.3 g, 87%) as a clear and colorless oil. $^1$H NMR (400 MHz, DMSO-d$_6$) δ 7.74 (s, 1H), 7.61 (dd, J=9.5, 1.5 Hz, 1H), 4.37-4.24 (m, 2H), 2.29 (t, J=7.2 Hz, 3H), 1.37-1.25 (m, 3H).

To a solution of ethyl 3-chloro-5-fluoro-4-methylbenzoate (5.3 g, 24.46 mmol) in CCl$_4$ (100 mL) was added NBS (4.79 g, 26.91 mmol) followed by AIBN (0.4 g, 2.45 mmol). The reaction mixture was heated at 80° C. overnight. After cooling, the reaction mixture was diluted with H$_2$O and washed with DCM (2×). The combined extracts were dried (Na$_2$SO$_4$), concentrated and purified by flash chromatography (12% EtOAc/Hex) to yield ethyl 4-(bromomethyl)-3-chloro-5-fluorobenzoate (3.53 g, 49%) as a light yellow solid. $^1$H NMR (400 MHz, DMSO-d$_6$) δ 7.96-7.85 (m, 1H), 7.83 (dd, J=9.6, 1.5 Hz, 1H), 4.80 (t, J=5.7 Hz, 2H), 4.41 (q, J=7.1 Hz, 2H), 3.47 (s, 1H), 1.47-1.30 (m, 3H).

Preparation of 4-((5-(2-(4-chloro-3-methoxyphenyl)propan-2-yl)-1-(4-fluorophenyl)-1H-imidazol-2-ylthio)methyl)-3,5-difluorobenzoic acid

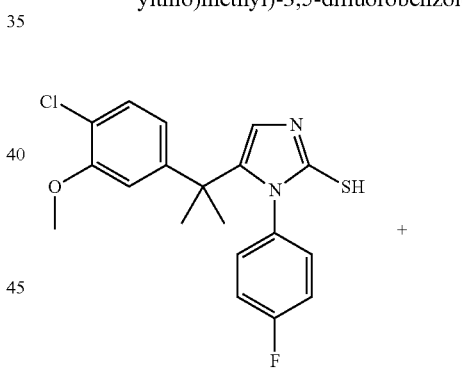

-continued

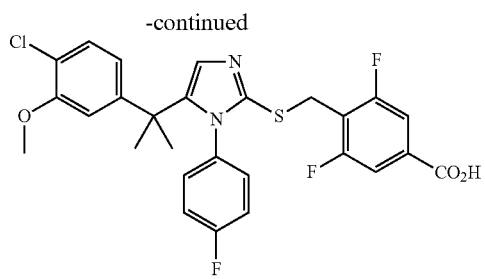

A mixture of 5-(2-(4-chloro-3-methoxyphenyl)propan-2-yl)-1-(4-fluorophenyl)-1H-imidazole-2-thiol (60 g, 0.16 mmol), tert-butyl 3,5-difluoro-4-((methylsulfonyloxy)methyl)benzoate (51 g, 0.16 mol, 1.0 eq.) and $Cs_2CO_3$ (62 g, 0.19 mol, 1.2 eq.) in MeCN (680 mL) was stirred for 2 h and evaporated to give a residue. The residue was diluted with water (1.5 L) and extracted with $CH_2Cl_2$ (1 L). The organic layer was washed with brine, dried over $MgSO_4$, filtered and concentrated in vacuo to give tert-butyl 4-((5-(2-(4-chloro-3-methoxyphenyl)propan-2-yl)-1-(4-fluorophenyl)-1H-imidazol-2-ylthio)methyl)-3,5-difluorobenzoate (95 g, quant). $^1$H NMR (400 MHz, $CDCl_3$) δ 7.40-7.42 (d, 2H), 7.19 (s, 1H), 7.14-7.16 (d, 1H), 6.76-6.80 (t, 2H), 6.51 (s, 1H), 6.41-6.49 (m, 3H), 4.07 (s, 2H), 3.75 (s, 3H), 1.58 (s, 9H), 1.47 (s, 6H).

To a solution of tert-butyl 4-((5-(2-(4-chloro-3-methoxyphenyl)propan-2-yl)-1-(4-fluorophenyl)-1H-imidazol-2-ylthio)methyl)-3,5-difluorobenzoate (95 g, 0.16 mmol) in $CH_2Cl_2$ (500 mL) at 0° C. was added TFA (500 mL) and then was stirred at room temperature. After 3 h, the reaction mixture was evaporated and the residue was diluted with $CH_2Cl_2$ (1.5 L), washed with water (600 mL×2). To the organic layers more water (600 mL) was added, it was neutralized with slow addition of aq. $NaHCO_3$ solution and organic layer was separated. Water (600 mL) was added to the organic layer and adjusted aqueous layer to pH 3-4 with 1N HCl. The organic layer was separated, dried over $MgSO_4$, filtered and concentrated under reduced pressure to give a residue. Toluene (600 mL) was added to the residue and the solution was evaporated and same process was repeated one more time to give the title compound as a white solid (88 g, quant). $^1$H NMR (400 MHz, $CDCl_3$) δ 7.55 (s, 1H), 7.46-7.49 (d, 2H), 7.16-7.19 (m, 1H), 6.92-6.97 (t, 2H), 6.69-6.71 (t, 2H), 6.62 (s, 1H), 6.49-6.51 (d, 1H), 3.84 (s, 3H), 3.53 (s, 2H), 1.58 (s, 6H); MS (EI) m/z 547 (MH$^+$).

4-((5-(2-(3-Chloro-4-sulfamoylphenyl)propan-2-yl)-1-(4-fluoro-3-methoxyphenyl)-1H-imidazol-2-ylthio)methyl)-3,5-difluorobenzoic acid

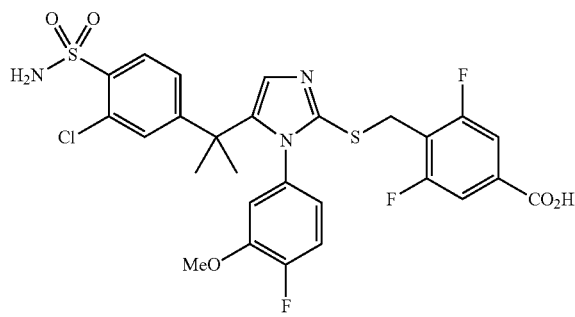 [SMILES: COc1cc(-n2c(C(C)(C)c3ccc(S(N)(=O)=O)c(Cl)c3)cnc2SCc2c(F)cc(C(=O)O)cc2F)ccc1F]

$^1$H NMR (400 MHz, $CDCl_3$+MeOD) δ 7.95 (d, J=8.4 Hz, 1H), 7.46 (d, J=7.6 Hz, 2H), 7.33 (s, 1H), 7.12 (d, J=2.0 Hz, 1H), 7.05 (d, J=8.4 Hz, 1H), 6.81 (m, 1H), 5.89 (m, 1H), 5.81 (dd, J=7.2 Hz, 1H), 4.04 (s, 2H), 3.40 (s, 3H), 1.51 (d, J=13.6 Hz, 6H); MS (EI) m/z 626 (MH$^+$).

3-Chloro-4-((5-(2-(4-chloro-3-methoxyphenyl)propan-2-yl)-1-(4-fluorophenyl)-1H-imidazol-2-ylthio)methyl)-5-fluorobenzoic acid

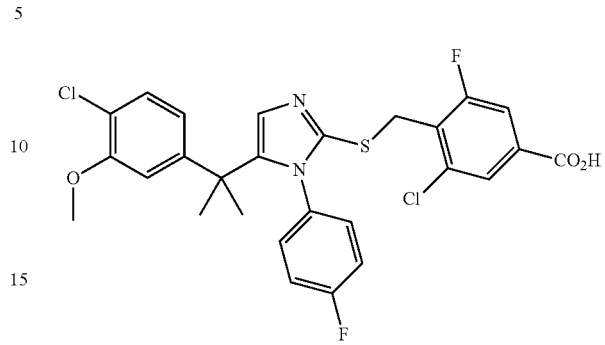

$^1$H NMR (400 MHz, DMSO) δ 13.63 (s, 1H), 7.72 (s, 1H), 7.59 (dd, J=9.6, 1.5 Hz, 1H), 7.22 (d, J=8.3 Hz, 1H), 7.19 (s, 1H), 6.94 (d, J=8.4 Hz, 1H), 6.92 (d, J=8.2 Hz, 1H), 6.54 (d, J=2.0 Hz, 1H), 6.51-6.45 (m, 3H), 4.08 (s, 2H), 3.67 (s, 3H), 1.46 (s, 6H); MS EI m/z 563.3 (MH$^+$).

4-((5-(2-(3-cyano-4-fluorophenyl)propan-2-yl)-1-(4-fluoro-3-methoxyphenyl)-1H-imidazol-2-ylthio)methyl)-3,5-difluorobenzoic acid

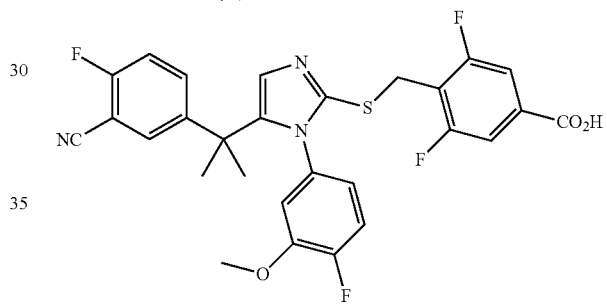

$^1$H NMR (400 MHz, $CDCl_3$) δ 7.52 (d, J=7.6 Hz, 2H), 7.31-7.12 (m, 4H), 6.87 (t, J=2.0 Hz, 1H), 6.05-5.98 (m, 2H), 4.01 (dd, J=7.8, 4.4 Hz, 2H), 3.61 (s, 3H), 1.59 (s, 6H); MS (EI) m/z 556 (MH$^+$).

4-((5-(2-(3-aminobenzo[d]isoxazol-5-yl)propan-2-yl)-14-(4-fluoro-3-methoxyphenyl)-1H-imidazol-2-ylthio)methyl)-3,5-difluorobenzoic acid

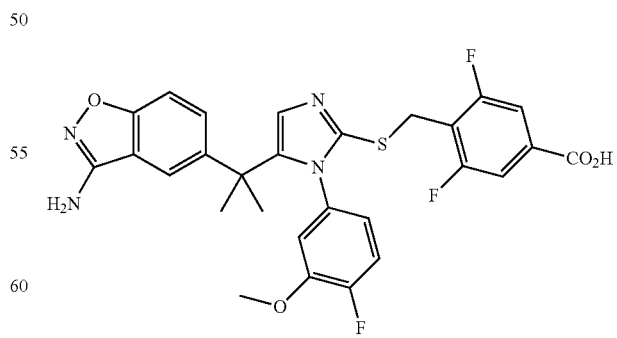

$^1$H NMR (400 MHz, $CDCl_3$) δ 7.52 (d, J=7.2 Hz, 2H), 7.32-7.26 (m, 2H), 7.15 (d, J=8.0 Hz, 1H), 6.83 (t, J=9.6 Hz, 1H), 6.05 (bs, 1H), 5.74 (d, J=5.6 Hz, 1H), 4.16 (s, 2H), 3.25 (s, 3H), 1.52 (d, J=24 Hz, 6H); MS (EI) m/z 569 (MH$^+$).

3-Chloro-4-((5-(2-(4-chloro-3-methoxyphenyl)propan-2-yl)-1-(4-fluorophenyl)-1H-imidazol-2-ylthio)methyl)-5-fluoroaniline

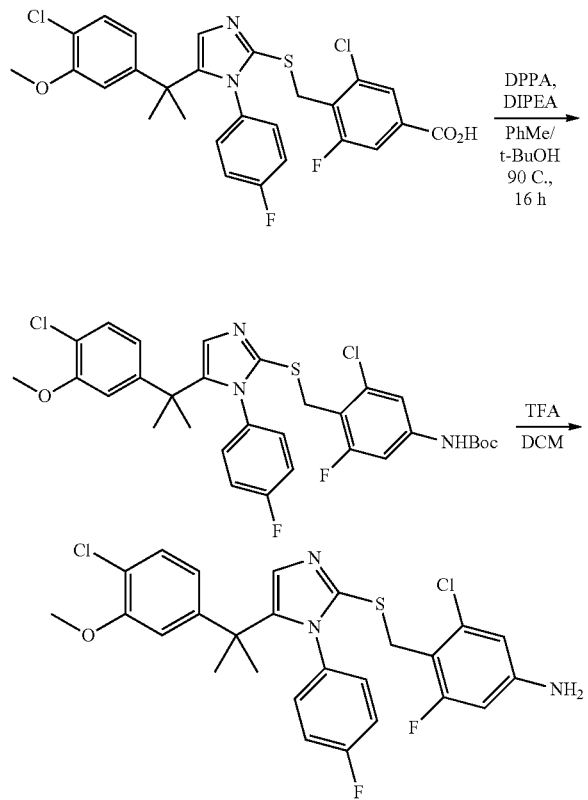

To a suspension of 3-chloro-4-((5-(2-(4-chloro-3-methoxyphenyl)propan-2-yl)-1-(4-fluorophenyl)-1H-imidazol-2-ylthio)methyl)-5-fluorobenzoic acid (540 mg) in a mixture of toluene (5 mL) and t-BuOH (1.5 mL) cooled to 0° C. was added diphenyl phosphoryl azide (DPPA) (302 mg, 1.1 eq) followed by DIPEA (1.3 eq, 0.23 mL). During addition of base, white slurry became clear solution. Reaction mixture was heated at 80° C. overnight. LC-MS showed complete conversion. After cooling to ambient temperature, the reaction mixture was diluted with EtOAc and washed with satd NaHCO$_3$. The organic layer was dried, concentrated and purified by chromatography (silica, EtOAc/Hex, 10-60%) to yield tert-butyl 3-chloro-4-((5-(2-(4-chloro-3-methoxyphenyl)propan-2-yl)-1-(4-fluorophenyl)-1H-imidazol-2-ylthio)methyl)-5-fluorophenylcarbamate (230 mg). MS (EI) m/z 634 (MH$^+$).

A solution of tert-butyl 3-chloro-4-((5-(2-(4-chloro-3-methoxyphenyl)propan-2-yl)-1-(4-fluorophenyl)-1H-imidazol-2-ylthio)methyl)-5-fluorophenylcarbamate (200 mg) in DCM (1 mL) was treated with TFA (1 mL) with stirring. After 1 h, the solution was concentrated under reduced pressure, diluted with DCE (5 mL). The organic layer was washed with water, satd NaHCO$_3$ and brine, then dried (MgSO$_4$) and concentrated to afford the title compound (152 mg, 90%). $^1$H NMR (400 MHz, MeOD) δ 7.40 (s, 1H), 7.36 (d, J=9.1 Hz, 1H), 6.93 (d, J=8.4, 1H), 6.87 (d, J=8.4 Hz, 1H), 6.68-6.61 (m, 2H), 6.53 (s, 1H), 6.40-6.27 (m, 3H), 4.01 (s, 2H), 3.76 (s, 3H), 1.58 (s, 6H); MS (EI) m/z 534 (MH$^+$).

Preparation of 4-(bromomethyl)-3,5-difluorobenzenesulfonamide

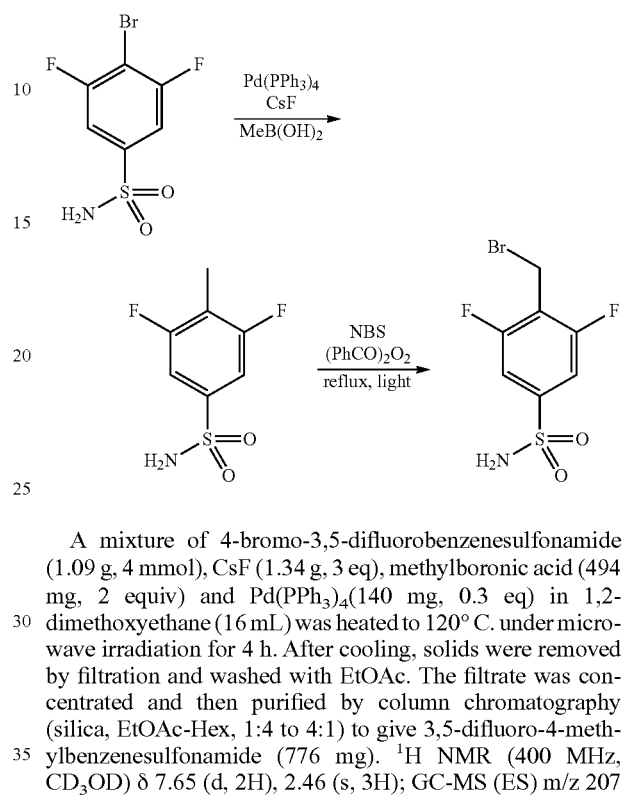

A mixture of 4-bromo-3,5-difluorobenzenesulfonamide (1.09 g, 4 mmol), CsF (1.34 g, 3 eq), methylboronic acid (494 mg, 2 equiv) and Pd(PPh$_3$)$_4$ (140 mg, 0.3 eq) in 1,2-dimethoxyethane (16 mL) was heated to 120° C. under microwave irradiation for 4 h. After cooling, solids were removed by filtration and washed with EtOAc. The filtrate was concentrated and then purified by column chromatography (silica, EtOAc-Hex, 1:4 to 4:1) to give 3,5-difluoro-4-methylbenzenesulfonamide (776 mg). $^1$H NMR (400 MHz, CD$_3$OD) δ 7.65 (d, 2H), 2.46 (s, 3H); GC-MS (ES) m/z 207 (M$^+$).

A mixture of 3,5-difluoro-4-methylbenzenesulfonamide (1.237 g, 6 mmol), N-bromosuccinimide (1.4 g, 1.3 eq) and benzoyl peroxide (87 mg, 0.1 eq) in carbon tetrachloride (24 mL) was heated to reflux for 6 h under a halogen light. After the reaction was determined to be complete by GC-MS, the mixture was concentrated and purified by column chromatography (silica, EtOAc-hexane, 1:4 to 4:1) to give the title compound (524 mg). $^1$H NMR (400 MHz, CD$_3$OD) δ 7.75 (d, 2H), 4.83 (s, 3H); GC-MS (ES) m/z 285 (M$^+$), 287 (M+2).

Preparation of 4-((5-(2-(4-chloro-3-methoxyphenyl)propan-2-yl)-1-(4-fluorophenyl)-1H-imidazol-2-ylthio)methyl)-3,5-difluorobenzenesulfonamide

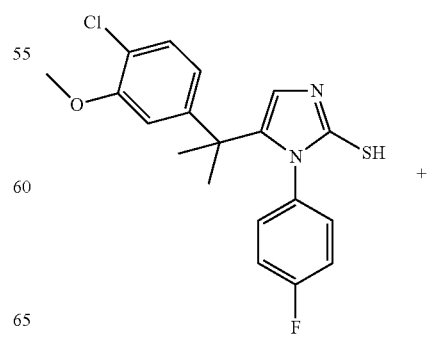

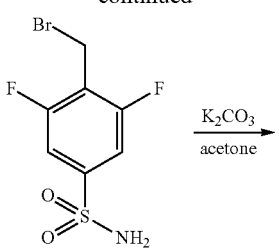

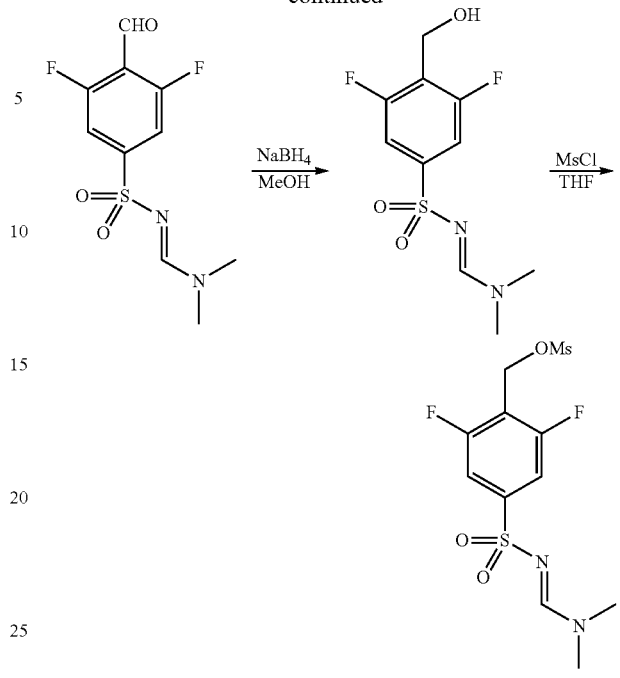

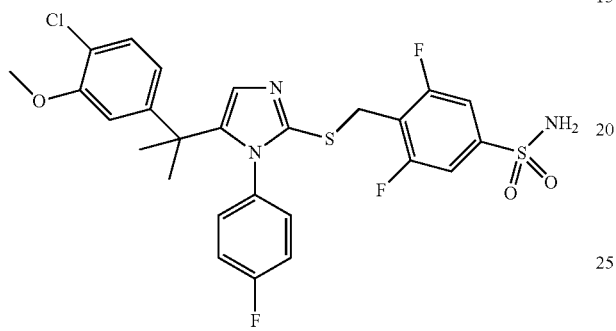

A mixture of 5-(2-(4-chloro-3-methoxyphenyl)propan-2-yl)-1-(4-fluorophenyl)-1H-imidazole-2-thiol (170 mg, 0.45 mmol, 1.0 eq), 4-(bromomethyl)-3,5-difluorobenzenesulfonamide (155 mg, 0.54 mmol, 1.2 eq) and K$_2$CO$_3$ (94 mg, 0.68 mmol, 1.5 eq) in acetone (2.3 mL) was stirred for 30 min. The reaction mixture was filtered, and the filtrate was concentrated and purified (silica, 0-75% EtOAc/Hex) to afford the title compound (252 mg, 96%) as a white solid. MS (EI) m/z 584 (MH$^+$).

Preparation of 4-(N-((dimethylamino)methylene)sulfamoyl)-2,6-difluorobenzyl methanesulfonate

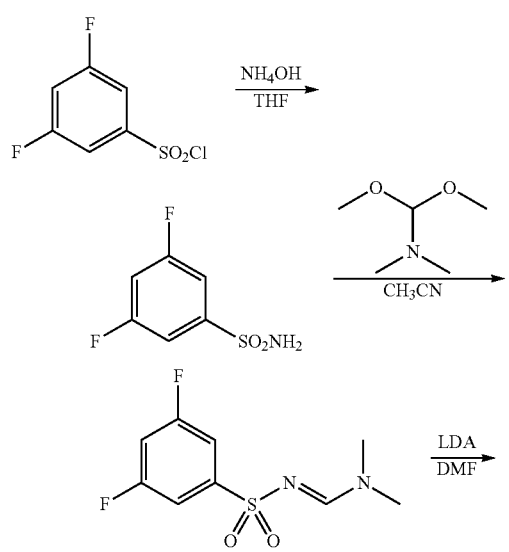

To a solution of 3,5-difluorobenzenesulfonyl chloride (25 g, 0.117 mol) in THF (150 mL) was added 35% aq. NH$_4$OH (120 mL) over 1 h in an ice-bath. After the reaction was complete, it was evaporated in vacuo. To a solution of this residue in water (150 mL) was added 2N HCl (1 mL). After stirring 1 h, the reaction mixture was filtered and dried under high vacuum to give 3,5-difluorobenzenesulfonamide as a light brown solid (19.9 g, 88%). $^1$H NMR (400 MHz, CDCl$_3$) δ 7.49-7.44 (m, 2H), 7.04-6.99 (m, 2H).

To a solution of 3,5-difluorobenzenesulfonamide (154 g, 0.797 mol) in CH$_3$CN (1 L) was added N,N-dimethylformamide dimethylacetal (224 mL, 1.67 mmol, 2.1 eq). After stirring 1 h, the reaction mixture was concentrated under reduced pressure. This material was triturated with Et$_2$O and dried in vacuo to give N'-(3,5-difluorophenylsulfonyl)-N,N-dimethylformimidamide (190 g, 96%) as a light brown solid. $^1$H NMR (400 MHz, CDCl$_3$) δ 8.12 (s, 1H), 7.44-7.38 (m, 2H), 6.98-6.91 (m, 1H), 3.17 (s, 3H), 3.05 (s, 3H).

To a solution of diisopropylamine (231 mL, 1.63 mmol, 2.1 eq) in THF (1 L) was slowly added BuLi (2.5M in Hex, 653 mL, 1.63 mmol, 2.1 eq) at 0° C. The solution was cooled to −78° C., and then a solution of N'-(3,5-difluorophenylsulfonyl)-N,N-dimethylformimidamide (193 g, 777 mmol) in THF (1 L) was added dropwise to the stirred LDA solution over 1 h at −78° C. and allowed to stir another 2 h at same temperature. To the reaction mixture was added anhyd DMF (72 mL, 932 mmol, 1.2 eq) and, 30 minutes later, was added AcOH (50 mL) and water. The reaction mixture was extracted with EtOAc (500 mL×3). The combined extracts were washed with brine (1 L), dried over MgSO$_4$ and concentrated in vacuo to give N'-(3,5-difluoro-4-formylphenylsulfonyl)-N,N-dimethylformimidamide (171 g), which was used in the next step without further purification.

To a solution of N'-(3,5-difluoro-4-formylphenylsulfonyl)-N,N-dimethylformimidamide (171 g, 619 mmol) in MeOH (1 L) was added NaBH$_4$ (23.4 g, 619 mmol) at 0° C. After 1 h, the reaction mixture was concentrated, neutralized to pH 6 with 1N HCl, and extracted with EtOAc. The combined extracts were washed with water and brine, dried over MgSO₄ and evaporated in vacuo. To a solution of this residue in CH₃CN (1 L) was added N,N-dimethylformamide dimethylacetal (166 mL, 1.24 mmol, 2 eq). The solution was evaporated in vacuo and then purified by chromatography (silica, DCM/EtOAc, 1:1) to give N'-(3,5-difluoro-4-(hydroxymethyl)phenylsulfonyl)-N,N-dimethylformimidamide (80 g). ¹H NMR (400 MHz, CDCl₃) δ 8.10 (s, 1H), 7.45-7.40 (m, 2H), 4.8 (d, J=3.6 Hz), 3.17 (s, 3H), 3.05 (s, 3H).

To a solution of N'-(3,5-difluoro-4-(hydroxymethyl)phenylsulfonyl)-N,N-dimethyl-formimidamide (80 g, 287 mmol) in DCM (500 mL) was added Et₃N (121 mL, 862 mmol, 3 eq) and methanesulfonylchloride (27 mL, 245 mmol, 1.2 eq) successively at 0° C. After 30 min, the reaction mixture was extracted with DCM (300 mL×3). The combined extracts were washed with water (1 L), dried over MgSO₄, concentrated and then purified by chromatography (silica, DCM/EtOAc, 1:1) to give 4-(N-((dimethylamino)methylene)sulfamoyl)-2,6-difluorobenzyl methanesulfonate (77.5 g, 28% over 4 steps) as a ivory solid. ¹H NMR (400 MHz, CDCl₃) δ 8.11 (s, 1H), 7.59-7.39 (m, 2H), 5.32 (s, 2H), 3.18 (s, 3H), 3.09 (s, 3H), 3.08 (s, 3H).

Preparation of N'-(4-(bromomethyl)-3-chloro-5-fluorophenylsulfonyl)-N,N-dimethylformimidamide

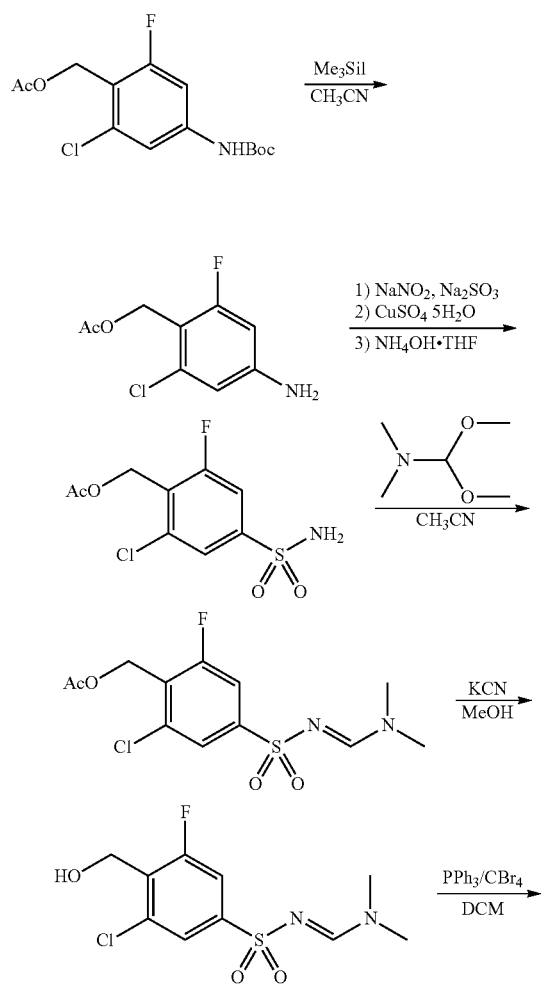

-continued

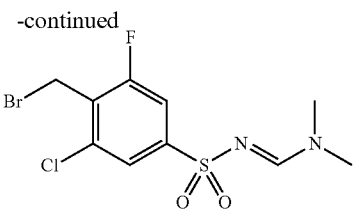

To a solution of 4-(tert-butoxycarbonylamino)-2-chloro-6-fluorobenzyl acetate (8.5 g, 24 mmol) in CH₃CN (300 mL) was added trimethylsilyl iodide (4.12 mL, 28 mmol) at 0° C. under N₂.2 After stirring 15 min, the reaction mixture was quenched with 5% Na₂S₂O₃ (10 mL) in ice-bath, concentrated in vacuo, and extracted with EtOAc. The combined extracts were washed with H₂O and brine successively, dried over anhyd MgSO₄, concentrated and purified by column chromatography (Hex/DCM=1:1) to afford 4-amino-2-chloro-6-fluorobenzyl acetate as yellow solid. ¹H NMR (400 MHz, CDCl₃) δ 6.55-6.49 (m, 1H), 6.33-6.27 (m, 1H), 5.15 (d, 2H), 3.97 (d, 2H), 2.07 (s, 3H).

To a solution of 4-amino-2-chloro-6-fluorobenzyl acetate (5.2 g, 0.024 mol) in DMF (10 mL) at 0° C. was added slowly 3M HCl (100 mL) followed by NaNO₂ (2 g, 0.029 mol). After stirring at the same temperature for 20 min, the mixture was added dropwise to a solution of Na₂SO₃ (12 g, 0.096 mol) and CuSO₄5H₂O in 3N HCl (100 mL). After stirring for 30 min, the reaction mixture was then poured into ice-water and extracted with EtOAc. The combined extracts were concentrated, dried over anhydrous MgSO₄, filtered and concentrated in vacuo. The material was dissolved in THF and added dropwise to a stirred solution of NH₄OH (17 mL) in THF (17 mL) at 5° C. After stirring 30 min, the mixture was concentrated under reduced pressure and extracted with EtOAc. The combined extracts were washed with H₂O, dried over anhyd MgSO₄, concentrated and purified by column chromatography (Hex/EtOAc=5:1) to afford 2-chloro-6-fluoro-4-sulfamoylbenzyl acetate (1.02 g, 15%, 3 steps) as an orange solid. ¹H NMR (400 MHz, CDCl₃) δ 7.80 (t, 1H), 7.59 (dd, 1H), 5.28 (d, 2H), 5.16 (s, 2H), 2.10 (d, 3H); MS (EI) m/z 303 (M+Na⁺).

To a solution of 2-chloro-6-fluoro-4-sulfamoylbenzyl acetate (1 g, 3.6 mmol) in CH₃CN (20 mL2) at 0° C. under N₂ was added 1,1-dimethoxy-N,N-dimethylmethanamine (0.7 ml, 5.4 mmol). The resulting solution was stirred at room temperature 1 h, concentrated under reduced pressure, and purified by column chromatography (DCM/EtOAc=9:1) to afford 2-chloro-4-(N-((dimethylamino)methylene)sulfamoyl)-6-fluorobenzyl acetate (850 mg, 76%) as ivory solid. ¹H NMR (400 MHz, CDCl₃) δ 8.12 (s, 1H), 7.76 (s, 1H), 7.55 (d, 1H), 5.26 (s, 2H), 3.18 (s, 3H), 3.05 (s, 3H), 2.08 (s, 3H).

To a solution of KCN (82 mg, 1.26 mmol) in MeOH (80 mL) was added 2-chloro-4-(N-((dimethylamino)methylene)sulfamoyl)-6-fluorobenzyl acetate (850 mg, 2.52 mmol) at 0° C. The mixture was allowed to attain room temperature and then refluxed 1 h. After cooling, the reaction mixture was quenched with H₂O, concentrated, and extracted with EtOAc. The combined extracts were washed with brine, dried over anhyd MgSO₄, filtered and concentrated under reduced pressure to give N'-(3-chloro-5-fluoro-4-(hydroxymethyl)phenylsulfonyl)-N,N-dimethylformimidamide (600 mg, 80%) as ivory solid. ¹H NMR (400 MHz, CDCl₃) δ 8.10(s, 1H), 7.74 (s, 1H), 7.55 (d, 1H), 4.86 (d, 2H), 3.17 (s, 3H), 3.05 (s, 3H), 2.07 (s, 1H).

To a solution of N'-(3-chloro-5-fluoro-4-(hydroxymethyl)phenylsulfonyl)-N,N-dimethylformimidamide (600 mg, 2 mmol) in DCM (10 mL) at 0° C. were added PPh₃ (1.06 g, 4.06 mmol) and CBr₄ (1.3 g, 4.06 mmol). The resulting solution was stirred at room temperature for 30 min, concentrated, and purified by column chromatography (silica, DCM/EtOAc=20:1) to afford N'-(4-(bromomethyl)-3-chloro-5-fluorophenylsulfonyl)-N,N-dimethylformimidamide (673 mg, 92%) as ivory solid. ¹H NMR (400 MHz, CDCl₃) δ 8.18-8.11 (m, 1H), 7.78 (d, 1H), 7.57 (dd, 1H), 4.64 (d, 2H), 3.22 (d, 3H), 3.10 (t, 3H); MS (EI) m/z 379 (M+Na⁺).

Preparation of 3-chloro-4-((5-(2-(4-chloro-3-methoxyphenyl)propan-2-yl)-1-(4-fluorophenyl)-1H-imidazol-2-ylthio)methyl)-5-fluorobenzenesulfonic acid

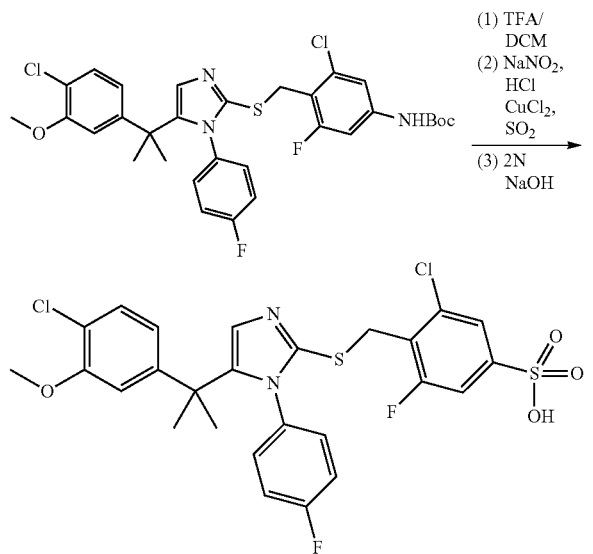

To a solution of tert-butyl 3-chloro-4-((5-(2-(4-chloro-3-methoxyphenyl)propan-2-yl)-1-(4-fluorophenyl)-1H-imidazol-2-ylthio)methyl)-5-fluorophenylcarbamate (12.0 g, 19 mmol) in DCM (anhyd, 30 mL) at 5° C. was added slowly TFA (30 mL). The flask was removed from the ice bath and stirred at ambient temperature. After 60 min, the deprotection was complete by LCMS and TLC. The mixture was concentrated to a minimum volume and then diluted with HOAc (64 mL). Added slowly mixture of conc HCl (21 mL) and water (12 mL), then submerged flask in ice bath to attain temperature of 5° C. While maintaining a temperature of 4-6° C., added dropwise a solution of sodium nitrite (3.1 g, 1.24 eq, 44.9 mmol) in water (4 mL).

In a 1000 mL 3-neck flask added CuCl₂ (0.509 g, 0.2 eq, 3.8 mmol), acetic acid (61 mL) and water (1.0 mL). Bubbled sulfur dioxide through the mixture at a slow rate for 10 min, then submerged flask in ice bath at 5° C. Continued bubbling sulfur dioxide through mixture with stirring. After diazotization reaction has stirred 30-40 min at 5° C., transfer mixture in small portions via cannula into other flask at 5° C. Addition of diazonium salt took 20 min and temperature held steady at 5° C. After stirring 60 min, an aliquot from the mixture showed 90-95% sulfonyl chloride present by LCMS. Diluted with water (400 mL), sulfonyl chloride was extracted into DCM (2×400 mL) and concentrated under reduced pressure to remove DCM. This material was dissolved in THF (200 mL), chilled to 5° C. with an ice bath, and then treated with 2N NaOH dropwise until slightly basic (pH 8). After stirring 10 min, the mixture was concentrated under reduced pressure, diluted with water (100 mL) and acidified with 1N HCl. The aqueous layer was extracted with DCM (4×150 mL). Combined extracts were washed with brine, dried (Na₂SO₄) and concentrated. The residue was purified by column chromatography (silica, DCM/MeOH, 0-20%) to afford the title compound (8.05 g, 70.9%). ¹H NMR (400 MHz, MeOD) δ 7.63 (s, 1H), 7.48 (s, 1H), 7.40 (dd, J=9.1, 1.4 Hz, 1H), 7.22-7.16 (m, 1H), 6.90 (d, J=8.7, 1H), 6.88 (d, J=8.7, 1H), 6.56-6.50 (m, 2H), 6.44-6.36 (m, 2H), 4.10 (s, 2H), 3.71 (s, 3H), 1.57 (s, 6H); MS (EI) m/z 599 (MH⁺).

Preparation of 4-((5-(2-(4-Chloro-3-methoxyphenyl)propan-2-yl)-1-(4-fluorophenyl)-1H-imidazol-2-ylthio)methyl)-3,5-difluorobenzenesulfonic acid

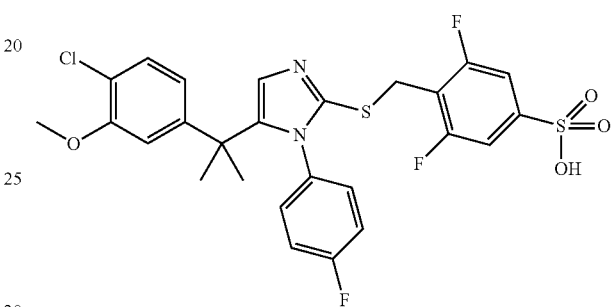

To a solution of 4-((5-(2-(4-chloro-3-methoxyphenyl)propan-2-yl)-1-(4-fluorophenyl)-1H-imidazol-2-ylthio)methyl)-3,5-difluorobenzoic acid (88 g, 0.16 mmol) in toluene (590 mL) and tert-butanol (200 mL) were added DPPA (49 g, 0.178 mol) and DIPEA (272 g, 0.21 mol) at 0° C. The reaction mixture was warmed to room temperature, stirred 30 min and heated at 80° C. overnight. After cooling, the reaction mixture was diluted with EtOAc (800 mL) and washed with 10% citric acid (1.5 L), satd NaHCO₃ (1.5 L) and brine (1.5 L), dried over MgSO₄, filtered and concentrated under reduced pressure to give a residue. The resulting residue was purified by column chromatography (Hex/EtOAc=3:1 to 2:1, v/v) to afford tert-butyl 4-((5-(2-(4-chloro-3-methoxyphenyl)propan-2-yl)-1-(4-fluorophenyl)-1H-imidazol-2-ylthio)methyl)-3,5-difluorophenylcarbamate (75 g, 74%) as a light-pink foam. ¹H NMR (400 MHz, CDCl₃): δ 7.22 (s, 1H), 7.14-7.16 (d, 1H), 6.88-6.92 (d, 2H), 6.85 (s, 1H), 6.75-6.80 (t, 2H), 6.48-6.53 (m, 2H), 6.33-6.37 (m, 2H), 3.99 (s, 2H), 3.76 (s, 3H), 1.52 (s, 9H), 1.49 (s, 6H).

To a solution of tert-butyl 4-((5-(2-(4-chloro-3-methoxyphenyl)propan-2-yl)-1-(4-fluorophenyl)-1H-imidazol-2-ylthio)methyl)-3,5-difluorophenylcarbamate (75 g, 0.12 mmol) in DCM (300 mL) was added TFA (300 mL) at 0° C. The reaction mixture was warmed to room temperature, stirred for 2 h and evaporated to give 4-((5-(2-(4-chloro-3-methoxyphenyl)propan-2-yl)-1-(4-fluorophenyl)-1H-imidazol-2-ylthio)methyl)-3,5-difluorobenzenamine as a light-pink foam (62 g, quant). ¹H NMR (400 MHz, CDCl₃): δ 7.65 (s, 1H), 7.20-7.23 (d, 1H), 6.92-6.96 (t, 2H), 6.41-6.50 (m, 6H), 3.91 (s, 2H), 3.79 (s, 3H), 1.58 (s, 6H).

To a solution of 4-((5-(2-(4-chloro-3-methoxyphenyl)propan-2-yl)-1-(4-fluorophenyl)-1H-imidazol-2-ylthio)methyl)-3,5-difluorobenzenamine (62 g, 0.12 mol) in AcOH (330 mL) was added slowly conc HCl (104 mL) and water (40 mL), and then the flask was submerged in ice-bath to attain constant temperature of 5° C. A solution of NaNO₂ (9.52 g, 0.14 mol) in water (20 mL) was added dropwise to the reaction mixture, while maintaining a temperature at 4-6° C. In a flask containing CuCl$_2$ (3.22 g, 0.02 mol), AcOH (288 mL) and water (12 mL) was bubbled sulfur dioxide through at a slow rate for 10 min, then the mixture was submerged in ice-bath at 5° C. Bubbling of sulfur dioxide through mixture was continued with stirring for 30 min at 5° C. The prepared diazonium salt was transferred to the mixture in small portions via cannula at 5° C. Addition of diazonium salt took 20 min and temperature held steady at 5° C. After 30 min at same temperature, the reaction mixture was then poured into a ice-water and stirred 30 min. After filtration, the resulting solid was dissolved in THF (250 mL), and then the solution was chilled to 5° C. with an ice bath. 2N NaOH solution was added dropwise until the mixture was basic. The solution was stirred for 10 min and evaporated to give a residue. The residue was diluted with water, acidified with 1N HCl, stirred 30 min and filtered give a residue which was purified by column chromatography (MC/MeOH=20:1, 10:1 to 5:1, v/v) to afford the title compound (23 g, 33%) as a light beige solid. $^1$H NMR (400 MHz, DMSO-d$_6$): δ 7.55 (s, 1H), 7.16-7.24 (d, 1H), 7.14-7.16 (d, 2H), 7.00-7.04 (t, 2H), 6.63-6.66 (t, 2H), 6.55 (s, 1H), 6.46-6.48 (d, 1H), 3.96 (s, 2H), 3.70 (s, 3H), 1.48 (s, 6H); MS (EI) m/z 581.0 (M$^+$).

4-Chloro-5-((5-(2-(4-chloro-3-methoxyphenyl)propan-2-yl)-1-(4-fluorophenyl)-1H-imidazol-2-ylthio)methyl)-2-fluorobenzenesulfonamide

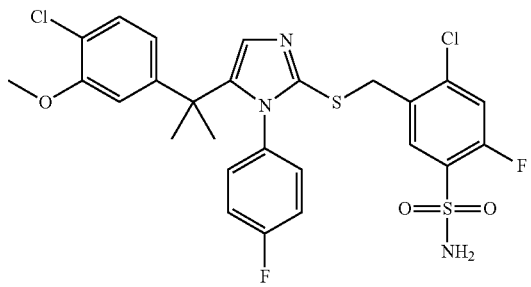 [SMILES: COc1cc(C(C)(C)c2cnc(SCc3cc(S(N)(=O)=O)c(F)cc3Cl)n2-c2ccc(F)cc2)ccc1Cl]

To a solution of 2-chloro-4-fluoro-5-sulfamoylbenzoic acid (3.2 g, 12.65 mmol) in THF (10 mL) was added 1M BH$_3$ THF (38 mL, 38.0 mmol). After stirring 12 h, the reaction mixture was quenched with MeOH and concentrated in vacuo. The residue was purified by chromatography (silica, EtOAc-Hex) to afford 4-chloro-2-fluoro-5-(hydroxymethyl) benzenesulfonamide (1.9 g). To a suspension of 4-chloro-2-fluoro-5-(hydroxymethyl)benzenesulfonamide (1.78 g, 7.43 mmol) in DCM (10 mL) was added PBr$_3$ (2.21 g, 8.17 mmol). The reaction was stirred for 24 h when it was determined to be complete by GCMS. The reaction was carefully quenched with H$_2$O and then partitioned between THF and brine. The organic layer was dried over Na$_2$SO$_4$ and concentrated in vacuo to afford 5-(bromomethyl)-4-chloro-2-fluorobenzenesulfonamide (1.98 g) as an off-white solid. $^1$H-NMR (DMSO-d$_6$, 400 MHz) δ 8.08 (d, J=7.8 Hz, 1H), 7.84 (s, 2H), 7.80 (d, J=9.9 Hz, 1H), 4.83 (s, 2H).

To a mixture of 5-(2-(4-chloro-3-methoxyphenyl)propan-2-yl)-1-(4-fluorophenyl)-1H-imidazole-2-thiol (0.94 g, 2.49 mmol) and K$_2$CO$_3$ in acetone (5 mL) was added 5-(bromomethyl)-4-chloro-2-fluorobenzenesulfonamide (0.83 g, 2.73 mmol). After stirring 3 h, the reaction mixture was filtered. The filtrate was concentrated and purified by chromatography (silica, EtOAc-Hex) to afford the title compound (1.21 g). $^1$H-NMR (DMSO-d$_6$, 400 MHz) δ 7.81 (d, J=7.8 Hz, 1H), 7.77 (s, 2H), 7.70 (d, J=9.7 Hz, 1H), 7.22-7.19 (m, 1H), 7.16 (s, 1H), 7.01-6.97 (m, 2H), 6.56-6.49 (m, 4H), 4.26 (s, 2H), 3.64 (s, 3H), 1.46 (s, 6H); MS (EI) m/z 598 [M]$^+$.

3-((5-(2-(4-Chloro-3-methoxyphenyl)propan-2-yl)-(4-fluorophenyl)-1H-imidazol-2-ylthio)methyl)-2,4-difluorobenzenesulfonamide

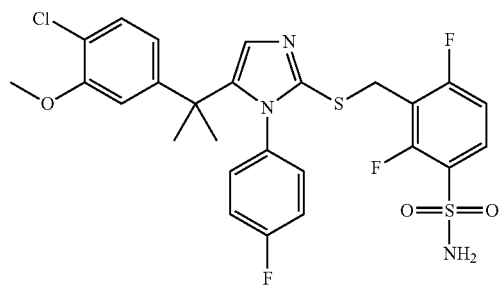 [SMILES: COc1cc(C(C)(C)c2cnc(SCc3c(F)ccc(S(N)(=O)=O)c3F)n2-c2ccc(F)cc2)ccc1Cl]

$^1$H NMR (400 MHz, DMSO-d$_6$) δ 7.80-7.68 (m, 3H), 7.27-7.12 (m, 3H), 7.03-6.92 (m, 2H), 6.61-6.46 (m, 4H), 4.06 (s, 2H), 3.67 (s, 3H), 1.46 (s, 6H); MS (EI) m/z 582 [M]$^+$.

(R)-Methyl 2-(4-((5-(2-(4-chloro-3-methoxyphenyl) propan-2-yl)-1-(4-fluorophenyl)-1H-imidazol-2-ylthio)methyl)-3,5-difluorophenylsulfonamido)propanoate

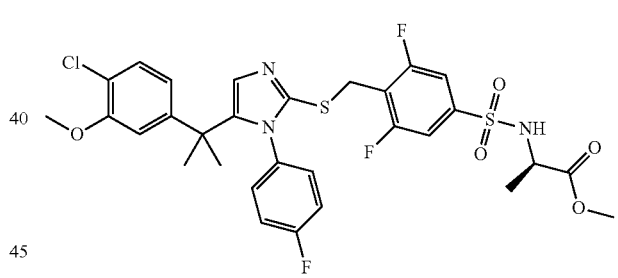

To a solution of 4-((5-(2-(4-chloro-3-methoxyphenyl)propan-2-yl)-1-(4-fluorophenyl)-1H-imidazol-2-ylthio)methyl)-3,5-difluorbenzenesulfonic acid (3.0 g, 5.1 mmol) in DCM (15 mL) was added thionyl chloride (7.5 mL) and DMF (0.1 mL). The mixture was heated at 65° C. for 1 h then concentrated in vacuo and azeotroped with toluene (10 mL) and DCM (10 mL). The pale yellow foam was dissolved in DCM (15 mL) and was added dropwise to a solution of D-alanine methyl ester (2.9 g, 20.6 mmol) in 2M Na$_2$CO$_3$ (30 mL) with vigorous stirring. Upon complete addition the layers were separated and the organics were dried over Na$_2$SO$_4$, filtered and concentrated in vacuo. The residue was purified by flash chromatography eluting with 0-70% ethyl acetate/ hexane to afford a white foam (2.4 g, 77%). MS (EI) m/z 601.3 (M$^+$).

Preparation of 3-(4-((5-(2-(4-chloro-3-methoxyphenyl)propan-2-yl)-1-(4-fluorophenyl)-1H-imidazol-2-ylthio)methyl)-3,5-difluorophenyl)propan-1-ol

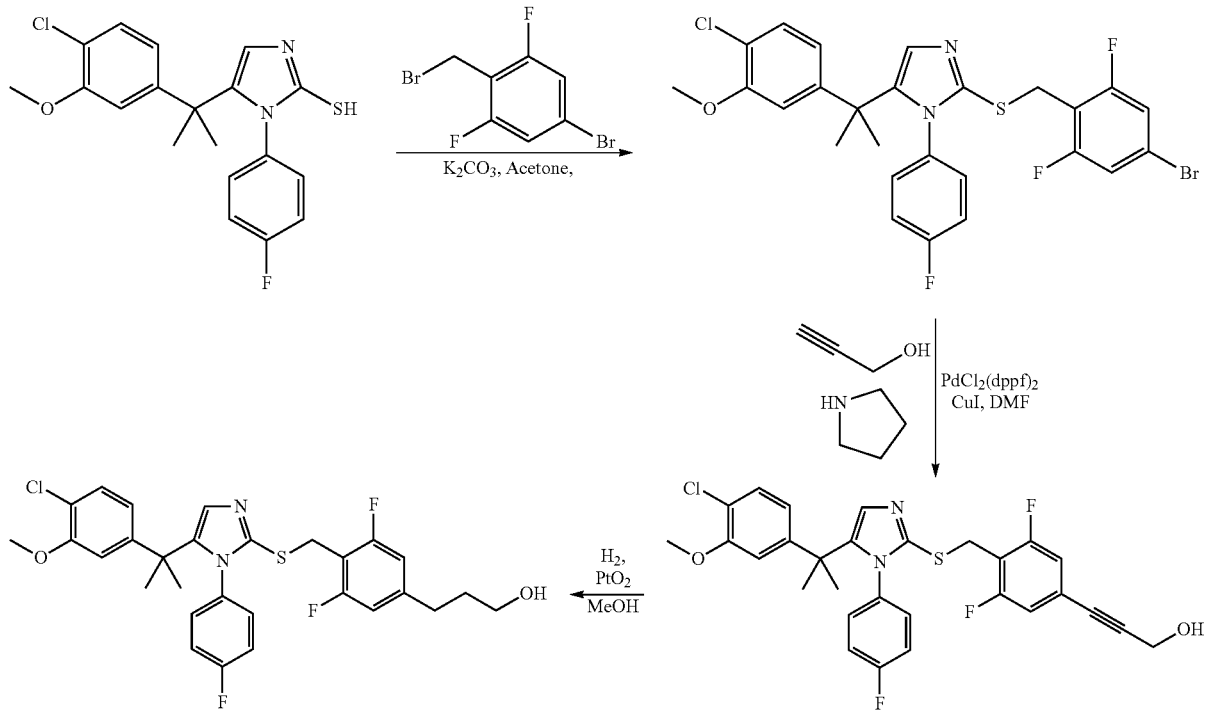

To a mixture of 5-(2-(4-chloro-3-methoxyphenyl)propan-2-yl)-1-(4-fluorophenyl)-1H-imidazole-2-thiol (1.00 g, 2.65 mmol) and K$_2$CO$_3$ (0.51 g, 3.70 mmol) in acetone (13 mL) was added 5-bromo-2-(bromomethyl)-1,3-difluorobenzene (0.91 g, 3.18 mmol). The reaction mixture was stirred 1 h and then filtered. The filtrate was concentrated under reduced pressure and purified by chromatography (10% MeOH/DCM) to yield 2-(4-bromo-2,6-difluorobenzylthio)-5-(2-(4-chloro-3-methoxyphenyl)propan-2-yl)-1-(4-fluorophenyl)-1H-imidazole as a tan solid (1.34 g, 87%). MS (EI) m/z 581 (MH$^+$).

A mixture of 2-(4-bromo-2,6-difluorobenzylthio)-5-(2-(4-chloro-3-methoxyphenyl)propan-2-yl)-1-(4-fluorophenyl)-1H-imidazole (0.79 g, 1.35 mmol), propargyl alcohol (122 μL, 2.03 mmol), pyrrolidine (169 μL, 2.03 mmol), CuI (26 mg, 0.13 mmol) and PdCl$_2$(dppf)$_2$ (50 mg, 0.07 mmol) in DMF (6.80 mL) was purged with argon and then heated to 80° C. for 3 h. The reaction mixture was filtered through to remove solids. The filter agent was rinsed with EtOAc and the filtrate was extracted with EtOAc (3×75 mL). The combined extracts were washed with water and brine, dried over anhyd Na$_2$SO$_4$, concentrated and purified by flash chromatography (80% EtOAc/hexanes) to get 3-(4-((5-(2-(4-chloro-3-methoxyphenyl)propan-2-yl)-1-(4-fluorophenyl)-1H-imidazol-2-ylthio)methyl)-3,5-difluorophenyl)prop-2-yn-1-ol (714 mg, 94%) as a yellow solid. MS (EI) m/z 557 (MH$^+$).

A solution of 3-(4-((5-(2-(4-chloro-3-methoxyphenyl)propan-2-yl)-1-(4-fluorophenyl)-1H-imidazol-2-ylthio)methyl)-3,5-difluorophenyl)prop-2-yn-1-ol (714 mg, 1.28 mmol) in MeOH (75 mL) was sparged with argon, charged with PtO$_2$ (30 wt %, 214 mg) and then pressurized to 65 psi under hydrogen atmosphere in a Parr shaker for 36 h. The reaction was monitored by LCMS and upon completion the mixture was filtered through Celite™ to remove the catalyst. The filtrate was concentrated and purified by flash chromatography (80% EtOAc/hexanes) to yield the title compound (560 mg, 0.99 mmol). MS (EI) m/z 561 (MH$^+$).

Preparation of 3-chloro-4-((5-(2-(3,4-dichlorophenyl)propan-2-yl)-1-(4-fluorophenyl)-1H-imidazol-2-yl)methoxy)-5-fluorobenzoic acid

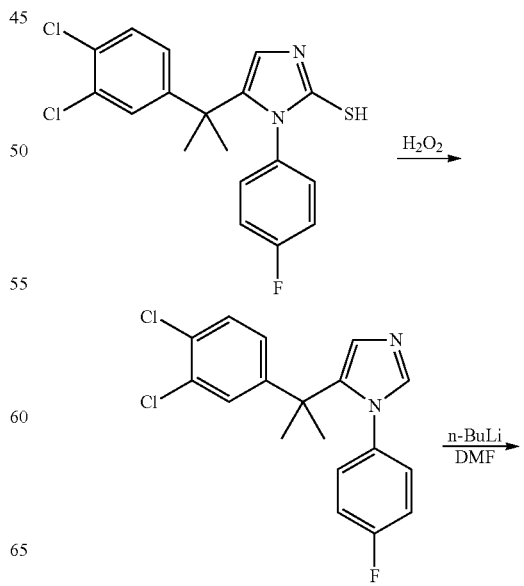

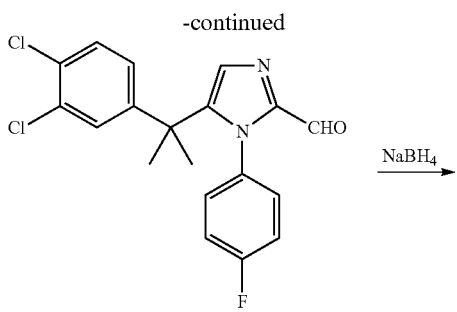

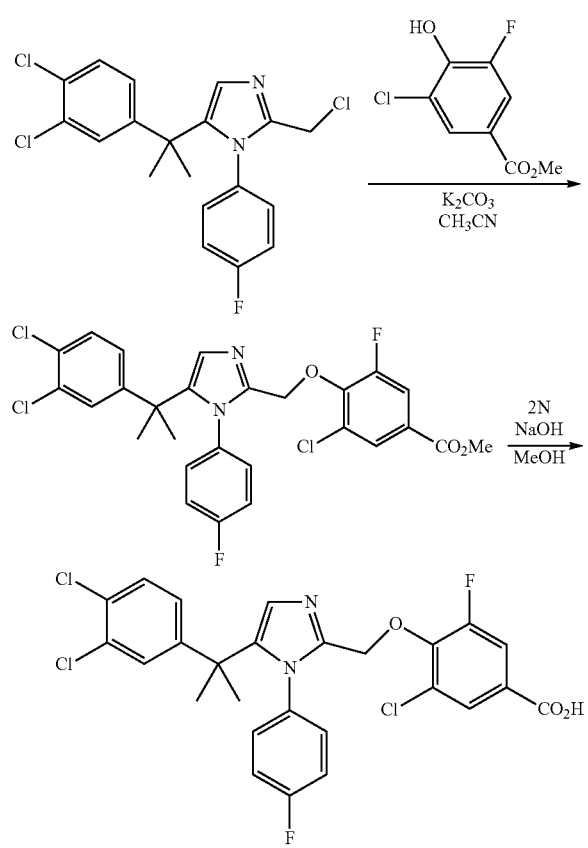

To a suspension of 5-(2-(3,4-dichlorophenyl)propan-2-yl)-1-(4-fluorophenyl)-1H-imidazole-2-thiol (737 mg, 1.9 mmol) in DCM (4 mL) at 0° C. was added a solution of 0.6 mL H₂O₂ (35% wt.) in HOAc (2 mL). After stirring 40 min, the mixture was allowed to warm to room temperature. After stirring 6 h, the reaction mixture was neutralized to pH 9 using 2N NaOH and was extracted with DCM. The combined extracts were washed with brine, dried over Na₂SO₄, and concentrated in vacuo. The crude material was purified by chromatography (silica, 0-95% EtOAc/Hex) to give 5-(2-(3,4-dichlorophenyl)propan-2-yl)-1-(4-fluorophenyl)-1H-imidazole as a white solid (455 mg, 69% yield).

To a solution of 5-(2-(3,4-dichlorophenyl)propan-2-yl)-1-(4-fluorophenyl)-1H-imidazole (770 mg, 2.2 mmol) in anhyd THF (10 mL) at −78° C. was added n-BuLi (1.4 mL, 2.0M in hexane, 2.8 mmol) dropwise. After stirring 1 h at −78° C., anhyd DMF (0.85 mL) was added in one portion. After stirring another 3 h at −78° C., the reaction was quenched with water. After warming to ambient temperature, the mixture was extracted with EtOAc. The combined extracts were washed with brine, dried over Na₂SO₄, and concentrated in vacuo. The crude material was purified by column chromatography (silica gel, 0-90% EtOAc/Hex) to give 5-(2-(3,4-dichlorophenyl)propan-2-yl)-1-(4-fluorophenyl)-1H-imidazole-2-carbaldehyde as a white solid (740 mg, 89% yield).

To a solution of 5-(2-(3,4-dichlorophenyl)propan-2-yl)-1-(4-fluorophenyl)-1H-imidazole-2-carbaldehyde (740 mg, 1.96 mmol) in anhyd ethanol (15 mL) was added NaBH₄ (91 mg, 2.4 mmol). After stirring 3 h, the mixture was poured into water, and extracted with EtOAc. The combined extracts were washed with brine, dried over Na₂SO₄, and concentrated in vacuo to give (5-(2-(3,4-dichlorophenyl)propan-2-yl)-1-(4-fluorophenyl)-1H-imidazol-2-yl)methanol as a white solid (670 mg, 88% yield).

To a solution of (5-(2-(3,4-dichlorophenyl)propan-2-yl)-1-(4-fluorophenyl)-1H-imidazol-2-yl)methanol (402 mg, 1.06 mmol) in CH₃CN (6 mL) at 0° C. was added thionyl chloride. After stirring 3 h, the solution was concentrated under reduced pressure, and azeotroped with DCM (3×) to give 2-(chloromethyl)-5-(2-(3,4-dichlorophenyl)propan-2-yl)-1-(4-fluorophenyl)-1H-imidazole as a yellow solid (420 mg) that was used directly for the next step without purification.

A mixture of 2-(chloromethyl)-5-(2-(3,4-dichlorophenyl)propan-2-yl)-1-(4-fluorophenyl)-1H-imidazole (154 mg, 0.39 mmol), methyl 3-chloro-5-fluoro-4-hydroxybenzoate (118 mg 0.57 mmol), potassium carbonate (79 mg, 0.57 mmol), and 18-crown-6 (11 mg, 0.04 mmol) in CH₃CN (4 mL) was heated 8 h at 60° C. After cooling, the reaction mixture was filtered, combined with water and DCM, and then extracted further with DCM. The combined extracts were washed with brine, dried over Na₂SO₄, and concentrated in vacuo. The material was purified by chromatography (silica, 0-70% EtOAc/Hex) to give methyl 3-chloro-4-((5-(2-(3,4-dichlorophenyl)propan-2-yl)-1-(4-fluorophenyl)-1H-imidazol-2-yl)methoxy)-5-fluorobenzoate as a white solid (150 mg, 68% yield). MS (EI) m/z 567.3 [M+H]⁺.

A mixture of methyl 3-chloro-4-((5-(2-(3,4-dichlorophenyl)propan-2-yl)-1-(4-fluorophenyl)-1H-imidazol-2-yl)methoxy)-5-fluorobenzoate (120 mg, 0.21 mmol) and 2N NaOH (0.31 mL, 0.63 mmol) in MeOH (3 mL) was heated 3 h at 65° C. After cooling, the reaction was neutralized to pH 3 with 3N HCl, concentrated under reduced pressure, diluted with water, and then extracted with EtOAc. The combined extracts were washed with brine, dried over Na₂SO₄, and concentrated in vacuo. The crude material was purified by

3-chloro-4-((5-(2-(4-chloro-3-methoxyphenyl)propan-2-yl)-1-(4-fluorophenyl)-1H-imidazol-2-yl)methoxy)-5-fluorobenzoic acid

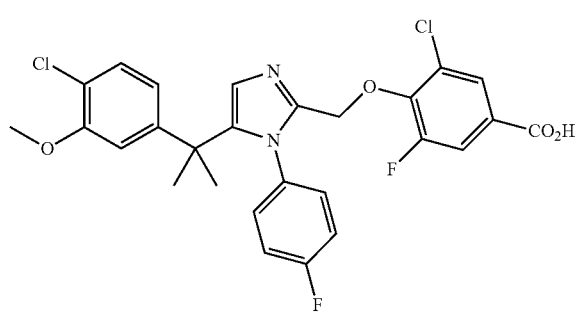 [SMILES: COc1cc(C(C)(C)c2cnc(COc3c(F)cc(C(=O)O)cc3Cl)n2-c2ccc(F)cc2)ccc1Cl]

The title compound was prepared from 5-(2-(4-chloro-3-methoxyphenyl)propan-2-yl)-1-(4-fluorophenyl)-1H-imidazole-2-thiol under similar conditions. $^1$H NMR (400 MHz, DMSO) δ 7.72 (t, J=1.6 Hz, 1H), 7.64 (dd, J=11.0, 1.9 Hz, 1H), 7.22 (d, J=8.3 Hz, 1H), 7.11 (s, 1H), 7.05 (d, J=8.1 Hz, 1H), 7.03 (d, J=8.7 Hz, 1H), 6.82-6.76 (m, 2H), 6.57 (d, J=2.0 Hz, 1H), 6.51 (dd, J=8.3, 2.0 Hz, 1H), 4.77 (s, 2H), 3.68 (s, 3H), 1.49 (s, 6H).

3-chloro-4-((5-(2-(4-chloro-3-methoxyphenyl)propan-2-yl)-1-(4-fluorophenyl)-1H-imidazol-2-yl)methoxy)-5-fluorobenzenesulfonic acid

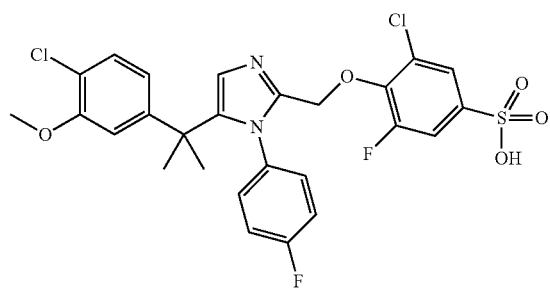 [SMILES: COc1cc(C(C)(C)c2cnc(COc3c(F)cc(S(=O)(=O)O)cc3Cl)n2-c2ccc(F)cc2)ccc1Cl]

The title compound was prepared from 3-chloro-4-((5-(2-(4-chloro-3-methoxyphenyl)propan-2-yl)-1-(4-fluorophenyl)-1H-imidazol-2-yl)methoxy)-5-fluorobenzoic acid under conditions previously described. $^1$H NMR (400 MHz, DMSO) δ 7.87 (s, 1H), 7.42 (t, J=1.6 Hz, 1H), 7.34 (dd, J=10.1, 1.8 Hz, 1H), 7.25 (d, J=8.3 Hz, 1H), 7.16 (d, J=8.4 Hz, 1H), 7.14 (d, J=8.7 Hz, 1H), 6.97-6.92 (m, 2H), 6.58 (d, J=2.0 Hz, 1H), 6.52 (dd, J=8.3, 2.1 Hz, 1H), 4.84 (s, 2H), 3.71 (s, 3H), 1.56 (s, 6H); MS (EI) m/z 583.2 [M+]$^+$.

3-chloro-4-(2-(5-(2-(4-chloro-3-methoxyphenyl)propan-2-yl)-1-(4-fluorophenyl)-1H-imidazol-2-yl)ethyl)-5-fluorobenzoic acid

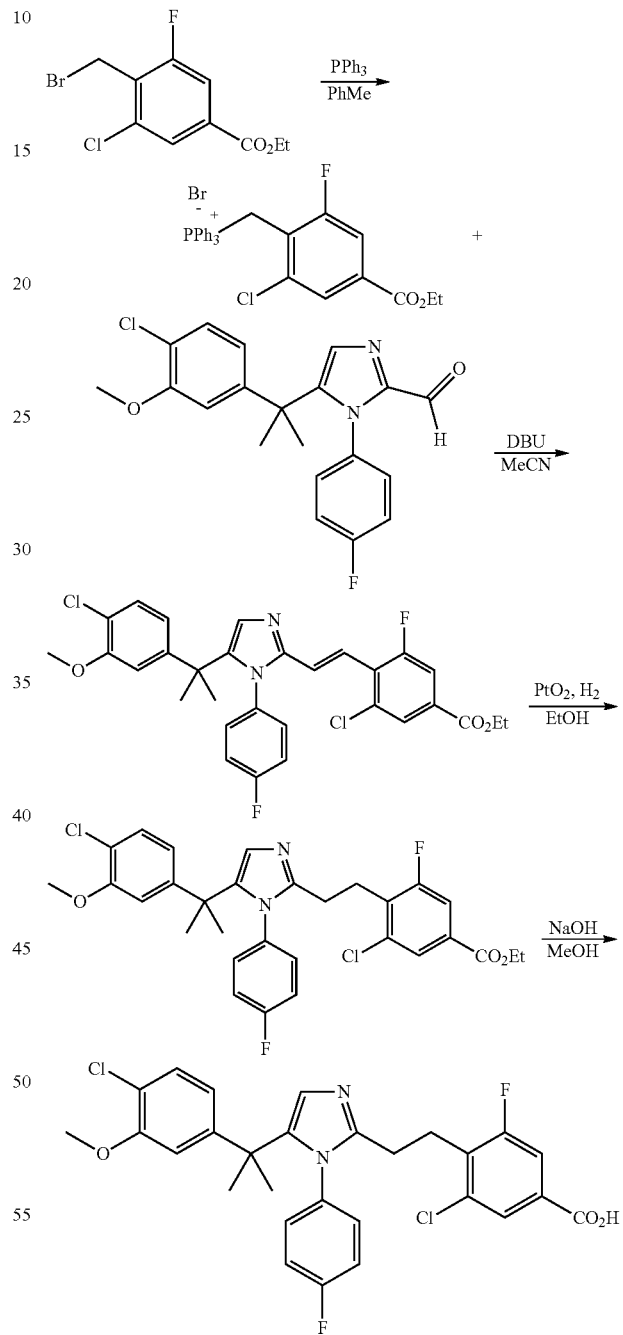

To a solution of ethyl 4-(bromomethyl)-3-chloro-5-fluorobenzoate (531 mg, 1.797 mmol) in toluene (10 mL) was added PPh$_3$ (471 mg, 1.797 mmol). The solution was refluxed at 90° C. overnight. Upon cooling a white precipitate formed. The mixture was diluted with hexanes, filtered and dried under vacuum to yield (2-chloro-4-(ethoxycarbonyl)-6-fluorobenzyl)triphenylphosphonium bromide (0.874 g, 86%) as a white solid. $^1$H NMR (400 MHz, DMSO-d$_6$) δ 8.05-7.87 (m, 3H), 7.85-7.58 (m, 13H), 7.20 (tt, J=15.1, 7.1 Hz, 1H), 5.21 (d, J=15.0 Hz, 2H), 4.34 (dq, J=14.2, 7.1 Hz, 2H), 1.33 (dt, J=14.2, 7.1 Hz, 3H).

To a mixture of 5-(2-(4-chloro-3-methoxyphenyl)propan-2-yl)-1-(4-fluorophenyl)-1H-imidazole-2-carbaldehyde (304 mg, 0.815 mmol) and (2-chloro-4-(ethoxycarbonyl)-6-fluorobenzyl)triphenylphosphonium bromide (454 mg, 0.815 mmol) in MeCN (5 mL) was added dropwise DBU (136 mg, 0.896 mmol). After stirring at 50° C. overnight, the mixture was diluted with H$_2$O and extracted with DCM. The combined extracts were dried (MgSO$_4$), filtered, concentrated and purified by flash chromatography (20-90% EtOAc/hexanes) to yield ethyl 3-chloro-4-(2-(5-(2-(4-chloro-3-methoxyphenyl)propan-2-yl)-1-(4-fluorophenyl)-1H-imidazol-2-yl)vinyl)-5-fluorobenzoate (0.241 g, 51%) as a yellow oil. $^1$H NMR (400 MHz, DMSO-d$_6$) δ 8.05-7.87 (m, 3H), 7.85-7.58 (m, 13H), 7.20 (tt, J=15.1, 7.1 Hz, 1H), 5.21 (d, J=15.0 Hz, 2H), 4.34 (dq, J=14.2, 7.1 Hz, 2H), 1.33 (dt, J=14.2, 7.1 Hz, 3H).

A solution of ethyl 3-chloro-4-(2-(5-(2-(4-chloro-3-methoxyphenyl)propan-2-yl)-1-(4-fluorophenyl)-1H-imidazol-2-yl)vinyl)-5-fluorobenzoate (224 mg, 0.392 mmol) in EtOH (10 mL) was degassed using N$_2$ for 5-10 minutes prior to the addition of PtO$_2$ (42 mg, 0.184 mmol). The resulting suspension was pressurized with 70 psi H$_2$ and agitated overnight. The catalyst was removed by filtration through Celite™ and eluting with more EtOH. The filtrate was concentrated in vacuo to provide ethyl 3-chloro-4-(2-(5-(2-(4-chloro-3-methoxyphenyl)propan-2-yl)-1-(4-fluorophenyl)-1H-imidazol-2-yl)ethyl)-5-fluorobenzoate (153 mg, 68%) as a gray oil. $^1$H NMR (400 MHz, CDCl$_3$) δ 7.87-7.61 (m, 1H), 7.50 (td, J=9.4, 1.4 Hz, 1H), 7.15 (d, J=8.4 Hz, 1H), 7.11-6.98 (m, 1H), 6.98-6.65 (m, 2H), 6.65-6.32 (m, 4H), 4.38 (dq, J=21.4, 7.1 Hz, 2H), 3.74 (d, J=3.3 Hz, 3H), 3.25-2.83 (m, 2H), 2.52 (dd, J=16.6, 8.9 Hz, 2H), 1.50 (s, 6H), 1.39 (dt, J=14.3, 7.2 Hz, 3H).

To a solution of ethyl 3-chloro-4-(2-(5-(2-(4-chloro-3-methoxyphenyl)propan-2-yl)-1-(4-fluorophenyl)-1H-imidazol-2-yl)ethyl)-5-fluorobenzoate (151 mg, 0.263 mmol) in MeOH (1.0 mL) was added dropwise a 2N solution of NaOH in H$_2$O (0.5 mL). After stirring 1 h, the reaction mixture was concentrated under reduced pressure, diluted with H$_2$O (1.5 mL), neutralized with 1N HCl and then extracted with DCM (10 mL×2). The combined extracts were dried (MgSO$_4$), filtered and concentrated to give the title compound (116 mg, 81%) as gray solid. $^1$H NMR (400 MHz, DMSO) δ 7.69 (s, 1H), 7.57 (d, J=9.6 Hz, 1H), 7.27-7.17 (m, 2H), 7.05 (d, J=8.6 Hz, 1H), 7.03 (d, J=8.6 Hz, 1H), 6.69 (dd, J=8.6, 4.8 Hz, 2H), 6.54 (s, 1H), 6.53-6.48 (m, 1H), 3.69 (s, 3H), 2.94 (t, J=7.2 Hz, 2H), 2.57 (t, J=7.2 Hz, 2H), 1.48 (s, 6H).

Preparation of 3-chloro-4-(2-(5-(2-(4-chloro-3-methoxyphenyl)propan-2-yl)-1-(4-fluorophenyl)-1H-imidazol-2-yl)ethyl)-5-fluorobenzenesulfonic acid

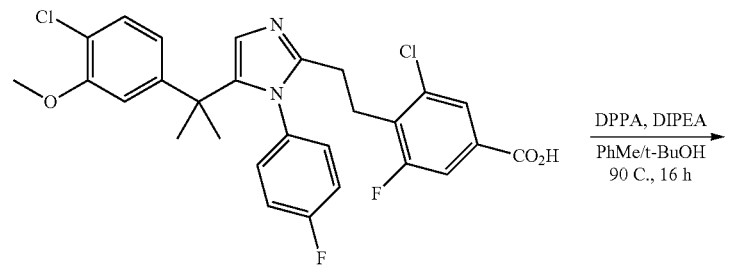

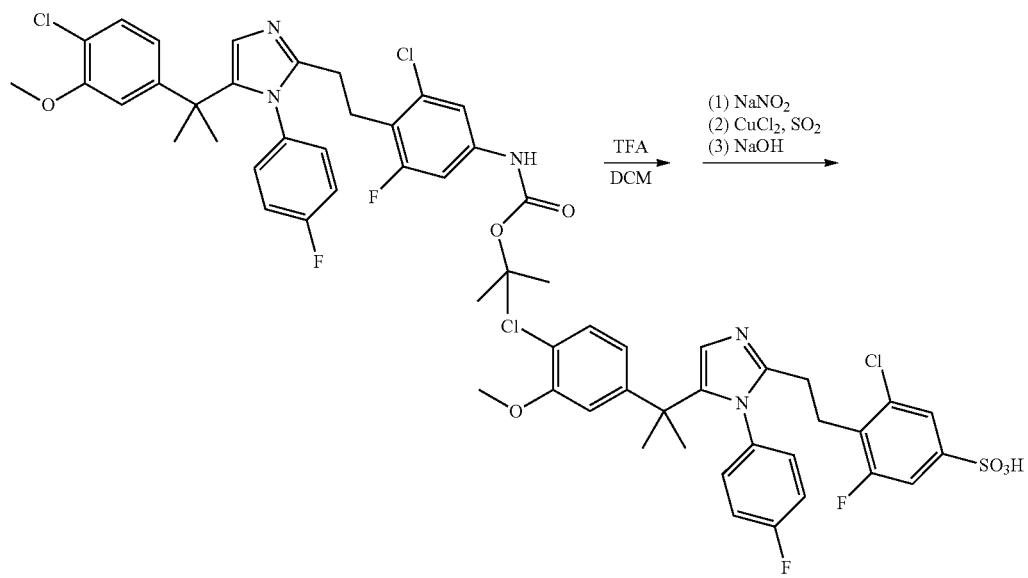

To solution of 3-chloro-4-(2-(5-(2-(4-chloro-3-methoxyphenyl)propan-2-yl)-1-(4-fluorophenyl)-1H-imidazol-2-yl)ethyl)-5-fluorobenzoic acid (540 mg) in a mixture of toluene (5 mL) and tert-butanol (1.5 mL) cooled to 0° C. was added diphenyl phosphoryl azide (DPPA) (1.1 eq, 302 mg) followed by DIPEA (1.3 eq, 226 μL). During addition of base, the white slurry became a clear solution, which was heated at 80° C. After 16 h, complete conversion was observed by LC-MS. The reaction was diluted with EtOAc, washed with satd NaHCO₃, dried (Na₂SO₄), concentrated and purified by chromatography (silica, EtOAc/Hex, 10-60%) to yield tert-butyl 3-chloro-4-(2-(5-(2-(4-chloro-3-methoxyphenyl)propan-2-yl)-1-(4-fluorophenyl)-1H-imidazol-2-yl)ethyl)-5-fluorophenylcarbamate (230 mg). MS (EI) m/z 616 (MH⁺).

To a solution of tert-butyl 3-chloro-4-(2-(5-(2-(4-chloro-3-methoxyphenyl)propan-2-yl)-1-(4-fluorophenyl)-1H-imidazol-2-yl)ethyl)-5-fluorophenylcarbamate (230 mg, 0.373 mmol) in DCM (anhyd, 3 mL) at 5° C. was added slowly TFA (3 mL). The flask was removed from the ice bath and stirred at ambient temperature. After 30 min, the deprotection was complete by LCMS and TLC. The mixture was concentrated to minimum volume and diluted with HOAc (1.34 mL). To this flask was added slowly conc HCl (387 μL) and water (231 μL). Then submerged flask in ice bath to attain constant temperature of 5° C. To this acidic mixture added dropwise a solution of sodium nitrite (31.7 mg, 0.458 mmol) in minimum water, while maintaining a temperature of 4-6° C. In another flask a mixture of CuCl₂ (10 mg, 0.0746 mmol), HOAc (1 mL) and H₂O (4 drops) was sparged with sulfur dioxide at a slow rate for 10 min, then submerged flask in ice bath at 5° C. After diazotization reaction has stirred 30-40 min at 5° C., this mixture was transferred to the second flask in small portions. After stirring 1 h, an aliquot from the mixture showed 90-95% sulfonyl chloride present by LCMS. The mixture was diluted with H₂O (5 mL) and extracted with DCM (2×5 mL). Combined extracts were concentrated under reduced pressure and then dissolved in THF (3 mL). To this solution chilled to 5° C. was added dropwise 2N NaOH until the mixture attained pH 8. After stirring 10 min, the reaction mixture was concentrated under reduced pressure, diluted with H₂O (3 mL) and acidified with 1N HCl. The aqueous mixture was extracted with DCM (4×5 mL). Combined extracts were washed with brine, dried (Na₂SO₄) and concentrated. The residue was purified by chromatography (silica, MeOH/DCM, 0-20%) to afford 3-chloro-4-(2-(5-(2-(4-chloro-3-methoxyphenyl)propan-2-yl)-1-(4-fluorophenyl)-1H-imidazol-2-yl)ethyl)-5-fluorobenzenesulfonic acid (201 mg). ¹H NMR (400 MHz, DMSO) δ 7.68 (s, 1H), 7.37 (s, 1H), 7.26-7.19 (m, 2H), 7.11 (d, J=8.4 Hz, 1H), 7.09 (d, J=8.7 Hz, 1H), 6.87-6.81 (m, 2H), 6.55 (d, J=2.0 Hz, 1H), 6.50 (dd, J=8.3, 2.1 Hz, 1H), 3.70 (d, J=8.1 Hz, 3H), 2.84 (t, J=7.2 Hz, 2H), 2.68 (t, J=7.3 Hz, 2H), 1.51 (s, 6H).

Preparation of (S)-4-amino-5-methoxy-N,N,N-trimethyl-5-oxopentan-1-aminium chloride hydrochloride

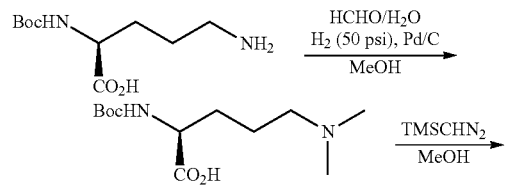

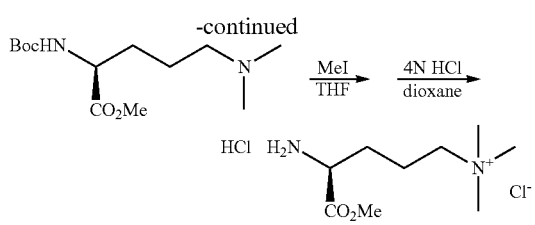

To a solution of (S)-5-amino-2-(tert-butoxycarbonylamino)pentanoic acid (15.0 g, 64.6 mmol, 1.0 eq) in MeOH (200 mL) was added 37% wt. aq. formaldehyde (28 mL, 387 mmol, 6.0 eq). The solution was degassed using N₂ (g) for 5-10 min. prior to the addition Pd/C (1.8 g, 5% wt, Degussa, wet), then degassed for an additional 5 min. The resulting mixture was pressurized to 50 psi H₂ (g) and agitated overnight. The palladium catalyst was removed by passing the reaction mixture through Celite™ and eluting with additional MeOH. The solvent was removed by rotary evaporation, and the product was co-evaporated with MeOH (3×) to yield 17.5 g (over theoretical) of (S)-2-(tert-butoxycarbonylamino)-5-(dimethylamino)pentanoic acid as an off-white solid. ¹H NMR (400 MHz, CDCl₃) δ 5.72 (d, J=5.0 Hz, 1H), 4.13-4.06 (m, 1H), 3.03-2.75 (m, 2H), 2.70 (s, 6H), 1.91-1.55 (m, 4H), 1.44 (s, 9H); MS (EI) m/z 261 (MH⁺).

To (S)-2-(tert-butoxycarbonylamino)-5-(dimethylamino)pentanoic acid (129 mmol, 1.0 eq) in MeOH (130 mL) under N₂ (g) at 0° C. was added TMSCHN₂ (84 mL, 168 mmol, 1.3 eq, 2.0 M in diethyl ether) slowly via addition funnel over 40 minutes. The ice-water bath was removed and the reaction mixture was warmed to room temperature and stirred 16 h. The volatiles were removed in vacuo and the residue was partitioned between EtOAc (250 mL) and satd NaHCO₃ (200 mL). Additional H₂O was added to form a clear aqueous layer, which was extracted with EtOAc (2×175 mL). The combined extracts were then washed with additional satd NaHCO₃ (100 mL) and brine, dried over MgSO₄, filtered and concentrated to afford (S)-methyl 2-(tert-butoxycarbonylamino)-5-(dimethylamino)pentanoate (16.8 g, 47%) as a yellow oil. ¹H NMR (400 MHz, CDCl₃) δ 5.85 (d, J=6.8 Hz, 1H), 4.15-4.04 (m, 1H), 3.58 (s, 3H), 2.12 (t, J=6.9 Hz, 2H), 2.06 (s, 6H), 1.73-1.51 (m, 4H), 1.29 (s, 9H); MS (EI) m/z 275 (MH⁺).

To a solution of (S)-methyl 2-(tert-butoxycarbonylamino)-5-(dimethylamino)pentanoate (5.62 g, 20.5 mmol, 1.0 eq) in THF (40 mL), was added iodomethane (1.4 mL, 22.5 mmol, 1.1 eq). The mixture was stirred at room temperature for 1 h, until the starting material was consumed as determined by LCMS analysis. The reaction mixture was concentrated and then dried under high vacuum to provide (S)-4-(tert-butoxycarbonylamino)-5-methoxy-N,N,N-trimethyl-5-oxopentan-1-aminium iodide as a white solid, which was used in the next step without purification. MS (EI) m/z 289 (M⁺).

To a solution of (S)-4-(tert-butoxycarbonylamino)-5-methoxy-N,N,N-trimethyl-5-oxopentan-1-aminium iodide (20.5 mmol, 1.0 eq) in anhyd dioxane (10 mL), was added HCl (51 mL, 205 mmol, 10 eq, 4M in dioxane). The orange slurry was stirred at room temperature for 1 h, the solids were broken up, then stirred vigorously for another 1 h. The suspension was allowed to settle before cannulating off the dioxane layer. The remaining yellow slurry was rinsed with Et₂O, stirred and cannulated out the ether layer (4×). The solids were dried under high vacuum to give the title compound (5.68 g) as a light yellow powder. ¹H NMR (400 MHz, DMSO) δ 8.75 (s, 3H), 4.03-3.93 (m, 1H), 3.68 (s, 3H), 3.30-3.20 (m, 2H), 2.98 (s, 9H), 1.89-1.69 (m, 4H); MS (EI) m/z 189 (M+).

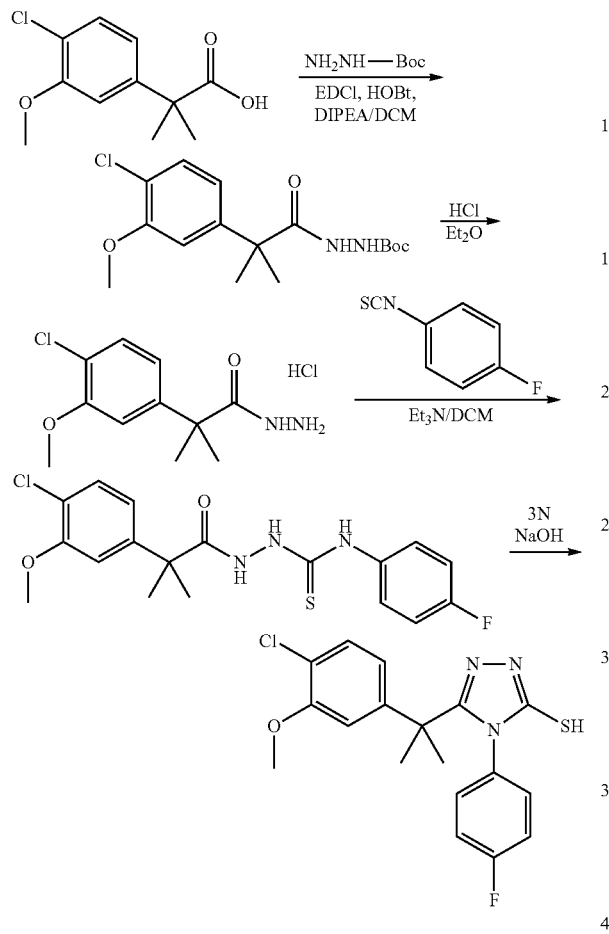

To a solution of carboxylic acid 1 (10 g, 0.04 mol) in CH₂Cl₂ (100 mL) was added DIPEA (38 mL, 0.22 mol, 5.0 eq.), tert-butyl carbazate (6.94 g, 0.05 mol, 1.2 eq.), HOBt (0.3 g, 0.002 mol, 0.05 eq.) and EDCI (25.15 g, 0.13 mol, 3.0 eq.). The reaction mixture was stirred for 15 h and tmixture was washed with 10% citric acid, sat'd NaHCO₃ and brine successively, dried over MgSO₄, filtered and concentrated under reduced pressure to give tert-butyl 2-(2-(4-chloro-3-methoxyphenyl)-2-methylpropanoyl)hydrazine carboxylate as a brown solid (12.63 g, 84%).

¹H NMR (400 MHz, CDCl₃) δ 7.35-7.34 (d, 1H), 6.99 (s, 1H), 6.96-6.93 (dd, 1H), 6.86 (s, 1H), 6.28 (s, 1H), 3.94 (s, 3H), 1.60 (s, 6H), 1.45 (s, 9H).

To a solution of tert-butyl 2-(2-(4-chloro-3-methoxyphenyl)-2-methylpropanoyl)hydrazine carboxylate (12.63 g, 0.04 mol) in EtOAc (100 mL) at 0° C. was added 2M HCl in Et₂O (92 mL). The resulting solution was stirred at room temperature 18 h and concentrated in vacuo. The residue was triturated with Et₂O, collected by filtration and dried to give 2-(4-chloro-3-methoxyphenyl)-2-methylpropanehydrazide hydrochloride (6.88 g, 67%) as a white solid. ¹H NMR (400 MHz, DMSO) δ 11.64 (s, 1H), 7.41-7.39 (d, 1H), 7.01 (s, 1H), 6.92-6.89 (d, 1H), 3.91 (s, 3H), 1.53 (s, 6H).

To a solution of 2-(4-chloro-3-methoxyphenyl)-2-methylpropanehydrazide hydrochloride (6.88 g, 0.02 mol) and 4-fluorophenylisothiocyanate (3.96 g, 0.03 mol, 1.05 eq.) in DCM (500 mL) at 0° C. was added Et₃N (7 mL, 1.29 mol, 2.0 eq.) and the resulting solution was stirred for 1.5 h at room temperature. The reaction mixture was washed with 1M HCl, satd NaHCO₃ and brine, dried over MgSO₄, filtered and concentrated in vacuo. The residue was triturated with DCM/Et₂O, collected by filtration and dried to give 2-(2-(4-Chloro-3-methoxyphenyl)-2-methylpropanoyl)-N-(4-fluorophenyl) hydrazine carbothioamide (8.13 g, 83% as a white solid. ¹H NMR (400 MHz, CDCl₃) δ 7.32-7.30 (d, 1H), 7.25-7.22 (m, 2H), 7.01-7.05 (t, 2H), 6.95-6.94 (d, 1H), 6.93-6.90 (dd, 1H), 3.88 (s, 3H), 1.64 (s, 6H).

A solution of 2-(2-(4-chloro-3-methoxyphenyl)-2-methylpropanoyl)-N-(4-fluorophenyl)-hydrazine carbothioamide (8.13 g, 0.02 mol) in 3N NaOH (270 mL) was heated at reflux 4 h with mechanical stirring. The reaction mixture was cooled to 5° C. and acidified with 5N HCl to pH=4. The resulting whited solids were collected by filtration, washed with diethyl ether and dried to give 5-(2-(4-chloro-3-methoxyphenyl)propan-2-yl)-4-(4-fluorophenyl)-4H-1,2,4-triazole-3-thiol (7.5 g, 96%). ¹H NMR (400 MHz, DMSO-d₆) δ 7.23-7.21 (d, 1H), 6.95-6.91 (t, 2H), 6.54 (d, 1H), 6.52-6.49 (dd, 1H), 6.45-6.41 (m, 2H), 3.67 (s, 3H), 1.45 (s, 6H).

Preparation of 5-(2-(3-chloro-4-fluorophenyl)propan-2-yl)-1-(4-fluorophenyl)-1H-imidazole-2-thiol

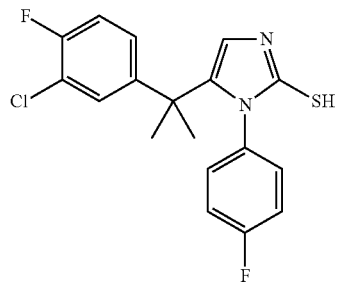 [SMILES: CC(C)(c1ccc(F)c(Cl)c1)c1cnc(S)n1-c1ccc(F)cc1]

¹H NMR (400 MHz, CDCl₃) δ 7.03-6.91 (m, 4H), 6.85 (ddd, J=9.26, 4.74, 2.44 Hz, 2H), 6.67-6.61 (m, 2H), 1.47 (d, J=8.61 Hz, 6H).

Preparation of 5-(2-(3,4-difluoro-5-methoxyphenyl)propan-2-yl)-1-(4-fluorophenyl)-1H-imidazole-2-thiol

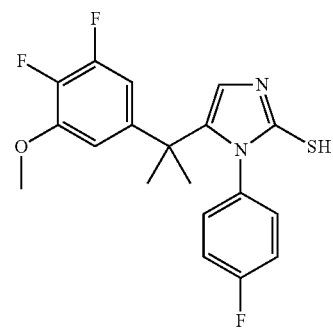 [SMILES: COc1cc(C(C)(C)c2cnc(S)n2-c2ccc(F)cc2)cc(F)c1F]

¹H NMR (400 MHz, CDCl₃) δ 11.20 (s, 1H), 6.92-6.96 (t, 2H), 6.80 (s, 1H), 6.64-6.68 (m, 2H), 6.36-6.40 (dd, 1H), 6.28-6.30 (d, 1H), 3.77 (s, 3H), 1.45 (s, 6H).

TGR5 cAMP Assay Using Cisbio™ cAMP Dynamic 2 htrf Assay Kit

Compounds were diluted in DPBS with 5% DMSO (8-point serial dilution by half logs) in a 96-well plate and 1 µL was transferred to a 384-well assay plate in quadruplicate. The d2-cAMP and anti-cAMP Ab-cryptate stock solution were prepared as per the instructions in the Cisbio™ (Bedford, Mass.) kit. Cells (hTGR5CRE-luc HEK 293 and mTGR5CRE-luc HEK 293) were harvested using cell dissociation buffer and resuspended in DPBS. Cells were adjusted to $0.44 \times 10^6$ cells/ml followed by addition of IBMX to a final concentration of 0.5 mM. The cells were then mixed with d2-cAMP solution (7.1 mL cells+100 ul d2-cAMP) and 4000 cells (9 µL) were transferred to each well of the 384-well assay plate. Cells without d2-cAMP were added to eight wells as a negative control. The plate was covered and incubated at room temp for 30 min. Then 10 µL of Ab-cryptate solution was added to each well of the assay plate and incubated for 1 hr. The plate was read on an EnVision™ plate reader (Perkin-Elmer, Waltham, Mass.) and the DeltaF value was calculated as per the instructions in the Cisbio™ kit.

Glucagon-Like Peptide-1 (GLP-1) Secretion Assays

Mouse enteroendocrine STC-1 cells were cultured and maintained in high glucose DMEM (31053-036; Invitrogen, Carlsbad, Calif.) supplemented with 2 mM L-GlutaMAX-I (35050-079; Invitrogen), 15% horse serum, 5% fetal bovine serum (FBS), and 1% penicillin/streptomycin. Two days prior to analysis of GLP-1 secretion, $2 \times 10^5$ cells were seeded in 24-well culture plates in 500 L of high glucose DMEM media containing 2 mM GlutaMAX-I, 10% charcoal-dextran stripped fetal bovine serum (CD-FBS) (100-119; GEMINI, West Sacramento, Calif.), and 50 µg/mL Gentamicin. On the day of the experiment, cells were washed twice with Hanks' Balanced Salt solution (HBSS) (H8264; Sigma, St. Louis, Mo.) and pre-incubated for 1 hour in 500 µL HBSS. After removal of the HBSS, cells were treated with test compounds in HBSS containing protease inhibitor cocktail (11836153001; Roche, Indianapolis, Ind.), DPP-IV inhibitor (DPP4-010; St. Charles, Mo.), aprotinin, and 0.1% fatty acid free bovine serum albumin (FAF-BSA) (A-0281, Sigma). Supernatants were then collected and 25 µL were used to measure GLP-1 using the Mouse/Rat Total Active GLP-1 MSD Assay Kit (K150 HZC; Meso Scale Discovery, Gaithersburg, Md.).

Murine enteroendocrine GLUTag cells were cultured and maintained in low glucose DMEM (10567-014; Invitrogen) supplemented with 2 mM L-GlutaMAX-I, 10% FBS, and 1% penicillin/streptomycin. The day before analysis of GLP-1 secretion, $2.5 \times 10^5$ cells were seeded in 24-well Matrigel-coated plates in 500 µL of DMEM containing 3 mM glucose, 10% CD-FBS, and 50 µg/mL Gentamicin. On the day of the experiment, cells were washed with PBS and treated with test compounds for 1 hour in 200 µL DMEM containing 15 mM glucose, protease inhibitor cocktail, DPP-IV inhibitor, aprotinin, and 0.1% FAF-BSA. Supernatants were then collected and 25 µL were used to measure GLP-1 using the Mouse/Rat Total Active GLP-1 MSD Assay Kit. The data are presented in FIG. 2.

TGRS/CRE-Luciferiase Assay

HEK 293 cells stably expressing human TGR5 (h-TGR5) or mouse TGR5 (m-TGR5) were generated from HEK 293 CRE-Luciferase cells. The day before the assay, HEK 293 hTGR5/CRE-Luc cells were plated in DMEM in a 384 well assay plate at a density of 25 k cells/45 µL per well and grown for 18-20 hours. Compounds were serially diluted in DMEM containing 5% DMSO and 5 L of compound or media alone was transferred to each well and plates were incubated for 6 hours. Following incubation, 30 µL of lysis/luciferase buffer was added to each well. The luciferase activity was then measured on the EnVision™ plate reader and the dose response data was analyzed using ActivityBase.

TGR5 Assay Results

In the following tables, ECso values determined according to the TGR5 cAMP Assay are noted (cAMP); $EC_{50}$ values determined according to the TGR5/CRE-Luciferiase Assay are noted (CRE-Luc). Table 1 display h-TGR5 CRE-Luc $EC_{50}$ (nM) and h-TGR5 cAMP $EC_{50}$ (nM) data, coded as follows: A<100 nM; B=100-1000 nM; C>1000 nM and less than 10,000 nM.

All of the compounds in Table 1 have quaternary ammonium ion moieties, and it is understood to one skilled in the art that these compounds are all in in the presence of a pharmaceutically acceptable counter ion. The pharmaceutically acceptable counter ion for each of the quaternary ammonium ion moieties present in the compounds of the invention can be any pharmaceutically acceptable counter ion known to one skilled in the art. Non-limiting examples of the pharmaceutically acceptable counter ions that can be used include chloride, bromide, 2,2,2-trifluoroacetate, methanesulfonate, sulfate, tosylate, phosphate, tartrate, maleate, acetate, formate, fumarate, mesylate, nitrate, oxalate, ascorbate, citrate, ammonium, arginine, diethylamine, ethylenediamine, magnesium, sodium, calcium, and potassium. It is also understood that the source of the counter ions can be from either intermolecular sources, or, when possible, intramolecular sources. When Example numbers and compounds numbers above corresponds to the numbers in Table 1. All compound numbers and example numbers that contain parenthesis above correspond to the Example/Compound numbers in table 1 that do not have the parenthesis (for example, Example 6 corresponds to 6 in the table, and compound 6(d) above corresponds to 6d in the table).

TABLE 1

| NAME | cAMP (EC50) (nM) | CRE-Luc Agonist (EC50) (nM) | Example Number |
|---|---|---|---|
| 2-({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]carbonyl}amino)-N,N,N-trimethylethanaminium | A | A | 1 |
| 2-{[(4-{[(5-{1-[4-(aminosulfonyl)-3-chlorophenyl]-1-methylethyl}-1-[4-fluoro-3-(methyloxy)phenyl]-1H-imidazol-2-yl)thio]methyl}-3-chloro-5- | A | A | 1a |

TABLE 1-continued

| NAME | cAMP (EC50) (nM) | CRE-Luc Agonist (EC50) (nM) | Example Number |
|---|---|---|---|
| fluorophenyl)carbonyl]amino}-N,N,N-trimethylethanaminium | | | |
| 2-[({4-[({5-[1-(3-amino-1,2-benzisoxazol-5-yl)-1-methylethyl]-1-[4-fluoro-3-(methyloxy)phenyl]-1H-imidazol-2-yl}thio)methyl]-3-chloro-5-fluorophenyl}carbonyl)amino]-N,N,N-trimethylethanaminium | A | A | 1b |
| 2-[({4-[({5-[1-(3-amino-1,2-benzisoxazol-5-yl)-1-methylethyl]-1-(4-fluorophenyl)-1H-imidazol-2-yl}thio)methyl]-3-chloro-5-fluorophenyl}carbonyl)amino]-N,N,N-trimethylethanaminium | A | A | 1c |
| 2-({[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]carbonyl}amino)-N,N,N-trimethylethanaminium | A | A | 1d |
| 2-({[3-chloro-4-({[5-{1-[4-chloro-3-(methyloxy)phenyl]-1-methylethyl}-1-(4-fluorophenyl)-1H-imidazol-2-yl]methyl}oxy)-5-fluorophenyl]carbonyl}amino)-N,N,N-trimethylethanaminium | A | A | 1e |
| 2-{[(3-chloro-4-{2-[5-{1-[4-chloro-3-(methyloxy)phenyl]-1-methylethyl}-1-(4-fluorophenyl)-1H-imidazol-2-yl]ethyl}-5-fluorophenyl)carbonyl]amino}-N,N,N-trimethylethanaminium | A | A | 1f |
| 1-[2-({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]carbonyl}amino)ethyl]-4-aza-1-azoniabicyclo[2.2.2]octane | A | A | 2 |
| 1-[2-({[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]carbonyl}amino)ethyl]-4-aza-1-azoniabicyclo[2.2.2]octane | A | A | 2a |
| 1-{2-[({3-chloro-4-[({5-[1-(3,4-dichlorophenyl)-1-methylethyl]-1-[4-fluoro-3-(methyloxy)phenyl]-1H-imidazol-2-yl}thio)methyl]-5-fluorophenyl}carbonyl)amino]ethyl}-4-aza-1-azoniabicyclo[2.2.2]octane | A | A | 2b |
| 4-({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]carbonyl}amino)-1,1-dimethylpiperidinium | A | A | 2c |
| (3S)-3-({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]carbonyl}amino)-1,1-dimethylpiperidinium | A | A | 2d |
| (3S)-3-({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]carbonyl}amino)-1-[(4-fluorophenyl)methyl]-1-methylpyrrolidinium | A | A | 2e |
| (3S)-3-({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]carbonyl}amino)-1,1-dimethylpyrrolidinium | A | A | 2f |
| (3R)-3-({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]carbonyl}amino)-1,1-dimethylpiperidinium | A | A | 2g |
| (3R)-3-({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]carbonyl}amino)-1,1-dimethylpyrrolidinium | A | A | 2h |
| 1-[2-({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]carbonyl}amino)ethyl]-1,4,4-trimethylpiperazinediium | B | B | 2i |
| 4-[2-({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]carbonyl}amino)ethyl]-4-methylmorpholin-4-ium | C | C | 2j |
| (3S)-3-[({4-[({5-[1-(3-amino-1,2-benzisoxazol-5-yl)-1-methylethyl]-1-[4-fluoro-3-(methyloxy)phenyl]-1H-imidazol-2-yl}thio)methyl]-3,5-difluorophenyl}carbonyl)amino]-1,1-dimethylpyrrolidinium | A | A | 2k |
| 1-{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]carbonyl}-N,N,N-trimethylpiperidin-4-aminium | A | A | 2l |
| 4-[({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]carbonyl}amino)methyl]-4-hydroxy-1,1-dimethylpiperidinium | A | A | 2m |
| 2-[({3-chloro-4-[({5-[1-(3,4-dichlorophenyl)-1-methylethyl]-1-[4-fluoro-3-(methyloxy)phenyl]-1H-imidazol-2-yl}thio)methyl]-5-fluorophenyl}carbonyl)amino]-N,N,N-trimethylethanaminium | A | A | 2n |
| (3S)-3-[({3-chloro-4-[({5-[1-(3,4-dichlorophenyl)-1-methylethyl]-1-[4-fluoro-3-(methyloxy)phenyl]-1H-imidazol-2-yl}thio)methyl]-5-fluorophenyl}carbonyl)amino]-1,1-dimethylpiperidinium | A | A | 2o |
| (3S)-3-({[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]carbonyl}amino)-1,1-dimethylpiperidinium | A | A | 2p |
| (3S)-3-({[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]carbonyl}amino)-1,1-dimethylpyrrolidinium | A | A | 2q |
| (3S)-3-[({3-chloro-4-[({5-[1-(3,4-dichlorophenyl)-1-methylethyl]-1-[4-fluoro-3-(methyloxy)phenyl]-1H-imidazol-2-yl}thio)methyl]-5- | A | A | 2r |

TABLE 1-continued

| NAME | cAMP (EC50) (nM) | CRE-Luc Agonist (EC50) (nM) | Example Number |
|---|---|---|---|
| fluorophenyl}carbonyl)amino]-1,1-dimethylpyrrolidinium | | | |
| 1-(carboxymethyl)-4-({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]carbonyl}amino)-1-methylpiperidinium | A | A | 3 |
| N-[2-({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]carbonyl}amino)ethyl]-N,N-dimethyl-3-sulfopropan-1-aminium | A | A | 4 |
| 2-[({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]amino}carbonyl)amino]-N,N,N-trimethylethanaminium | A | A | 5 |
| 3-({[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}amino)-N,N,N-trimethylpropan-1-aminium | A | A | 6 |
| 3-({[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]sulfonyl}amino)-N,N,N-trimethylpropan-1-aminium | A | A | 6a |
| 3-{[(4-{[(5-{1-[4-(aminosulfonyl)-3-chlorophenyl]-1-methylethyl}-1-[4-fluoro-3-(methyloxy)phenyl]-1H-imidazol-2-yl)thio]methyl}-3,5-difluorophenyl)sulfonyl]amino}-N,N,N-trimethylpropan-1-aminium | A | A | 6b |
| 3-({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}amino)-N,N,N-triethylpropan-1-aminium | A | A | 6c |
| 3-({[4-({[5-{1-[4-chloro-3-(methyloxy)phenyl]-1-methylethyl}-4-(4-fluorophenyl)-4H-1,2,4-triazol-3-yl]thio}methyl)-3,5-difluorophenyl]sulfonyl}amino)-N,N,N-trimethylpropan-1-aminium | A | A | 6d |
| 3-[({4-[({5-[1-(3,4-dichlorophenyl)-1-methylethyl]-1-[4-fluoro-3-(methyloxy)phenyl]-1H-imidazol-2-yl}thio)methyl]-3,5-difluorophenyl}sulfonyl)amino]-N,N,N-trimethylpropan-1-aminium | A | A | 6e |
| 3-({[3,5-difluoro-4-({[5-{1-[4-fluoro-3-(methyloxy)phenyl]-1-methylethyl}-1-(4-fluorophenyl)-1H-imidazol-2-yl]thio}methyl)phenyl]sulfonyl}amino)-N,N,N-trimethylpropan-1-aminium | A | A | 6f |
| 3-{[(4-{[(5-{1-[4-chloro-3-(methyloxy)phenyl]-1-methylethyl}-1-{4-fluoro-3-[(methyloxy)carbonyl]phenyl}-1H-imidazol-2-yl)thio]methyl}-3,5-difluorophenyl)sulfonyl]amino}-N,N,N-trimethylpropan-1-aminium | B | B | 6g |
| 3-[({4-[({5-[1-(3-chloro-4-fluorophenyl)-1-methylethyl]-1-[4-fluoro-3-(methyloxy)phenyl]-1H-imidazol-2-yl}thio)methyl]-3,5-difluorophenyl}sulfonyl)amino]-N,N,N-trimethylpropan-1-aminium | A | A | 6h |
| 3,3'-({[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}imino)bis(N,N,N-trimethylpropan-1-aminium) | A | B | 6i |
| 3-({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}amino)-N,N,N-trimethylpropan-1-aminium | A | A | 6j |
| 2-({[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}amino)-N,N,N-trimethylethanaminium | A | A | 6k |
| 3-({[2-chloro-5-({[5-{1-[4-chloro-3-(methyloxy)phenyl]-1-methylethyl}-1-(4-fluorophenyl)-1H-imidazol-2-yl]thio}methyl)phenyl]sulfonyl}amino)-N,N,N-trimethylpropan-1-aminium | A | A | 6l |
| 3-({[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}amino)-N,N,N-triethylpropan-1-aminium | A | A | 6m |
| 3-({[4-({[5-{1-[3-chloro-4-(methyloxy)phenyl]-1-methylethyl}-1-(4-fluorophenyl)-1H-imidazol-2-yl]thio}methyl)-3,5-difluorophenyl]sulfonyl}amino)-N,N,N-trimethylpropan-1-aminium | A | A | 6n |
| 3-({[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]sulfonyl}amino)-N,N,N-triethylpropan-1-aminium | A | A | 6o |
| 3,3'-({[4-chloro-5-({[5-{1-[4-chloro-3-(methyloxy)phenyl]-1-methylethyl}-1-(4-fluorophenyl)-1H-imidazol-2-yl]thio}methyl)-2-fluorophenyl]sulfonyl}imino)bis(N,N,N-trimethylpropan-1-aminium) | B | B | 6p |
| 3-({[2-chloro-5-({[5-{1-[4-chloro-3-(methyloxy)phenyl]-1-methylethyl}-1-(4-fluorophenyl)-1H-imidazol-2-yl]thio}methyl)-4-fluorophenyl]sulfonyl}amino)-N,N,N-trimethylpropan-1-aminium | A | A | 6q |
| 4-({[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}amino)-N,N,N-trimethylbutan-1-aminium | A | A | 6r |
| 3-({[4-chloro-5-({[5-{1-[4-chloro-3-(methyloxy)phenyl]-1-methylethyl}-1-(4-fluorophenyl)-1H-imidazol-2-yl]thio}methyl)-2-fluorophenyl]sulfonyl}amino)-N,N,N-trimethylpropan-1-aminium | A | A | 7 |
| 3-({[3-({[5-{1-[4-chloro-3-(methyloxy)phenyl]-1-methylethyl}-1-(4-fluorophenyl)-1H-imidazol-2-yl]thio}methyl)-2,4-difluorophenyl]sulfonyl}amino)-N,N,N-trimethylpropan-1-aminium | A | A | 7a |

TABLE 1-continued

| NAME | cAMP (EC50) (nM) | CRE-Luc Agonist (EC50) (nM) | Example Number |
|---|---|---|---|
| 3-{[({[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}amino)carbonyl]amino}-N,N,N-triethylpropan-1-aminium | A | A | 8 |
| 1-[3-({[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]sulfonyl}amino)propyl]pyridinium | A | A | 9 |
| 3-[3-({[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]sulfonyl}amino)propyl]-1-methyl-1H-imidazol-3-ium | A | A | 10 |
| 3-(2-(3-chloro-5-fluoro-4-((5-(2-(4-fluoro-3-methoxyphenyl)propan-2-yl)-1-(4-fluorophenyl)-1H-imidazol-2-ylthio)methyl)phenylsulfonamido)ethyl)-1-methylpyridinium | A | A | 11 |
| (3S)-3-({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}amino)-1,1-dimethylpiperidinium | A | A | 11a |
| 4-({[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}amino)-1,1-dimethylpiperidinium | A | A | 11b |
| 1-{[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}-N,N,N-trimethylpiperidin-4-aminium | A | A | 11c |
| (3R)-3-({[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}amino)-1,1-dimethylpiperidinium | A | A | 11d |
| (3S)-3-({[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}amino)-1,1-dimethylpiperidinium | A | A | 11e |
| 1-{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}-N,N,N-trimethylpiperidin-4-aminium | A | A | 11f |
| (3R)-1-{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}-N,N,N-trimethylpiperidin-3-aminium | A | A | 11g |
| (3S)-1-{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}-N,N,N-trimethylpiperidin-3-aminium | A | A | 11h |
| (3R)-1-{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}-N,N,N-trimethylpyrrolidin-3-aminium | A | A | 11i |
| 1-{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}-N-ethyl-N,N-dimethylpiperidin-4-aminium | A | A | 11j |
| 4-{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}-1,1-dimethylpiperazin-1-ium | A | A | 11k |
| (3S)-1-{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}-N,N,N-trimethylpyrrolidin-3-aminium | A | A | 11l |
| 3-[{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}(methyl)amino]-N-ethyl-N,N-dimethylpropan-1-aminium | A | A | 11m |
| 1-{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}-N,N,N-trimethylazetidin-3-aminium | A | A | 11n |
| 1-{[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]sulfonyl}-N,N,N-trimethylpiperidin-4-aminium | A | A | 11o |
| (3R)-1-{[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]sulfonyl}-N,N,N-trimethylpiperidin-3-aminium | A | A | 11p |
| 1-{[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]sulfonyl}-N-ethyl-N,N-dimethylpiperidin-4-aminium | A | A | 11q |
| (1-{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}azetidin-3-yl)-N,N,N-trimethylmethanaminium | A | A | 11r |
| 4-[({[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]sulfonyl}amino)methyl]-1,1-dimethylpiperidinium | A | A | 11s |
| 2-({[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]sulfonyl}amino)-1-methylpyridinium | A | A | 11t |

TABLE 1-continued

| NAME | cAMP (EC50) (nM) | CRE-Luc Agonist (EC50) (nM) | Example Number |
|---|---|---|---|
| [(3S)-1-{[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]sulfonyl}piperidin-3-yl]-N,N,N-trimethylmethanaminium | A | A | 11u |
| [(3S)-1-{[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]sulfonyl}pyrrolidin-3-yl]-N,N,N-trimethylmethanaminium | A | A | 11v |
| [(3R)-1-{[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]sulfonyl}piperidin-3-yl]-N,N,N-trimethylmethanaminium | A | A | 11w |
| (4-carboxy-1-{[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}piperidin-4-yl)-N,N,N-trimethylmethanaminium | A | A | 11x |
| 3-[(carboxymethyl){4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}amino]-N,N,N-trimethylpropan-1-aminium | A | A | 12 |
| 3-[{[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}(methyl)amino]-N,N,N-trimethylpropan-1-aminium | A | A | 12a |
| 3-[{[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}(ethyl)amino]-N,N,N-trimethylpropan-1-aminium | A | A | 12b |
| 3-[{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}(methyl)amino]-N,N,N-trimethylpropan-1-aminium | A | A | 12c |
| 3-[{[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]sulfonyl}(methyl)amino]-N,N,N-trimethylpropan-1-aminium | A | A | 12d |
| 3-[{[3-chloro-4-({[5-{1-[4-chloro-3-(methyloxy)phenyl]-1-methylethyl}-1-(4-fluorophenyl)-1H-imidazol-2-yl]methyl}oxy)-5-fluorophenyl]sulfonyl}(methyl)amino]-N,N,N-trimethylpropan-1-aminium | A | A | 12e |
| 3-[{[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}(2-hydroxyethyl)amino]-N,N,N-trimethylpropan-1-aminium | A | A | 12f |
| 3-[{[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}(3-hydroxypropyl)amino]-N,N,N-trimethylpropan-1-aminium | A | A | 12g |
| 3-[(2-amino-2-oxoethyl){[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}amino]-N,N,N-trimethylpropan-1-aminium | A | A | 12h |
| 3-([(4-carboxyphenyl)methyl]{[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}amino)-N,N,N-trimethylpropan-1-aminium | A | A | 12 |
| 3-[({4-[({5-[1-(4-chloro-3-hydroxyphenyl)-1-methylethyl]-1-(4-fluorophenyl)-1H-imidazol-2-yl}thio)methyl]-3,5-difluorophenyl}sulfonyl)amino]-N,N,N-trimethylpropan-1-aminium | B | B | 13a |
| 3-({[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}[(1R)-1-methyl-2-(methyloxy)-2-oxoethyl]amino)-N,N,N-trimethylpropan-1-aminium | A | A | 14 |
| 3-([(1R)-1-carboxyethyl]{[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}amino)-N,N,N-trimethylpropan-1-aminium | A | A | 14a |
| 3-([(1S)-1-carboxyethyl]{[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}amino)-N,N,N-trimethylpropan-1-aminium | A | A | 14b |
| 3-([(1R)-1-carboxyethyl]{[3-chloro-4-({[5-{1-[3,4-difluoro-5-(methyloxy)phenyl]-1-methylethyl}-1-(4-fluorophenyl)-1H-imidazol-2-yl]thio}methyl)-5-fluorophenyl]sulfonyl}amino)-N,N,N-trimethylpropan-1-aminium | A | A | 14c |
| 4-([(1R)-1-carboxyethyl]{[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}amino)-N,N,N-trimethylbutan-1-aminium | A | A | 14d |
| N-{(4S)-4-carboxy-4-[{[3,5-difluoro-4-({[5-{1-[4-fluoro-3-(methyloxy)phenyl]-1-methylethyl}-1-(4-fluorophenyl)-1H-imidazol-2-yl]thio}methyl)phenyl]sulfonyl}(methyl)amino]butyl}-N,N-dimethylmethanaminium | A | A | 14e |
| N-{(4S)-4-carboxy-4-[{[4-({[5-{1-[3,4-difluoro-5-(methyloxy)phenyl]-1-methylethyl}-1-(4-fluorophenyl)-1H-imidazol-2-yl]thio}methyl)-3,5-difluorophenyl]sulfonyl}(methyl)amino]butyl}-N,N-dimethylmethanaminium | A | A | 14f |

TABLE 1-continued

| NAME | cAMP (EC50) (nM) | CRE-Luc Agonist (EC50) (nM) | Example Number |
|---|---|---|---|
| N-{(4S)-4-carboxy-4-[{[4-({[5-{1-[3-chloro-4-(methyloxy)phenyl]-1-methylethyl}-1-(4-fluorophenyl)-1H-imidazol-2-yl]thio}methyl)-3,5-difluorophenyl]sulfonyl}(methyl)amino]butyl}-N,N-dimethylmethanaminium | A | A | 14g |
| N-{(4S)-4-carboxy-4-[({4-[({5-[1-(3-chloro-4-fluorophenyl)-1-methylethyl]-1-(4-fluorophenyl)-1H-imidazol-2-yl}thio)methyl]-3,5-difluorophenyl}sulfonyl)(methyl)amino]butyl}-N,N-dimethylmethanaminium | A | A | 14h |
| (6S)-6-carboxy-6-[{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}(methyl)amino]-N,N,N-trimethylhexan-1-aminium | A | A | 14i |
| 3-[{[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]sulfonyl}(ethyl)amino]-N,N,N-trimethylpropan-1-aminium | A | A | 14j |
| 3-[{[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]sulfonyl}(cyclopropyl)amino]-N,N,N-trimethylpropan-1-aminium | A | A | 14k |
| 3-[{[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]sulfonyl}(1-methylethyl)amino]-N,N,N-trimethylpropan-1-aminium | A | A | 14l |
| 3-[{[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]sulfonyl}(methyl)amino]-N-ethyl-N,N-dimethylpropan-1-aminium | A | A | 14m |
| 3-[(carboxymethyl){[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]sulfonyl}amino]-N,N,N-trimethylpropan-1-aminium | A | A | 14n |
| 4-[(carboxymethyl){[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}amino]-N,N,N-trimethylbutan-1-aminium | A | A | 14o |
| 3-({(1S)-1-carboxy-2-methylpropyl}{[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}amino)-N,N,N-trimethylpropan-1-aminium | A | A | 14p |
| 3-({(1R)-1-carboxy-2-methylpropyl}{[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}amino)-N,N,N-trimethylpropan-1-aminium | A | A | 14q |
| 3-[(2-carboxyethyl){[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}amino]-N,N,N-trimethylpropan-1-aminium | A | A | 14r |
| 3-[(carboxymethyl){[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}amino]-N,N,N-trimethylpropan-1-aminium | A | A | 14s |
| 3-({(1S)-1-carboxy-2-hydroxyethyl}{[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}amino)-N,N,N-trimethylpropan-1-aminium | A | A | 14t |
| 3-[(2-carboxyethyl){[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}amino]-N,N,N-trimethylpropan-1-aminium | A | A | 14u |
| 3-({[(3-carboxyphenyl)methyl]{[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}amino)-N,N,N-trimethylpropan-1-aminium | A | A | 14v |
| 3-({(1S)-1-carboxypropyl}{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}amino)-N,N,N-trimethylpropan-1-aminium | A | A | 14w |
| 3-({[(1S)-1-carboxyethyl]{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}amino)-N,N,N-trimethylpropan-1-aminium | A | A | 14x |
| 3-({[(1R)-1-carboxyethyl]{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}amino)-N,N,N-trimethylpropan-1-aminium | A | A | 14y |
| 3-[(1-carboxycyclopropyl){[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}amino]-N,N,N-trimethylpropan-1-aminium | A | A | 14z |

TABLE 1-continued

| NAME | cAMP (EC50) (nM) | CRE-Luc Agonist (EC50) (nM) | Example Number |
|---|---|---|---|
| 4-([(1R)-1-carboxyethyl]{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}amino)-N,N,N-trimethylbutan-1-aminium | A | A | 14aa |
| 3-([(1R)-1-carboxypropyl]{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}amino)-N,N,N-trimethylpropan-1-aminium | A | A | 14ab |
| 3-([(1S,2R)-1-carboxy-2-hydroxypropyl]{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}amino)-N,N,N-trimethylpropan-1-aminium | A | A | 14ac |
| 5-([(1R)-1-carboxyethyl]{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}amino)-N,N,N-trimethylpentan-1-aminium | A | A | 14ad |
| 3-({[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}{[4-(methyloxy)phenyl]methyl}amino)-N,N,N-trimethylpropan-1-aminium | B | A | 14ae |
| 3-({[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}[1,1-dimethyl-2-(methyloxy)-2-oxoethyl]amino)-N,N,N-trimethylpropan-1-aminium | A | A | 14af |
| (S)-3-(4-((5-(2-(4-chloro-3-methoxyphenyl)propan-2-yl)-1-(4-fluorophenyl)-1H-imidazol-2-ylthio)methyl)-N-(1,3-dicarboxypropyl)-3,5-difluorophenylsulfonamido)-N,N,N-trimethylpropan-1-aminium | B | A | 14ag |
| 3-[(1-carboxy-1-methylethyl){[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}amino]-N,N,N-trimethylpropan-1-aminium | A | A | 14ah |
| 4-[(1-carboxy-1-methylethyl){[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}amino]-N,N,N-trimethylbutan-1-aminium | A | A | 14ai |
| 3-([(1R)-2-carboxy-1-methylethyl]{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}amino)-N,N,N-trimethylpropan-1-aminium | A | A | 14aj |
| N-{[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}-N-[(1,1-dimethylpiperidinium-4-yl)methyl]-D-alanine | A | A | 15 |
| N-{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}-N-(3-pyridinium-1-ylpropyl)-D-alanine | A | A | 15a |
| N-{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}-N-[3-(1-methyl-1H-imidazol-3-ium-3-yl)propyl]-D-alanine | A | A | 15b |
| N-{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}-N-[2-(1-methylpyridinium-3-yl)ethyl]-D-alanine | A | A | 16 |
| N-{(4S)-4-carboxy-4-[{[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}(methyl)amino]butyl}-N,N-dimethylmethanaminium | A | A | 17 |
| N-{(4S)-4-carboxy-4-[{[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}(ethyl)amino]butyl}-N,N-dimethylmethanaminium | A | A | 17a |
| N-{(4S)-4-carboxy-4-[{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}(methyl)amino]butyl}-N,N-dimethylmethanaminium | A | A | 17b |
| N-{(4R)-4-carboxy-4-[{[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}(methyl)amino]butyl}-N,N-dimethylmethanaminium | A | A | 17c |
| N-{(4R)-4-carboxy-4-[{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}(methyl)amino]butyl}-N,N-dimethylmethanaminium | A | A | 17d |
| N-[(5S)-5-carboxy-5-({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}amino)pentyl]-N,N-dimethylmethanaminium | A | A | 17e |
| N-{(5S)-5-carboxy-5-[{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}(methyl)amino]pentyl}-N,N-dimethylmethanaminium | A | A | 17f |
| N-{(5S)-5-carboxy-5-[{[4-({[5-{1-[4-chloro-3-(methyloxy)phenyl]-1-methylethyl}-1-(4-fluorophenyl)-1H-imidazol-2-yl]thio}methyl)-3,5- | A | A | 17g |

TABLE 1-continued

| NAME | cAMP (EC50) (nM) | CRE-Luc Agonist (EC50) (nM) | Example Number |
|---|---|---|---|
| difluorophenyl]sulfonyl}(methyl)amino]pentyl}-N,N-dimethylmethanaminium | | | |
| N-{(5S)-5-carboxy-5-[({3-chloro-4-[({5-[1-(3,4-dichlorophenyl)-1-methylethyl]-1-(4-fluorophenyl)-1H-imidazol-2-yl}thio)methyl]-5-fluorophenyl}sulfonyl)(methyl)amino]pentyl}-N,N-dimethylmethanaminium | A | A | 17h |
| N-{(5R)-5-carboxy-5-({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}amino)pentyl}-N,N-dimethylmethanaminium | A | A | 17i |
| N-{(5R)-5-carboxy-5-[{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}(methyl)amino]pentyl}-N,N-dimethylmethanaminium | A | A | 17j |
| N-{(5R)-5-carboxy-5-[{[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}(methyl)amino]pentyl}-N,N-dimethylmethanaminium | A | A | 17k |
| (6S)-6-carboxy-6-[{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}(methyl)amino]-N,N,N-trimethylhexan-1-aminium | A | A | 17l |
| 3-{[(1R)-1-carboxyethyl][(3-chloro-4-{2-[5-{1-[4-chloro-3-(methyloxy)phenyl]-1-methylethyl}-1-(4-fluorophenyl)-1H-imidazol-2-yl]ethyl}-5-fluorophenyl)sulfonyl]amino}-N,N,N-trimethylpropan-1-aminium | A | A | 17m |
| N-[(5S)-5-carboxy-5-{[(3-chloro-4-{2-[5-{1-[4-chloro-3-(methyloxy)phenyl]-1-methylethyl}-1-(4-fluorophenyl)-1H-imidazol-2-yl]ethyl}-5-fluorophenyl)sulfonyl]amino}pentyl]-N,N-dimethylmethanaminium | A | A | 17n |
| N-[(5S)-5-carboxy-5-{[(3-chloro-4-{2-[5-{1-[4-chloro-3-(methyloxy)phenyl]-1-methylethyl}-1-(4-fluorophenyl)-1H-imidazol-2-yl]ethyl}-5-fluorophenyl)sulfonyl](methyl)amino}pentyl]-N,N-dimethylmethanaminium | A | A | 17o |
| 3-[4-({5-{1-[4-chloro-3-(methyloxy)phenyl]-1-methylethyl}-1-(4-fluorophenyl)-1H-imidazol-2-yl]thio}methyl)-3,5-difluorophenyl]-N,N,N-trimethylprop-2-yn-1-aminium | A | A | 18 |
| 3-[4-({5-{1-[4-chloro-3-(methyloxy)phenyl]-1-methylethyl}-1-(4-fluorophenyl)-1H-imidazol-2-yl]thio}methyl)-3,5-difluorophenyl]-N,N,N-triethylprop-2-yn-1-aminium | A | A | 18a |
| 1-(3-(4-((5-(2-(4-chloro-3-methoxyphenyl)propan-2-yl)-1-(4-fluorophenyl)-1H-imidazol-2-ylthio)methyl)-3,5-difluorophenyl)propyl)-4-aza-1-azoniabicyclo[2.2.2]octane | A | A | 19 |
| 3-[4-({[5-{1-[4-chloro-3-(methyloxy)phenyl]-1-methylethyl}-1-(4-fluorophenyl)-1H-imidazol-2-yl]thio}methyl)-3,5-difluorophenyl]-N,N,N-trimethylpropan-1-aminium | A | A | 19a |
| 3-{4-[({5-[1-(3-chloro-4-fluorophenyl)-1-methylethyl]-1-[4-fluoro-3-(methyloxy)phenyl]-1H-imidazol-2-yl}thio)methyl]-3,5-difluorophenyl}-N,N,N-trimethylpropan-1-aminium | A | A | 19b |
| 3-[4-({[5-{1-[3-chloro-4-(methyloxy)phenyl]-1-methylethyl}-1-(4-fluorophenyl)-1H-imidazol-2-yl]thio}methyl)-3,5-difluorophenyl]-N,N,N-trimethylpropan-1-aminium | A | A | 19c |
| 3-[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]-N,N,N-trimethylpropan-1-aminium | A | A | 19d |
| 4-[4-({[5-{1-[4-chloro-3-(methyloxy)phenyl]-1-methylethyl}-1-(4-fluorophenyl)-1H-imidazol-2-yl]thio}methyl)-3,5-difluorophenyl]-N,N,N-trimethylbutan-1-aminium | A | A | 19e |
| 3-(4-{[(5-{1-[4-(aminosulfonyl)-3-chlorophenyl]-1-methylethyl}-1-[4-fluoro-3-(methyloxy)phenyl]-1H-imidazol-2-yl)thio]methyl}-3,5-difluorophenyl)-N,N,N-trimethylpropan-1-aminium | A | A | 19f |
| 2-{[4-({[5-{1-[4-chloro-3-(methyloxy)phenyl]-1-methylethyl}-1-(4-fluorophenyl)-1H-imidazol-2-yl]thio}methyl)-3,5-difluorophenyl]oxy}-N,N,N-trimethylethanaminium | A | A | 20 |
| 2-{[4-({[5-{1-[4-chloro-3-(methyloxy)phenyl]-1-methylethyl}-1-(4-fluorophenyl)-1H-imidazol-2-yl]thio}methyl)-3,5-difluorophenyl]oxy}-N,N,N-triethylethanaminium | A | A | 20a |
| (4-carboxy-1-{[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}piperidin-4-yl)-N,N,N-trimethylmethanaminium | A | A | 21 |
| N-[3-(4-aza-1-azoniabicyclo[2.2.2]oct-1-yl)propyl]-N-{[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}-D-alanine | A | A | 22 |
| N-[4-(4-aza-1-azoniabicyclo[2.2.2]oct-1-yl)butyl]-N-{[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}-D-alanine | A | A | 22a |

All of the above compounds having quaternary ammonium ion moieties have more non-systemic than with the same compounds without quaternary ammonium ion moieties.

From the foregoing it will be appreciated that, although specific embodiments of this disclosure have been described herein for purposes of illustration, various modifications may be made without deviating from the spirit and scope of the invention. Accordingly, the invention is not limited except as by the appended claims.

What is claimed is:

1. A compound of Formula VIII(Q):

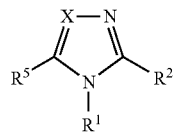

VIII(Q)

or pharmaceutically acceptable salt thereof, wherein:

X is =N— or =C($R^4$)—;

$R^1$ is $R^C$;

or X can be =C($R^C$)— only when $R^1$ is phenyl optionally substituted with one, two, or three $R^{C10}$ groups;

$R^C$ is selected from phenyl, —($C_5$-$C_6$)-cycloalkyl, —$CH_2$-phenyl, heteroaryl, and —($C_1$-$C_4$)alkyl optionally substituted with —$OR^{C13}$, —N($R^{C13}$)$_2$ or —S($R^{C13}$), wherein the cyclic group of $R^C$ can be optionally substituted with 1, 2, 3, 4 or 5 $R^{C10}$ groups, wherein the 1, 2, 3, 4, or 5 $R^{C10}$ groups are independently selected from $R^{C10A}$ and $R^{C10B}$, provided that $R^C$ cannot be substituted with more than 2 $R^{C10B}$ groups, wherein each $R^{C10A}$ is independently selected from halo, methoxy, —$CF_3$, cyano and —($C_1$-$C_4$)alkyl optionally substituted with 1-3 groups selected from —OH, methoxy, —$CF_3$, and halo;

each $R^{C10B}$ is independently selected from —C(O)$NH_2$, (5-6 membered)heterocycloalkyl, —O—($C_1$-$C_4$)alkyl-$R^{C11}$, —N[—($C_1$-$C_4$)alkyl]$_2$, —($C_1$-$C_4$)alkyl substituted with —N[—($C_1$-$C_4$)alkyl]$_2$, —C(O)$OR^{C12}$, —OC(O)$OR^{C12}$ and —O—($C_1$-$C_4$)alkyl optionally substituted with —OH or —C(O)OH;

$R^{C11}$ is cyano, nitro, —N($R^{C12}$)$_2$, —$OR^{C12}$, —$SR^{C12}$, —C(O)$R^{C12}$, —C(O)$OR^{C12}$, —C(O)N($R^{C12}$)$_2$, —S(O)N($R^{C12}$)$_2$, —S(O)$_2$N($R^{C12}$)$_2$, —S(O)$_2$$R^{C12}$, —OC(O)$R^{C12}$, —OC(O)$OR^{C12}$, —OC(O)N($R^{C12}$)$_2$, —N($R^{C12}$)C(O)$R^{C12}$, —N($R^{C12}$)C(O)$OR^{C12}$, —N($R^{C12}$)C(O)N($R^{C12}$)$_2$, or —N($R^{C12}$)C(=N$R^{C12}$)N($R^{C12}$)$_2$;

each $R^{C12}$ is independently selected from hydrogen, —($C_1$-$C_4$)alkyl, and —($C_1$-$C_4$)haloalkyl;

each $R^{C13}$ is independently selected from hydrogen, —($C_1$-$C_4$)alkyl, and —($C_1$-$C_4$)haloalkyl;

$R^2$ is -$L^D$-$R^{D1}$;

$L^D$ is —[C(R)$_2$]$_p$—Y—[C(R)$_2$]$_q$—;

p is 0 or 1:

q is 0 or 1;

each R is independently selected from H, —($C_1$-$C_3$)alkyl, halo, —OH, and —$CH_2$OH;

Y is a bond, —S—, —S(O)$_2$—, —CH(OH)—, —O—, —C(H)=C(H)—, —C(O)—($C_1$-$C_4$)alkyl-, —($C_1$-$C_4$)alkyl-S—($C_1$-$C_4$)alkyl-, —($C_1$-$C_4$)alkyl-N($R^Y$)—($C_1$-$C_4$)alkyl-, —C(H)(halo)-, —($C_1$-$C_4$)alkyl-S(O)$_2$—, —S(O)$_2$—N($R^Y$)—, —($C_1$-$C_4$)alkyl—O—, or —C(O)—N($R^Y$)—, wherein $R^Y$ is H, —($C_1$-$C_4$)alkyl, hydroxyl($C_1$-$C_4$)alkyl or —C≡C—($C_1$-$C_3$)alkyl-;

$R^{D1}$ is selected from —($C_6$-$C_{10}$)aryl, —N(H)-phenyl, cycloalkyl, heterocycloalkyl, and heteroaryl, wherein $R^{D1}$ is substituted with 1-5 $R^{D10}$ groups, wherein the 1-5 $R^{D10}$ groups are independently selected from A groups and B groups, provided that $R^{D1}$ is substituted with 1-2 B groups;

each A group, when they occur, is independently selected from halo, —$CF_3$, —CN, —$NO_2$, —OH, —O—($C_1$-$C_4$) alkyl optionally substituted at the alkyl group with 1-3 substituents independently selected from —OH and halo, and —($C_1$-$C_4$)alkyl optionally substituted with 1-3 substituents independently selected from —OH and halo;

each B group is selected from —($C_1$-$C_4$)alkyl-N($R^{D11}$)$R^{D11B}$, —C(O)—N($R^{D11D}$)$R^{D11}$, —C(O)—($C_1$-$C_4$)alkyl-$Q^A$, —C(O)O—($C_1$-$C_4$)alkyl-$Q^A$, —C(O)-heterocycloalkyl-$R^{D11}$, —S(O)$_2$—($C_1$-$C_4$)alkyl-N($R^{D11B}$)$R^{D11}$, —S(O)$_2$—$R^{D11}$, —S(O)$_2$—N($R^{D11D}$)$Q^R$, —S(O)$_2$—N(H)C(O)—($C_1$-$C_4$)alkyl-$Q^A$, —S(O)$_2$—N($R^{D11D}$)C(O)O—($C_1$-$C_4$)alkyl-$Q^A$, —S(O)$_2$—N(H)C(O)—N(H)$R^{D11}$, —S(O)$_2$-(4-6 membered)heterocycloalkyl-($C_0$-$C_4$)alkyl-$Q^A$, wherein a carbon of the heterocycloalkyl group of —S(O)$_2$-(4-6 membered)heterocycloalkyl-($C_0$-$C_4$)alkyl-$Q^A$ can be substituted with $R^{D11D}$, —S(O)$_2$—($C_1$-$C_4$)alkyl-$Q^A$, —O—($C_1$-$C_4$)alkyl-$Q^A$ optionally substituted at the alkyl group with 1 or 2 $R^{D11B}$, —C(O)—N($R^{D11D}$)—($C_1$-$C_6$)alkyl substituted at the alkyl group with 1 or 2 $R^{D11}$, heterocycloalkyl-$Q^A$ optionally substituted with oxo or $R^{D11D}$, —S(O)$_2$—N($R^{D11D}$)$R^{D11}$, —C(O)—($C_1$-$C_4$alkyl substituted at the alkyl group with 1 or 2 $R^{D11}$, —N(H)—C(O)—N($R^{D11D}$)—($C_1$-$C_3$)alkyl substituted at the —($C_1$-$C_3$)alkyl group with $R^{D11}$, —($C_1$-$C_6$)alkyl substituted with 1 or 2 $R^{D11}$, and —C≡C—($C_0$-$C_3$)alkyl substituted with $R^{D11}$;

each $R^{D11}$ is independently selected from —($C_3$-$C_6$)cycloalkyl-$Q^A$, —($C_0$-$C_6$)alkyl-$Q^A$ optionally substituted with halo or COOH, —($C_0$-$C_6$)alkyl—(5-6 membered)heterocycloalkyl-$Q^A$, and a PEG polymer substituted with $Q^A$, $R^{D11B}$ is selected from $Q^A$, H, —OH, —$CF_3$, —N($R^{D11E}$)$_2$, —C(O)OH, —O—($C_1$-$C_4$)alkyl, —S(O)$_2$OH, —C(=NH)—$NH_2$, —N(H)C(=NH)$NH_2$, —C(H)=NC(=NH)$NH_2$, —C(H)=NN(H)C(=NH)$NH_2$, 1,4-diazabicyclo[2.2.2]octanyl, —N(H)C(=NH)—N(H)C(=NH)$NH_2$, —C(O)—($C_1$-$C_3$)alkyl, —O—($C_1$-$C_4$)alkyl-C(O)OH, (5-6 membered)heteroaryl, —($C_1$-$C_4$)alkyl optionally substituted with 1-3 groups independently selected from halo, —OH, —S(O)$_2$OH, C(O)OH, —$NH_2$, —N[($C_1$-$C_3$)alkyl]$_3$$^+$, 1,4-diazabicyclo[2.2.2]octanyl, and —N(H)C(=NH)$NH_2$, —($C_0$-$C_3$)alkyl—(5-8 membered)heterocycloalkyl optionally substituted at the heterocycloalkyl group with 1-3 $R^{D11}$, —($C_0$-$C_3$)alkyl-($C_3$-$C_6$)cycloalkyl optionally substituted with $R^{D11}$, and aryl optionally substituted with 1-5 halo;

$R^{D11D}$ is selected from H, —($C_3$-$C_6$)cycloalkyl, —($C_1$-$C_6$) alkyl optionally substituted with 1 or 2 substituents selected from —N[($C_1$-$C_3$)alkyl]$_3$$^+$, gem-cyclopropyl, —OH, —C(O)OH, —C(O)O—($C_1$-$C_3$)alkyl, and —C(O)$NH_2$, and —($C_1$-$C_6$)alkyl-phenyl optionally substituted at the phenyl group with —($C_1$-$C_3$)alkoxy, —C(O)OH, or —C(O)O—($C_1$-$C_3$)alkyl;

each $R^{D11E}$ is independently selected from H, —($C_1$-$C_3$) alkyl, and —($C_1$-$C_3$)haloalkyl;

$R^4$ is H, —($C_1$-$C_3$)alkyl or halo;

R⁵ is —[C(R⁸)₂]-phenyl, —[C(R⁸)₂]—Naphthalenyl, or —[C(R⁸)₂]—(5-10 membered) heteroaryl, wherein the heteroaryl is selected from (benzo[d][1,3]dioxolyl, benzo[d]isoxazole, quinoxalinyl, quinolinyl and 2,3,4a, 8a-tetrahydrobenzo[b][1,4]dioxinyl, wherein the cyclic group of R⁵ is optionally substituted with 1-5 R⁴¹⁰ groups, wherein the 1-5 R⁴¹⁰ groups are independently selected from R⁴¹⁰ᴬ groups and R⁴¹⁰ᴮ groups, provided that R⁵ cannot be substituted with more than 2R⁴¹⁰ᴮ groups;

each R⁴¹⁰ᴬ, when they occur, is independently selected from halo, alkoxyl, hydroxyl, —CN, —OCF₃, —(C₁-C₄)alkyl and —NH₂, each R⁴¹⁰ᴮ, when they occur, is selected from —O—(C₁-C₄)alkyl—R⁴¹¹, —S(O)₂—NH₂, —S(O)₂CH₃, —N(H)—S(O)₂CH₃, —S(O)₂N(H)—CH₃ —C(O)OH, —(C₁-C₄)alkyl—OH, —C(O)NH₂, and —(C₁-C₄)alkyl substituted with 1-3 groups selected from —OH and halo;

R⁴¹¹ is selected —C(O)OH, (5-6 membered)heterocycloalkyl, halogen, cyano, nitro, —(C₁-C₄)alkyl, —N(R⁴¹²)₂ —OR⁴¹², —SR⁴¹², —N(OR⁴¹²)R⁴¹², —C(O)R⁴¹², —C(O)OR⁴¹², —C(O)N(R⁴¹²)₂, —N(R⁴¹²)S(O)R⁴¹², —N(R¹²)S(O)₂R⁴¹², —S(O)N(R⁴¹²)², —S(O)₂N(R⁴¹²)₂, —S(O)₂R⁴¹², —OC(O)R⁴¹², —OC(O)OR⁴¹², —OC(O)N(R⁴¹²)₂, —N(R⁴¹²)C(O)R⁴¹², —N(R¹²)S(O)₂R⁴¹², —N(R⁴¹²)C(O)OR⁴¹², —N(R⁴¹²) C(O)N(R⁴¹²)₂, —N(R⁴¹²)C(=NR⁴¹²)N(R⁴¹²)₂, and heteroaryl, wherein each R⁴¹² is independently hydrogen, —(C₁-C₄)alkyl, or —(C₁-C₄)haloalkyl;

each R⁸ is independently hydrogen, halogen, or methyl, or both R⁸ taken together with the carbon to which they are both attached form either a (C₃-C₆)cycloalkyl or a (3-6 membered)heterocycloalkyl;

Qᴬ is Qᴸ or Qᴿ;

Qᴸ is —N[(C1-C3)alkyl]₃⁺wherein an alkyl group of —N[(C₁-C₃)alkyl]₃⁺is optionally substituted with —(C₀-C₆)alkyl—S(O)₂OH;

Qᴿ is selected from:

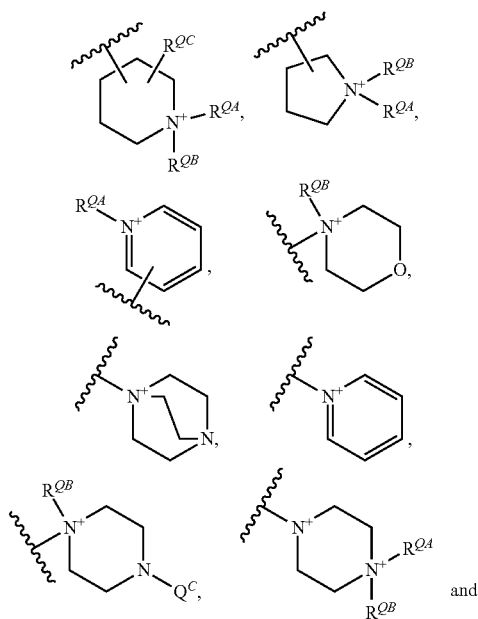

-continued

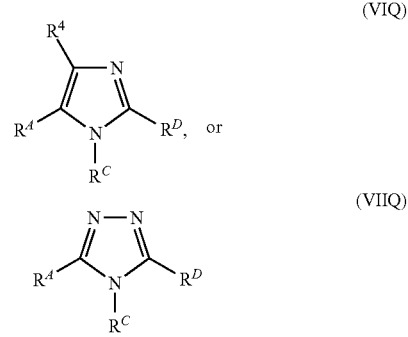

Rᵠᴬ is —(C₁-C₆)alkyl;
Rᵠᴮ is —(C₁-C₆)alkyl optionally substituted with —C(O)OH; and
Rᵠᶜ is H, —OH, —(C₀-C₄)alkyl—C(O)OH or —(C₁-C₆)alkyl.

2. The compound a according to claim 1 having structural formulae (VIQ) or (VIIQ):

(VIQ)

(VIIQ)

or pharmaceutically acceptable salt thereof, wherein:

Rᴬ is —[C(CH₃)₂]—phenyl, —[C(CH₃)₂]—naphthalenyl, or —[C(CH₃)₂]—(5-10 membered)heteroaryl, wherein the heteroaryl is selected from (benzo[d][1,3]dioxolyl, benzo[d]isoxazole, quinoxalinyl, quinolinyl and 2,3,4a, 8a-tetrahydrobenzo[b][1,4]dioxinyl, wherein the cyclic group of Rᴬ is optionally substituted with 1, 2 or 3 R⁴¹⁰;

each R⁴¹⁰ is independently selected from halo, alkoxyl, hydroxyl, —NH₂, —S(O)₂—NH₂, —S(O)₂CH₃, —N(H)—S(O)₂CH₃, —SO₂N(H)—CH₃, —CN, —C(O)OH, —(C₁-C₄)alkyl—OH, —OCF₃, —C(O)NH₂, and —(C₁-C₄)alkyl optionally substituted with 1-3 groups independently selected from —OH and halo;

Rᶜ is phenyl, —CH₂—phenyl, —(C₅-C₆)—cycloalkyl, —CH₂—phenyl, or pyridinyl, wherein the cyclic group of Rᶜ can be optionally substituted with 1, 2 or 3 Rᶜ¹⁰, wherein the 1, 2, or 3 Rᶜ¹⁰ groups are independently selected from Rᶜ¹⁰ᴬ and Rᶜ¹⁰ᴮ, provided that Rᶜ cannot be substituted with more than 1 Rᶜ¹⁰ᴮ group;

each Rᶜ¹⁰ᴬ is independently selected from halo and —(C₁-C₃)alkyl optionally substituted with 1-3 groups selected from —OH, methoxy, —CF₃ and halo;

Rᶜ¹⁰ᴮ is selected from —C(O)NH₂, (5-6 membered)heterocycloalkyl, —C(O)OH, or —N[—(C₁-C₄)alkyl]₂, —O—(C₁-C₄)alkyl optionally substituted with —OH, and —(C₁-C₄)alkyl substituted with —N[(C₁-C₄)alkyl]₂;

Rᴰ is -Lᴰ-Rᴰ¹;
Lᴰ is —Y—[C(R)₂]_q—;
q is 0 or 1;
each R is independently selected from H, —(C₁-C₃)alkyl (—CH₃), halo, —OH, and —CH₂OH;
Y is a bond, —S—, —S(O)₂—, —CH(OH)—, —O—, —C(H)=C(H)—, —C(O)—(C₁-C₄)alkyl-, —C₁-C₄)

alkyl—S—(C$_1$-C$_4$)alkyl-, —(C$_1$-C$_4$)alkyl—N(R$^Y$)—(C$_1$-C$_4$)alkyl-, —C(H)(halo)-, —(C$_1$-C$_4$)alkyl—S(O)$_2$—, —S(O)$_2$—N(R$^Y$)—, —(C$_1$-C$_4$)alkyl—O—, or —C(O)—N(R$^Y$)—, wherein R$^Y$ is H, —(C$_1$-C$_4$)alkyl, hydroxyl(C$_1$-C$_4$)alkyl or —C≡C—(C$_1$-C$_3$)alkyl-;

R$^{D1}$ is selected from —(C$_6$-C$_{10}$)aryl, —N(H)-phenyl, cycloalkyl, heterocycloalkyl, and heteroaryl, wherein R$^{D1}$ is substituted with 1-5 R$^{10}$ groups, wherein the 1-4 R$^{D10}$ groups are independently selected from A groups and B groups, provided that R$^{D1}$ is substituted with 1-2 B groups;

each A group, when they occur, is independently selected from halo, —CF$_3$, —CN, —NO$_2$, —OH, —O—(C$_1$-C$_4$)alkyl optionally substituted at the alkyl group with 1-3 substituents independently selected from —OH and halo, and —(C$_1$-C$_4$)alkyl optionally substituted with 1-3 substituents independently selected from —OH and halo;

each B group is selected from —(C$_1$-C$_4$)alkylN(R$^{D11}$)R$^{D11B}$, —C(O)—N(R$^{D11D}$)R$^{D11}$, —C(O)—(C$_1$-C$_4$)alkyl-Q$^A$, —C(O)O—(C$_1$-C$_4$)alkyl-Q$^A$, —C(O)—heterocycloalkyl—R$^{d11}$, —S(O)$_2$—(C$_1$-C$_4$)alkyl—N(R$^{D11B}$)R$^{D11}$, —S(O)$_2$—R$^{D11}$, —S(O)$_{2-N(R^{D11D})}$Q$^R$, —S(O)$_2$—N(H)C(O)—(C$_1$-C$_4$)alkyl-Q$^A$, —S(O)$_2$—N((R$^{D11D}$)C(O)O—(C$_1$-C$_4$)alkyl-Q$^A$, —S(O)$_2$—N(H)C(O)—N(H)R$^{D11}$, —S(O)$_2$—(C$_1$-C$_4$)alkyl-Q$^A$, —O—(C$_1$-C$_4$)alkyl-Q$^A$ optionally substituted at the alkyl group with 1 or 2 R$^{D11B}$, —C(O)—N(R$^{D11D}$)—(C$_1$-C$_6$)alkyl substituted at the alkyl group with 1 or 2 R$^{D11}$, heterocycloalkyl-Q$^A$ optionally substituted with oxo or R$^{D11D}$, —S(O)$_2$—N(R$^{D11D}$)R$^{D11}$, —S(O)$_2$—(4-6 membered)heterocycloalkyl—(C$_0$-C$_4$)alkyl-Q$^A$, wherein a carbon of the heterocycloalkyl group of —S(O)$_2$—(4-6 membered)heterocycloalkyl—(C$_0$-C$_4$)alkyl-Q$^A$ can be substituted with R$^{D11D}$, —N(RD11D)—C(O)—(C$_1$-C$_4$)alkyl substituted at the alkyl group with 1 or 2 R$^{D11}$, —N(H)—C(O)—N(R$^{D11D}$)—(C$_1$-C$_3$)alkyl substituted at the —C$_1$-C$_3$)alkyl group with R$^{D11}$, —(C$_1$-C$_6$)alkyl substituted with 1 or 2 R$^{D11}$, and —C≡C—(C$_0$-C$_3$)alkyl substituted with R$^{D11}$;

each R$^{D11}$ is independently selected from —(C$_3$-C$_6$)cycloalkyl-Q$^A$, —(C$_0$-C$_6$)alkyl—(5-6 membered) heterocycloalkyl-Q$^A$, —(C$_0$-C$_6$)alkyl-Q$^A$ optionally substituted with halo or —COOH, and a PEG polymer substituted with Q$^A$;

R$^{D11B}$ is selected from Q$^A$, H, —OH, —CF$_3$, —N(R$^{D11E}$)$_2$, —C(O)OH, —O—(C$_1$-C$_4$)alkyl, —S(O)$_2$OH, —C(=NH)—NH$_2$, —N(H)C(=NH)NH$_2$, —C(H)=NC(=NH)NH$_2$, —C(H)=NN(H)C(=NH)NH$_2$, 1,4-diazabicyclo[2.2.2]octanyl, —O—(C$_1$-C$_4$)alkyl—C(O)OH, —N(H)C(=NH)—N(H)C(=NH)NH$_2$, (5-6 membered)heteroaryl, —C(O)—(C$_1$-C$_3$)alkyl, —(C$_1$-C$_4$)alkyl optionally substituted with 1-3 groups independently selected from halo, —OH, —S(O)$_2$OH, C(O)OH, —NH$_2$, —N[(C$_1$-C$_3$)alkyl]$_3$$^+$, 1,4-diazabicyclo[2.2.2]octanyl, and —N(H)C(=NH)NH$_2$, —(C$_0$-C$_3$)alkyl—(5-8 membered)heterocycloalkyl optionally substituted at the heterocycloalkyl group with 1-3 R$^{D11}$, —(C$_0$-C$_3$)alkyl—(C$_3$-C$_6$)cycloalkyl optionally substituted with R$^{D"}$, and aryl optionally substituted with 1-3 halo;

R$^{D11D}$ is selected from H, —(C$_3$-C$_6$)cycloalkyl, —(C$_1$-C$_6$)alkyl optionally substituted with 1 or 2 substituents independently selected from —N[(C$_1$-C$_3$)alkyl]$_3$$^+$, —OH, gem-cyclopropyl, —C(O)OH, —C(O)O—(C$_1$-C$_3$)alkyl, and —C(O)NH$_2$, and —(C$_1$-C$_6$)alkyl-phenyl optionally substituted at the phenyl group with —(C$_1$-C$_3$)alkoxy, —C(O)OH, or —C(O)O—(C$_1$-C$_3$)alkyl;

Q$^A$ is Q$^L$ or Q$^R$;

Q$^L$ is —N[(C$_1$-C$_3$)alkyl]$_3$$^+$ wherein an alkyl group of —N[(C$_1$-C$_3$)alkyl]$_3$$^+$ is optionally substituted with —(C$_0$-C$_6$)alkyl—S(O)$_2$$_0$OH;

Q$^R$ is selected from:

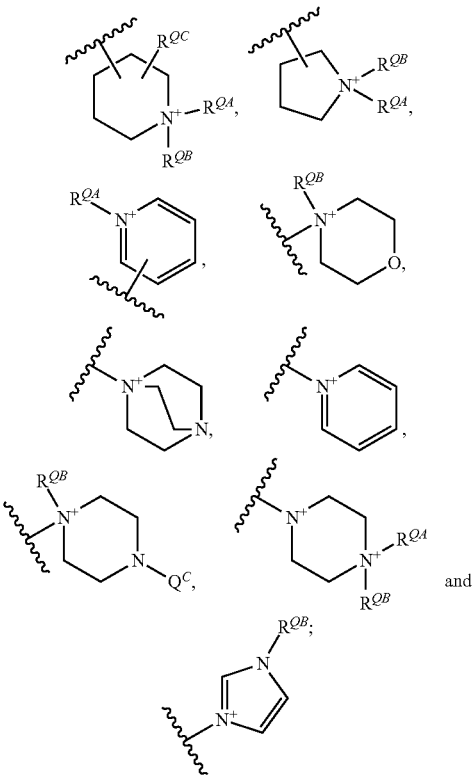

R$^{QA}$ is —(C$_1$-C$_6$)alkyl;
R$^{QB}$ is —(C$_1$-C$_6$)alkyl optionally substituted with —C(O)OH; and
R$^{QC}$ is H, —OH, —(C$_0$-C$_4$)alkyl—C(O)OH or —(C$_1$-C$_6$)alkyl.

3. The compound according to claim 1, or a pharmaceutically acceptable salt thereof, wherein:

X is =C(R$^4$)—;

each R is independently selected from H, —(C$_1$-C$_3$)alkyl, —OH, and —CH$_2$OH;

Y is —S—, —S(O)$_2$—, —C(H)=C(H)—, —C(O)—, —(C$_1$-C$_4$)alkyl—S—, —(C$_1$-C$_4$)alkyl—N(R$^Y$)—, —C(H)(halo)-, —(C$_1$-C$_4$)alkyl—S(O)$_2$—, —S(O)$_2$—N(R$^Y$)—, —(C$_1$-C$_4$)alkyl—O—, or —C(O)—N(R$^Y$)—, wherein R$^Y$ is H, —(C$_1$-C$_4$)alkyl or hydroxyl(C$_1$-C$_4$)alkyl;

R$^{D1}$ is selected from phenyl —(C$_6$-C$_{10}$)aryl, —N(H)—phenyl, —(C$_5$-C$_6$)cycloalkyl, heterocycloalkyl, or heteroaryl, wherein R$^{D1}$ is substituted with 1, 2, 3 or 4 R$^{10}$, wherein the 1-4 R$^{D10}$ groups are 0-3 A groups and 1 B group;

each A group, when they occur, is independently selected from halo, —CF$_3$, —CN, —NO$_2$, —OH, —O—(C$_1$-C$_4$)alkyl optionally substituted at the alkyl group with 1-3 substituents independently selected from —OH and halo, and —(C$_1$-C$_4$)alkyl optionally substituted with 1-3 substituents independently selected from —OH and halo;

each B group is selected from —($C_1$-$C_4$)alkylN($R^{D11}$)$R^{D11B}$, —C(O)—N($R^{D11D}$)$R^{D11}$, —C(O)—($C_1$-$C_4$)alkyl-$Q^A$, —C(O)O—($C_1$-$C_4$)alkyl-$Q^A$, —S(O)$_2$—($C_1$-$C_4$)alkyl—N($R^{D11B}$)$R^{D11}$, —S(O)$_2$—$R^D$, —S(O)$_2$—N($R^{D11D}$)$Q^R$, —C(O)—heterocycloalkyl—$R^D$, —S(O)$_2$—N(H)C(O)—($C_1$-$C_4$)alkyl-$Q^A$, —S(O)$_2$—N(($R^{D11B}$)C(O)O—($C_1$-$C_4$)alkyl-$Q^A$, —S(O)$_2$—N(H)C(O)—N(H)$R^{D11}$, —S(O)$_2$—($C_1$-$C_4$)alkyl-$Q^A$,—O—($C_1$-$C_4$)alkyl-$Q^A$ optionally substituted at the alkyl group with 1 or 2 $R^{D11B}$, —C(O)—N($R^{D11D}$)—($C_1$-$C_6$) alkyl substituted at the alkyl group with 1 or 2 $R^{D11}$, heterocyloalkyl—$Q^A$ optionally substituted with oxo or $R^{D11D}$, —S(O)$_2$—N($R^{D11D}$)$R^{D11}$, —S(O)$_2$—(4-6 membered)heterocycloalkyl—($C_0$-$C_4$)alkyl-$Q^A$, wherein a carbon of the heterocycloalkyl group of —S(O)$_2$—(4-6 membered)heterocycloalkyl—($C_0$-$C_4$)alkyl-$Q^A$ can be substituted with $R^{D11F}$, —N($R^{D11D}$)—C(O)—($C_1$-$C_4$)alkyl substituted at the alkyl group with 1 or 2 $R^{D11}$, —N(H)—C(O)—N($R^{D11D}$)—($C_1$-$C_3$)alkyl substituted at the —($C_1$-$C_3$)alkyl group with $R^{D11}$, —($C_1$-$C_6$)alkyl substituted with 1 or 2 $R^{D11}$, and —C≡C—($C_0$-$C_3$)alkyl substituted with $R^{D11}$;

each $R^{D11}$ is independently selected from —($C_3$-$C_6$)cycloalkyl—$Q^A$, —($C_0$-$C_6$)alkyl—(5-6 membered) heterocycloalkyl-$Q^A$, —($C_0$-$C_6$)alkyl—$Q^A$ optionally substituted with halo or —COOH, and a PEG polymer substituted with $Q^A$;

$R^{D11B}$ is selected from $Q^A$, H, —OH, —CF$_3$, —N($R^{D11E}$)$_2$, —C(O)OH, —O—($C_1$-$C_4$)alkyl, —S(O)$_2$OH, —C(=NH)—NH$_2$, —N(H)C(=NH)NH$_2$, —C(H)=NC(=NH)NH$_2$, —C(H)=NN(H)C(=NH)NH$_2$, 1,4-diazabicyclo[2.2.2]octanyl, —O—($C_1$-$C_4$)alkyl—C(O)OH, —N(H)C(=NH)—N(H)C(=NH)NH$_2$, —C(O)—($C_1$-$C_3$)alkyl, (5-6 membered)heteroaryl, —($C_1$-$C_4$)alkyl optionally substituted with 1-3 groups independently selected from halo, —OH, —S(O)$_2$OH, C(O)OH, —NH$_2$, —N[($C_1$-$C_3$)alkyl]$_3^+$, 1,4-diazabicyclo[2.2.2]octanyl, and —N(H)C(=NH)NH$_2$, —($C_0$-$C_3$)alkyl—(5-8 membered)heterocycloalkyl optionally substituted at the heterocycloalkyl group with 1 to 3 $R^{D11}$, —($C_0$-$C_3$)alkyl—($C_3$-$C_6$)cycloalkyl optionally substituted with $R^{D11}$, and aryl optionally substituted with 1-5 halo;

$R^{D11D}$ is selected from H, —($C_3$-$C_6$)cycloalkyl, —($C_1$-$C_6$) alkyl optionally substituted with 1 or 2 substituents selected from —OH, gem-cyclopropyl, —C(O)OH, —C(O)O—($C_1$-$C_3$)alkyl, and —C(O)NH$_2$, and —($C_1$-$C_6$)alkyl-phenyl optionally substituted at the phenyl group with —($C_1$-$C_3$)alkoxy, —C(O)OH, or —C(O)O—($C_1$-$C_3$)alkyl;

$R^{D11E}$ is H or —($C_1$-$C_3$)alkyl; and $R^{D11F}$ is H or —C(O)OH.

4. The compound according to claim 1, or a pharmaceutically acceptable salt thereof, wherein:

X is =C($R^4$)—;

Y is a bond, —S—, —S(O)$_2$—, —CH(CH$_3$)—S(O)$_2$—, —CH(CH$_3$)—S—, —CH(OH)—, —CH(CH$_3$)—O—, —C(O)—, —(CH$_2$)—S—, —CH$_2$—N($R^Y$)—, —CH(halo)—, —CH$_2$—S(O)$_2$—, —S(O)$_2$—N($R^Y$)—, —(CH$_2$)—O—, or —C(O)—N($R^Y$)—, wherein $R^1$(is H, —($C_1$-$C_3$)alkyl or hydroxyl($C_1$-$C_3$)alkyl;

each R is independently selected from H, —CH$_3$, —OH, F and —CH$_2$OH;

$R^{D1}$ is selected from phenyl, —N(H)—phenyl, —($C_3$-$C_6$) cycloalkyl, —(5-6 membered)heterocycloalkyl, —(5-6 membered)heteroaryl—(5-6 membered)heterocycloalkyl, —(5-6 membered)heteroaryl, wherein $R^{D1}$ is substituted with 1, 2, or 3 $R^{D10}$, wherein the 1-3 $R^{D10}$ groups are 0-2 A groups and 1 B group;

each A group, when they occur, is independently selected from halo, —CF$_3$, —CN, —NO$_2$, —OH, —O—($C_1$-$C_4$) alkyl optionally substituted with 1—3 substituents independently selected from —OH and halo, and —($C_1$-$C_4$) alkyl optionally substituted with 1—3 substituents independently selected from —OH and halo;

each B group is selected from —($C_1$-$C_4$)alkylN($R^{D11}$)$R^{D11B}$, —C(O)—N($R^{D11D}$)$R^{D11}$, —C(O)—($C_1$-$C_4$)alkyl-$Q^A$, —C(O)O—($C_1$-$C_4$)alkyl-$Q^A$, —C(O)—heterocycloalkyl—$R^{D11}$, —S(O)$_2$-($C_1$-$C_4$)alkyl—N($R^{D11B}$)$R^{D11}$, —S(O)$_2$—$R^{D11}$, —S(O)$_2$—N($R^{D11D}$)$Q^R$,—S(O)$_2$—N(H)C(O)—($C_1$-$C_4$)alkyl- $Q^A$, —S(O)$_2$—N(($R^{D11D}$)C(O)O—($C_1$-$C_4$)alkyl-$Q^A$, —S(O)$_2$—N(H)C(O)—N(H)$R^{D11}$, —S(O)$_2$—($C_1$-$C_4$)alkyl-$Q^A$, —C(O)—N($R^{D11D}$)—($C_1$-$C_6$)alkyl substituted at the alkyl group with 1 or 2 $R^{D11}$, heterocyloalkyl-$Q^A$ optionally substituted with oxo or $R^{D11D}$, —O—($C_1$-$C_4$)alkyl-$Q^A$ optionally substituted at the alkyl group with 1 or 2 $R^{D11B}$, —S(O)$_2$—N($R^{D11D)RD11}$, —S(O)$_2$—(4-6 membered)heterocycloalkyl—($C_0$-$C_4$)alkyl-$Q^A$, wherein a carbon of the heterocycloalkyl group of —S(O)$_2$—(4-6 membered)heterocycloalkyl—($C_0$ -$C_4$)alkyl-$Q^A$ can be substituted with $R^{D11F}$, —N($R^{D11D}$)—C(O)—($C_1$-$C_4$) alkyl substituted at the alkyl group with 1 or 2 $R^{D11}$, —N(H)—C(O)—N($R^{D11D}$)—($C_1$-$C_3$)alkyl substituted at the —($C_1$-$C_3$)alkyl group with $R^{D11}$, —($C_1$-$C_6$)alkyl substituted with 1 or 2 $R^{D11}$, and —C≡C—($C_0$-$C_3$) alkyl substituted with $R^{D11}$;

each $R^{D11}$ is independently selected from —($C_3$-$C_6$)cycloalkyl-$Q^A$, —($C_0$-$C_6$)alkyl—(5-6 membered) heterocycloalkyl-$Q^A$, —($C_0$-$C_6$)alkyl-$Q^A$ optionally substituted with halo or —COOH, and a PEG polymer substituted with $Q^A$;

$R^{D11B}$ is selected from H, —OH, —CF$_3$, —N($R^{D11E}$)$_2$, —C(O)OH, —O—($C_1$-$C_4$)alkyl, —S(O)$_2$OH, —C(O)—($C_1$-$C_3$)alkyl, —O—($C_1$-$C_4$)alkyl—C(O)OH, (5-6 membered)heteroaryl, —($C_1$-$C_4$)alkyl optionally substituted with 1-3 groups independently selected from halo, —OH, —S(O)$_2$OH, C(O)OH, —NH$_2$, —NR[($C_1$-$C_3$)alkyl]$_3^+$, 1,4-diazabicyclo[2.2.2]octanyl, and —N(H)C(=NH)NH$_2$, —($C_0$-$C_3$)alkyl—(5-8 membered)heterocycloalkyl optionally substituted at the heterocycloalkyl group with 1 to 3 $R^{D11}$, —($C_0$-$C_3$)alkyl—($C_3$-$C_6$)cycloalkyl optionally substituted with $R^{D11}$, and aryl optionally substituted with 1-3 halo;

$R^{D11D}$ is selected from H, —($C_3$-$C_6$)cycloalkyl, —($C_1$-$C_6$) alkyl optionally substituted with 1 or 2 substituents selected from —OH, gem-cylcopropyl, —C(O)OH, —C(O)O—($C_1$-$C_3$)alkyl, and —C(O)NH$_2$, and —($C_1$-$C_6$)alkyl-phenyl optionally substituted at the phenyl group with —($C_1$-$C_3$)alkoxy, —C(O)OH, or —C(O)O—($C_1$-$C_3$)alkyl;

$R^{D11E}$ is H or —($C_1$-$C_3$)alkyl; and $R^{D11F}$ is H or —C(O)OH.

5. The compound aaccording to claim 1, or a pharmaceutically acceptable salt thereof, wherein:

p is 0;

Y is a bond, —S—, —S(O)$_2$—, —CH(CH$_3$)—S(O)$_2$—, —CH(CH$_3$)—S—, —CH(OH)—, —CH(CH$_3$)—O—, —C(H)=C(H)—, —C(O)—, —(CH$_2$)—S—, —CH$_2$—N($R^Y$)—, —CH(halo)-, —CH$_2$—S(O)$_2$—, —S(O)$_2$—N($R^Y$)—, —(CH$_2$)—O—, or —C(O)—N($R^Y$)—, wherein $R^1$(is H, —($C_1$-$C_4$)alkyl or hydroxyl($C_1$-$C_4$)alkyl;

each R is independently selected from H, —($C_1$-$C_2$)alkyl, fluoro, —OH and —$CH_2$OH;

$R^{D1}$ is selected from phenyl, —N(H)-phenyl, cyclohexyl, cyclopentyl, piperidinyl, piperazinyl, pyrrolidinyl, morpholinyl, 1,2,3,6-tetrahydropyridine, heteroarylheterocycloalkyl, pyridinyl, oxazolyl, pyrazinyl, quinolinyl, 1,2,4-oxadiazolyl, 1,2,3,4-tetrahydroquinolinyl, and pyrazolyl, wherein $R^{D1}$ is substituted 1, 2 or 3 $R^{D10}$, wherein the 1-3 $R^{D10}$ groups are independently selected from A groups and B groups, provided that $R^{D1}$ is substituted with 1 B group;

each A group, when they occur is independently selected from halo, —$CF_3$, —CN, —$NO_2$, —OH, —O—($C_1$-$C_4$) alkyl optionally substituted with 1-3 substituents independently selected from —OH and halo, and —($C_1$-$C_4$) alkyl optionally substituted with 1-3 substituents independently selected from —OH and halo;

each B group is selected from —O—($C_1$-$C_4$)alkyl-$Q^L$, —S(O)$_2$—N($R^{D11D}$)$Q^R$, —C(O)—N($R^{D11D}$)$Q^R$, —S(O)$_2$—$R^{D11}$, —C(O)—($C_1$-$C_4$)alkyl-$Q^A$, —C(O)—heterocycloalkyl-$Q^L$, —S(O)$_2$—N($R^{D11D}$)—C($R^{D11F}$)—($C_1$-$C_5$)alkyl-$Q^A$, —C(O)—N($R^{D11E}$)—($C_1$-$C_6$)alkyl substituted at the alkyl group with $Q^A$, —S(O)$_2$—N($R^{D11D}$)$R^{D11}$, —S(O)$_2$—(4-6 membered)heterocycloalkyl—($C_0$-$C_4$)alkyl-$Q^L$, wherein a carbon of the heterocycloalkyl group of —S(O)$_2$—(4-6 membered)heterocycloalkyl—($C_0$-$C_4$)alkyl-$Q^L$ can be substituted with $R^{D11F}$, —N(H)—C(O)—N($R^{D11D}$)—($C_1$-$C_3$)alkyl substituted at the —($C_1$-$C_3$)alkyl group with $Q^L$, —($C_1$-$C_6$)alkyl substituted with $Q^A$, and —C≡C—($C_0$-$C_3$)alkyl substituted with $Q^A$;

$R^{D11D}$ is selected from H, —($C_3$-$C_6$)cycloalkyl, —($C_1$-$C_6$)alkyl optionally substituted with 1 or 2 substituents selected from —OH, gem-cyclopropyl, —C(O)OH, —C(O)O—($C_1$-$C_3$)alkyl, and —C(O)$NH_2$, and —($C_1$-$C_6$)alkyl-phenyl optionally substituted at the phenyl group with —($C_1$-$C_3$)alkoxy, —C(O)OH, or —C(O)O—($C_1$-$C_3$)alkyl;

$R^{D11E}$ is H or —($C_1$-$C_3$)alkyl; and $R^{D11F}$ is H or —C(O)OH.

6. The compound aaccording to claim 1, or a pharmaceutically acceptable salt thereof, wherein:

X is =C(H)—;

p is 0;

Y is a bond, —S—, —S(O)$_2$—, —CH($CH_3$)—S(O)$_2$—, —CH($CH_3$)—S—, —CH(OH)—, —CH($CH_3$)—O—, —C(H)=C(H)—, —C(O)—, —($CH_2$)—S—, —$CH_2$—N($R^Y$)—, —CH(halo)-, —$CH_2$—S(O)$_2$—, —S(O)$_2$—N($R^Y$)—, —($CH_2$)—O—, or —C(O)—N($R^Y$)—, wherein $R^Y$ is H, —($C_1$-$C_4$)alkyl or hydroxyl ($C_1$-$C_4$)alkyl;

each R is independently selected from H, —($C_1$-$C_2$)alkyl, fluoro, —OH and —$CH_2$OH;

$R^{D1}$ is selected from phenyl, —N(H)—phenyl, cyclohexyl, cyclopentyl, piperidinyl, piperazinyl, pyrrolidinyl, morpholinyl, 1,2,3,6-tetrahydropyridine, heteroarylheterocycloalkyl, pyridinyl, oxazolyl, pyrazinyl, quinolinyl, 1,2,4-oxadiazolyl, 1,2,3,4-tetrahydroquinolinyl, and pyrazolyl, wherein $R^{D1}$ is substituted with 1, 2 or 3 $R^{D10}$, wherein the 1-3 $R^{D10}$ groups are 0-2A groups and 1B group;

each A group, when they occur, is independently selected from halo, —$CF_3$, —CN, —$NO_2$, —OH, —O—($C_1$-$C_4$) alkyl optionally substituted with 1-3 substituents independently selected from —OH and halo, and —($C_1$-$C_4$) alkyl optionally substituted with 1-3 substituents independently selected from —OH and halo;

the B group is selected from —O—($C_1$-$C_4$)alkyl-$Q^L$, —C(O)—N($R^{D11D}$)$Q^R$, —C(O)—($C_1$-$C_4$)alkyl-$Q^A$, —C(O)—heterocycloalkyl-$Q^L$, —S(O)$_2$—N($R^{D11D}$)$Q^R$, —S(O)$_2$—$R^{D11}$, —S(O)$_2$—N($R^{D11D}$)—($C_1$-$C_6$)alkyl-$Q^A$, —S(O)$_2$—$R^{D11}$, —S(O)$_2$—N$R^{D11D}$—C($R^{D11F}$)—($C_1$-$C_5$)alkyl-$Q^A$, —C(O)—N($R^{D11E}$)—($C_1$-$C_6$)alkyl substituted at the alkyl group with $Q^A$, —S(O)$_2$—(4-6 membered)heterocycloalkyl—($C_0$-$C_4$)alkyl-$Q^L$, wherein a carbon of the heterocycloalkyl group of —S(O)$_2$—(4-6 membered)heterocycloalkyl—($C_0$-$C_4$)akyl-$Q^L$ can be substituted with $R^{D11F}$, —N(H)—C(O)—N($R^{D11D}$)—($C_1$-$C_3$)akyl substituted at the —($C_1$-$C_3$)alkyl group with $Q^L$, —($C_1$-$C_6$)alkyl substituted with $Q^A$, and —C≡C—($C_0$-$C_3$)alkyl substituted with $Q^A$;

$R^{D11D}$ is selected from H, —($C_1$-$C_6$)alkyl optionally substituted with 1 or 2substituents selected from —OH, gem-cyclopropyl, —C(O)OH, —C(O)O—($C_1$-$C_3$) alkyl, and —C(O)$NH_2$ and —($C_1$-$C_6$)alkyl-phenyl optionally substituted at the phenyl group with —($C_1$-$C_3$)alkoxy or —C(O)OH;

$R^{D11E}$ is H or —($C_1$-$C_3$)alkyl; and $R^{D11F}$ is H or —C(O)OH.

7. The compound according to claim 1, or a pharmaceutically acceptable salt thereof, wherein:

X is =C($R^4$)—;

p is 0;

Y is a bond, —S—, —S(O)$_2$—, —CH($CH_3$)—S(O)$_2$—, —CH($CH_3$)—S—, —CH(OH)—, —CH($CH_3$)—O—, —C(H)=C(H)—, —C(O)—, —($CH_2$)—S—, —$CH_2$—N($R^Y$)—, —CH(halo)-, —$CH_2$—S(O)$_2$—, —S(O)$_2$—N($R^Y$)—, —($CH_2$)—O—, or —C(O)—N($R^Y$)—, wherein $R^Y$ is H, —($C_1$-$C_4$)alkyl or hydroxyl ($C_1$-$C_4$)alkyl;

each R is independently selected from H, —($C_1$-$C_2$)alkyl, fluoro, —OH and —$CH_2$OH;

$R^{D1}$ is selected from phenyl, —N(H)-phenyl, cyclohexyl, cyclopentyl, piperidinyl, piperazinyl, pyrrolidinyl, morpholinyl, 1,2,3,6-tetrahydropyridine, heteroarylheterocycloalkyl, pyridinyl, oxazolyl, pyrazinyl, quinolinyl, 1,2,4-oxadiazolyl, 1,2,3,4-tetrahydroquinolinyl, and pyrazolyl, wherein $R^{D1}$ is substituted with 1, 2 or 3 $R^{D10}$, wherein the 1-3 $R^{D10}$ groups are 0-2 A groups and 1 B group;

each A group, when they occur, is independently selected from halo, —$CF_3$, —CN, —$NO_2$, —OH, —O—($C_1$-$C_4$) alkyl optionally substituted with 1-3 substituents independently selected from —OH and halo, and —($C_1$-$C_4$) alkyl optionally substituted with 1-3 substituents independently selected from —OH and halo;

the B group is selected from —O—($C_1$-$C_4$)alkyl-$Q^L$, —C(O)—N($R^{D11D}$)$Q^R$, —C(O)—($C_1$-$C_4$)alkyl-$Q^A$, —C(O)—heterocycloalkyl-$Q^L$, —S(O)$_2$—$R^{D11}$, —C(O)—N($R^{D11E}$)—($C_1$-$C_6$)alkyl substituted at the alkyl group with $Q^A$, —S(O)$_2$—N($R^{D11D}$)$Q^R$, —S(O)$_2$—N($R^{D11D}$)—($C_1$-$C_6$)alkyl-$Q^A$, —S(O)$_2$—N($R^{D11E}$)—C($R^{D11F}$)—($C_1$-$C_5$)alkyl-$Q^A$, —S(O)$_2$—(4-6 membered)heterocycloalkyl—($C_0$-$C_4$)alkyl-$Q^L$, wherein a carbon of the heterocycloalkyl group of —S(O)$_2$—(4-6 membered)heterocycloalkyl—($C_0$-$C_4$) alkyl-$Q^L$ can be substituted with $R^{D11F}$, —N(H)—C(O)—N($R^{D11D}$)—($C_1$-$C_3$)alkyl substituted at the —($C_1$-$C_3$)alkyl group with $Q^L$, —($C_1$-$C_6$)alkyl substituted with $Q^A$, and —C≡C—($C_0$-$C_3$)alkyl substituted with $Q^A$;

$R^{D11D}$ is selected from H, —($C_1$-$C_6$)alkyl optionally substituted with 1 or 2 substituents selected from —OH, gem-cyclopropyl, —C(O)OH, —C(O)O—($C_1$-$C_3$)

alkyl, and —C(O)NH$_2$, and —(C$_1$-C$_6$)alkyl-phenyl optionally substituted at the phenyl group with —(C$_1$-C$_3$)alkoxy or —C(O)OH;
R$^{D11E}$ is H or —(C$_1$-C$_2$)alkyl; and
R$^{D11F}$ is —C(O)OH.

8. The compound aaccording to claim 1, or a pharmaceutically acceptable salt thereof, wherein L$^D$ is selected from: —(CH$_2$)$_{1-3}$—O—, —(CH$_2$)$_{1-3}$—NR$^Y$—, —(C$_0$-C$_3$)alkyl—S—(C$_0$-C$_3$)alkyl-; —(CH$_2$)$_{1-3}$—S—, —S—(CH$_2$)$_{1-3}$, —S(O)$_2$—(CH$_2$)$_{1-3}$—, —S(O)$_2$—C(O)N(H)—(CH$_2$)$_{1-3}$—, —S(O)$_2$—N(H)—(CH$_2$)$_{1-3}$—, —C(O)—(CH$_2$)$_{1-2}$—, —C≡C—(C$_0$-C$_3$)alkyl-, a bond, and —(C$_1$-C$_4$)alkyl-optionally substituted with halo or —OH.

9. The compound according to claim 1, or a pharmaceutically acceptable salt thereof, wherein: L$^D$ is selected from —(CH$_2$)—O—, —(CH$_2$)—NR$^Y$—, —(CH$_2$)—S—, —S—(CH$_2$)—, —S(O)$_2$—, —S(O)$_2$—(CH$_2$)—, —C(O)N(R$^Y$)—(C$_0$-C$_3$)alkyl-, —S(O)$_2$—N(H)—(CH$_2$)$_{1-3}$—, —C(O)—(CH$_2$)$_{1-2}$—, —C≡C—(C$_2$-C$_3$)alkyl-, and —(C$_1$-C$_4$)alkyl-optionally substituted with halo or —OH.

10. The compound aaccording to claim 1, or a pharmaceutically acceptable salt thereof, wherein: L$^D$ is selected from —(CH$_2$)—O—, —(CH$_2$)—NH—, —(CH$_2$)—S—, —S—(CH$_2$)—, —S(O)$_2$—, —S(O)$_2$—(CH$_2$)—, —C(O)N(H)—(CH$_2$)$_{1-3}$—, —S(O)$_2$—N(H)—(CH$_2$)$_{1-3}$—, —C(O)—(CH$_2$)$_{1-2}$—, —C≡C—(C$_2$-C$_3$)alkyl- and —(C$_1$-C$_4$)alkyl-optionally substituted with halo or —OH.

11. The compound according to claim 1, or a pharmaceutically acceptable salt thereof, wherein the B group of R$^{D1}$ is selected from:

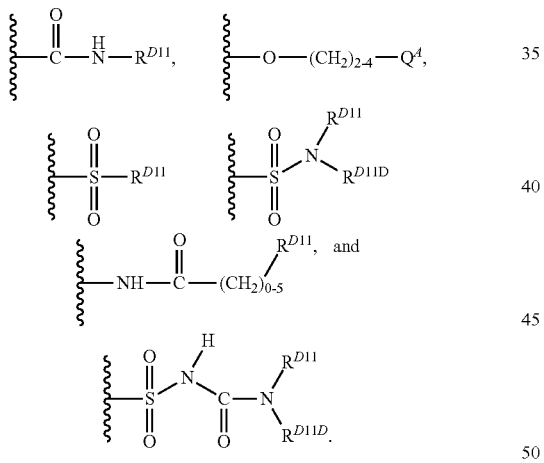

12. The compound according to claim 1, or a pharmaceutically acceptable salt thereof, wherein:
R$^C$ is phenyl, —CH$_2$-phenyl, —(C$_5$-C$_6$)-cycloalkyl, or pyridinyl, wherein the cyclic group of R$^C$ can be optionally substituted with one, two, or three R$^{C10}$ groups and, wherein the one, two, or three R$^{C10}$ groups are independently selected from R$^{C10A}$ and R$^{C10B}$, provided that R$^C$ cannot be substituted with more than 1 R$^{C10B}$ group;
each R$^{C10A}$, when they occur, is independently selected from methoxy, —CF$_3$, halo, and —(C$_1$-C$_3$)alkyl optionally substituted with 1-3 groups selected from halo and —OH; and
R$^{C10B}$ is selected from (5-6 membered)heterocycloalkyl, —(C$_1$-C$_4$)alkyl substituted with —N[—(C$_1$-C$_4$)alkyl]$_2$, —C(O)NH$_2$, and —O—(C$_1$-C$_4$)alkyl optionally substituted with —OH, —C(O)OH, or —N[—(C$_1$-C$_4$)alkyl]$_2$.

13. The compound according to claim 1, or a pharmaceutically acceptable salt thereof, wherein R$^C$ is phenyl or pyridinyl, wherein the cyclic group of R$^C$ can be optionally substituted with 1, 2 or 3 R$^{C10}$, wherein the 1, 2 or 3 R$^{C10}$ groups are independently selected from R$^{C10A}$ and R$^{C10B}$, provided that R$^C$ cannot be substituted with more than 1 R$^{C10B}$ group;
each R$^{C10A}$, when they occur, is independently selected from methoxy and halo; and
R$^{C10B}$ is selected from —C(O)NH$_2$, (5-6 membered)heterocycloalkyl, —(C$_1$-C$_4$)alkyl substituted with —N[—(C$_1$-C$_4$)alkyl]$_2$, and —O—(C$_1$-C$_4$)alkyl optionally substituted with —OH, —C(O)OH, or —N[—(C$_1$-C$_4$)alkyl]$_2$.

14. The compound according to claim 1, or a pharmaceutically acceptable salt thereof, wherein R$^C$ is phenyl or pyridinyl, wherein the cyclic group of R$^C$ can be optionally substituted 1 or 2 groups selected from methoxy, methyl, fluoro and chloro.

15. The compound according to claim 1, or a pharmaceutically acceptable salt thereof, wherein R$^C$ is phenyl substituted with one or two groups selected from methoxy, fluoro or chloro.

16. The compound according to claim 1, or a pharmaceutically acceptable salt thereof, having formula IX, X, XI, XII, XIII, XIV or XV:

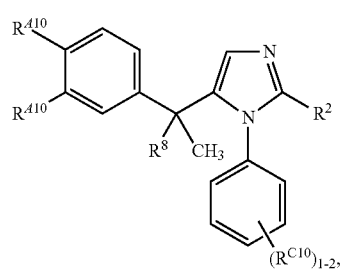

IX

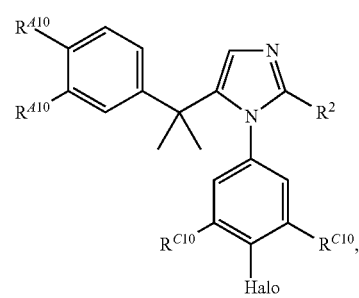

X

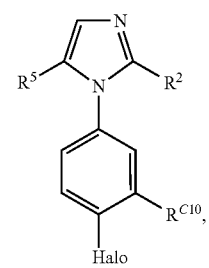

XI

XII

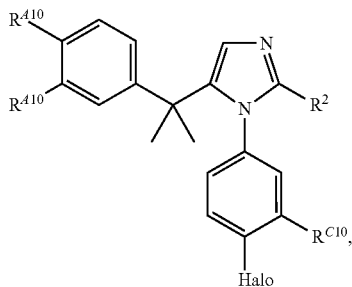

XIII

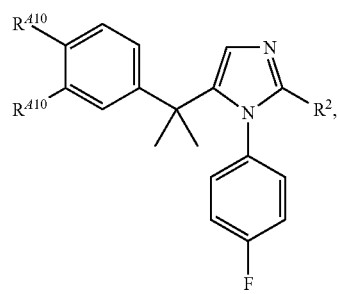

XIV

XV

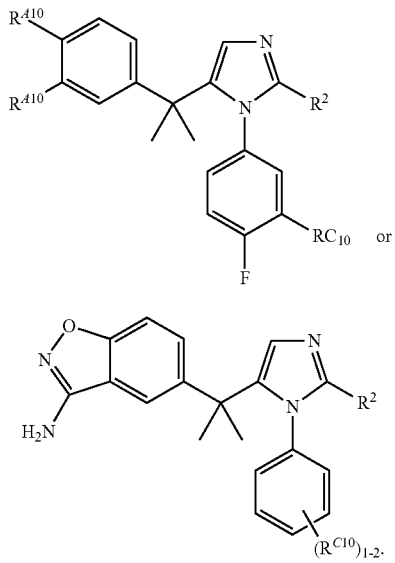

17. The compound according to claim 16, or a pharmaceutically acceptable salt thereof, wherein each $R^{A10}$ is selected from fluoro, chloro and methoxy;
each $R^{C10}$ is selected from fluoro, chloro and methoxy;
$R^2$ is $-L^D-R^{D1}$ wherein:
$L^D$ is selected from $-(CH_2)-O-$, $-(CH_2)-NH-$, $-(CH_2)-S-$, $-S-(CH_2)-$, $-S(O)_2-$, $-S(O)_2-(CH_2)-$, $-C(O)N(H)-(CH_2)_{1-3}-$, $-S(O)_2-N(H)-(CH_2)_{1-3}-$, $-C(O)-(CH_2)_{1-2}-$, $-(C_1-C_3)$ alkyl- optionally substituted with halo or $-OH$, and $-C\equiv C-(C_2-C_3)$alkyl; and $R^{D1}$ is one of:

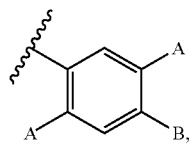 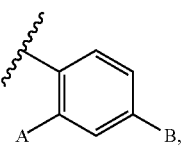

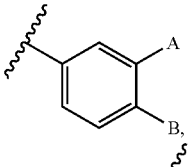

,,

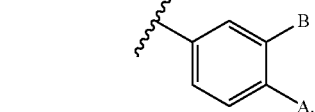 or

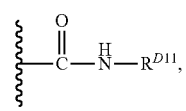

wherein each A is chloro or fluoro, and B is selected from:

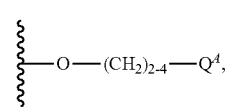

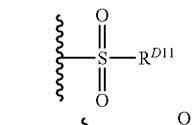 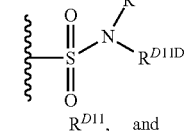

, and

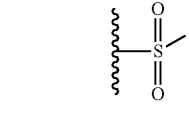 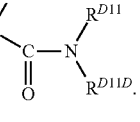

18. The compound according to claim 1, or a pharmaceutically acceptable salt thereof, wherein $L^D$ is selected from $-S-(C_1-C_3)$alkyl-, $-(CH_2)_2-$and $-(C_1-C_3)$alkyl$-O-$.

19. The compound according to claim 1, or a pharmaceutically acceptable salt thereof, wherein $R^5$ is $-[C(CH_3)_2]-$phenyl, and the phenyl group of $R^5$ is optionally substituted with one, two, or three $R^{A10}$ groups, wherein the one, two, or three $R^{A10}$ groups are independently selected from $R^{A10A}$ and $R^{A10B}$, provided that $R^5$ cannot be substituted with more than 1 $R^{A10B}$ group;

each $R^{A10A}$, when they occur, is independently selected from halo, methoxy and hydroxyl; and $R^{A10B}$ is $-O-(C_1-C_4)$alkyl$-C(O)OH$, $O-(C_1-C_4)$alkyl$-N[(C_{1-C3})$alkyl$]_2$, $-NH_2$, $-S(O)_2-NH_2$, $-SO_2CH_3$, $-N(H)-SO_2CH_3$, $-SO_2N(H)-CH_3$, $-CN$, $-C(O)OH$, $-(C_1-C_4)$alkyl$-OH$, $-OCF_3$, $-C(O)NH_2$ or $-(C_1-C_4)$alkyl optionally substituted with 1-3 groups selected from $-OH$ and halo.

20. The compound according to claim 1, or a pharmaceutically acceptable salt thereof, wherein $R^5$ is $-[C(CH_3)_2]-$ phenyl, wherein the phenyl group is optionally substituted with one or two groups selected from halo and methoxy.

21. The compound according to claim 1, or a pharmaceutically acceptable salt thereof, wherein $R^5$ is:

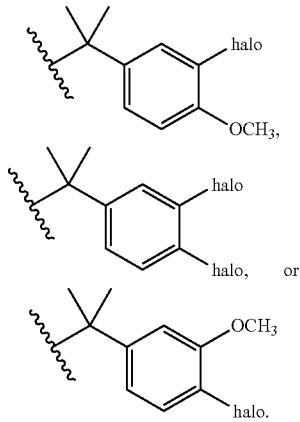

22. A compound selected from one of the following compounds, or a pharmaceutically acceptable salt thereof:

2-({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]carbonyl}amino)-N,N,N-trimethylethanaminium;

2-{[(4-{[(5-{1-[4-(aminosulfonyl)-3-chlorophenyl]-1-methylethyl}-1-[4-fluoro-3-(methyloxy)phenyl]-1H-imidazol-2-yl)thio]methyl}-3-chloro-5-fluorophenyl)carbonyl]amino}-N,N,N-trimethylethanaminium;

2-[({4-[({5-[1-(3-amino-1,2-benzisoxazol-5-yl)-1-methylethyl]-1-[4-fluoro-3-(methyloxy)phenyl]-1H-imidazol-2-yl}thio)methyl]-3-chloro-5-fluorophenyl}carbonyl)amino]-N,N,N-trimethylethanaminium;

2-[({4-[({5-[1-(3-amino-1,2-benzisoxazol-5-yl)-1-methylethyl]-1-(4-fluorophenyl)-1H-imidazol-2-yl}thio)methyl]-3-chloro-5-fluorophenyl}carbonyl)amino]-N,N,N-trimethylethanaminium;

2-({[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]carbonyl}amino)-N,N,N-trimethylethanaminium;

2-({[3-chloro-4-({[5-{1-[4-chloro-3-(methyloxy)phenyl]-1-methylethyl}-1-(4-fluorophenyl)-1H-imidazol-2-yl]methyl}oxy)-5-fluorophenyl]carbonyl}amino)-N,N,N-trimethylethanaminium;

2-{[(3-chloro-4-{2-[5-{1-[4-chloro-3-(methyloxy)phenyl]-1-methylethyl}-1-4-fluorophenyl)-1H-imidazol-2-yl]ethyl}-5-fluorophenyl)carbonyl]amino]-N,N,N-trimethylethanaminium;

1-[2-({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]carbonyl}amino)ethyl]-4-aza-1-azoniabicyclo[2.2.2]octane;

1-[2-({[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]carbonyl}amino)ethyl]-4-aza-1-azoniabicyclo[2.2.2]octane;

1-{2-[({3-chloro-4-[({5-[1-(3,4-dichlorophenyl)-1-methylethyl]-1-[4-fluoro-3-(methyloxy)phenyl]-1H-imidazol-2-yl}thio)methyl]-5-fluorophenyl}carbonyl)amino]ethyl}-4-aza-1-azoniabicyclo[2.2.2]octane;

4-({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]carbonyl}amino)-1,1-dimethylpiperidinium;

(3S)-3-({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]carbonyl}amino)-1,1-dimethylpiperidinium;

(3S)-3-({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]carbonyl}amino)-1-[(4-fluorophenyl)methyl]-1-methylpyrrolidinium;

(3S)-3-({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]carbonyl}amino)-1,1-dimethylpyrrolidinium;

(3R)-3-({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]carbonyl}amino)-1,1-dimethylpiperidinium;

(3R)-3-({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]carbonyl}amino)-1,1-dimethylpyrrolidinium;

1-[2-({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]carbonyl}amino)ethyl]-1,4,4-trimethylpiperazinediium;

4-[2-({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]carbonyl}amino)ethyl]-4-methylmorpholin-4-ium;

(3S)-3-[({4-[({5-[1-(3-amino-1,2-benzisoxazol-5-yl)-1-methylethyl]-1-[4-fluoro-3-(methyloxy)phenyl]-1H-imidazol-2-yl}thio)methyl]-3,5-difluorophenyl}carbonyl)amino]-1,1-dimethylpyrrolidinium;

1-{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]carbonyl}-N,N,N-trimethylpiperidin-4-aminium;

4-[({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]carbonyl}amino)methyl]-4-hydroxy-1,1-dimethylpiperidinium;

2-[({3-chloro-4-[({5-[1-(3,4-dichlorophenyl)-1-methylethyl]-1-[4-fluoro-3-(methyloxy)phenyl]-1H-imidazol-2-yl}thio)methyl]-5-fluorophenyl}carbonyl)amino]-N,N,N-trimethylethanaminium;

(3S)-3-[({3-chloro-4-[({5-[1-(3,4-dichlorophenyl)-1-methylethyl]-1-[4-fluoro-3-(methyloxy)phenyl]-1H-imidazol-2-yl}thio)methyl]-5-fluorophenyl}carbonyl)amino]-1,1-dimethylpiperidinium;

(3S)-3-({[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]carbonyl}amino)-1,1-dimethylpiperidinium;

(3S)-3-({[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]carbonyl}amino)-1,1-dimethylpyrrolidinium;

(3S)-3-[({3-chloro-4-[({5-[1-(3,4-dichlorophenyl)-1-methylethyl]-1-[4-fluoro-3-(methyloxy)phenyl]-1H-imidazol-2-yl}thio)methyl]-5-fluorophenyl}carbonyl)amino]-1,1-dimethylpyrrolidinium;

1-(carboxymethyl)-4-({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]carbonyl}amino)-1-methylpiperidinium;

N-[2-({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]carbonyl}amino)ethyl]-N,N-dimethyl-3-sulfopropan-1-aminium;

2-[({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]amino}carbonyl)amino]-N,N,N-trimethylethanaminium;

-3-({[4-({[5-{1-[4-chloro-3-(methyloxy)phenyl]-1-methylethyl}-1-4-fluorophenyl)-1H-imidazol-2-yl]thio}methyl)-3,5-difluorophenyl]sulfonyl}amino)-N,N,N-trimethylpropan-1-aminium;

-3-({[3-chloro-5-fluoro-4-({[5-{1-[4-fluoro-3-(methyloxy)phenyl]-1-methylethyl}-1-4-fluorophenyl)-1H-imidazol-2-yl]thio}methyl)phenyl]sulfonyl}amino)-N,N,N-trimethylpropan-1-aminium;

3-{[(4-{[(5-{1-[4-(aminosulfonyl)-3-chlorophenyl]-1-methylethyl}-1-[4-fluoro-3-(methyloxy)phenyl]-1H-imidazol-2-yl]thio]methyl}-3,5-difluorophenyl)sulfonyl]amino}-N,N,N-trimethylpropan-1-aminium;

-3-({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}amino)-N,N,N-triethylpropan-1-aminium;

3-({[4-({[5-{1-[4-chloro-3-(methyloxy)phenyl]-1-methylethyl}-4-(4-fluorophenyl)-4H-1,2,4-triazol-3-yl]thio}methyl)-3,5-difluorophenyl]sulfonyl}amino)-N,N,N-trimethylpropan-1-aminium;

3-[({4-[({5-[1-(3,4-dichlorophenyl)-1-methylethyl]-1-[4-fluoro-3-(methyloxy)phenyl]-1H-imidazol-2-yl}thio)methyl]-3,5-difluorophenyl}sulfonyl)amino]-N,N,N-trimethylpropan-1-aminium;

-3-({[3,5-difluoro-4-({[5-{1-[4-fluoro-3-(methyloxy)phenyl]-1-methylethyl}-1-(4-fluorophenyl)-1H-imidazol-2-yl]thio}methyl)phenyl]sulfonyl}amino)-N,N,N-trimethylpropan-1-aminium;

3-{[(4-{[(5-{1-[4-chloro-3-(methyloxy)phenyl]-1-methylethyl}-1-{4-fluoro-3-[(methyloxy)carbonyl]phenyl}-1H-imidazol-2-yl)thio]methyl}-3,5-difluorophenyl)sulfonyl]amino}-N,N,N-trimethylpropan-1-aminium;

3-[({4-[({5-[1-(3-chloro-4-fluorophenyl)-1-methylethyl]-1-[4-fluoro-3-(methyloxy)phenyl]-1H-imidazol-2-yl}thio)methyl]-3,5-difluorophenyl}sulfonyl)amino]-N,N,N-trimethylpropan-1-aminium;

3,3'-({[4-({[5-{1-[4-chloro-3-(methyloxy)phenyl]-1-methylethyl}-1-4-fluorophenyl)-1H-imidazol-2-yl]thio}methyl)-3,5-difluorophenyl]sulfonyl}imino)bis(N,N,N-trimethylpropan-1-aminium);

-3-({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}amino)-N,N,N-trimethylpropan-1-aminium;

2-({[4-({[5-{1-[4-chloro-3-(methyloxy)phenyl]-1-methylethyl}-1-4-fluorophenyl)-1H-imidazol-2-yl]thio}methyl)-3,5-difluorophenyl]sulfonyl}amino)-N,N,N-trimethylethanaminium;

-3-({[2-chloro-5-({[5-{1-[4-chloro-3-(methyloxy)phenyl]-1-methylethyl}-1-(4-fluorophenyl)-1H-imidazol-2-yl]thio}methyl)phenyl]sulfonyl}amino)-N,N,N-trimethylpropan-1-aminium;

3-({[4-({[5-{1-[4-chloro-3-(methyloxy)phenyl]-1-methylethyl}-1-4-fluorophenyl)-1H-imidazol-2-yl]thio}methyl)-3,5-difluorophenyl]sulfonyl}amino)-N,N,N-triethylpropan-1-aminium;

3-({[4-({[5-{1-[3-chloro-4-(methyloxy)phenyl]-1-methylethyl}-1-(4-fluorophenyl)-1H-imidazol-2-yl]thio}methyl)-3,5-difluorophenyl]sulfonyl}amino)-N,N,N-trimethylpropan-1-aminium;

3-({[3-chloro-5-fluoro-4-({[5-1-[4-fluoro-3-(methyloxy)phenyl]-1-methylethyl]-1-4-fluorophenyl)-1H-imidazol-2-yl]thio}methyl)phenyl]sulfonyl}amino)-N,N,N-triethylpropan-1-aminium;

3,3'-({[4-chloro-5-({[5-{1-[4-chloro-3-(methyloxy)phenyl]-1-methylethyl}-1-(4-fluorophenyl)-1H-imidazol-2-yl]thio}methyl)-2-fluorophenyl]sulfonyl}imino)bis(N,N,N-trimethylpropan-1-aminium);

3-({[2-chloro-5-({[5-{1-[4-chloro-3-(methyloxy)phenyl]-1-methylethyl}-1-(4-fluorophenyl)-1H-imidazol-2-yl]thio}methyl)-4-fluorophenyl]sulfonyl}amino)-N,N,N-trimethylpropan-1-aminium;

4-({[4-({[5-{1-[4-chloro-3-(methyloxy)phenyl]-1-methylethyl}-1-4-fluorophenyl)-1H-imidazol-2-yl]thio}methyl)-3,5-difluorophenyl]sulfonyl}amino)-N,N,N-trimethylbutan-1-aminium;

3-({[4-chloro-5-({[5-{1-[4-chloro-3-(methyloxy)phenyl]-1-methylethyl}-1-(4-fluorophenyl)-1H-imidazol-2-yl]thio}methyl)-2-fluorophenyl]sulfonyl}amino)-N,N,N-trimethylpropan-1-aminium;

3-({[-3-({[5-{1-[4-chloro-3-(methyloxy)phenyl]-1-methylethyl}-1-4-fluorophenyl)-1H-imidazol-2-yl]thio}methyl)-2,4-difluorophenyl]sulfonyl}amino)-N,N,N-trimethylpropan-1-aminium;

3-{[({4-({[5-{1-[4-chloro-3-(methyloxy)phenyl]-1-methylethyl}-1-4-fluorophenyl)-1H-imidazol-2-yl]thio}methyl)-3,5-difluorophenyl]sulfonyl}amino)carbonyl]amino}-N,N,N-triethylpropan-1-aminium;

1-[-3-({[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]sulfonyl}amino)propyl]pyridinium;

3-[-3-({[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]sulfonyl}amino)propyl]-1-methyl-1H-imidazol-3-ium;

3-(2(3-chloro-5-fluoro-4-((5-(2-(4-fluoro-3-methoxyphenyl)propan-2-yl)-1-(4-fluorophenyl)-1H-imidazol-2-ylthio)methyl)phenylsulfonamido)ethyl)-1-methylpyridinium;

(3S)-3-({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}amino)-1,1-dimethylpiperidinium;

4-({[4-({[5-{1-[4-chloro-3-(methyloxy)phenyl]-1-methylethyl}-1-4-fluorophenyl)-1H-imidazol-2-yl]thio}methyl)-3,5-difluorophenyl]sulfonyl}amino)-1,1-dimethylpiperidinium;

1-{[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}-N,N,N-trimethylpiperidin-4-aminium;

(3R)-3-({[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}amino)-1,1-dimethylpiperidinium;

(3S)-3-({[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}amino)-1,1-dimethylpiperidinium;

1-{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}-N,N,N-trimethylpiperidin-4-aminium;

(3R)-1-{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}-N,N,N-trimethylpiperidin-3-aminium;

(3S)-1-{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}-N,N,N-trimethylpiperidin-3-aminium;

(3R)-1-{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}-N,N,N-trimethylpyrrolidin-3-aminium;

1-{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}-N-ethyl-N,N-dimethylpiperidin-4-aminium;

4-{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}-1,1-dimethylpiperazin-1-ium;

(3S)-1-{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}-N,N,N-trimethylpyrrolidin-3-aminium;

3-[{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}(methyl)amino]-N-ethyl-N,N-dimethylpropan-1-aminium;

1-{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}-N,N,N-trimethylazetidin-3-aminium;

1-{[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]sulfonyl}-N,N,N-trimethylpiperidin-4-aminium;

(3R)-1-{[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]sulfonyl}-N,N,N-trimethylpiperidin-3-aminium;

1-{[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]sulfonyl}-N-ethyl-N,N-dimethylpiperidin-4-aminium;

(1-{[3-chloro-4-({[5-{1-[4chloro-3-(methyloxy)phenyl]-1-methylethyl}-1-(4-fluorophenyl)-1H-imidazol-2-yl]thio}methyl)-5-fluorophenyl]sulfonyl}azetidin-3-yl)-N,N,N-trimethylmethanaminium;

4-[({[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]sulfonyl}amino)methyl]-1,1-dimethylpiperidinium;

2-({[3-chloro-5-fluoro-4-({[5-{1-[4-fluoro-3-(methyloxy)phenyl]-1-methylethyl}-1-4-fluorophenyl)-1H-imidazol-2-yl]thio}methyl)phenyl]sulfonyl}amino)-1-methylpyridinium;

[(3S)-1-{[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]sulfonyl}piperidin-3-yl]-N,N,N-trimethylmethanaminium;

[(3S)-1-{[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]sulfonyl}pyrrolidin-3-yl]-N,N,N-trimethylmethanaminium;

[(3R)-1-{[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]sulfonyl}piperidin-3-yl]-N,N,N-trimethylmethanaminium;

3-[(carboxymethyl){[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}amino]-N,N,N-trimethylpropan-1-aminium;

3-[{[4-({[5-{1-[4-chloro-3-(methyloxy)phenyl]-1-methylethyl}-1-4-fluorophenyl)-1H-imidazol-2-yl]thio}methyl)-3,5-difluorophenyl]sulfonyl}(methyl)amino]-N,N,N-trimethylpropan-1-aminium;

3-[{[4-({[5-{1-[4-chloro-3-(methyloxy)phenyl]-1-methylethyl}-1-4-fluorophenyl)-1H-imidazol-2-yl]thio}methyl)-3,5-difluorophenyl]sulfonyl}(ethyl)amino]-N,N,N-trimethylpropan-1-aminium;

3-[{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}(methyl)amino]-N,N,N-trimethylpropan-1-aminium;

3-[{[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]sulfonyl}(methyl)amino]-N,N,N-trimethylpropan-1-aminium;

3-[{[3-chloro-4-({[5-{1-[4-chloro-3-(methyloxy)phenyl]-1-methylethyl}-1-(4-fluorophenyl)-1H-imidazol-2-yl]methyl}oxy)-5-fluorophenyl]sulfonyl}(methyl)amino]-N,N,N-trimethylpropan-1-aminium;

3-[{[4-({[5-{1-[4-chloro-3-(methyloxy)phenyl]-1-methylethyl}-1-4-fluorophenyl)-1H-imidazol-2-yl]thio}methyl)-3,5-difluorophenyl]sulfonyl}(2-hydroxyethyl)amino]-N,N,N-trimethylpropan-1-aminium;

3-[{[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}(3-hydroxypropyl)amino]-N,N,N-trimethylpropan-1-aminium;

3-[(2-amino-2-oxoethyl){[4-({[5-{1-[4-chloro-3-(methyloxy)phenyl]-1-methylethyl}-1-4-fluorophenyl)-1H-imidazol-2-yl]thio}methyl)-3,5-difluorophenyl]sulfonyl}amino]-N,N,N-trimethylpropan-1-aminium;

3-([(4-carboxyphenyl)methyl]{[4-({[5-{1-[4-chloro-3-(methyloxy)phenyl]-1-methylethyl}-1-4-fluorophenyl)-1H-imidazol-2-yl]thio}methyl)-3,5-difluorophenyl]sulfonyl}amino)-N,N,N-trimethylpropan-1-aminium;

3-[({4-[({5-[1-(4-chloro-3-hydroxyphenyl)-1-methylethyl]-1-(4-fluorophenyl) 1H-imidazol-2-yl}thio)methyl]-3,5-difluorophenyl}sulfonyl)amino]-N,N,N-trimethylpropan-1-aminium;

3-({[4-({[5-{1-[4-chloro-3-(methyloxy)phenyl]-1-methylethyl}-1-4-fluorophenyl)-1H-imidazol-2-yl]thio}methyl)-3,5-difluorophenyl]sulfonyl}[(1R)-1-methyl-2-(methyloxy)-2-oxoethyl]amino)-N,N,N-trimethylpropan-1-aminium;

3-([(1R)-1-carboxyethyl]{[4-({[5-{1-[4-chloro-3-(methyloxy)phenyl]-1-methylethyl}-1-4-fluorophenyl)-1H-imidazol-2-yl]thio}methyl)-3,5-difluorophenyl]sulfonyl}amino)-N,N,N-trimethylpropan-1-aminium;

3-([(1S)-1-carboxyethyl]{[4-({[5-{1-[4-chloro-3-(methyloxy)phenyl]-1-methylethyl}-1-4-fluorophenyl)-1H-imidazol-2-yl]thio}methyl)-3,5-difluorophenyl]sulfonyl}amino)-N,N,N-trimethylpropan-1-aminium;

3-([(1R)-1-carboxyethyl]{[3-chloro-4-({[5-{1-[3,4-difluoro-5-(methyloxy)phenyl]-1-methylethyl}-1-(4-fluorophenyl)-1H-imidazol-2-yl]thio}methyl)-5-fluorophenyl]sulfonyl}amino)-N,N,N-trimethylpropan-1-aminium;

4-([(1R)-1-carboxyethyl]{[4-({[5-{1-[4-chloro-3-(methyloxy)phenyl]-1-methylethyl}-1-4-fluorophenyl)-1H-imidazol-2-yl]thio}methyl)-3,5-difluorophenyl]sulfonyl}amino)-N,N,N-trimethylbutan-1-aminium;

3-[{[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]sulfonyl}(ethyl)amino]-N,N,N-trimethylpropan-1-aminium;

3-[{[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]sulfonyl}(cyclopropyl)amino]-N,N,N-trimethylpropan-1-aminium;

3-[{[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]sulfonyl}(1-methylethyl)amino]-N,N,N-trimethylpropan-1-aminium;

3-[{[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]sulfonyl}(methyl)amino]-N-ethyl-N,N-dimethylpropan-1-aminium;

3-[(carboxymethyl){[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]sulfonyl}amino]-N,N,N-trimethylpropan-1-aminium;

4-[(carboxymethyl){[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}amino]-N,N,N-trimethylbutan-1-aminium;

3-([(1S)-1-carboxy-2-methylpropyl]{[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}amino)-N,N,N-trimethylpropan-1-aminium;

3-([(1R)-1-carboxy-2-methylpropyl]{[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}amino)-N,N,N-trimethylpropan-1-aminium;

3-[(2-carboxyethyl){[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}amino]-N,N,N-trimethylpropan-1-aminium;

3-[(carboxymethyl){[3-chloro-4-({[5-{1-[4-chloro-3-(methyloxy)phenyl]-1-methylethyl}-1-4-fluorophenyl)-1H-imidazol-2-yl]thio}methyl)-5-fluorophenyl]sulfonyl}amino]-N,N,N-trimethylpropan-1-aminium;

3-([(1S)-1-carboxy-2-hydroxyethyl]{[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}amino)-N,N,N-trimethylpropan-1-aminium;

3-[(2-carboxyethyl){[3-chloro-4-({[5-{1-[4-chloro-3-(methyloxy)phenyl]-1-methylethyl}-1-4-fluorophenyl)-1H-imidazol-2-yl]thio}methyl)-5-fluorophenyl]sulfonyl}amino]-N,N,N-trimethylpropan-1-aminium;

3-([(3-carboxyphenyl)methyl]{[4-({[5-{1-[4-chloro-3-(methyloxy)phenyl]-1-methylethyl}-1-4-fluorophenyl)-1H-imidazol-2-yl]thio}methyl)-3,5-difluorophenyl]sulfonyl}amino)-N,N,N-trimethylpropan-1-aminium;

3-([(1S)-1-carboxypropyl]{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}amino)-N,N,N-trimethylpropan-1-aminium;

3-([(1S)-1-carboxyethyl]{[3-chloro-4-({[5-{1-[4-chloro-3-(methyloxy)phenyl]-1-methylethyl}-1-4-fluorophenyl)-1H-imidazol-2-yl]thio}methyl)-5-fluorophenyl]sulfonyl}amino)-N,N,N-trimethylpropan-1-aminium;

3-([(1R)-1-carboxyethyl]{[3-chloro-4-({[5-{1-[4-chloro-3-(methyloxy)phenyl]-1-methylethyl}-1-4-fluorophenyl)-1H-imidazol-2-yl]thio}methyl)-5-fluorophenyl]sulfonyl}amino)-N,N,N-trimethylpropan-1-aminium;

3-[(1-carboxycyclopropyl){[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}amino]-N,N,N-trimethylpropan-1-aminium;

4-([(1R)-1-carboxyethyl]{[3-chloro-4-({[5-{1-[4-chloro-3-(methyloxy)phenyl]-1-methylethyl}-1-4-fluorophenyl)-1H-imidazol-2-yl]thio}methyl)-5-fluorophenyl]sulfonyl}amino)-N,N,N-trimethylbutan-1-aminium;

3-([(1R)-1-carboxypropyl]{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}amino)-N,N,N-trimethylpropan-1-aminium;

3-([(1S,2R)-1-carboxy-2-hydroxypropyl]{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}amino)-N,N,N-trimethylpropan-1-aminium;

5-([(1R)-1-carboxyethyl]{[3-chloro-4-({[5-{1-[4-chloro-3-(methyloxy)phenyl]-1-methylethyl}-1-4-fluorophenyl)-1H-imidazol-2-yl]thio}methyl)-5-fluorophenyl]sulfonyl}amino)-N,N,N-trimethylpentan-1-aminium;

3-({[4-({[5-{1-[4-chloro-3-(methyloxy)phenyl]-1-methylethyl}-1-4-fluorophenyl)-1H-imidazol-2-yl]thio}methyl)-3,5-difluorophenyl]sulfonyl}{[4-(methyloxy)phenyl]methyl}amino)-N,N,N-trimethylpropan-1-aminium;

3-({[4-({[5-{1-[4-chloro-3-(methyloxy)phenyl]-1-methylethyl}-1-4-fluorophenyl)-1H-imidazol-2-yl]thio}methyl)-3,5-difluorophenyl]sulfonyl}[1,1-dimethyl-2-(methyloxy)-2-oxoethyl]amino)-N,N,N-trimethylpropan-1-aminium;

(S)-3-(4((5-(2-(4-chloro-3-methoxyphenyl)propan-2-yl)-1-(4-fluorophenyl)-1H-imidazol-2-ylthio)methyl)-N-(1,3-dicarboxypropyl)-3,5-difluorophenylsulfonamido)-N,N,N-trimethylpropan-1-aminium;

3-[(1-carboxy-1-methylethyl){[4-({[5-{1-[4-chloro-3-(methyloxy)phenyl]-1-methylethyl}-1-4-fluorophenyl)-1H-imidazol-2-yl]thio}methyl)-3,5-difluorophenyl]sulfonyl}amino]-N,N,N-trimethylpropan-1-aminium;

4-[(1-carboxy-1-methylethyl){[4-({[5-{1-[4-chloro-3-(methyloxy)phenyl]-1-methylethyl}-1-4-fluorophenyl)-1H-imidazol-2-yl]thio}methyl)-3,5-difluorophenyl]sulfonyl}amino]-N,N,N-trimethylbutan-1-aminium;

3-([(1R)-2-carboxy-1-methylethyl]{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}amino)-N,N,N-trimethylpropan-1-aminium;

N-{[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}-N-[(1,1-dimethylpiperidinium-4-yl)methyl]-D-alanine;

N-{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}-N-(3-pyridinium-1-ylpropyl)-D-alanine;

N-{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}-N-[-3-(1-methyl-1H-imidazol-3-ium-3-yl)propyl]-D-alanine;

N-{[3-chloro-4-({[5-{1-[4-chloro-3-methyloxy)phenyl]-1-methylethyl}-1-(4-fluorophenyl)-1H-imidazol-2-yl]thio}methyl)-5-fluorophenyl]sulfonyl}-N-[2-(1-methylpyridinium-3-yl)ethyl]-D-alanine;

N-{(4S)-4-carboxy-4-[{[4-({[5-{1-[4-chloro-3-(methyloxy)phenyl]-1-methylethyl}-1-4-fluorophenyl)-1H-imidazol-2-yl]thio}methyl)-3,5-difluorophenyl]sulfonyl}(methyl)amino]butyl}-N,N-dimethylmethanaminium;

N-{(4S)-4-carboxy-4-[{[4-({[5-{1-[4-chloro-3-(methyloxy)phenyl]-1-methylethyl}-1-4-fluorophenyl)-1H-imidazol-2-yl]thio}methyl)-3,5-difluorophenyl]sulfonyl}(ethyl)amino]butyl}-N,N-dimethylmethanaminium;

N-{(4S)-4-carboxy-4-[[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}(methyl)amino]butyl}-N,N-dimethylmethanaminium;

N-{(4R)-4-carboxy-4-[{[4-({[5-{1-[4-chloro-3-(methyloxy)phenyl]-1-methylethyl}-1-4-fluorophenyl)-1H-imidazol-2-yl]thio}methyl)-3,5-difluorophenyl]sulfonyl}(methyl)amino]butyl}-N,N-dimethylmethanaminium;

N-{(4R)-4-carboxy-4-[{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}(methyl)amino]butyl}-N,N-dimethylmethanaminium;

N-[(5S)-5-carboxy-5-({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}amino)pentyl]-N,N-dimethylmethanaminium;

N-{(5S)-5-carboxy-5-[{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}(methyl)amino]pentyl}-N,N-dimethylmethanaminium;

N-{(5S)-5-carboxy-5-[{[4-({[5-{1-[4-chloro-3-(methyloxy)phenyl]-1-methylethyl}-1-4-fluorophenyl)-1H-imidazol-2-yl]thio}methyl)-3,5-difluorophenyl]sulfonyl}(methyl)amino]pentyl}-N,N-dimethylmethanaminium;

N-{(5S)-5-carboxy-5-[({3-chloro-4-[({5-[1-(3,4-dichlorophenyl]-1-methylethyl]-1-(4-fluorophenyl)-1H-imidazol-2-yl}thio)methyl]-5-fluorophenyl}sulfonyl)(methyl)amino]pentyl}-N,N-dimethylmethanaminium N-[(5R)-5-carboxy-5-({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}amino)pentyl]-N,N-dimethylmethanaminium;

N-{(5R)-5-carboxy-5-[{[3-chloro-4-({[5-{1-[4-chloro-3-(methyloxy)phenyl]-1-4-fluorophenyl)-1H-imidazol-2-yl]thio}methyl)-5-fluorophenyl]sulfonyl}(methyl)amino]pentyl}-N,N-dimethylmethanaminium;

N-{(5R)-5-carboxy-5-[{[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}(methyl)amino]pentyl}-N,N-dimethylmethanaminium;

(6S)-6-carboxy-6-[{[3-chloro-4-({[5-{1-[4-chloro-3-(methyloxy)phenyl]-1-methylethyl}-1-4-fluorophenyl)-1H-imidazol-2-yl]thio}methyl)-5-fluorophenyl]sulfonyl}(methyl)amino]-N,N,N-trimethylhexaN-1-aminium;

3-{[(1R)-1-carboxyethyl][(3-chloro-4-{2-[5-{1-[4-chloro-3-(methyloxy)phenyl]-1-methylethyl}-1-(4-fluorophenyl)-1H-imidazol-2-yl]ethyl}-5-fluorophenyl)sulfonyl]amino}-N,N,N-trimethylpropan-1-aminium;

N-[(5S)-5-carboxy-5-{[(3-chloro-4-{2-[5-{1-[4-chloro-3-(methyloxy)phenyl]-1-methylethyl}-1-4-fluorophenyl)-1H-imidazol-2-yl]ethyl}-5-fluorophenyl)sulfonyl]amino}pentyl]-N,N-dimethylmethanaminium;

N-[(5S)-5-carboxy-5-{[(3-chloro-4-{2-[5-{1-[4-chloro-3-(methyloxy)phenyl]-1-methylethyl}-1-4-fluorophenyl)-1H-imidazol-2-yl]ethyl}-5-fluorophenyl)sulfonyl](methyl)amino}pentyl]-N,N-dimethylmethanaminium;

3-[4-({[5-{1-[4-chloro-3-(methyloxy)phenyl]-1-methylethyl}-1-(4-fluorophenyl)-1H-imidazol-2-yl]thio}methyl)-3,5-difluorophenyl]-N,N,N-trimethylprop-2-yn-1-aminium;

3-[4-({[5-{1-[4-chloro-3-(methyloxy)phenyl]-1-methylethyl}-1-(4-fluorophenyl)-1H-imidazol-2-yl]thio}methyl)-3,5-difluorophenyl]-N,N,N-triethylprop-2-yn-1-aminium;

1-(3(4-((5-(2-(4-chloro-3-methoxyphenyl)propan-2-yl)-1-(4-fluorophenyl)-1H-imidazol-2-ylthio)methyl)-3,5-difluorophenyl)propyl)-4-aza-1-azoniabicyclo[2.2.2]octane;

3-[4-({[5-{1-[4chloro-3-(methyloxy)phenyl]-1-methylethyl}-1-(4-fluorophenyl)-1H-imidazol-2-yl]thio}methyl)-3,5-difluorophenyl]-N,N,N-trimethylpropan-1-aminium;

3-{4-[({5-[1-(3-chloro-4-fluorophenyl)-1-methylethyl]-1-[4-fluoro-3-(methyloxy)phenyl]-1H-imidazol-2-yl}thio)methyl]-3,5-difluorophenyl}-N,N,N-trimethylpropan-1-aminium;

3-[4-({[5-{1[3-chloro-4-(methyloxy)phenyl]-1-methylethyl}-1-(4-fluorophenyl)-1H-imidazol-2-yl]thio}methyl)-3,5-difluorophenyl]-N,N,N-trimethylpropan-1-aminium;

3-[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]-N,N,N-trimethylpropan-1-aminium;

4-[4-({[5-{1-[4-chloro-3-(methyloxy)phenyl]-1-methylethyl}-1-(4-fluorophenyl)-1H-imidazol-2-yl]thio}methyl)-3,5difluorophenyl]-N,N,N-trimethylbutan-1-aminium;

-3-(4-{[(5-{1-[4-(aminosulfonyl)-3-chlorophenyl]-1-methylethyl}-1-[4-fluoro-3-(methyloxy)phenyl]-1H-imidazol-2-yl)thio]methyl}-3,5-difluorophenyl)-N,N,N-trimethylpropan-1-aminium;

2-{[4-({[5-{1-[4-chloro-3-(methyloxy)phenyl]-1-methylethyl}-1-(4-fluorophenyl)-1H-imidazol-2-yl]thio}methyl)-3,5-difluorophenyl]oxy}-N,N,N-trimethylethanaminium;

2-{[4-({[5-{1-[4-chloro-3-(methyloxy)phenyl]-1-methylethyl}-1-(4-fluorophenyl)-1H-imidazol-2-yl]thio}methyl)-3,5-difluorophenyl]oxy}-N,N,N-triethylethanaminium;

(4-carboxy-1-{[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}piperidin-4-y1)-N,N,N-trimethylmethanaminium;

N-{(4S)-4-carboxy-4-[{[3,5-difluoro-4-({[5-{1-[4-fluoro-3-(methyloxy)phenyl]-1-methylethyl}-1-(4-fluorophenyl)-1H-imidazol-2-yl]thio}methyl)phenyl]sulfonyl}(methyl)amino]butyl}-N,N-dimethylmethanaminium;

N-{(4S)-4-carboxy-4-[{[4-({[5-{1-[3,4-difluoro-5-(methyloxy)phenyl]-1-methylethyl}-1-4-fluorophenyl)-1H-imidazol-2-yl]thio}methyl)-3,5-difluorophenyl]sulfonyl}(methyl)amino]butyl}-N,N-dimethylmethanaminium;

N-{(4S)-4-carboxy-4-[{[4-({[5-{1-[3-chloro-4-(methyloxy)phenyl]-1-methylethyl}-1-4-fluorophenyl)-1H-imidazol-2-yl]thio}methyl)-3,5-difluorophenyl]sulfonyl}(methyl)amino]butyl}-N,N-dimethylmethanaminium;

N-{(4S)-4-carboxy-4-[({4-[({5-[1-(3-chloro-4-fluorophenyl]-1-methylethyl]-1-(4-fluorophenyl)-1H-imidazol-2-yl}thio)methyl]-3,5-difluorophenyl}sulfonyl)(methyl)amino]butyl}-N,N-dimethylmethanaminium;

(6S)-6-carboxy-6-[{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}(methyl)amino]-N,N,N-trimethylhexaN-1-aminium;

N-[3-(4-aza-1-azoniabicyclo[2.2.2]oct-1-yl)propyl]-N-{[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}-D-alanine;

(S)-5-carboxy-5-(3-chloro-4-((5-(2-(3,4-dichlorophenyl)propan-2-yl)-1-(4-fluorophenyl)-1H-imidazol-2-ylthio)methyl)-5-fluoro-N-methylphenylsulfonamido)-N,N,N-trimethylpentan-1-aminium N-[4-(4-aza-1-azoniabicyclo[2.2.2]oct-1-yl)butyl]-N-{[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}-D-alanine; and (4-carboxy-1-{[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl }piperidin-4-y1)-N,N,N-trimethylmethanaminium, wherein each of the above compounds are in the presence of a pharmaceutically acceptable counter ion.

23. A composition comprising a compound according to claim 1 and a pharmaceutically acceptable diluent, excipient, or carrier.

\* \* \* \* \*